US010246491B2

(12) United States Patent
Guerlavais et al.

(10) Patent No.: US 10,246,491 B2
(45) Date of Patent: Apr. 2, 2019

(54) PEPTIDOMIMETIC MACROCYCLES AND USE THEREOF IN REGULATING HIF1ALPHA

(71) Applicant: AILERON THERAPEUTICS, INC., Cambridge, MA (US)

(72) Inventors: Vincent Guerlavais, Arlington, MA (US); Noriyuki Kawahata, West Roxbury, MA (US); Huw M. Nash, Lexington, MA (US); Carl Elkin, Arlington, MA (US); Eric Feyfant, Lexington, MA (US)

(73) Assignee: AILERON THERAPEUTICS, INC., Watertown, MA (US)

( * ) Notice: Subject to any disclaimer, the term of this patent is extended or adjusted under 35 U.S.C. 154(b) by 62 days.

(21) Appl. No.: 14/843,079

(22) Filed: Sep. 2, 2015

(65) Prior Publication Data

US 2016/0052970 A1    Feb. 25, 2016

Related U.S. Application Data

(63) Continuation of application No. PCT/US2014/021292, filed on Mar. 6, 2014.

(60) Provisional application No. 61/798,026, filed on Mar. 15, 2013, provisional application No. 61/776,663, filed on Mar. 11, 2013, provisional application No. 61/773,769, filed on Mar. 6, 2013.

(51) Int. Cl.
*C07K 7/56* (2006.01)
*A61K 47/54* (2017.01)
*A61K 38/00* (2006.01)

(52) U.S. Cl.
CPC .............. *C07K 7/56* (2013.01); *A61K 47/54* (2017.08); *A61K 38/00* (2013.01)

(58) Field of Classification Search
None
See application file for complete search history.

(56) References Cited

U.S. PATENT DOCUMENTS

| | | | |
|---|---|---|---|
| 6,936,586 B1 | 8/2005 | Larsen et al. |
| 7,192,713 B1 | 3/2007 | Verdine et al. |
| 7,786,072 B2 | 8/2010 | Verdine et al. |
| 8,324,428 B2 | 12/2012 | Verdine et al. |
| 8,895,699 B2 | 11/2014 | Verdine et al. |
| 9,074,009 B2 | 7/2015 | Bradner et al. |
| 9,458,189 B2 | 10/2016 | Verdine et al. |
| 9,487,562 B2 | 11/2016 | Moellering et al. |
| 9,617,309 B2 | 4/2017 | Verdine et al. |
| 9,845,287 B2 | 12/2017 | Darlak et al. |
| 9,951,099 B2 | 4/2018 | Verdine et al. |
| 9,957,296 B2 | 5/2018 | Nash et al. |
| 9,957,299 B2 | 5/2018 | Guerlavais et al. |
| 10,022,422 B2 | 7/2018 | Nash et al. |
| 10,023,613 B2 | 7/2018 | Guerlavais et al. |
| 10,030,049 B2 | 7/2018 | Nash |
| 10,059,741 B2 | 8/2018 | Annis et al. |
| 2004/0230380 A1 | 11/2004 | Chirino et al. |
| 2007/0161690 A1 | 7/2007 | Castro et al. |
| 2012/0149648 A1 | 6/2012 | Nash et al. |
| 2012/0190818 A1 | 7/2012 | Nash |
| 2013/0210745 A1 | 8/2013 | Guerlavais et al. |
| 2016/0122405 A1 | 5/2016 | Palchaudhuri et al. |
| 2016/0215036 A1 | 7/2016 | Verdine et al. |
| 2016/0244494 A1 | 8/2016 | Verdine et al. |
| 2016/0257725 A1 | 9/2016 | Verdine et al. |
| 2017/0008930 A1 | 1/2017 | Walensky et al. |
| 2017/0107252 A1 | 4/2017 | Guerlavais et al. |
| 2017/0114098 A1 | 4/2017 | Aivado et al. |
| 2017/0212125 A1 | 7/2017 | Nash et al. |
| 2017/0226177 A1 | 8/2017 | Kawahata et al. |
| 2017/0266254 A1 | 9/2017 | Nash et al. |
| 2017/0281720 A1 | 10/2017 | Guerlavais et al. |
| 2017/0296620 A1 | 10/2017 | Nash |
| 2017/0298099 A1 | 10/2017 | Nash et al. |
| 2017/0360881 A1 | 12/2017 | Samant et al. |
| 2018/0085426 A1 | 3/2018 | Nash et al. |
| 2018/0100001 A1 | 4/2018 | Verdine et al. |

FOREIGN PATENT DOCUMENTS

| | | |
|---|---|---|
| AU | 2008232709 A1 | 10/2008 |
| CA | 2700925 A1 | 4/2009 |
| EP | 2488193 A1 | 8/2012 |
| EP | 2489360 A1 | 8/2012 |
| EP | 2114428 B1 | 10/2012 |
| JP | 2010510236 A | 4/2010 |
| JP | 2010518017 A | 5/2010 |
| JP | 2012503025 A | 2/2012 |
| WO | WO-2005001023 A2 | 1/2005 |
| WO | WO-2008040000 A2 | 4/2008 |
| WO | WO-2008104000 A3 | 11/2008 |
| WO | WO-2009126292 A2 | 10/2009 |
| WO | WO-2009042237 A3 | 12/2009 |
| WO | WO-2010121288 A1 | 10/2010 |
| WO | WO-2013062923 A1 | 5/2013 |
| WO | WO-2013116829 A1 | 8/2013 |
| WO | WO-2014047673 A1 | 4/2014 |
| WO | WO-2014115080 A1 | 7/2014 |
| WO | WO-2014134201 A1 | 9/2014 |
| WO | WO-2015017803 A1 | 2/2015 |
| WO | WO-2015097622 A1 | 7/2015 |
| WO | WO-2015097621 A3 | 10/2015 |
| WO | WO-2017165299 A2 | 9/2017 |
| WO | WO-2017205786 A1 | 11/2017 |
| WO | WO-2017218949 A2 | 12/2017 |

OTHER PUBLICATIONS

Adamski, et al. The cellular adaptations to hypoxia as novel therapeutic targets in childhood cancer. Cancer Treat Rev. May 2008;34(3):231-46. doi: 10.1016/j.ctrv.2007.11.005. Epub Jan. 18, 2008.

(Continued)

*Primary Examiner* — Thomas S Heard
(74) *Attorney, Agent, or Firm* — Wilson Sonsini Goodrich & Rosati

(57) ABSTRACT

The present invention provides peptidomimetic macrocycles capable of regulating HIF1α and methods of using such macrocycles for the treatment of diseases.

3 Claims, 4 Drawing Sheets

Specification includes a Sequence Listing.

(56) References Cited

OTHER PUBLICATIONS

Caramelo, et al. [Response to hypoxia. A systemic mechanism based on the control of gene expression]. Medicina (B Aires). 2006;66(2):155-64 (in French with English abstract).
Co-pending U.S. Appl. No. 13/494,846, filed Jun. 12, 2012.
Co-pending U.S. Appl. No. 15/493,301, filed Apr. 21, 2017.
Ding, et al. Retinal disease in mice lacking hypoxia-inducible transcription factor-2alpha. Invest Ophthalmol Vis Sci. Mar. 2005;46(3):1010-6.
Fields, et al. Chapter 3 in Synthetic Peptides: A User's Guide. Grant W.H. Freeman & Co. New York, NY. 1992. p. 77.
Fields, G. B. Chapter 3: Principles and Practice of Solid-Phase Peptide Synthesis. Synthetic Peptides: A User's Guide, GA Grant Edition, (1992), pp. 77-183.
Forooghian, et al. Anti-angiogenic effects of ribonucleic acid interference targeting vascular endothelial growth factor and hypoxia-inducible factor-1alpha. Am J Ophthalmol. Nov. 2007;144(5):761-8. Epub Sep. 17, 2007.
Freedman, et al. Structural basis for negative regulation of hypoxia-inducible factor-1alpha by CITED2. Nat Struct Biol. Jul. 20003;10(7):504-12.
Freedman, et al. Structural basis for recruitment of CBP/p300 by hypoxia-inducible factor-1 alpha. Proc Natl Acad Sci U S A. Apr. 16, 2002;99(8):5367-72.
Galanis, et al. Reactive oxygen species and HIF-1 signalling in cancer. Cancer Lett. Jul. 18, 2008;266(1):12-20. doi: 10.1016/j.canlet.2008.02.028. Epub Apr. 18, 2008.
Henchey, et al. Inhibition of Hypoxia Inducible Factor 1-Transcription Coactivator Interaction by a Hydrogen Bond Surrogate α-Helix. J Am Chem Soc. Jan. 27, 2010;132(3):941-3.
Inoue, et al. Expression of hypoxia-inducible factor 1alpha and 2alpha in choroidal neovascular membranes associated with age-related macular degeneration. Br J Ophthalmol. Dec. 2007;91(12):1720-1.
Marignol, et al. Hypoxia in prostate cancer: a powerful shield against tumour destruction? Cancer Treat Rev. Jun. 2008;34(4):313-27. doi: 10.1016/j.ctrv.2008.01.006. Epub Mar. 10, 2008.
Min, et al. Structure of an HIF-1alpha-pVHL complex: hydroxyproline recognition in signaling. Science. Jun. 7, 2002;296(5574):1886-9.
Rankin, et al. The role of hypoxia-inducible factors in tumorigenesis. Cell Death Differ. Apr. 2008;15(4):678-85. doi: 10.1038/cdd.2008.21. Epub Feb. 15, 2008.
Semenza, GL. HIF-1 and mechanisms of hypoxia sensing. Curr Opin Cell Biol. Apr. 2001;13(2):167-71.
Simon, et al. Hypoxia-induced signaling in the cardiovascular system. Annu Rev Physiol. 2008;70:51-71.
Tazuke, et al. Hypoxia stimulates insulin-like growth factor binding protein 1 (IGFBP-1) gene expression in HepG2 cells: a possible model for IGFBP-1 expression in fetal hypoxia. Proc Natl Acad Sci U S A. Aug. 18, 1998;95(17):10188-93.
Toffoli, et al. Intermittent hypoxia is a key regulator of cancer cell and endothelial cell interplay in tumours. FEBS J. Jun. 2008;275(12):2991-3002. doi: 10.1111/j.1742-4658.2008.06454.x. Epub Apr. 25, 2008.
Verdine et al., Stapled peptides for intracellular drug targets. Methods Enzymol. 2012;503:3-33. doi: 10.1016/B978-0-12-396962-0.00001-X.
Zhang, et al. 310 Helix versus alpha-helix: a molecular dynamics study of conformational preferences of Aib and Alanine. J. American Cancer Society. Dec. 1994; 116(26):11915-11921.
Zhu, et al. Long-term tolerance to retinal ischemia by repetitive hypoxic preconditioning: role of HIF-1alpha and heme oxygenase-1. Invest Ophthalmol Vis Sci. Apr. 2007;48(4):1735-43.
Zimm & Bragg, "Theory of the Phase Transition between Helix and Random Coil in Polypeptide Chains," J. Chem. Phys. 31(2):526-535 (1959).
Co-pending U.S. Appl. No. 15/711,576, filed Sep. 21, 2017.
Co-pending U.S. Appl. No. 15/794,355, filed Oct. 26, 2017.
Co-pending U.S. Appl. No. 15/956,333, filed Apr. 18, 2018.
Co-pending U.S. Appl. No. 15/917,054, filed Mar. 9, 2018.
Co-pending U.S. Appl. No. 15/917,560, filed Mar. 9, 2018.
Co-pending U.S. Appl. No. 15/975,298, filed May 9, 2018.
Co-pending U.S. Appl. No. 15/982,700, filed May 17, 2018.
Co-pending U.S. Appl. No. 16/002,977, filed Jun. 7, 2018.
Co-pending U.S. Appl. No. 16/009,755, filed Jun. 15, 2018.
Co-pending U.S. Appl. No. 16/023,606, filed Jun. 29, 2018.
Co-pending U.S. Appl. No. 16/050,380, filed Jul. 31, 2018.
Co-pending U.S. Appl. No. 16/051,744, filed Aug. 1, 2018.
Co-pending U.S. Appl. No. 16/053,015, filed Aug. 2, 2018.

PEPTIDOMIMETIC MACROCYCLES AND USE THEREOF IN REGULATING HIF1ALPHA

CROSS-REFERENCE

This application is a continuation of PCT/US14/21292, filed Mar. 6, 2014, which claims priority to U.S. Provisional Application No. 61/798,026, filed Mar. 15, 2013, U.S. Provisional Application No. 61/776,663, filed Mar. 11, 2013, and U.S. Provisional Application No. 61/773,769, filed Mar. 6, 2013, each of which applications are hereby incorporated by reference in their entirety.

SEQUENCE LISTING

The instant application contains a Sequence Listing which has been submitted electronically in ASCII format and is hereby incorporated by reference in its entirety. Said ASCII copy, created on Mar. 24, 2014, is named 35224-790.601_SL.txt and is 392,916 bytes in size.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND OF THE INVENTION

Hypoxia-inducible factors (HIFs) are transcription factors that respond to changes in available oxygen in the cellular environment, in specific, to decreases in oxygen, or hypoxia. Most, if not all, oxygen-breathing species express the highly-conserved transcriptional complex HIF-1, which is a heterodimer composed of an alpha and a beta subunit, the latter being a constitutively-expressed aryl hydrocarbon receptor nuclear translocator (ARNT). HIF-1 belongs to the PER-ARNT-SIM (PAS) subfamily of the basic-helix-loop-helix (bHLH) family of transcription factors. The alpha subunit of HIF-1 is a target for prolyl hydroxylation by HIF prolyl-hydroxylase, which makes HIF1α a target for degradation by the E3 ubiquitin ligase complex, leading to quick degradation by the proteasome. This occurs only in normoxic conditions. In hypoxic conditions, HIF prolyl-hydroxylase is inhibited, since it utilizes oxygen as a cosubstrate.

HIFs facilitate both oxygen delivery and adaptation to oxygen deprivation by regulating the expression of genes that are involved in many cellular processes, including glucose uptake and metabolism, angiogenesis, erythropoiesis, cell proliferation, and apoptosis (Semenza G L. Curr Opin Cell Biol 2001; 13: 167-171). They are members of the PAS (PER-ARNT (arylhydrocarbon receptor nuclear translocator)-SIM) family of basic helix-loop-helix (bHLH) transcription factors that bind to DNA as heterodimers composed of an oxygen-sensitive α subunit and a constitutively expressed β subunit, also known as ARNT. To date, three HIFs (HIF-1, -2, and -3) have been identified that regulate transcriptional programs in response to low oxygen levels.

HIFs are transcription factors that mediate cellular adaptations to oxygen deprivation. Over 100 direct HIF target genes have been identified that regulate a number of cellular processes, including glucose metabolism, angiogenesis, erythropoiesis, proliferation, and invasion. HIF can also indirectly regulate cellular processes such as proliferation and differentiation through interactions with other signaling proteins such as C-Myc and Notch (Rankin E B and A J Giaccia, Cell Death and Differentiation, 15, 2008).

Chronic hypoxia is a hallmark of many tumors and is associated with angiogenesis and more aggressive tumor phenotype. HIFs regulate multiple steps of tumorigenesis including tumor formation, progression, and response to therapy. There are multiple mechanisms by which HIF can become activated and promote tumor progression. Thus, it is apparent that downregulation of the HIF system is an attractive target for cancer therapy.

Cited2 is a cAMP-responsive element-binding protein (CBP)/p300 interacting transcriptional modulator, with Glu/Asp-rich carboxy-terminal domain, 2. Cited2 has been seen as a negative regulator of HIF1α-mediated signaling by competing with HIF1α for binding to CBP/p300 (Freedman et al., Nat Struct Biol. 2003 July; 10(7):504-12; Bhattacharya et al., Genes Dev. 13, 64-75, 1999).

SUMMARY OF THE INVENTION

The present invention provides pharmaceutical formulations comprising an effective amount of peptidomimetic macrocycles or pharmaceutically acceptable salts thereof. The peptidomimetic macrocycles of the invention are cross-linked (e.g., stapled) and possess improved pharmaceutical properties relative to their corresponding uncross-linked peptidomimetic macrocycles. These improved properties include improved bioavailability, enhanced chemical and in vivo stability, increased potency, and reduced immunogenicity (i.e., fewer or less severe injection site reactions).

In some embodiments, the present invention provides a peptidomimetic macrocycle comprising an amino acid sequence which is at least about 60% identical to an amino acid sequence selected from the group consisting of the amino acid sequences in Tables 1a, 1b and 1c, further comprising at least one macrocycle-forming linker, wherein the macrocycle-forming linker connects a first amino acid to a second amino acid. In some embodiments, the peptidomimetic macrocycle comprises an amino acid sequence which is at least about 65%, 70%, 75%, 80%, 85%, 90% or 95% an amino acid sequence identical to selected from the group consisting of the amino acid sequences in Tables 1a, 1b and 1c. In some embodiments, the peptidomimetic macrocycle comprises an amino acid sequence selected from the group consisting of the amino acid sequences in Tables 1a, 1b and 1c. In some embodiments, a macrocycle-forming linker of the peptidomimetic macrocycle of the invention connects one of the following pairs of amino acids: 9 and 13, 9 and 16, 10 and 14, 10 and 17, 11 and 15, 11 and 18, 12 and 16, 12 and 19, 13 and 17, 13 and 20, 14 and 18, and 15 and 19. In some embodiments, the macrocycle-forming linker connects amino acids 10 and 14. In some embodiments, the macrocycle-forming linker connects amino acids 14 and 18.

In some embodiments, the present invention provides a peptidomimetic macrocycle comprising an amino acid sequence which is at least about 60% identical to an amino acid sequence selected from the group consisting of the amino acid sequences in Table 2, further comprising at least one macrocycle-forming linker, wherein the macrocycle-forming linker connects a first amino acid to a second amino acid. In some embodiments, the peptidomimetic macrocycle comprises an amino acid sequence which is at least about 65%, 70%, 75%, 80%, 85%, 90% or 95% identical to an amino acid sequence selected from the group consisting of the amino acid sequences in Table 2. In some embodiments, the peptidomimetic macrocycle comprises an amino acid sequence selected from the group consisting of the amino acid sequences in Table 2. In some embodiments, one or more macrocycle-forming linkers of the peptidomimetic macrocycle of the invention connect one or more of the following pairs of amino acids: 4 and 8, 4 and 11, 5 and 9, 5 and 12, 6 and 10, 6 and 13, 7 and 11, 8 and 12, 9 and 13, 19 and 23, 19 and 26, 20 and 27, 21 and 25, 21 and 28, 23 and 27, and 41 and 45. In some embodiments, the peptidomimetic macrocycle comprise two macrocycle-forming linkers. In some embodiments, the macrocycle-forming linkers connect amino acids 6 and 13 and amino acids 23 and 27. In some embodiments, the macrocycle-forming linkers connect amino acids 8 and 12 and amino acids 19 and 26. In some embodiments, the macrocycle-forming linkers connect amino acids 8 and 12 and amino acids 23 and 27. In some embodiments, the macrocycle-forming linkers connect amino acids 23 and 27 and amino acids 41 and 45.

In some embodiments, a peptidomimetic macrocycle of the invention comprises a helix, for example an α-helix. In some embodiments, a peptidomimetic macrocycle of the invention comprises an α,α-disubstituted amino acid. In some embodiments, each amino acid connected by the macrocycle-forming linker is an α,α-disubstituted amino acid.

In some embodiments, the present invention provides a peptidomimetic macrocycle having Formula (I):

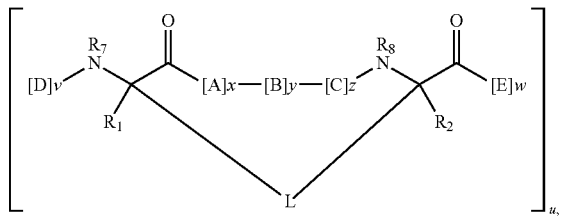

Formula (I)

wherein:
each A, C, D, and E is independently an amino acid,
B is an amino acid

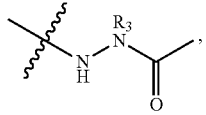

[—NH-L₃-CO—], [—NH-L₃-SO₂—], or [—NH-L₃-],
wherein A, B, C, D, and E, taken together with the cross-linked amino acids connected by the macrocycle-forming linker L, form the amino acid sequence of the peptidomimetic macrocycle;
L is a macrocycle-forming linker of the formula -L₁-L₂- or the formula

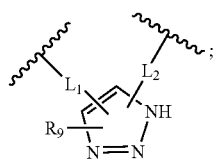

R₁ and R₂ are independently —H, alkyl, alkenyl, alkynyl, arylalkyl, cycloalkyl, cycloalkylalkyl, heteroalkyl, or heterocycloalkyl, each of which except for —H is optionally substituted with halo-;

R₃ is —H, alkyl, alkenyl, alkynyl, arylalkyl, heteroalkyl, cycloalkyl, heterocycloalkyl, cycloalkylalkyl, cycloaryl, or heterocycloaryl, each of which except for —H is optionally substituted with R₅;

L₁, L₂, and L₃ are independently alkylene, alkenylene, alkynylene, heteroalkylene, cycloalkylene, heterocycloalkylene, cycloarylene, heterocycloarylene, or [—R₄—K—R₄—]ₙ, each being optionally substituted with R₅;

each R₄ is alkylene, alkenylene, alkynylene, heteroalkylene, cycloalkylene, heterocycloalkylene, arylene, or heteroarylene;

each K is O, S, SO, SO₂, CO, CO₂, or CONR₃;

each R₅ is independently halogen, alkyl, —OR₆, —N(R₆)₂, —SR₆, —SOR₆, —SO₂R₆, —CO₂R₆, a fluorescent moiety, a radioisotope, or a therapeutic agent;

each R₆ is independently —H, alkyl, alkenyl, alkynyl, arylalkyl, cycloalkylalkyl, heterocycloalkyl, a fluorescent moiety, a radioisotope, or a therapeutic agent;

R₇ is —H, alkyl, alkenyl, alkynyl, arylalkyl, cycloalkyl, heteroalkyl, cycloalkylalkyl, heterocycloalkyl, cycloaryl, or heterocycloaryl, each of which except for —H is optionally substituted with R₅, or part of a cyclic structure with a D residue;

R₈ is —H, alkyl, alkenyl, alkynyl, arylalkyl, cycloalkyl, heteroalkyl, cycloalkylalkyl, heterocycloalkyl, cycloaryl, or heterocycloaryl, each of which except for —H is optionally substituted with R₅, or part of a cyclic structure with an E residue;

R₉ is alkyl, alkenyl, alkynyl, aryl, cycloalkyl, cycloalkenyl, heteroaryl, or heterocyclyl group, unsubstituted or optionally substituted with Rₐ and/or R_b;

Rₐ and R_b are independently alkyl, OCH₃, CF₃, NH₂, CH₂NH₂, F, Br, I,

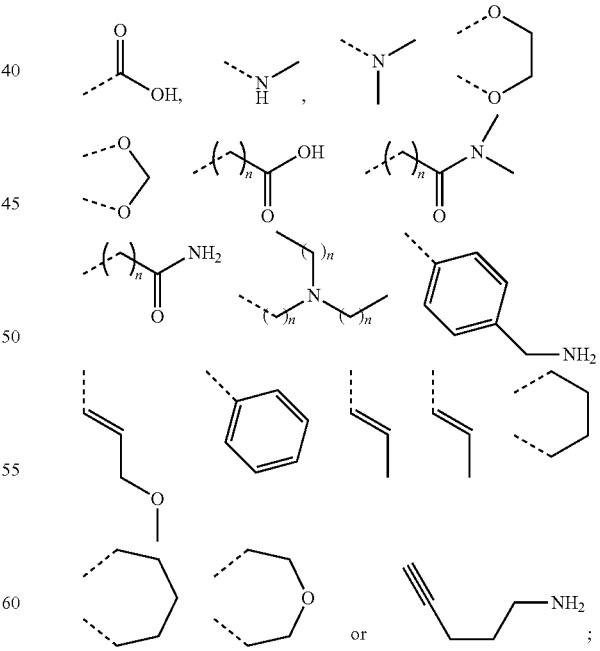

v and w are independently integers from 1-100;
u is an integer from 1 to 3;
x, y and z are independently integers from 0-10; and
n is an integer from 1-5.

In some embodiments, u is 1.

In some embodiments, the sum of x+y+z is 2, 3 or 6, for example 3.

In some embodiments, each of v and w is independently an integer from 1 to 10, 1 to 15, 1 to 20, or 1 to 25, for example from 1 to 15.

In some embodiments. $L_1$ and $L_2$ are independently alkylene, alkenylene or alkynylene. In some embodiments, $L_1$ and $L_2$ are independently $C_3$-$C_{10}$ alkylene or alkenylene, for example $C_3$-$C_6$ alkylene or alkenylene. For example, L is

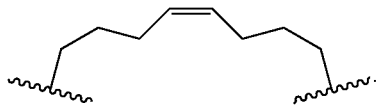 [SMILES: *CCC/C=C\CCC*]

In some embodiments, L is

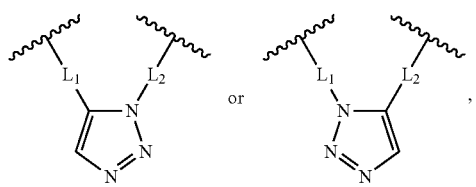

for example

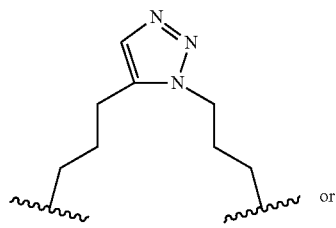

or

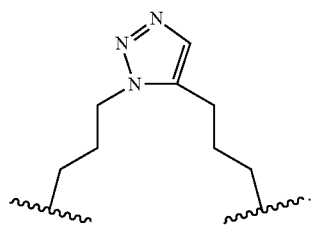

In some embodiments, $R_1$ and $R_2$ are H. In some embodiments, $R_1$ and $R_2$ are independently alkyl, for example methyl.

In some embodiments, the present invention provides a peptidomimetic macrocycle having the formula

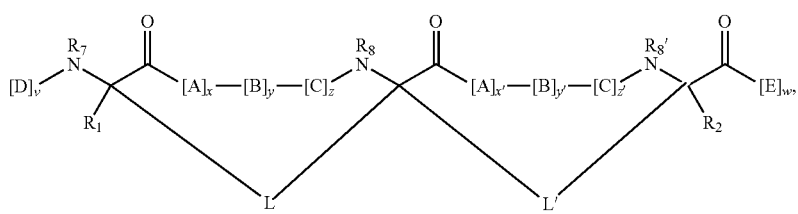

wherein:

L' is a macrocycle-forming linker of the formula -$L_1$'-$L_2$'- or the formula

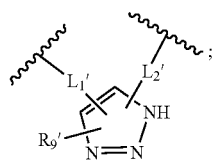

$L_1$' and $L_2$' are independently alkylene, alkenylene, alkynylene, heteroalkylene, cycloalkylene, heterocycloalkylene, cycloarylene, heterocycloarylene, or [—$R_4$—K—$R_4$—]$_n$, each being optionally substituted with $R_5$;

$R_8$' is —H, alkyl, alkenyl, alkynyl, arylalkyl, cycloalkyl, heteroalkyl, cycloalkylalkyl, heterocycloalkyl, cycloaryl, or heterocycloaryl, each of which except for —H is optionally substituted with $R_5$, or part of a cyclic structure with an E residue;

$R_9$' is alkyl, alkenyl, alkynyl, aryl, cycloalkyl, cycloalkenyl, heteroaryl, or heterocyclyl group, unsubstituted or optionally substituted with $R_a$' and/or $R_b$';

$R_a$' and $R_b$' are independently alkyl, $OCH_3$, $CF_3$, $NH_2$, $CH_2NH_2$, F, Br, I,

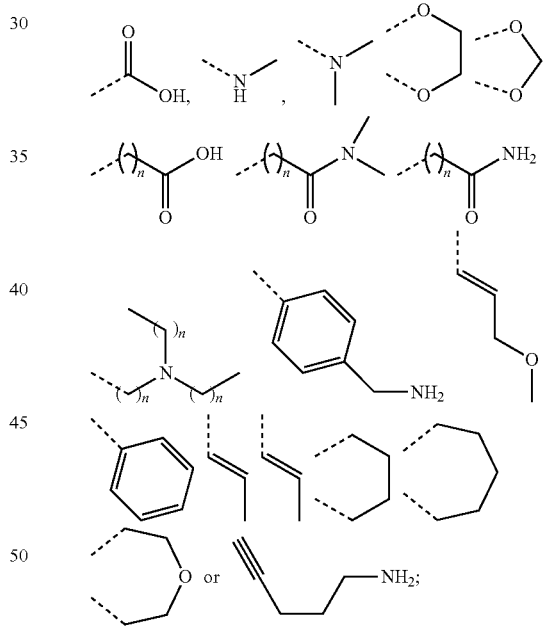

and x', y', and z' are independently integers from 0-10.

In some embodiments, the sum of x+y+z and the sum of x'+y'+z' are independently 2, 3 or 6, for example 3.

In some embodiments, each of v, w, v' and w' is independently an integer from 1 to 10, 1 to 15, 1 to 20, or 1 to 25.

In some embodiments, each of v, w, v' and w' is independently an integer from 1 to 15.

In some embodiments, $L_1$, $L_2$, $L_1'$, and $L_2'$ are independently alkylene, alkenylene or alkynylene. In some embodiments, $L_1$, $L_2$, $L_1'$, and $L_2'$ are independently $C_3$-$C_{10}$ alkylene or alkenylene, for example $C_3$-$C_6$ alkylene or alkenylene. In some embodiments, L and L' are both

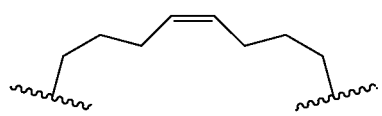 [SMILES: *CCC/C=C\CCC*]

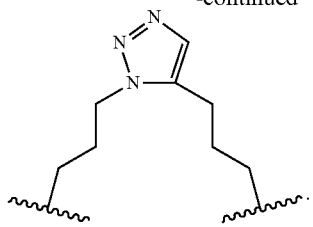

In some embodiments. $R_1$ and $R_2$ are H. In some embodiments, $R_1$ and $R_2$ are independently alkyl, for example methyl.

In some embodiments, a peptidomimetic macrocycle of the invention is (SEQ ID NO: 1)

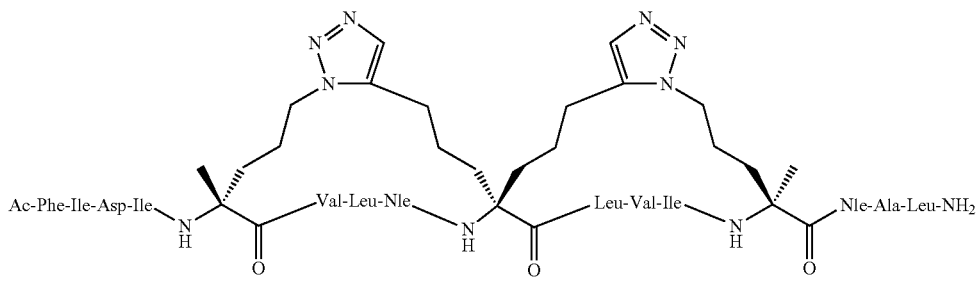

In some embodiments, L is

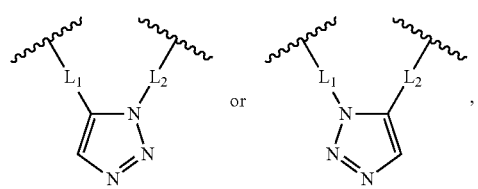

and L' is

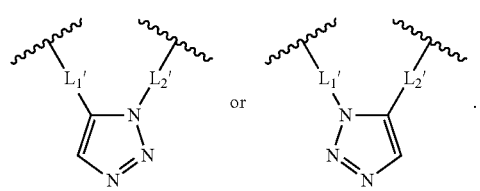

For example, L and L' are independently

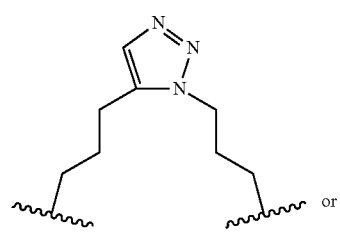

or a pharmaceutically acceptable salt thereof.

In some embodiments, a peptidomimetic macrocycle of the invention comprises a macrocycle-forming linker connecting a backbone amino group of a first amino acid to a second amino acid within the peptidomimetic macrocycle.

In some embodiments, the present invention provides a peptidomimetic macrocycle having Formula (II) or (IIa):

Formula (II)

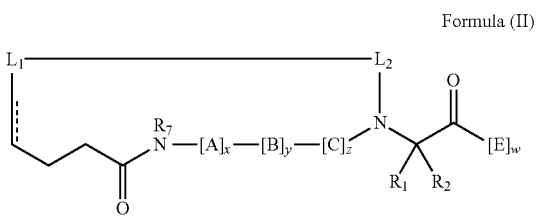

Formula (IIa)

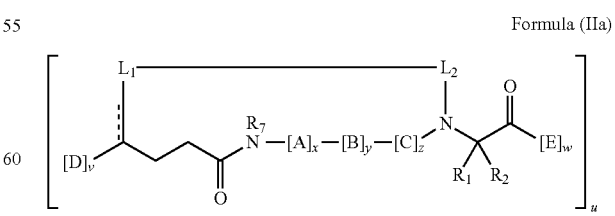

wherein:
each A, C, D, and E is independently an amino acid,
B is an amino acid,

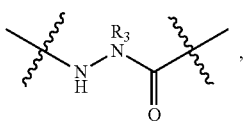

[—NH-L₃-CO—], [—NH-L₃-SO₂—], or [—NH-L₃-], wherein A, B, C, D, and E, taken together with the cross-linked amino acids connected by the macrocycle-forming linker -$L_1$-$L_2$-, form the amino acid sequence of the peptidomimetic macrocycle which is at least about 65%, 70%, 75%, 80%, 85%, 90%, 95% or is about 100% identical to an amino acid sequence selected from the group consisting of the amino acid sequences in Tables 1a, 1b, 1c and 2;

$R_1$ and $R_2$ are independently —H, alkyl, alkenyl, alkynyl, arylalkyl, cycloalkyl, cycloalkylalkyl, heteroalkyl, or heterocycloalkyl, unsubstituted or substituted with halo-, or part of a cyclic structure with an E residue;

$R_3$ is hydrogen, alkyl, alkenyl, alkynyl, arylalkyl, heteroalkyl, cycloalkyl, heterocycloalkyl, cycloalkylalkyl, cycloaryl, or heterocycloaryl, optionally substituted with $R_5$;

$L_1$ and $L_2$ are independently alkylene, alkenylene, alkynylene, heteroalkylene, cycloalkylene, heterocycloalkylene, cycloarylene, heterocycloarylene, or [—$R_4$—K—$R_4$—]$_n$, each being optionally substituted with $R_5$;

each $R_4$ is alkylene, alkenylene, alkynylene, heteroalkylene, cycloalkylene, heterocycloalkylene, arylene, or heteroarylene;

each K is O, S, SO, $SO_2$, CO, $CO_2$, or $CONR_3$:

each $R_5$ is independently halogen, alkyl, —$OR_6$, —$N(R_6)_2$, —$SR_6$, —$SO_6$, —$SO_2R_6$, —$CO_2R_6$, a fluorescent moiety, a radioisotope, or a therapeutic agent;

each $R_6$ is independently —H, alkyl, alkenyl, alkynyl, arylalkyl, cycloalkylalkyl, heterocycloalkyl, a fluorescent moiety, a radioisotope or a therapeutic agent;

$R_7$ is —H, alkyl, alkenyl, alkynyl, arylalkyl, cycloalkyl, heteroalkyl, cycloalkylalkyl, heterocycloalkyl, cycloaryl, or heterocycloaryl, each of which except for —H is optionally substituted with $R_5$;

v and w are independently integers from 1-100;

u is an integer from 1 to 3;

x, y and z are independently integers from 0-10; and n is an integer from 1-5.

In some embodiments, u is 1.

In some embodiments, the sum of x+y+z is 2, 3 or 6, for example 3.

In some embodiments, each of v and w is independently an integer from 1 to 10, 1 to 15, 1 to 20, or 1 to 25, for example from 1 to 15.

In some embodiments, $L_1$ and $L_2$ are independently alkylene, alkenylene or alkynylene. In some embodiments, $L_1$ and $L_2$ are independently $C_3$-$C_{10}$ alkylene or alkenylene, for example $C_3$-$C_6$ alkylene or alkenylene. For example, L is

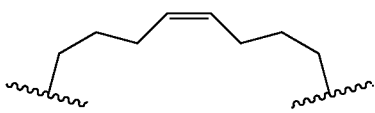

In some embodiments, L is

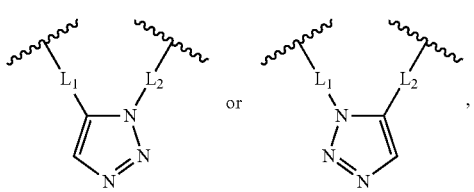

for example

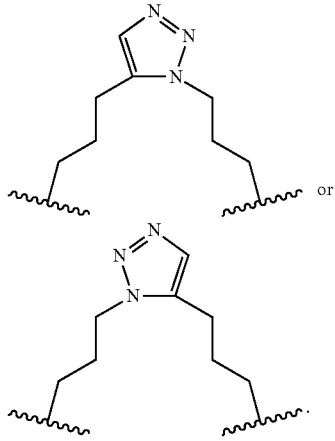

In some embodiments, $R_1$ and $R_2$ are H. In some embodiments, $R_1$ and $R_2$ are independently alkyl, for example methyl.

In some embodiments, the present invention provides a peptidomimetic macrocycle comprising an amino acid sequence of the formula:

X1-X2-X3-X4-X5-X6-X7-X8-X9-X10-X11-X12-
X13-X14-X15-X16-X17-X18-X19-X20-X21-
X22-X23-X24-X25-X26-X27-X28-X29-X30-
X31-X32                    (SEQ ID NO: 2)

wherein:

X1 is a hydrophobic amino acid, or absent;
X2 is a hydrophobic amino acid, or absent;
X3 is a negatively charged amino acid, a positively charged amino acid, or absent;
X4 is an uncharged polar amino acid, or absent;
X5 is a negatively charged amino acid or absent;
X6 is a hydrophobic amino acid, a negatively charged amino acid, a positively charged amino acid, an uncharged polar amino acid, or absent;
X7 is a hydrophobic amino acid, a negatively charged amino acid, or absent;
X8 is a negatively charged amino acid, a positively charged amino acid or absent;
X9 is a negatively charged amino acid, absent, or a cross-linked amino acid;
X10 is a negatively charged amino acid, a positively charged amino acid, an uncharged polar amino acid, or a cross-linked amino acid;
X11 is a hydrophobic amino acid, a negatively charged amino acid, a positively charged amino acid, or a cross-linked amino acid;
X12 is a hydrophobic amino acid, a negatively charged amino acid, or a cross-linked amino acid;
X13 is a hydrophobic amino acid, a hydrophobic amino acid, a negatively charged amino acid, or a cross-linked amino acid;
X14 is a cross-linked amino acid;
X15 is a hydrophobic amino acid, a negatively charged amino acid, or a cross-linked amino acid;
X16 is a hydrophobic amino acid, a negatively charged amino acid, or a cross-linked amino acid;
X17 is a hydrophobic amino acid, a negatively charged amino acid, a positively charged amino acid, or a cross-linked amino acid;
X18 is a cross-linked amino acid;

X19 is a hydrophobic amino acid, a negatively charged amino acid, a positively charged amino acid, or a cross-linked amino acid;
X20 is a negatively charged amino acid, a hydrophobic amino acid, or a cross-linked amino acid;
X21 is a hydrophobic amino acid, or a negatively charged amino acid;
X22 is a negatively charged amino acid, or absent;
X23 is a positively charged amino acid, a negatively charged amino acid or absent;
X24 is a hydrophobic amino acid, a negatively charged amino acid, or absent;
X25 is a hydrophobic amino acid, a negatively charged amino acid, or absent;
X26 is a negatively charged amino acid, or absent;
X27 is a hydrophobic amino acid or absent;
X28 is a hydrophobic amino acid, or absent;
X29 is a negatively charged amino acid, an uncharged polar amino acid, or absent;
X30 is a hydrophobic amino acid, or absent;
X31 is a hydrophobic amino acid, or absent; and
X32 is a hydrophobic amino acid, or absent;
wherein the peptidomimetic macrocycle comprises at least one macrocycle-forming linker connecting at least one pair of amino acids selected from X1-X28;
L is a macrocycle-forming linker of the formula -L$_1$-L$_2$- or the formula

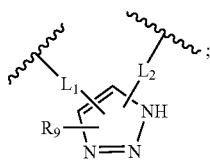

L$_1$ and L$_2$ are independently alkylene, alkenylene, alkynylene, heteroalkylene, cycloalkylene, heterocycloalkylene, cycloarylene, heterocycloarylene, or [—R$_4$—K—R$_4$—]$_n$, each being optionally substituted with R$_5$;
each the cross-linked amino acid is optionally substituted at the alpha carbon position with R$_1$ or R$_2$, wherein R$_1$ and R$_2$ are independently alkyl, alkenyl, alkynyl, arylalkyl, cycloalkyl, cycloalkylalkyl, heteroalkyl, or heterocycloalkyl, each being optionally substituted with halo-;
each R$_4$ is alkylene, alkenylene, alkynylene, heteroalkylene, cycloalkylene, heterocycloalkylene, arylene, or heteroarylene;
each K is O, S, SO, SO$_2$, CO, or CO$_2$;
each R$_5$ is independently halogen, alkyl, —OR$_6$, —N(R$_6$)$_2$, —SR$_6$, —SOR$_6$, —SO$_2$R$_6$, —CO$_2$R$_6$, a fluorescent moiety, a radioisotope, or a therapeutic agent;
each R$_6$ is independently —H, alkyl, alkenyl, alkynyl, arylalkyl, cycloalkylalkyl, heterocycloalkyl, a fluorescent moiety, a radioisotope, or a therapeutic agent;
R$_9$ is alkyl, alkenyl, alkynyl, aryl, cycloalkyl, cycloalkenyl, heteroaryl, or heterocyclyl group, unsubstituted or optionally substituted with R$_a$ and/or R$_b$; and
R$_a$ and R$_b$ are independently alkyl, OCH$_3$, CF$_3$, NH$_2$, CH$_2$NH$_2$, F, Br, I,

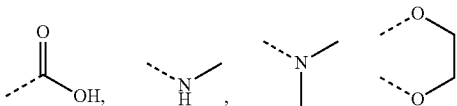

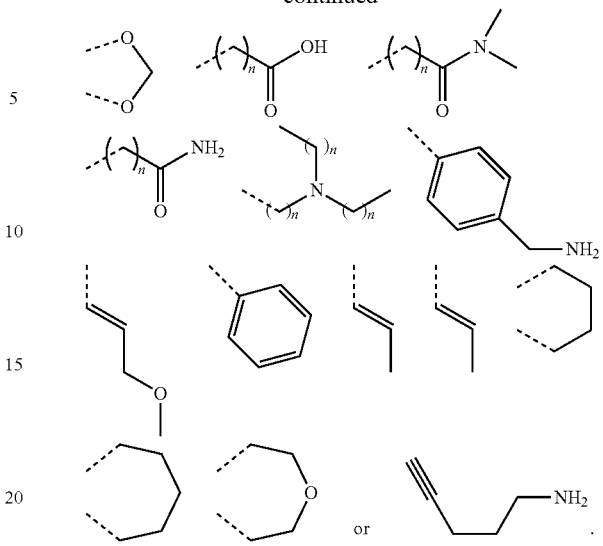

In some embodiments, the present invention provides a peptidomimetic macrocycle comprising an amino acid sequence of the formula:

X1-X2-X3-X4-X5-X6-X7-X8-X9-X10-X1-X12-X13-X14-X15-X16-X17-X18-X19-X20-X21-X22-X23-X24-X25-X26-X27-X28-X29-X30-X31-X32 (SEQ ID NO: 3)

wherein:
X1 is Val or absent;
X2 is Ile, Phe, or absent;
X3 is Asp, Arg, or absent;
X4 is Thr or absent;
X5 is Asp or absent;
X6 is Phe, Ala, Glu, Ser, Dpr, Asn, or absent;
X7 is Ile, Ala, Glu, Ser, or absent;
X8 is Asp, Ala, Ser, Dpr, or absent;
X9 is Glu, Ala, absent, or a cross-linked amino acid;
X10 is Glu, Ala, Ser, Dpr, Gln, or a cross-linked amino acid;
X11 is Val, Ala, Asp, Ser, Dpr, or a cross-linked amino acid;
X12 is Leu, Ala, Glu, Ser, pL, or a cross-linked amino acid;
X13 is Met, Nle, Ala, Asp, or a cross-linked amino acid;
X14 is Ser or a cross-linked amino acid;
X15 is Leu, Ala, Asp, Ser, or a cross-linked amino acid;
X16 is Val, Ala, Glu. Ser, pL, or a cross-linked amino acid;
X17 is Ile, Ala, Glu, Ser, Dpr, Bpa, or a cross-linked amino acid;
X18 is Glu or a cross-linked amino acid;
X19 is Met, Nle, Ala, Glu, Ser, Dpr, Bpa, or a cross-linked amino acid;
X20 is Gly, Ala, Glu, Ser, or a cross-linked amino acid;
X21 is Leu, Ala, Glu, or Ser;
X22 is Asp, Ala, Ser, or absent;
X23 is Arg, Ala, Glu, Ser, Dpr, or absent;
X24 is Ile, Ala, Glu, Ser, or absent;
X25 is Lys, Glu, or absent;
X26 is Glu or absent;
X27 is Leu or absent;
X28 is Pro or absent;
X29 is Glu, Gin, or absent;
X30 is Leu or absent;
X31 is Trp or absent; and
X32 is Leu or absent;

wherein the peptidomimetic macrocycle comprises at least one macrocycle-forming linker connecting at least one pair of amino acids selected from X1-X28;

L is a macrocycle-forming linker of the formula -L$_1$-L$_2$- or the formula $L_1$ and $L_2$ are independently alkylene, alkenylene, alkynylene, heteroalkylene, cycloalkylene, heterocycloalkylene, cycloarylene, heterocycloarylene, or [—R$_4$—K—R$_4$—]$_n$, each being optionally substituted with R$_5$;

each the cross-linked amino acid is optionally substituted at the alpha carbon position with R$_1$ or R$_2$, wherein R$_1$ and R$_2$ are independently alkyl, alkenyl, alkynyl, arylalkyl, cycloalkyl, cycloalkylalkyl, heteroalkyl, or heterocycloalkyl, each being optionally substituted with halo-;

each R$_4$ is alkylene, alkenylene, alkynylene, heteroalkylene, cycloalkylene, heterocycloalkylene, arylene, or heteroarylene;

each K is O, S, SO, SO$_2$, CO, or CO$_2$;

each R$_5$ is independently halogen, alkyl, —OR$_6$, —N(R$_6$)$_2$, —SR$_6$, —SOR$_6$, —SO$_2$R$_6$, —CO$_2$R$_6$, a fluorescent moiety, a radioisotope, or a therapeutic agent;

each R$_6$ is independently —H, alkyl, alkenyl, alkynyl, arylalkyl, cycloalkylalkyl, heterocycloalkyl, a fluorescent moiety, a radioisotope, or a therapeutic agent;

R$_9$ is alkyl, alkenyl, alkynyl, aryl, cycloalkyl, cycloalkenyl, heteroaryl, or heterocyclyl group, unsubstituted or optionally substituted with R$_a$ and/or R$_b$; and R$_a$ and R$_b$ are independently alkyl, OCH$_3$, CF$_3$, NH$_2$, CH$_2$NH$_2$, F, Br, I, A peptidomimetic macrocycle comprising an amino acid sequence of the formula:

X1-X2-X3-X4-X5-X6-X7-X8-X9-X10-X1-X12-X13-X14-X15-X16-X17-X18-X19-X20-X21-X22-X23-X24-X25-X26-X27-X28-X29-X30-X31-X32   (SEQ ID NO: 4)

wherein:
X1 is Val or absent;
X2 is Ile, Phe, or absent;
X3 is Asp, Arg, or absent;
X4 is Thr or absent;
X5 is Asp or absent;
X6 is Phe, Ala, Glu, Ser, Dpr, Asn, or absent;
X7 is Ile. Ala, Glu, Ser, or absent;
X8 is Asp, Ala, Ser, Dpr, or absent;
X9 is Glu. Ala, absent, or a cross-linked amino acid;
X10 is Glu, Ala, Ser, Dpr, Gin, or a cross-linked amino acid;
X11 is Val, Ala, Asp, Ser, Dpr, or a cross-linked amino acid;
X12 is Leu, Ala, Glu, Ser, pL, or a cross-linked amino acid;
X13 is Met. Nle, Ala. Asp, or a cross-linked amino acid;
X14 is Ser or a cross-linked amino acid;
X15 is Leu. Ala, Asp, Ser, or a cross-linked amino acid;
X16 is Val, Ala, Glu, Ser, pL, or a cross-linked amino acid;
X17 is Ile, Ala, Glu, Ser, Dpr, Bpa, or a cross-linked amino acid;
X18 is Glu or a cross-linked amino acid;
X19 is Met, Nle, Ala, Glu, Ser, Dpr, Bpa, or a cross-linked amino acid;
X20 is Gly, Ala, Glu, Ser, or a cross-linked amino acid;
X21 is Leu, Ala, Glu, or Ser;
X22 is Asp, Ala, Ser, or absent;
X23 is Arg, Ala, Glu, Ser, Dpr, or absent;
X24 is Ile, Ala, Glu, Ser, or absent;
X25 is Lys. Glu, or absent;
X26 is Glu or absent;
X27 is Leu or absent;
X28 is Pro or absent;
X29 is Glu, Gin, or absent;
X30 is Leu or absent;
X31 is Trp or absent; and
X32 is Leu or absent;

wherein the peptidomimetic macrocycle comprises at least one macrocycle-forming linker connecting at least one pair of amino acids selected from X1-X28;

L is a macrocycle-forming linker of the formula -L$_1$-L$_2$- or the formula $L_1$ and $L_2$ are independently alkylene, alkenylene, alkynylene, heteroalkylene, cycloalkylene, heterocycloalkylene, cycloarylene, heterocycloarylene, or [—R$_4$—K—R$_4$—]$_n$, each being optionally substituted with R$_5$;

each the cross-linked amino acid is optionally substituted at the alpha carbon position with R$_1$ or R$_2$, wherein R$_1$ and R$_2$ are independently alkyl, alkenyl, alkynyl, arylalkyl, cycloalkyl, cycloalkylalkyl, heteroalkyl, or heterocycloalkyl, each being optionally substituted with halo-;

each $R_4$ is alkylene, alkenylene, alkynylene, heteroalkylene, cycloalkylene, heterocycloalkylene, arylene, or heteroarylene;

each K is O, S, SO, $SO_2$, CO, or $CO_2$;

each $R_5$ is independently halogen, alkyl, $—OR_6$, $—N(R_6)_2$, $—SR_6$, $—SOR_6$, $—SO_2R_6$, $—CO_2R_6$, a fluorescent moiety, a radioisotope, or a therapeutic agent:

each $R_6$ is independently —H, alkyl, alkenyl, alkynyl, arylalkyl, cycloalkylalkyl, heterocycloalkyl, a fluorescent moiety, a radioisotope, or a therapeutic agent;

$R_9$ is alkyl, alkenyl, alkynyl, aryl, cycloalkyl, cycloalkenyl, heteroaryl, or heterocyclyl group, unsubstituted or optionally substituted with $R_a$ and/or $R_b$; and $R_a$ and $R_b$ are independently alkyl, $OCH_3$, $CF_3$, $NH_2$, $CH_2NH_2$, F, Br, I,

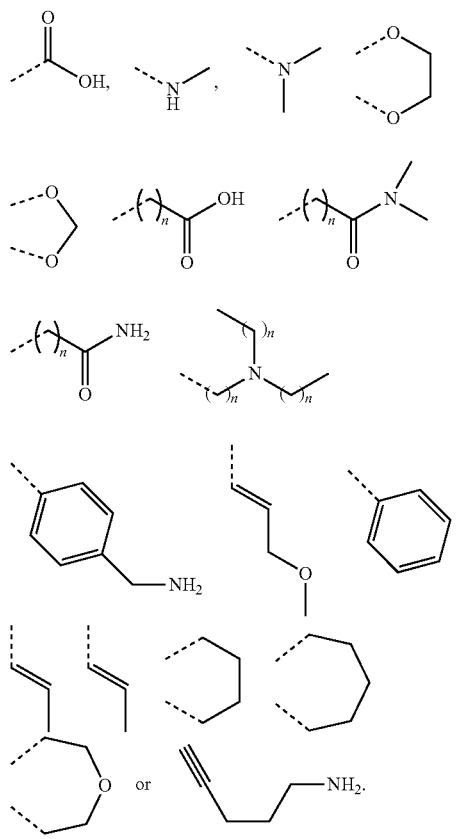

In some embodiments, the peptidomimetic macrocycle of the invention comprises one macrocycle-forming linker.

In some embodiments, the macrocycle-forming linker of the peptidomimetic macrocycle of the invention connects one of the following pairs of amino acids: X9 and X14, X9 and X16, X10 and X14, X10 and X17, X11 and X15, X11 and X18, X12 and X16, X12 and X19, X13 and X17. X13 and X20, X14 and X18, and X14 and X19. In some embodiments, the macrocycle-forming linker connects amino acids: X10 and X14. In some embodiments, the macrocycle-forming linker connects amino acids: X14 and X18.

In some embodiments, X9 is Glu. In some embodiments, X12 is Leu. In some embodiments, X13 is Nle or Met. In some embodiments, X16 is Val. In some embodiments, X18 is Glu. In some embodiments, X19 is Me or Met. In some embodiments, X20 is Ala. In some embodiments, X21 is Leu. In some embodiments, X22 is Asp. In some embodiments, X24 is Ile. In some embodiments, X30 is Leu. In some embodiments, X31 is Trp.

In some embodiments, $L_1$ and $L_2$ are independently alkylene, alkenylene or alkynylene. In some embodiments. $L_1$ and $L_2$ are independently $C_3$-$C_{10}$ alkylene or alkenylene, for example $C_3$-$C_6$ alkylene or alkenylene. For example, L is

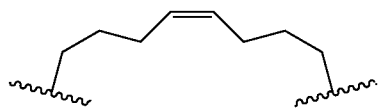 [SMILES: *CCC/C=C\CCC*]

In some embodiments, L is

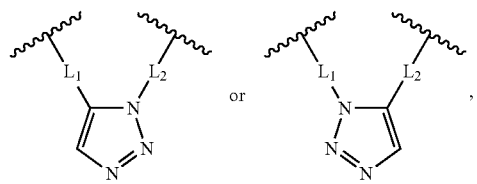

for example

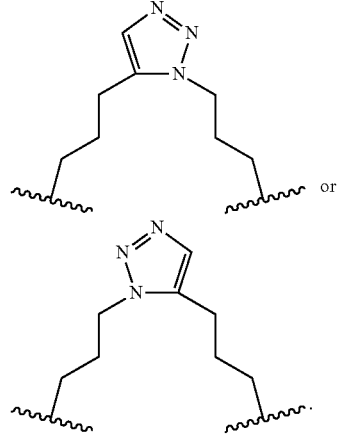

In some embodiments, $R_1$ and $R_2$ are H. In some embodiments. $R_1$ and $R_2$ are independently alkyl, for example methyl.

In some embodiments, the present invention provides a peptidomimetic macrocycle comprising an amino acid sequence which is about 60%, 65%, 70%, 75%, 80%, 85%, 90%, or 95% identical to an amino acid sequence of FIDEEVLMSLVIEMALDRI (SEQ ID NO: 5), for example an amino acid sequence of FIDEEVLM-Z-LVI-Z-MALDRI (SEQ ID NO: 6), wherein each Z is independently a cross-linked amino acid. In some embodiments, the peptidomimetic macrocycle is (SEQ ID NO: 6)

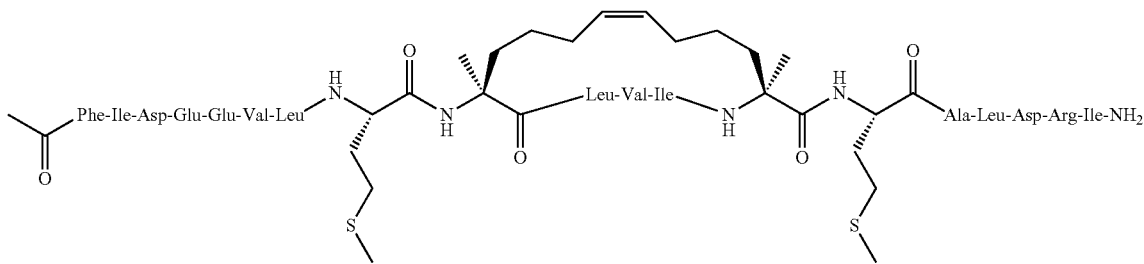

or a pharmaceutically acceptable salt thereof.

In some embodiments, the present invention provides a peptidomimetic macrocycle comprising an amino acid sequence which is about 60%, 65%, 70%, 75%, 80%, 85%, 90%, or 95% identical to an amino acid sequence of FIDEEVLNleSLVIENleALDRI (SEQ ID NO: 7), for example an amino acid sequence of FIDEEVLNle-Z-LVI-Z-NleALDRI (SEQ ID NO: 8), wherein each Z is independently a cross-linked amino acid. In some embodiments, the peptidomimetic macrocycle is 95% identical to an amino acid sequence of LLQGEELL-RALDQV (SEQ ID NO: 12) In some embodiments, the peptidomimetic macrocycle comprises an amino acid sequence of LLQGEEL-Z-RAL-Z-QV (SEQ ID NO: 13), wherein each Z is independently a cross-linked amino acid. In some embodiments, X6 is linked to the amino acid sequence of LLQGEEL-Z-RAL-Z-QV (SEQ ID NO: 13). In some embodiments, the peptidomimetic macrocycle comprises an amino acid sequence of LLQGE-Z-LLRALD-Z-V (SEQ ID NO: 14), wherein each Z is independently a (SEQ ID NO: 8)

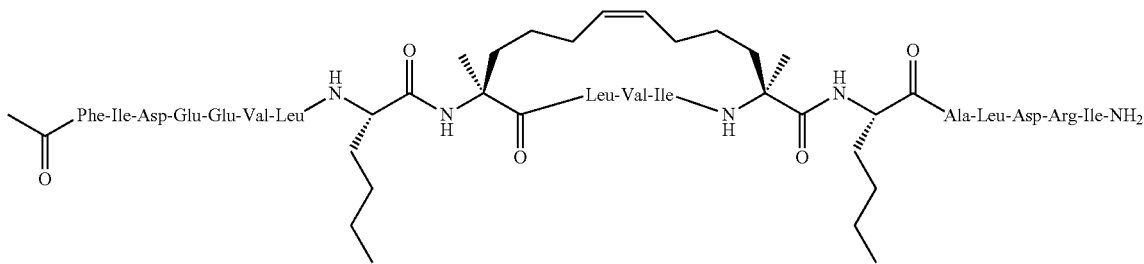

or a pharmaceutically acceptable salt thereof.

In some embodiments, the present invention provides a peptidomimetic macrocycle comprising an amino acid sequence which is about 60%, 65%, 70%, 75%, 80%, 85%, 90%, or 95% identical to an amino acid sequence of FIDEEVLMSLVIEMGLDRIKELPELWL (SEQ ID NO: 9), for example an amino acid sequence of FIDEEVLM-Z-LVI-Z-MGLDRIKELPELWL (SEQ ID NO: 10), wherein each Z is independently a cross-linked amino acid.

In some embodiments, a peptidomimetic macrocycle of the invention has a formula X6-X7-X8-X9-X10-X11-X12-X13-X14-X15-X16-X17-X18-X19-X20-X21-X22-X23-X24-X25-X26-X27-X28 (SEQ ID NO: 11). In some embodiments, a macrocycle-forming linker of the peptidomimetic macrocycle of the invention connects one of the following pairs of amino acids: X10 and X14, X10 and X17, X11 and X18. X12 and X16, X12 and X19, and X14 and X18, for example X14 and X18. In some embodiments, X13 is Nle. In some embodiments, X19 is Nle. In some embodiments, X20 is Ala.

In some embodiments, a peptidomimetic macrocycle of the invention further comprises an amino acid sequence which is about 60%, 65%, 70%, 75%, 80%, 85%, 90%, or cross-linked amino acid. In some embodiments, X6 is linked to the amino acid sequence of LLQGEEL-Z-RAL-Z-QV (SEQ ID NO: 13).

In some embodiments, a peptidomimetic macrocycle of the invention further comprises an amino acid sequence which is about 60%, 65%, 70%, 75%, 80%, 85%, 90%, or 95% identical to an amino acid sequence of QLTSYD-CEVNA (SEQ ID NO: 15), for example an amino acid sequence of QLT-Z-YDAbu-Z-VNA (SEQ ID NO: 16), wherein each Z is independently a cross-linked amino acid. In some embodiments, X28 is linked to the amino acid sequence of QLT-Z-YDAbu-Z-VNA (SEQ ID NO: 16).

In some embodiments, the present invention provides a pharmaceutical composition comprising a peptidomimetic macrocycle of the invention and a pharmaceutically acceptable carrier.

In some embodiments, the present invention provides a method of reducing transcription of a gene in a cell, wherein transcription of the gene is mediated by interaction of Hypoxia-Inducible Factor 1α (HIF1α) with CREB-binding protein and/or p300, comprising contacting the cell with an effective amount of a peptidomimetic macrocycle of the invention. In some embodiments, the gene is selected from the group consisting of adenylate kinase 3, aldolase A, aldolase C, enolase 1, glucose transporter 1, glucose transporter 3, glyceraldehyde-3-phosphate dehydrogenase, hexokinase 1, hexokinase 2, insulin-like growth factor 2, IGF binding protein 1, IGF binding protein 3, lactate dehydrogenase A, phosphoglycerate kinase 1, pyruvate kinase M, p21, transforming growth factor β3, ceruloplasmin, erythropoietin, transferrin, transferrin receptor, αiB-adrenergic receptor, adrenomedullin, endothelin-1, heme oxygenase 1, nitric oxide synthase 2, plasminogen activator inhibitor 1, vascular endothelial growth factor, vascular endothelial growth factor receptor FLT-1·vascular endothelial growth factor receptor KDR/FIk-1, and p35srg.

In some embodiments, the present invention provides a method of treating or preventing in a subject in need thereof a disorder mediated by interaction of HIF1α with CREB-binding protein and/or p300, comprising administering to the subject an effective amount of a peptidomimetic macrocycle of the invention. In some embodiments, the disorder is selected from the group consisting of retinal ischemia, pulmonary hypertension, intrauterine growth retardation, diabetic retinopathy, age-related macular degeneration, diabetic macular edema, and cancer.

In some embodiments, the present invention provides a method of reducing or preventing angiogenesis in a tissue, comprising contacting the tissue with an effective amount of a peptidomimetic macrocycle of the invention. In some embodiments, the method is carried out in vivo. In some embodiments, the tissue is a tumor.

In some embodiments, the present invention provides a method of inducing apoptosis in a cell, comprising contacting the cell with an effective amount of a peptidomimetic macrocycle of the invention.

In some embodiments, the present invention provides a method of decreasing survival and/or proliferation of a cell, comprising contacting the cell with an effective amount of a peptidomimetic macrocycle of the invention. In some embodiments, the cell is cancerous or is contained in the endothelial vasculature of a tissue that contains cancerous cells.

In some embodiments, the present invention provides a method of treating cancer in a subject comprising administering to the subject an effective amount of a peptidomimetic macrocycle of the invention.

In some embodiments, the present invention provides a method of treating age-related macular degeneration or diabetic retinopathy in a subject comprising administering to the subject an effective amount of a peptidomimetic macrocycle of the invention.

In some embodiments, the present invention provides a method of treating a disorder caused by excessive angiogenesis in a subject comprising administering to the subject an effective amount of a peptidomimetic macrocycle of the invention.

In some embodiments, the present invention provides a method of modulating the activity of HIF1α in a subject comprising administering to the subject a peptidomimetic macrocycle of the invention.

In some embodiments, the present invention provides a method of antagonizing the interaction between CBP/p300 and HIF1α proteins in a subject comprising administering to the subject an effective amount of a peptidomimetic macrocycle of the invention.

In some embodiments, the present invention provides a method of identifying a potential ligand of CREB-binding protein and/or p300, comprising: providing a peptidomimetic macrocycle of the invention, contacting the peptidomimetic macrocycle with a test agent, and detecting whether the test agent selectively binds to the peptidomimetic macrocycle, wherein a test agent that selectively binds to the peptidomimetic macrocycle is identified as a potential ligand of CREB-binding protein and/or p300.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
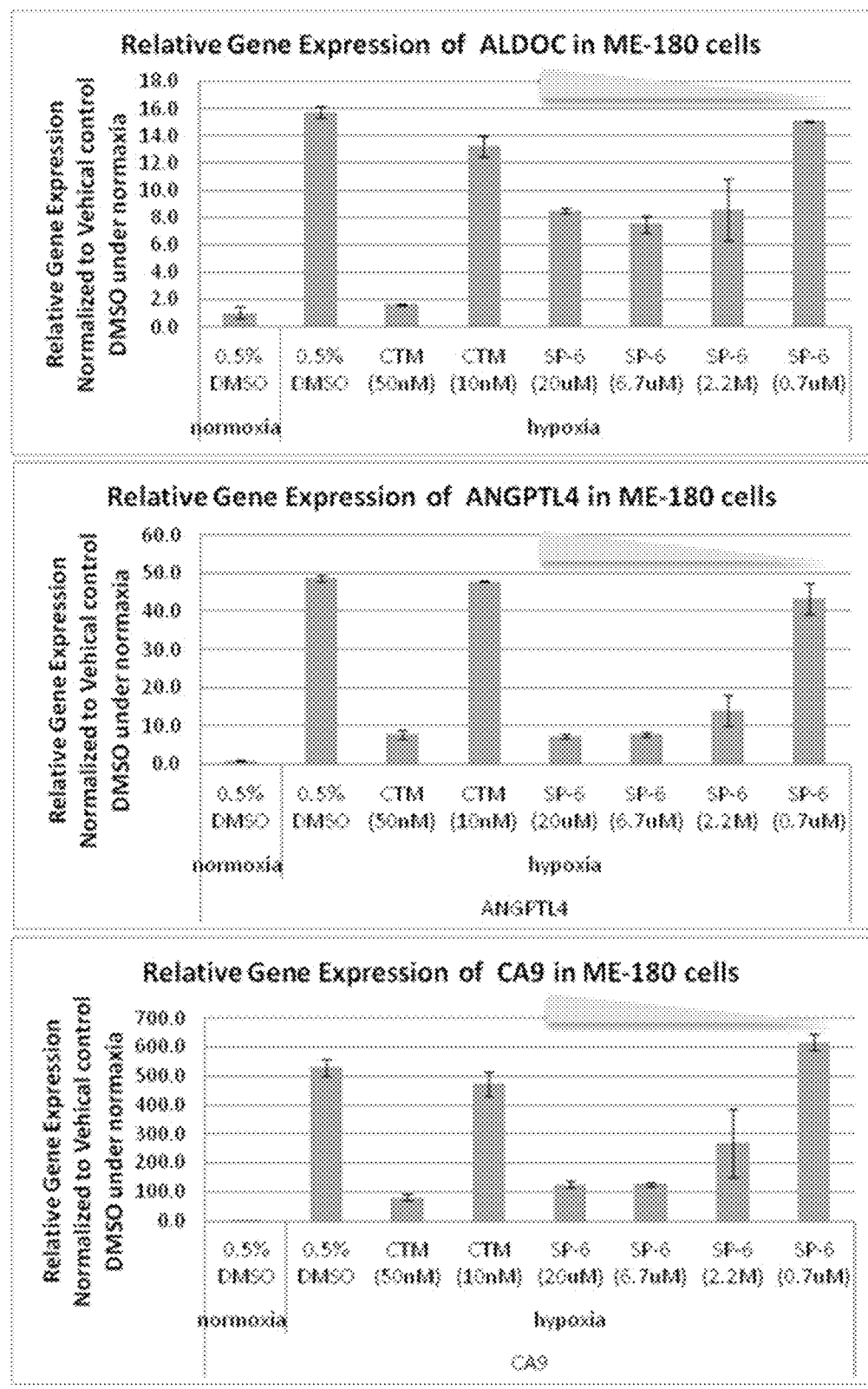
FIG. 1 is a set of bar graphs that show effects of the peptidomimetic macrocycle SP-6 in inhibiting gene expression of HIF1α targets including ANGPTL4, CA9 and ALDOC in ME-180 cells.

The term "about" has the meaning as commonly understood by one of ordinary skill in the art. In some embodiments, the term "about" refers to ±10%. In some embodiments, the term "about" refers to ±5%.

As used herein, the term "macrocycle" refers to a molecule having a chemical structure including a ring or cycle formed by at least 9 covalently bonded atoms.

As used herein, the term "peptidomimetic macrocycle" or "crosslinked polypeptide" refers to a compound comprising a plurality of amino acid residues joined by a plurality of peptide bonds and at least one macrocycle-forming linker which forms a macrocycle between a first naturally-occurring or non-naturally-occurring amino acid residue (or analog) and a second naturally-occurring or non-naturally-occurring amino acid residue (or analog) within the same molecule. Peptidomimetic macrocycles include embodiments where the macrocycle-forming linker connects the α carbon of the first amino acid residue (or analog) to the α carbon of the second amino acid residue (or analog). The peptidomimetic macrocycles optionally include one or more non-peptide bonds between one or more amino acid residues and/or amino acid analog residues, and optionally include one or more non-naturally-occurring amino acid residues or amino acid analog residues in addition to any which form the macrocycle. A "corresponding uncrosslinked polypeptide" when referred to in the context of a peptidomimetic macrocycle is understood to relate to a polypeptide of the same length as the macrocycle and comprising the equivalent natural amino acids of the wild-type sequence corresponding to the macrocycle.

As used herein, the term "stability" refers to the maintenance of a defined secondary structure in solution by a peptidomimetic macrocycle of the invention as measured by circular dichroism, NMR or another biophysical measure, or resistance to proteolytic degradation in vitro or in vivo.

Non-limiting examples of secondary structures contemplated in this invention are α-helices, $3_{10}$ helices, β-turns, and β-pleated sheets.

As used herein, the term "helical stability" refers to the maintenance of a helical structure by a peptidomimetic macrocycle of the invention as measured by circular dichroism or NMR. For example, in some embodiments, the peptidomimetic macrocycles of the invention exhibit at least a 1.25, 1.5, 1.75 or 2-fold increase in α-helicity as determined by circular dichroism compared to a corresponding uncrosslinked macrocycle.

The term "amino acid" refers to a molecule containing both an amino group and a carboxyl group. Suitable amino acids include, without limitation, both the D- and L-isomers of the naturally-occurring amino acids, as well as non-naturally occurring amino acids prepared by organic synthesis or other metabolic routes. The term amino acid, as used herein, includes without limitation, α-amino acids, natural amino acids, non-natural amino acids, and amino acid analogs.

The term "α-amino acid" refers to a molecule containing both an amino group and a carboxyl group bound to α carbon which is designated the α-carbon.

The term "β-amino acid" refers to a molecule containing both an amino group and a carboxyl group in a β configuration.

The term "naturally occurring amino acid" refers to any one of the twenty amino acids commonly found in peptides synthesized in nature, and known by the one letter abbreviations A, R, N, C, D, Q, E, G, H, I, L, K, M, F, P, S, T, W, Y and V.

The following table shows a summary of the properties of natural amino acids:

| Amino Acid | 3-Letter Code | 1-Letter Code | Side-chain Polarity | Side-chain charge (pH 7.4) | Hydropathy Index |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | polar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive(10%) neutral(90%) | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

"Hydrophobic amino acids" include small hydrophobic amino acids and large hydrophobic amino acids. "Small hydrophobic amino acids" are glycine, alanine, proline, and analogs thereof. "Large hydrophobic amino acids" are valine, leucine, isoleucine, phenylalanine, methionine, tryptophan, tyrosine, and analogs thereof. "Polar amino acids" are serine, threonine, asparagine, glutamine, cysteine, and analogs thereof. "Charged amino acids" include positively charged amino acids and negatively charged amino acids. "Positively charged amino acids" include lysine, arginine, histidine, and analogs thereof. "Negatively charged amino acids" include aspartate, glutamate, and analogs thereof.

The term "amino acid analog" refers to a molecule which is structurally similar to an amino acid and which can be substituted for an amino acid in the formation of a peptidomimetic macrocycle. Amino acid analogs include, without limitation, β-amino acids and amino acids where the amino or carboxy group is substituted by a similarly reactive group (e.g., substitution of the primary amine with a secondary or tertiary amine, or substitution of the carboxy group with an ester).

The term "non-natural amino acid" refers to an amino acid which is not one of the twenty amino acids commonly found in peptides synthesized in nature, and known by the one letter abbreviations A, R, N, C, D, Q, E, G, H, I, L, K, M, F, P. S, T, W, Y and V. Non-natural amino acids or amino acid analogs include, without limitation, structures according to the following:

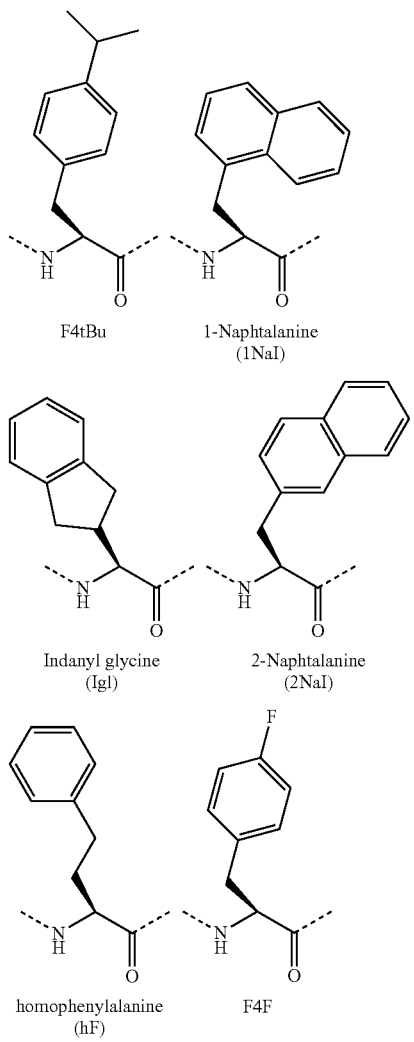

F4tBu     1-Naphtalanine (1NaI)

Indanyl glycine (Igl)     2-Naphtalanine (2NaI)

homophenylalanine (hF)     F4F

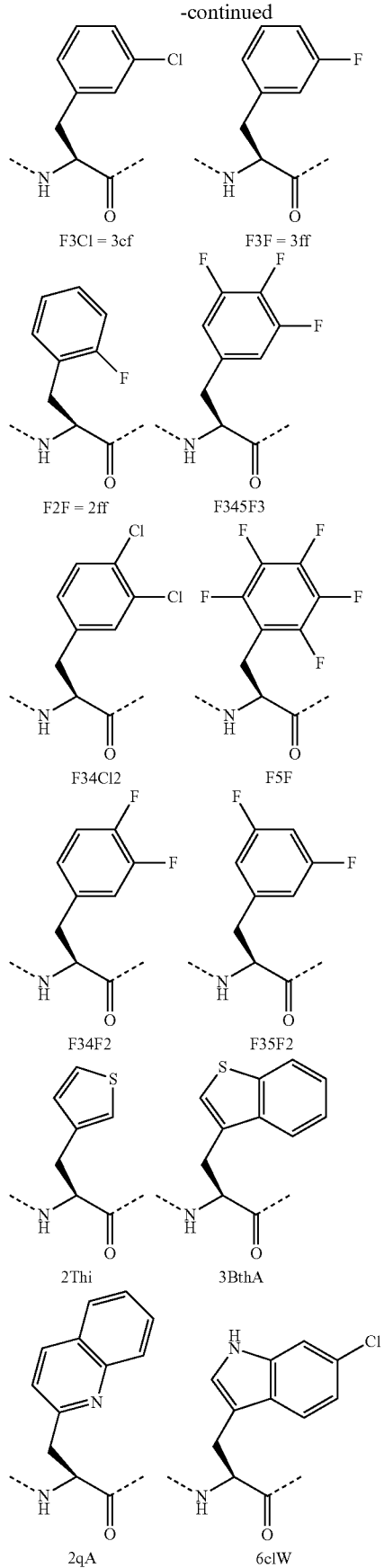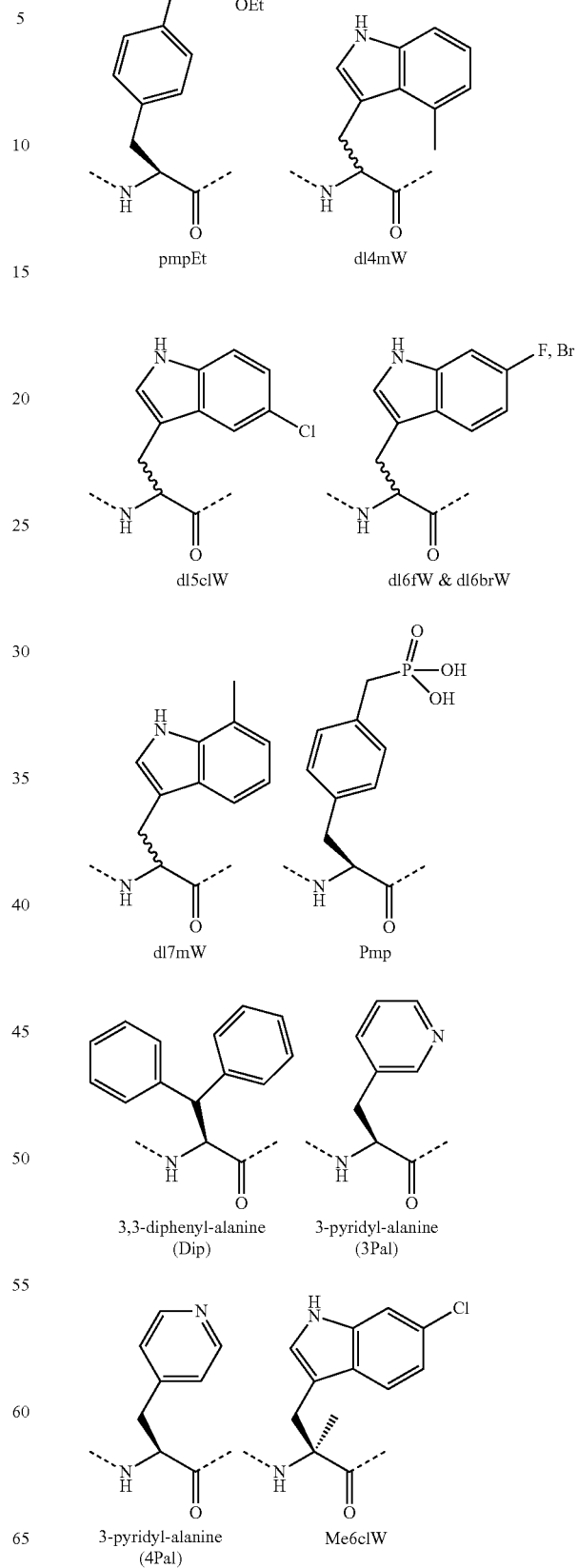

-continued
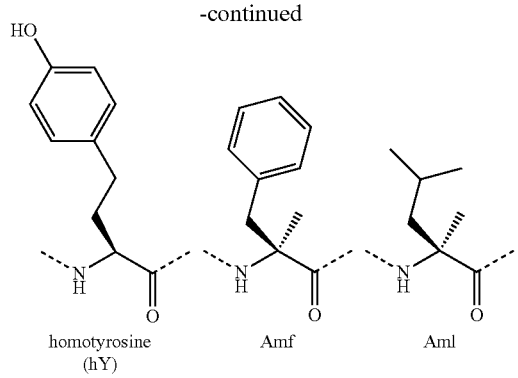
homotyrosine (hY)　　Amf　　Aml
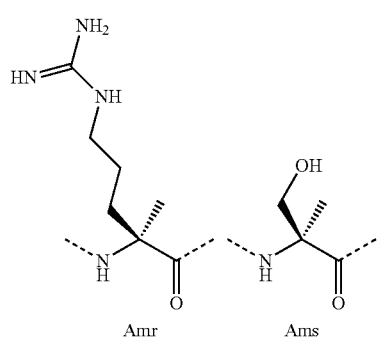
Amr　　Ams
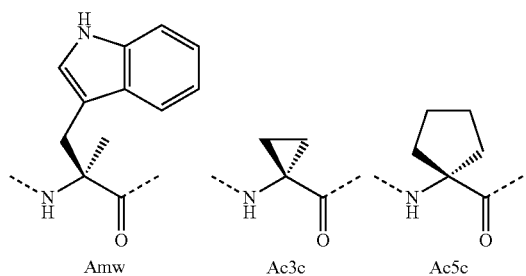
Amw　　Ac3c　　Ac5c
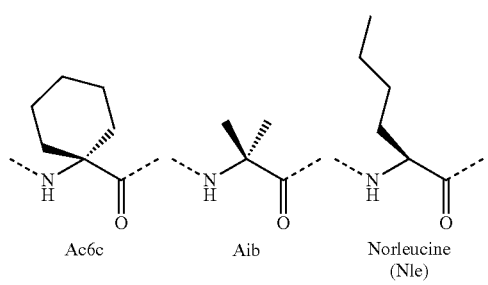
Ac6c　　Aib　　Norleucine (Nle)
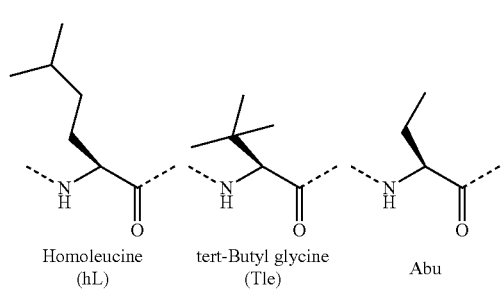
Homoleucine (hL)　　tert-Butyl glycine (Tle)　　Abu
-continued
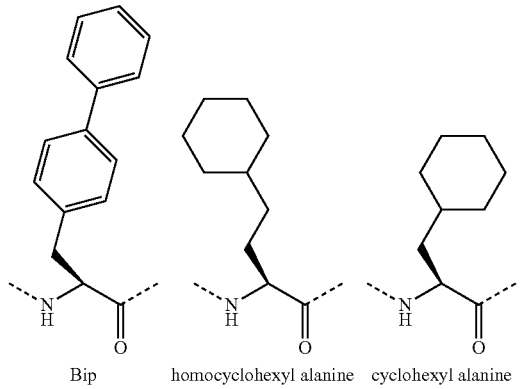
Bip　　homocyclohexyl alanine (hCha)　　cyclohexyl alanine (Cha)
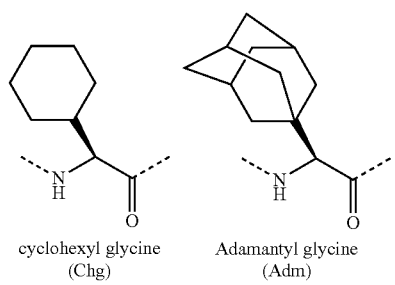
cyclohexyl glycine (Chg)　　Adamantyl glycine (Adm)
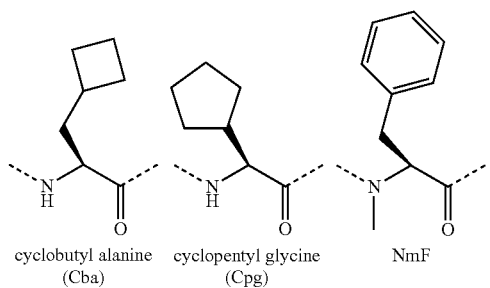
cyclobutyl alanine (Cba)　　cyclopentyl glycine (Cpg)　　NmF
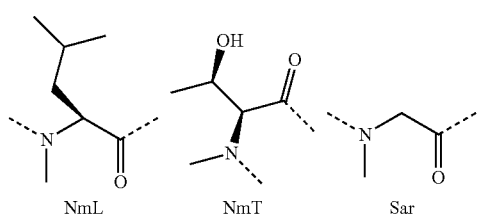
NmL　　NmT　　Sar
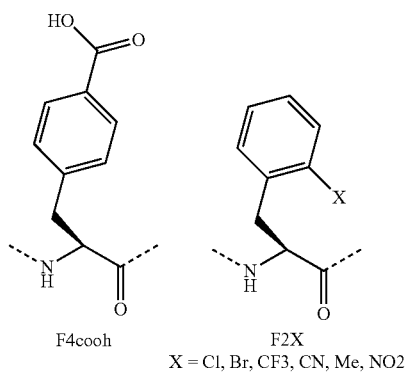
F4cooh　　F2X
X = Cl, Br, CF3, CN, Me, NO2

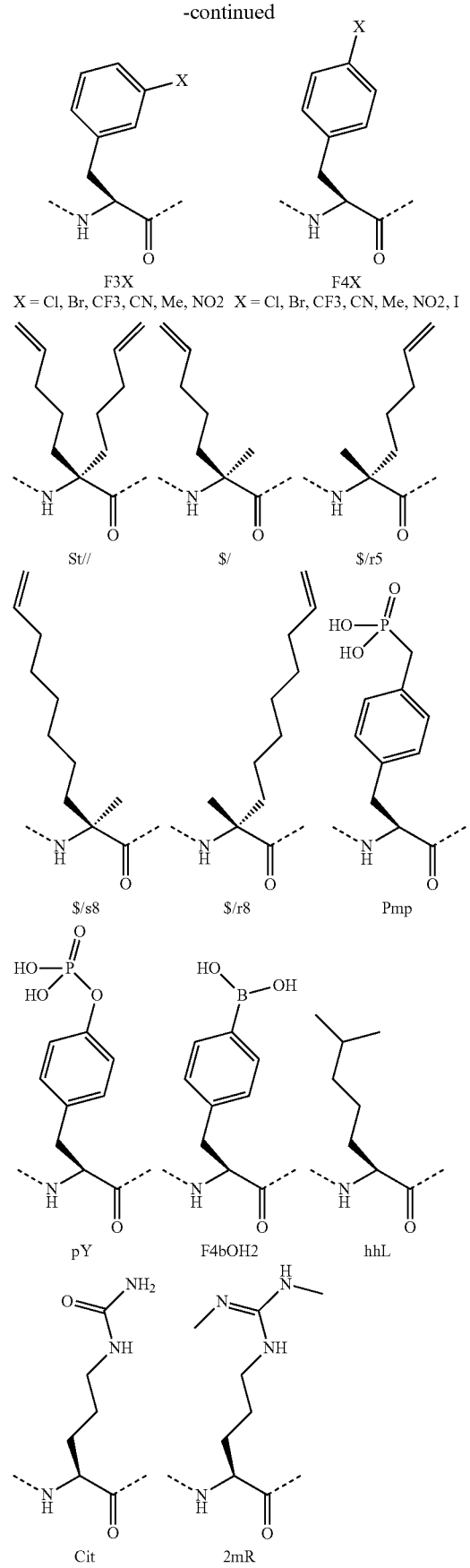
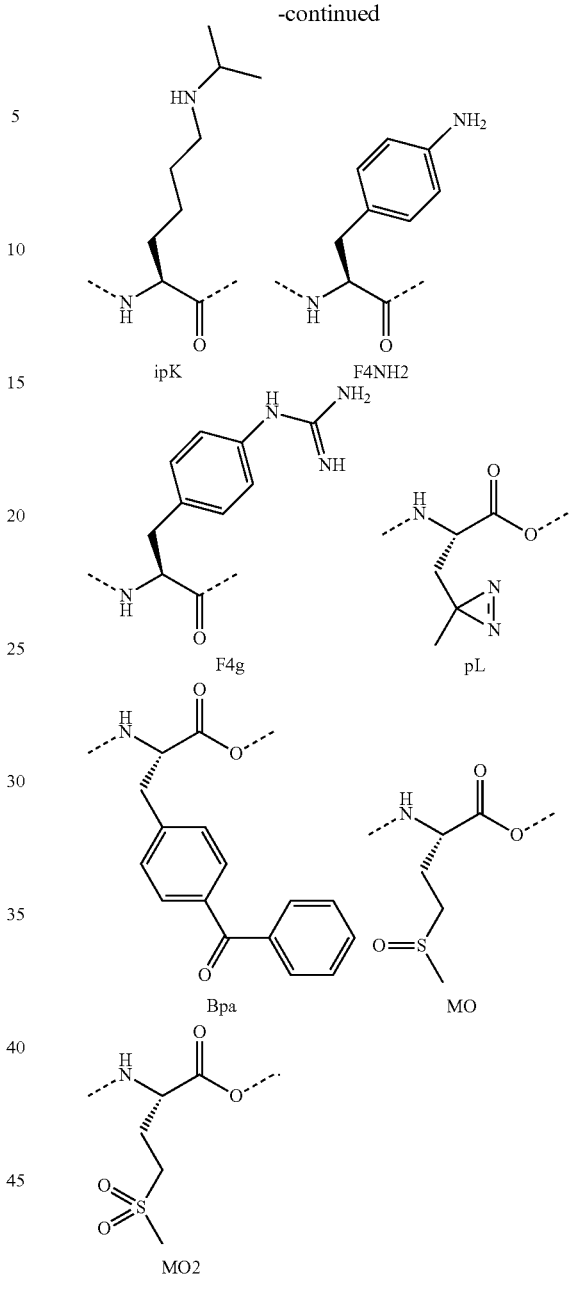

Amino acid analogs include β-amino acid analogs. Examples of β-amino acid analogs include, but are not limited to, the following: cyclic-amino acid analogs; β-alanine; (R)-β-phenylalanine; (R)-1,2,3,4-tetrahydro-isoquinoline-3-acetic acid; (R)-3-amino-4-(1-naphthyl)-butyric acid; (R)-3-amino-4-(2,4-dichlorophenyl)butyric acid; (R)-3-amino-4-(2-chlorophenyl)-butyric acid; (R)-3-amino-4-(2-cyanophenyl)-butyric acid; (R)-3-amino-4-(2-fluorophenyl)-butyric acid; (R)-3-amino-4-(2-furyl)-butyric acid; (R)-3-amino-4-(2-methylphenyl)-butyric acid; (R)-3-amino-4-(2-naphthyl)-butyric acid; (R)-3-amino-4-(2-thienyl)-butyric acid; (R)-3-amino-4-(2-trifluoromethylphenyl)-butyric acid; (R)-3-amino-4-(3,4-dichlorophenyl)butyric acid; (R)-3-amino-4-(3,4-difluorophenyl)butyric acid; (R)-3-amino-4-(3-benzothienyl)-butyric acid; (R)-3-amino-4-(3-chlorophenyl)-butyric acid; (R)-3-amino-4-(3-cyanophenyl)-butyric acid; (R)-3-amino-4-(3-fluorophenyl)-butyric acid; (R)-3-amino-4-(3-methylphenyl)-butyric acid; (R)-3-amino-4-(3-pyridyl)-butyric acid; (R)-3-amino-4-(3-thienyl)-butyric acid; (R)-3-amino-4-(3-trifluoromethylphenyl)-butyric acid; (R)-3-amino-4-(4-bromophenyl)-butyric acid; (R)-3-amino-4-(4-chlorophenyl)-butyric acid; (R)-3-amino-4-(4-cyanophenyl)-butyric acid; (R)-3-amino-4-(4-fluorophenyl)-butyric acid; (R)-3-amino-4-(4-iodophenyl)-butyric acid; (R)-3-amino-4-(4-methylphenyl)-butyric acid; (R)-3-amino-4-(4-nitrophenyl)-butyric acid; (R)-3-amino-4-(4-pyridyl)-butyric acid; (R)-3-amino-4-(4-trifluoromethylphenyl)-butyric acid; (R)-3-amino-4-pentafluoro-phenylbutyric acid; (R)-3-amino-5-hexenoic acid; (R)-3-amino-5-hexynoic acid; (R)-3-amino-5-phenylpentanoic acid; (R)-3-amino-6-phenyl-5-hexenoic acid; (S)-1,2,3,4-tetrahydro-isoquinoline-3-acetic acid; (S)-3-amino-4-(1-naphthyl)-butyric acid; (S)-3-amino-4-(2.4-dichlorophenyl)butyric acid; (S)-3-amino-4-(2-chlorophenyl)-butyric acid; (S)-3-amino-4-(2-cyanophenyl)-butyric acid; (S)-3-amino-4-(2-fluorophenyl)-butyric acid; (S)-3-amino-4-(2-furyl)-butyric acid; (S)-3-amino-4-(2-methylphenyl)-butyric acid; (S)-3-amino-4-(2-naphthyl)-butyric acid; (S)-3-amino-4-(2-thienyl)-butyric acid; (S)-3-amino-4-(2-trifluoromethylphenyl)-butyric acid; (S)-3-amino-4-(3,4-dichlorophenyl)butyric acid; (S)-3-amino-4-(3,4-difluorophenyl)butyric acid; (S)-3-amino-4-(3-benzothienyl)-butyric acid; (S)-3-amino-4-(3-chlorophenyl)-butyric acid; (S)-3-amino-4-(3-cyanophenyl)-butyric acid; (S)-3-amino-4-(3-fluorophenyl)-butyric acid; (S)-3-amino-4-(3-methylphenyl)-butyric acid; (S)-3-amino-4-(3-pyridyl)-butyric acid; (S)-3-amino-4-(3-thienyl)-butyric acid; (S)-3-amino-4-(3-trifluoromethylphenyl)-butyric acid; (S)-3-amino-4-(4-bromophenyl)-butyric acid; (S)-3-amino-4-(4-chlorophenyl)-butyric acid; (S)-3-amino-4-(4-cyanophenyl)-butyric acid; (S)-3-amino-4-(4-fluorophenyl)-butyric acid; (S)-3-amino-4-(4-iodophenyl)-butyric acid; (S)-3-amino-4-(4-methylphenyl)-butyric acid; (S)-3-amino-4-(4-nitrophenyl)-butyric acid; (S)-3-amino-4-(4-pyridyl)-butyric acid; (S)-3-amino-4-(4-trifluoromethylphenyl)-butyric acid; (S)-3-amino-4-pentafluoro-phenylbutyric acid; (S)-3-amino-5-hexenoic acid; (S)-3-amino-5-hexynoic acid; (S)-3-amino-5-phenylpentanoic acid; (S)-3-amino-6-phenyl-5-hexenoic acid; 1,2,5,6-tetrahydropyridine-3-carboxylic acid; 1,2,5,6-tetrahydropyridine-4-carboxylic acid; 3-amino-3-(2-chlorophenyl)-propionic acid; 3-amino-3-(2-thienyl)-propionic acid; 3-amino-3-(3-bromophenyl)-propionic acid; 3-amino-3-(4-chlorophenyl)-propionic acid; 3-amino-3-(4-methoxyphenyl)-propionic acid; 3-amino-4,4,4-trifluoro-butyric acid; 3-aminoadipic acid; D-β-phenylalanine; β-leucine; L-β-homoalanine; L-β-homoaspartic acid γ-benzyl ester; L-β-homoglutamic acid δ-benzyl ester; L-β-homoisoleucine; L-β-homoleucine; L-β-homomethionine; L-β-homophenylalanine; L-β-homoproline; L-β-homotryptophan; L-β-homovaline; L-Nω-benzyloxycarbonyl-β-homolysine; Nω-L-β-homoarginine; O-benzyl-L-β-homohydroxyproline; O-benzyl-L-β-homoserine; O-benzyl-L-β-homothreonine; O-benzyl-L -β-homotyrosine; γ-trityl-L-β-homoasparagine; (R)-β-phenylalanine; L-β-homoaspartic acid γ-t-butyl ester; L-β-homoglutamic acid δ-t-butyl ester; L-Nω-β-homolysine; Nδ-trityl-L-β-homoglutamine; Nω-2,2,4,6,7-pentamethyl-dihydrobenzofuran-5-sulfonyl-L-β-homoarginine; O-t-butyl-L-β-homohydroxy-proline; O-t-butyl-L-β-homoserine; O-t-butyl-L-β-homothreonine; O-t-butyl-L-β-homotyrosine; 2-aminocyclopentane carboxylic acid; and 2-aminocyclohexane carboxylic acid.

Amino acid analogs include analogs of alanine, valine, glycine or leucine. Examples of amino acid analogs of alanine, valine, glycine, and leucine include, but are not limited to, the following: α-methoxyglycine; α-allyl-L-alanine; α-aminoisobutyric acid; α-methyl-leucine; β-(1-naphthyl)-D-alanine; β-(1-naphthyl)-L-alanine; β-(2-naphthyl)-D-alanine; β-(2-naphthyl)-L-alanine; β-(2-pyridyl)-D-alanine; β-(2-pyridyl)-L-alanine; β-(2-thienyl)-D-alanine; β-(2-thienyl)-L-alanine; β-(3-benzothienyl)-D-alanine; β-(3-benzothienyl)-L-alanine; β-(3-pyridyl)-D-alanine; β-(3-pyridyl)-L-alanine; β-(4-pyridyl)-D-alanine; β-(4-pyridyl)-L-alanine; β-chloro-L-alanine; β-cyano-L-alanin; β-cyclohexyl-D-alanine; β-cyclohexyl-L-alanine; β-cyclopenten-1-yl-alanine; β-cyclopentyl-alanine; β-cyclopropyl-L-Ala-OH.dicyclohexylammonium salt; β-t-butyl-D-alanine; β-t-butyl-L-alanine; γ-aminobutyric acid; L-α,β-diaminopropionic acid; 2,4-dinitro-phenylglycine; 2,5-dihydro-D-phenylglycine; 2-amino-4,4,4-trifluorobutyric acid; 2-fluoro-phenylglycine; 3-amino-4,4,4-trifluoro-butyric acid; 3-fluoro-valine; 4,4,4-trifluoro-valine; 4,5-dehydro-L-leu-OH. dicyclohexylammonium salt; 4-fluoro-D-phenylglycine; 4-fluoro-L-phenylglycine; 4-hydroxy-D-phenylglycine; 5,5,5-trifluoro-leucine; 6-aminohexanoic acid; cyclopentyl-D-Gly -OH.dicyclohexylammonium salt; cyclopentyl-Gly-OH.dicyclohexylammonium salt; D-α,β-diaminopropionic acid; D-α-aminobutyric acid; D-α-t-butylglycine; D-(2-thienyl)glycine; D-(3-thienyl)glycine; D-2-aminocaproic acid; D-2-indanylglycine; D-allylglycine.dicyclohexylammonium salt; D-cyclohexylglycine; D-norvaline; D-phenylglycine; β-aminobutyric acid; β-aminoisobutyric acid; (2-bromophenyl)glycine; (2-methoxyphenyl)glycine; (2-methylphenyl)glycine; (2-thiazoyl)glycine; (2-thienyl)glycine; 2-amino-3-(dimethylamino)-propionic acid; L-α,β-diaminopropionic acid; L-α-aminobutyric acid; L-α-t-butylglycine; L-(3-thienyl) glycine; L-2-amino-3-(dimethylamino)-propionic acid; L-2-aminocaproic acid dicyclohexyl-ammonium salt; L-2-indanylglycine; L-allylglycine.dicyclohexyl ammonium salt; L-cyclohexylglycine; L-phenylglycine; L-propargylglycine; L-norvaline; N-α-aminomethyl-L-alanine; D-α,γ-diaminobutyric acid; L-α,γ-diaminobutyric acid; R-cyclopropyl-L-alanine; (N-β-(2,4-dinitrophenyl))-L-α,β-diaminopropionic acid; (N-β-1-(4,4-dimethyl-2,6-dioxocyclohex-1-ylidene) ethyl)-D-α,β-diaminopropionic acid; (N-β-1-(4,4-dimethyl-2,6-dioxocyclohex-1-ylidene)ethyl)-L-α,β-diaminopropionic acid; (N-β-4-methyltrityl)-L-α,β-diaminopropionic acid; (N-β-allyloxycarbonyl)-L-α,β-diaminopropionic acid; (N-γ-1-(4,4-dimethyl-2,6-dioxocyclohex-1-ylidene)ethyl)-D-α,γ-diaminobutyric acid; (N-γ-1-(4,4-dimethyl-2,6-dioxocyclohex-1-ylidene)ethyl)-L-α,γ-diaminobutyric acid; (N-γ-4-methyltrityl)-D-α,γ-diaminobutyric acid; (N-γ-4-methyltrityl)-L-α,γ-diaminobutyric acid; (N-γ-allyloxycarbonyl)-L-α,γ-diaminobutyric acid; D-α,γ-diaminobutyric acid; 4,5-dehydro-L-leucine; cyclopentyl-D-Gly-OH; cyclopentyl-Gly-OH; D-allylglycine; D-homocyclohexylalanine; L-1-pyrenylalanine; L-2-aminocaproic acid; L-allylglycine; L-homocyclohexylalanine; and N-(2-hydroxy-4-methoxy-Bzl)-Gly-OH.

Amino acid analogs include analogs of arginine or lysine. Examples of amino acid analogs of arginine and lysine include, but are not limited to, the following: citrulline; L-2-amino-3-guanidinopropionic acid; L-2-amino-3-ureido-propionic acid; L-citrulline; Lys(Me)-OH; Lys(N$_3$)-OH; Nδ-benzyloxycarbonyl-L-ornithine; Nω-nitro-D-arginine; Nω-nitro-L-arginine; α-methyl-ornithine; 2,6-diaminoheptanedioic acid; L-ornithine; (Nδ-1-(4,4-dimethyl-2,6-dioxo-cyclohex-1-ylidene)ethyl)-D-ornithine; (Nδ-1-(4,4-dimethyl-2,6-dioxo-cyclohex-1-ylidene)ethyl)-L-ornithine; (Nδ-4-methyltrityl)-D-ornithine; (Nδ-4-methyltrityl)-L-ornithine; D-ornithine; L-ornithine; Arg(Me)(Pbf)-OH; Arg(Me)$_2$-OH (asymmetrical); Arg(Me)$_2$-OH (symmetrical);

Lys(ivDde)-OH; Lys(Me)₂-OH.HCl; Lys(Me3)-OH chloride; Nω-nitro-D-arginine; and Nω-nitro-L-arginine.

Amino acid analogs include analogs of aspartic or glutamic acids. Examples of amino acid analogs of aspartic and glutamic acids include, but are not limited to, the following: α-methyl-D-aspartic acid; α-methyl-glutamic acid; α-methyl-L-aspartic acid; γ-methylene-glutamic acid; (N-γ-ethyl)-L-glutamine; [N-α-(4-aminobenzoyl)]-L-glutamic acid; 2,6-diaminopimelic acid; L-α-aminosuberic acid; D-2-aminoadipic acid; D-α-aminosuberic acid; α-aminopimelic acid; iminodiacetic acid; L-2-aminoadipic acid; threo-β-methyl-aspartic acid; γ-carboxy-D-glutamic acid γ,γ-di-t-butyl ester; γ-carboxy-L-glutamic acid γ,γ-di-t-butyl ester; Glu(OAll)-OH; L-Asu(OtBu)-OH; and pyroglutamic acid.

Amino acid analogs include analogs of cysteine and methionine. Examples of amino acid analogs of cysteine and methionine include, but are not limited to, Cys(famesyl)-OH, Cys(famesyl)-OMe, α-methyl-methionine, Cys(2-hydroxyethyl)-OH, Cys(3-aminopropyl)-OH, 2-amino-4-(ethylthio)butyric acid, buthionine, buthioninesulfoximine, ethionine, methionine methylsulfonium chloride, selenomethionine, cysteic acid, [2-(4-pyridyl)ethyl]-DL-penicillamine, [2-(4-pyridyl)ethyl]-L-cysteine, 4-methoxybenzyl-D-penicillamine, 4-methoxybenzyl-L-penicillamine, 4-methylbenzyl-D-penicillamine, 4-methylbenzyl-L-penicillamine, benzyl-D-cysteine, benzyl-L-cysteine, benzyl-DL-homocysteine, carbamoyl-L-cysteine, carboxyethyl-L-cysteine, carboxymethyl-L-cysteine, diphenylmethyl-L-cysteine, ethyl-L-cysteine, methyl-L-cysteine, t-butyl-D-cysteine, trityl-L-homocysteine, trityl-D-penicillamine, cystathionine, homocystine, L-homocystine, (2-aminoethyl)-L-cysteine, seleno-L-cystine, cystathionine, Cys (StBu)-OH, and acetamidomethyl-D-penicillamine.

Amino acid analogs include analogs of phenylalanine and tyrosine. Examples of amino acid analogs of phenylalanine and tyrosine include β-methyl-phenylalanine, β-hydroxyphenylalanine, α-methyl-3-methoxy-DL-phenylalanine, α-methyl-D-phenylalanine, α-methyl-L-phenylalanine, 1,2,3,4-tetrahydroisoquinoline-3-carboxylic acid, 2,4-dichlorophenylalanine, 2-(trifluoromethyl)-D-phenylalanine, 2-(trifluoromethyl)-L-phenylalanine, 2-bromo-D-phenylalanine, 2-bromo-L-phenylalanine, 2-chloro-D-phenylalanine, 2-chloro-L-phenylalanine, 2-cyano-D-phenylalanine, 2-cyano-L-phenylalanine, 2-fluoro-D-phenylalanine, 2-fluoro-L-phenylalanine, 2-methyl-D-phenylalanine, 2-methyl-L-phenylalanine, 2-nitro-D-phenylalanine, 2-nitro-L-phenylalanine, 2,4,5-trihydroxy-phenylalanine, 3,4,5-trifluoro-D-phenylalanine, 3,4,5-trifluoro-L-phenylalanine, 3,4-dichloro-D-phenylalanine, 3,4-dichloro-L-phenylalanine, 3,4-difluoro-D-phenylalanine, 3,4-difluoro-L-phenylalanine, 3,4-dihydroxy-L-phenylalanine, 3,4-dimethoxy-L-phenylalanine, 3,5,3'-triiodo-L-thyronine, 3,5-diiodo-D-tyrosine, 3,5-diiodo-L-tyrosine, 3,5-diiodo-L-thyronine, 3-(trifluoromethyl)-D-phenylalanine, 3-(trifluoromethyl)-L-phenylalanine, 3-amino-L-tyrosine, 3-bromo-D-phenylalanine, 3-bromo-L-phenylalanine, 3-chloro-D-phenylalanine, 3-chloro-L-phenylalanine, 3-chloro-L-tyrosine, 3-cyano-D-phenylalanine, 3-cyano-L-phenylalanine, 3-fluoro-D-phenylalanine, 3-fluoro-L-phenylalanine, 3-fluoro-tyrosine, 3-iodo-D-phenylalanine, 3-iodo-L-phenylalanine, 3-iodo-L-tyrosine, 3-methoxy-L-tyrosine, 3-methyl-D-phenylalanine, 3-methyl-L-phenylalanine, 3-nitro-D-phenylalanine, 3-nitro-L-phenylalanine, 3-nitro-L-tyrosine, 4-(trifluoromethyl)-D-phenylalanine, 4-(trifluoromethyl)-L-phenylalanine, 4-amino-D-phenylalanine, 4-amino-L-phenylalanine, 4-benzoyl-D-phenylalanine, 4-benzoyl-L-phenylalanine, 4-bis(2-chloroethyl)amino-L-phenylalanine, 4-bromo-D-phenylalanine, 4-bromo-L-phenylalanine, 4-chloro-D-phenylalanine, 4-chloro-L-phenylalanine, 4-cyano-D-phenylalanine, 4-cyano-L-phenylalanine, 4-fluoro-D-phenylalanine, 4-fluoro-L-phenylalanine, 4-iodo-D-phenylalanine, 4-iodo-L-phenylalanine, homophenylalanine, thyroxine, 3,3-diphenylalanine, thyronine, ethyl-tyrosine, and methyl-tyrosine.

Amino acid analogs include analogs of proline. Examples of amino acid analogs of proline include, but are not limited to, 3,4-dehydro-proline, 4-fluoro-proline, cis-4-hydroxy-proline, thiazolidine-2-carboxylic acid, and trans-4-fluoro-proline.

Amino acid analogs include analogs of serine and threonine. Examples of amino acid analogs of serine and threonine include, but are not limited to, 3-amino-2-hydroxy-5-methylhexanoic acid, 2-amino-3-hydroxy-4-methylpentanoic acid, 2-amino-3-ethoxybutanoic acid, 2-amino-3-methoxybutanoic acid, 4-amino-3-hydroxy-6-methylheptanoic acid, 2-amino-3-benzyloxypropionic acid, 2-amino-3-benzyloxypropionic acid, 2-amino-3-ethoxypropionic acid, 4-amino-3-hydroxybutanoic acid, and α-methylserine.

Amino acid analogs include analogs of tryptophan. Examples of amino acid analogs of tryptophan include, but are not limited to, the following: α-methyl-tryptophan; β-(3--benzothienyl)-D -alanine; β-(3-benzothienyl)-L-alanine; 1-methyl-tryptophan; 4-methyl-tryptophan; 5-benzyloxy-tryptophan; 5-bromo-tryptophan; 5-chloro-tryptophan; 5-fluoro-tryptophan; 5-hydroxy-tryptophan; 5-hydroxy-L-tryptophan; 5-methoxy-tryptophan; 5-methoxy-L-tryptophan; 5-methyl-tryptophan; 6-bromo-tryptophan; 6-chloro-D-tryptophan; 6-chloro-tryptophan; 6-fluoro-tryptophan; 6-methyl-tryptophan; 7-benzyloxy-tryptophan; 7-bromo-tryptophan; 7-methyl--tryptophan; D-1,2,3,4-tetrahydro-norharman-3-carboxylic acid; 6-methoxy-1,2,3,4-tetrahydronorharman-1-carboxylic acid; 7-azatryptophan; L-1,2,3,4-tetrahydro-norharman-3-carboxylic acid; 5-methoxy-2-methyl-tryptophan; and 6-chloro-L-tryptophan.

In some embodiments, amino acid analogs are racemic. In some embodiments, the D isomer of the amino acid analog is used. In some embodiments, the L isomer of the amino acid analog is used. In other embodiments, the amino acid analog comprises chiral centers that are in the R or S configuration. In still other embodiments, the amino group(s) of a β-amino acid analog is substituted with a protecting group, e.g., tert-butyloxycarbonyl (BOC group), 9-fluorenylmethyloxycarbonyl (FMOC), tosyl, and the like. In yet other embodiments, the carboxylic acid functional group of a β-amino acid analog is protected, e.g., as its ester derivative. In some embodiments the salt of the amino acid analog is used.

A "non-essential" amino acid residue is a residue that can be altered from the wild-type sequence of a polypeptide without abolishing or substantially abolishing its essential biological or biochemical activity (e.g., receptor binding or activation). An "essential" amino acid residue is a residue that, when altered from the wild-type sequence of the polypeptide, results in abolishing or substantially abolishing the polypeptide's essential biological or biochemical activity.

A "conservative amino acid substitution" is one in which the amino acid residue is replaced with an amino acid residue having a similar side chain. Families of amino acid residues having similar side chains have been defined in the art. These families include amino acids with basic side chains (e.g., K, R, H), acidic side chains (e.g., D, E), uncharged polar side chains (e.g., G, N, Q, S, T, Y, C), nonpolar side chains (e.g., A, V, L, I, P, F, M, W), beta-branched side chains (e.g., T, V, I) and aromatic side chains (e.g., Y, F, W, H). Thus, a predicted nonessential amino acid residue in a polypeptide, for example, is replaced with another amino acid residue from the same side chain family. Other examples of acceptable substitutions are substitutions based on isosteric considerations (e.g. norleucine for methionine) or other properties (e.g. 2-thienylalanine for phenylalanine).

The term "capping group" refers to the chemical moiety occurring at either the carboxy or amino terminus of the polypeptide chain of the subject peptidomimetic macrocycle. The capping group of a carboxy terminus includes an unmodified carboxylic acid (ie —COOH) or a carboxylic acid with a substituent. For example, the carboxy terminus can be substituted with an amino group to yield a carboxamide at the C-terminus. Various substituents include but are not limited to primary and secondary amines, including pegylated secondary amines. Representative secondary amine capping groups for the C-terminus include:

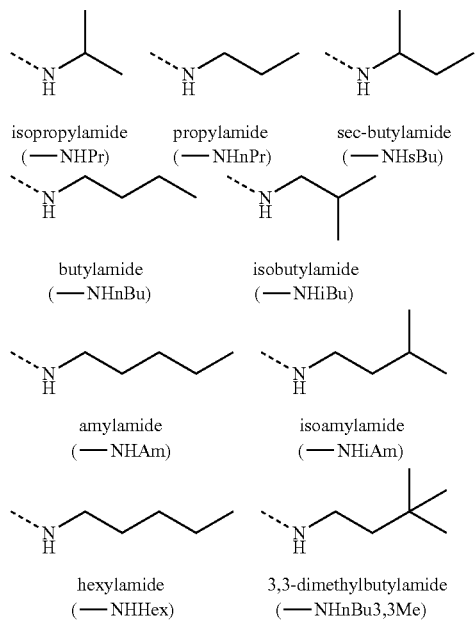

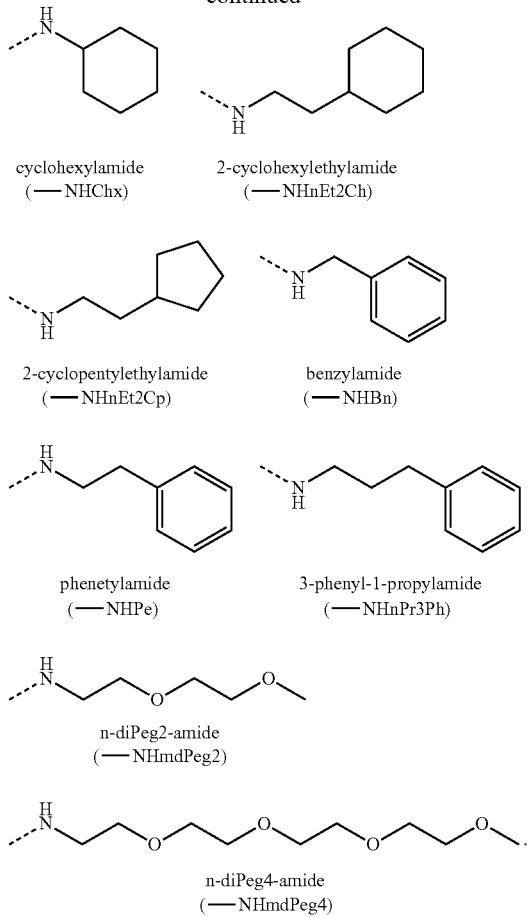

The capping group of an amino terminus includes an unmodified amine (ie —NH$_2$) or an amine with a substituent. For example, the amino terminus can be substituted with an acyl group to yield a carboxamide at the N-terminus. Various substituents include but are not limited to substituted acyl groups, including $C_1$-$C_6$ carbonyls, $C_7$-$C_{30}$ carbonyls, and pegylated carbamates. Representative capping groups for the N-terminus include:

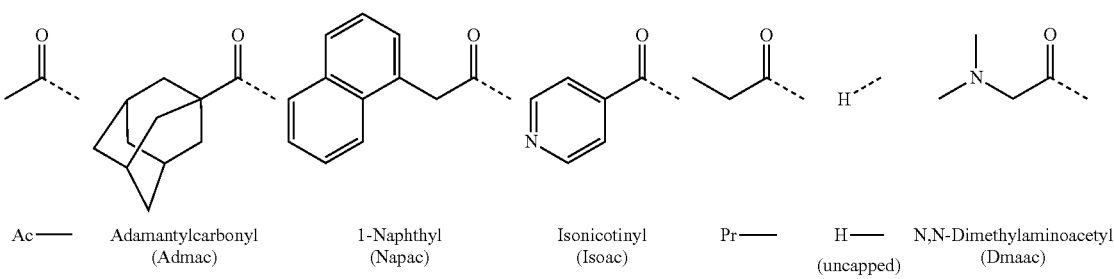

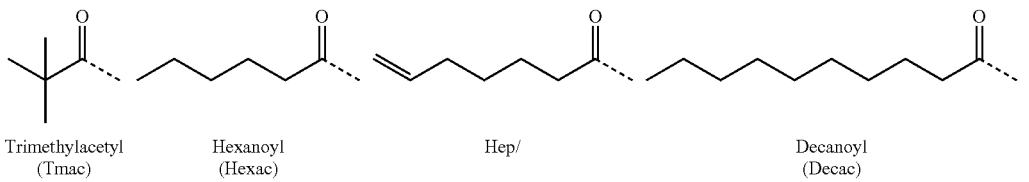

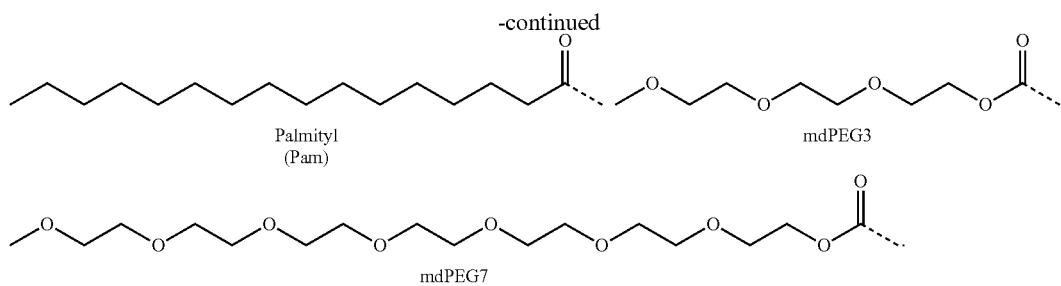

Palmityl (Pam)

mdPEG3 mdPEG7

The term "member" as used herein in conjunction with macrocycles or macrocycle-forming linkers refers to the atoms that form or can form the macrocycle, and excludes substituent or side chain atoms. By analogy, cyclodecane, 1,2-difluoro-decane and 1,3-dimethyl cyclodecane are all considered ten-membered macrocycles as the hydrogen or fluoro substituents or methyl side chains do not participate in forming the macrocycle.

The symbol "⫽" when used as part of a molecular structure refers to a single bond or a trans or cis double bond.

The term "amino acid side chain" refers to a moiety attached to the α-carbon (or another backbone atom) in an amino acid. For example, the amino acid side chain for alanine is methyl, the amino acid side chain for phenylalanine is phenylmethyl, the amino acid side chain for cysteine is thiomethyl, the amino acid side chain for aspartate is carboxymethyl, the amino acid side chain for tyrosine is 4-hydroxyphenylmethyl, etc. Other non-naturally occurring amino acid side chains are also included, for example, those that occur in nature (e.g., an amino acid metabolite) or those that are made synthetically (e.g., an α,α di-substituted amino acid).

The term "α·α di-substituted amino" acid refers to a molecule or moiety containing both an amino group and a carboxyl group bound to α carbon (the α-carbon) that is attached to two natural or non-natural amino acid side chains.

The term "polypeptide" encompasses two or more naturally or non-naturally-occurring amino acids joined by a covalent bond (e.g., an amide bond). Polypeptides as described herein include full length proteins (e.g., fully processed proteins) as well as shorter amino acid sequences (e.g., fragments of naturally-occurring proteins or synthetic polypeptide fragments).

The term "macrocyclization reagent" or "macrocycle-forming reagent" as used herein refers to any reagent which may be used to prepare a peptidomimetic macrocycle of the invention by mediating the reaction between two reactive groups. Reactive groups may be, for example, an azide and alkyne, in which case macrocyclization reagents include, without limitation, Cu reagents such as reagents which provide a reactive Cu(I) species, such as CuBr, CuI or CuOTf, as well as Cu(II) salts such as Cu(CO$_2$CH$_3$)$_2$, CuSO$_4$, and CuCl$_2$ that can be converted in situ to an active Cu(I) reagent by the addition of a reducing agent such as ascorbic acid or sodium ascorbate. Macrocyclization reagents may additionally include, for example, Ru reagents known in the art such as Cp*RuCl(PPh$_3$)$_2$, [Cp*RuCl]$_4$ or other Ru reagents which may provide a reactive Ru(II) species. In other cases, the reactive groups are terminal olefins. In such embodiments, the macrocyclization reagents or macrocycle-forming reagents are metathesis catalysts including, but not limited to, stabilized, late transition metal carbene complex catalysts such as Group VIII transition metal carbene catalysts. For example, such catalysts are Ru and Os metal centers having a +2 oxidation state, an electron count of 16 and pentacoordinated. In other examples, catalysts have W or Mo centers. Various catalysts are disclosed in Grubbs et al., "Ring Closing Metathesis and Related Processes in Organic Synthesis" Acc. Chem. Res. 1995, 28, 446-452, and U.S. Pat. Nos. 5,811,515; 7,932,397; U.S. Application No. 2011/0065915; U.S. Application No. 2011/0245477; Yu et al., "Synthesis of Macrocyclic Natural Products by Catalyst-Controlled Stereoselective Ring-Closing Metathesis," Nature 2011, 479, 88; and Peryshkov et al., "Z-Selective Olefin Metathesis Reactions Promoted by Tungsten Oxo Alkylidene Complexes," J. Am. Chem. Soc. 2011, 133, 20754. In yet other cases, the reactive groups are thiol groups. In such embodiments, the macrocyclization reagent is, for example, a linker functionalized with two thiol-reactive groups such as halogen groups.

The term "halo" or "halogen" refers to fluorine, chlorine, bromine or iodine or a radical thereof.

The term "alkyl" refers to a hydrocarbon chain that is a straight chain or branched chain, containing the indicated number of carbon atoms. For example, $C_1$-$C_{10}$ indicates that the group has from 1 to 10 (inclusive) carbon atoms in it. In the absence of any numerical designation, "alkyl" is a chain (straight or branched) having 1 to 20 (inclusive) carbon atoms in it.

The term "alkylene" refers to a divalent alkyl (i.e., —R—).

The term "alkenyl" refers to a hydrocarbon chain that is a straight chain or branched chain having one or more carbon-carbon double bonds. The alkenyl moiety contains the indicated number of carbon atoms. For example, $C_2$-$C_{10}$ indicates that the group has from 2 to 10 (inclusive) carbon atoms in it. The term "lower alkenyl" refers to a $C_2$-$C_6$ alkenyl chain. In the absence of any numerical designation, "alkenyl" is a chain (straight or branched) having 2 to 20 (inclusive) carbon atoms in it.

The term "alkynyl" refers to a hydrocarbon chain that is a straight chain or branched chain having one or more carbon-carbon triple bonds. The alkynyl moiety contains the indicated number of carbon atoms. For example, $C_2$-$C_{10}$ indicates that the group has from 2 to 10 (inclusive) carbon atoms in it. The term "lower alkynyl" refers to a $C_2$-$C_6$ alkynyl chain. In the absence of any numerical designation, "alkynyl" is a chain (straight or branched) having 2 to 20 (inclusive) carbon atoms in it.

The term "aryl" refers to a 6-carbon monocyclic or 10-carbon bicyclic aromatic ring system wherein 0, 1, 2, 3, or 4 atoms of each ring are substituted by a substituent. Examples of aryl groups include phenyl, naphthyl and the like. The term "arylalkoxy" refers to an alkoxy substituted with aryl.

"Arylalkyl" refers to an aryl group, as defined above, wherein one of the aryl group's hydrogen atoms has been replaced with a $C_1$-$C_5$ alkyl group, as defined above. Representative examples of an arylalkyl group include, but are not limited to, 2-methylphenyl, 3-methylphenyl, 4-methylphenyl, 2-ethylphenyl, 3-ethylphenyl, 4-ethylphenyl, 2-propylphenyl, 3-propylphenyl, 4-propylphenyl, 2-butylphenyl, 3-butylphenyl, 4-butylphenyl, 2-pentylphenyl, 3-pentylphenyl, 4-pentylphenyl, 2-isopropylphenyl, 3-isopropylphenyl, 4-isopropylphenyl, 2-isobutylphenyl, 3-isobutylphenyl, 4-isobutylphenyl, 2-sec-butylphenyl, 3-sec-butylphenyl, 4-sec-butylphenyl, 2-t-butylphenyl, 3-t-butylphenyl and 4-t-butylphenyl.

"Arylamido" refers to an aryl group, as defined above, wherein one of the aryl group's hydrogen atoms has been replaced with one or more —C(O)$NH_2$ groups. Representative examples of an arylamido group include 2-C(O)NH2-phenyl, 3-C(O)$NH_2$-phenyl, 4-C(O)$NH_2$-phenyl, 2-C(O)$NH_2$-pyridyl, 3-C(O)$NH_2$-pyridyl, and 4-C(O)$NH_2$-pyridyl, "Alkylheterocycle" refers to a $C_1$-$C_5$ alkyl group, as defined above, wherein one of the $C_1$-$C_5$ alkyl group's hydrogen atoms has been replaced with a heterocycle. Representative examples of an alkylheterocycle group include, but are not limited to, —$CH_2CH_2$-morpholine, —$CH_2CH_2$-piperidine, —$CH_2CH_2CH_2$-morpholine, and —$CH_2CH_2CH_2$-imidazole.

"Alkylamido" refers to a $C_1$-$C_5$ alkyl group, as defined above, wherein one of the $C_1$-$C_5$ alkyl group's hydrogen atoms has been replaced with a —C(O)$NH_2$ group. Representative examples of an alkylamido group include, but are not limited to, —$CH_2$—C(O)$NH_2$, —$CH_2CH_2$—C(O)$NH_2$, —$CH_2CH_2CH_2$C(O)$NH_2$, —$CH_2CH_2CH_2CH_2$C(O)$NH_2$, —$CH_2CH_2CH_2CH_2CH_2$C(O)$NH_2$, —$CH_2$CH(C(O)$NH_2$)$CH_3$, —$CH_2$CH(C(O)$NH_2$)$CH_2CH_3$, —CH(C(O)$NH_2$)$CH_2CH_3$, —C($CH_3$)$_2CH_2$C(O)$NH_2$, —$CH_2$—$CH_2$—NH—C(O)—$CH_3$, —$CH_2$—$CH_2$—NH—C(O)—$CH_3$—$CH_3$, and —$CH_2$—$CH_2$—NH—C(O)—CH=$CH_2$.

"Alkanol" refers to a $C_1$-$C_5$ alkyl group, as defined above, wherein one of the $C_1$-$C_5$ alkyl group's hydrogen atoms has been replaced with a hydroxyl group. Representative examples of an alkanol group include, but are not limited to, —$CH_2$OH, —$CH_2CH_2$OH, —$CH_2CH_2CH_2$OH, —$CH_2CH_2CH_2CH_2$OH, —$CH_2CH_2CH_2$ $CH_2CH_2$OH, —$CH_2$CH(OH)$CH_3$, —$CH_2$CH(OH)$CH_2CH_3$, —CH(OH)$CH_3$ and —C($CH_3$)$_2CH_2$OH.

"Alkylcarboxy" refers to a $C_1$-$C_5$ alkyl group, as defined above, wherein one of the $C_1$-$C_5$ alkyl group's hydrogen atoms has been replaced with a —COOH group. Representative examples of an alkylcarboxy group include, but are not limited to, —$CH_2$COOH, —$CH_2CH_2$COOH, —$CH_2CH_2CH_2$COOH, —$CH_2CH_2CH_2CH_2$COOH, —$CH_2$CH(COOH)$CH_3$, —$CH_2CH_2CH_2$CHCH COOH, —$CH_2$CH(COOH)$CH_2CH_3$, —CH(COOH)$CH_2CH_3$ and —C($CH_3$)$_2CH_2$COOH.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally is optionally substituted. Some cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of O, N, or S if monocyclic, bicyclic, or tricyclic, respectively), wherein 0, 1, 2, 3, or 4 atoms of each ring are substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like.

The term "heteroarylalkyl" or the term "heteroaralkyl" refers to an alkyl substituted with a heteroaryl. The term "heteroarylalkoxy" refers to an alkoxy substituted with heteroaryl.

The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of O, N, or S if monocyclic, bicyclic, or tricyclic, respectively), wherein 0, 1, 2 or 3 atoms of each ring are substituted by a substituent. Examples of heterocyclyl groups include piperazinyl, pyrrolidinyl, dioxanyl, morpholinyl, tetrahydrofuranyl, and the like.

The term "substituent" refers to a group replacing a second atom or group such as a hydrogen atom on any molecule, compound or moiety. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, and cyano groups.

In some embodiments, the compounds of this invention contain one or more asymmetric centers and thus occur as racemates and racemic mixtures, single enantiomers, individual diastereomers and diastereomeric mixtures. All such isomeric forms of these compounds are included in the present invention unless expressly provided otherwise. In some embodiments, the compounds of this invention are also represented in multiple tautomeric forms, in such instances, the invention includes all tautomeric forms of the compounds described herein (e.g., if alkylation of a ring system results in alkylation at multiple sites, the invention includes all such reaction products). All such isomeric forms of such compounds are included in the present invention unless expressly provided otherwise. All crystal forms of the compounds described herein are included in the present invention unless expressly provided otherwise.

As used herein, the terms "increase" and "decrease" mean, respectively, to cause a statistically significantly (i.e., $p<0.1$) increase or decrease of at least 5%.

As used herein, the recitation of a numerical range for a variable is intended to convey that the variable is equal to any of the values within that range. Thus, for a variable which is inherently discrete, the variable is equal to any integer value within the numerical range, including the end-points of the range. Similarly, for a variable which is inherently continuous, the variable is equal to any real value within the numerical range, including the end-points of the range. As an example, and without limitation, a variable which is described as having values between 0 and 2 takes the values 0, 1 or 2 if the variable is inherently discrete, and takes the values 0.0, 0.1, 0.01, 0.001, or any other real values $\geq 0$ and $\leq 2$ if the variable is inherently continuous.

As used herein, unless specifically indicated otherwise, the word "or" is used in the inclusive sense of "and/or" and not the exclusive sense of "either/or."

The term "on average" represents the mean value derived from performing at least three independent replicates for each data point.

The term "biological activity" encompasses structural and functional properties of a macrocycle of the invention. Biological activity is, for example, structural stability, alpha-helicity, affinity for a target, resistance to proteolytic degradation, cell penetrability, intracellular stability, in vivo stability, or any combination thereof.

The details of one or more particular embodiments of the invention are set forth in the accompanying drawings and the description below. Other features, objects, and advantages of the invention will be apparent from the description and drawings, and from the claims.

Peptidomimetic Macrocycles of the Invention

The present invention provides pharmaceutical formulations comprising an effective amount of peptidomimetic macrocycles or pharmaceutically acceptable salts thereof. The peptidomimetic macrocycles of the invention are cross-linked (e.g., stapled or stitched) and possess improved pharmaceutical properties relative to their corresponding uncross-linked peptidomimetic macrocycles. These improved properties include improved bioavailability, enhanced chemical and in vivo stability, increased potency, and reduced immunogenicity (i.e., fewer or less severe injection site reactions).

In some embodiments, the peptide sequences are derived from a Cited2 peptide. For example, the peptide sequences are derived from human Cited2 (222-244) or human Cited2 (217-248).

In some embodiments, the peptide sequences are derived from a Cited2 peptide and a HIF1α peptide. For example, the peptide sequences are derived from human Cited2 (222-244) and human HIF1α (812-826). For example, the peptide sequences are derived from human Cited2 (222-244) and human HIF1α (794-804).

Non-limiting exemplary lists of suitable Cited2-derived peptides for use in the present invention are given in Tables 1a, 1b, and 1c below; and a non-limiting exemplary list of suitable hybrid peptides derived from Cited2 and HIF1α for use in the present invention is given in Table 2.

TABLE 1a

| SP # | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|
| SP-1 | Ac- | | | | | | F | I | D | E | E | V | L | M | $ | L | V | I | $ | M | G | L | D |
| SP-2 | Ac- | | | | | | F | I | D | E | E | V | L | Nle | $ | L | V | I | $ | Nle | G | L | D |
| SP-3 | Ac- | | | | | | F | I | D | E | E | V | L | M | $ | L | V | I | $ | M | A | L | D |
| SP-4 | Ac- | | | | | | F | I | D | E | E | V | L | Nle | $ | L | V | I | $ | Nle | A | L | D |
| SP-5 | Ac- | | | | | | F | I | D | E | E | V | L | M | $ | L | V | I | $ | M | A | L | D |
| SP-6 | Ac- | | | | | | F | I | D | E | E | V | L | Nle | $ | L | V | I | $ | Nle | A | L | D |
| SP-7 | Ac- | | | | | | F | I | D | E | E | V | L | M | $ | L | V | I | $ | M | A | L | |
| SP-8 | Ac- | | | | | | F | I | D | E | E | V | L | Nle | $ | L | V | I | $ | Nle | A | L | |
| SP-9 | Ac- | | | | | | A | I | D | E | E | V | L | Nle | $ | L | V | I | $ | Nle | A | L | D |
| SP-10 | Ac- | | | | | | F | A | D | E | E | V | L | Nle | $ | L | V | I | $ | Nle | A | L | D |
| SP-11 | Ac- | | | | | | F | I | A | E | E | V | L | Nle | $ | L | V | I | $ | Nle | A | L | D |
| SP-12 | Ac- | | | | | | F | I | D | A | E | V | L | Nle | $ | L | V | I | $ | Nle | A | L | D |
| SP-13 | Ac- | | | | | | F | I | D | E | A | V | L | Nle | $ | L | V | I | $ | Nle | A | L | D |
| SP-14 | Ac- | | | | | | F | I | D | E | E | A | L | Nle | $ | L | V | I | $ | Nle | A | L | D |
| SP-15 | Ac- | | | | | | F | I | D | E | E | V | A | Nle | $ | L | V | I | $ | Nle | A | L | D |
| SP-16 | Ac- | | | | | | F | I | D | E | E | V | L | A | $ | L | V | I | $ | Nle | A | L | D |
| SP-17 | Ac- | | | | | | F | I | D | E | E | V | L | Nle | $ | A | V | I | $ | Nle | A | L | D |
| SP-18 | Ac- | | | | | | F | I | D | E | E | V | L | Nle | $ | L | A | I | $ | Nle | A | L | D |
| SP-19 | Ac- | | | | | | F | I | D | E | E | V | L | Nle | $ | L | V | A | $ | Nle | A | L | D |
| SP-20 | Ac- | | | | | | F | I | D | E | E | V | L | Nle | $ | L | V | I | $ | A | A | L | D |
| SP-21 | Ac- | | | | | | F | I | D | E | E | V | L | Nle | $ | L | V | I | $ | Nle | G | L | D |
| SP-22 | Ac- | | | | | | F | I | D | E | E | V | L | Nle | $ | L | V | I | $ | Nle | A | A | D |
| SP-23 | Ac- | | | | | | F | I | D | E | E | V | L | Nle | $ | L | V | I | $ | Nle | A | L | A |
| SP-24 | Ac- | | | | | | F | I | D | E | E | V | L | Nle | $ | L | V | I | $ | Nle | A | L | D |
| SP-25 | Ac- | | | | | | F | I | D | E | E | V | L | Nle | $ | L | V | I | $ | Nle | A | L | D |
| SP-26 | Ac- | | | | | | F | I | D | E | E | V | L | A | $ | L | V | I | $ | A | A | L | D |
| SP-27 | Ac- | | | | | | F | I | D | E | E | V | L | Nle | $ | L | V | I | $ | Nle | A | L | D |
| SP-28 | Ac- | | | | | | F | I | D | E | E | V | L | A | $ | L | V | I | $ | A | A | L | D |
| SP-29 | Ac- | | | | | D | F | I | D | E | E | V | L | Nle | $ | L | V | I | $ | Nle | A | L | D |
| SP-30 | Ac- | | | | | | E | I | D | E | E | V | L | Nle | $ | L | V | I | $ | Nle | A | L | D |
| SP-31 | Ac- | | | | | | F | E | D | E | E | V | L | Nle | $ | L | V | I | $ | Nle | A | L | D |
| SP-32 | Ac- | | | | | | F | I | D | E | E | D | L | Nle | $ | L | V | I | $ | Nle | A | L | D |
| SP-33 | Ac- | | | | | | F | I | D | E | E | E | L | Nle | $ | L | V | I | $ | Nle | A | L | D |
| SP-34 | Ac- | | | | | | F | I | D | E | E | V | L | D | $ | L | V | I | $ | Nle | A | L | D |
| SP-35 | Ac- | | | | | | F | I | D | E | E | V | L | Nle | $ | D | V | I | $ | Nle | A | L | D |
| SP-36 | Ac- | | | | | | F | I | D | E | E | V | L | Nle | $ | L | E | I | $ | Nle | A | L | D |
| SP-37 | Ac- | | | | | | F | I | D | E | E | V | L | Nle | $ | L | V | E | $ | Nle | A | L | D |
| SP-38 | Ac- | | | | | | F | I | D | E | E | V | L | Nle | $ | L | V | I | $ | E | A | L | D |
| SP-39 | Ac- | | | | | | F | I | D | E | E | V | L | Nle | $ | L | V | I | $ | Nle | E | L | D |
| SP-40 | Ac- | | | | | | F | I | D | E | E | V | L | Nle | $ | L | V | I | $ | Nle | A | E | D |
| SP-41 | Ac- | | | | | | F | I | D | E | E | V | L | Nle | $ | L | V | I | $ | Nle | A | L | D |
| SP-42 | Ac- | | | | | | F | I | D | E | E | V | L | Nle | $ | L | V | I | $ | Nle | A | L | D |
| SP-43 | Ac- | | | | | | F | I | D | E | E | V | L | Nle | $ | L | V | I | $ | Nle | A | L | D |
| SP-44 | Ac- | | | | | | S | I | D | E | E | V | L | Nle | $ | L | V | I | $ | Nle | A | L | D |
| SP-45 | Ac- | | | | | | F | S | D | E | E | V | L | Nle | $ | L | V | I | $ | Nle | A | L | D |
| SP-46 | Ac- | | | | | | F | I | S | E | E | V | L | Nle | $ | L | V | I | $ | Nle | A | L | D |
| SP-47 | Ac- | | | | | | F | I | D | E | S | V | L | Nle | $ | L | V | I | $ | Nle | A | L | D |
| SP-48 | Ac- | | | | | | F | I | D | E | E | S | L | Nle | $ | L | V | I | $ | Nle | A | L | D |
| SP-49 | Ac- | | | | | | F | I | D | E | E | V | S | Nle | $ | L | V | I | $ | Nle | A | L | D |
| SP-50 | Ac- | | | | | | F | I | D | E | E | V | L | S | $ | L | V | I | $ | Nle | A | L | D |

TABLE 1a-continued

| | | | | | | | | | | | | | | | | | | |
|---|---|---|---|---|---|---|---|---|---|---|---|---|---|---|---|---|---|---|
| SP-51 | Ac- | | F | I | D | E | E | V | L | Nle | $ | S | V | I | $ | Nle | A | L | D |
| SP-52 | Ac- | | F | I | D | E | E | V | L | Nle | $ | L | S | I | $ | Nle | A | L | D |
| SP-53 | Ac- | | F | I | D | E | E | V | L | Nle | $ | L | V | S | $ | Nle | A | L | D |
| SP-54 | Ac- | | F | I | D | E | E | V | L | Nle | $ | L | V | I | $ | S | A | L | D |
| SP-55 | Ac- | | F | I | D | E | E | V | L | Nle | $ | L | V | I | $ | Nle | S | L | D |
| SP-56 | Ac- | | F | I | D | E | E | V | L | Nle | $ | L | V | I | $ | Nle | A | S | D |
| SP-57 | Ac- | | F | I | D | E | E | V | L | Nle | $ | L | V | I | $ | Nle | A | L | S |
| SP-58 | Ac- | | F | I | D | E | E | V | L | Nle | $ | L | V | I | $ | Nle | A | L | D |
| SP-59 | Ac- | | F | I | D | E | E | V | L | Nle | $ | L | V | I | $ | Nle | A | L | D |
| SP-60 | Ac- | | F | I | D | E | E | V | L | A | $ | L | V | I | $ | A | A | L | D |
| SP-61 | Ac- | | Dpr | I | D | E | E | V | L | Nle | $ | L | V | I | $ | Nle | A | L | D |
| SP-62 | Ac- | | F | I | Dpr | E | E | V | L | Nle | $ | L | V | I | $ | Nle | A | L | D |
| SP-63 | Ac- | | F | I | D | Dpr | E | V | L | Nle | $ | L | V | I | $ | Nle | A | L | D |
| SP-64 | Ac- | | F | I | D | E | E | Dpr | L | Nle | $ | L | V | I | $ | Nle | A | L | D |
| SP-65 | Ac- | | F | I | D | E | E | V | L | Nle | $ | L | V | Dpr | $ | Nle | A | L | D |
| SP-66 | Ac- | | F | I | D | E | E | V | L | Nle | $ | L | V | I | $ | Dpr | A | L | D |
| SP-67 | Ac- | | F | I | D | E | E | V | L | Nle | $ | L | V | I | $ | Nle | A | L | D |
| SP-68 | Ac- | | F | I | D | E | E | V | L | Nle | $ | L | V | I | $ | Nle | A | L | D |
| SP-69 | Ac- | | F | I | D | E | Q | V | L | Nle | $ | L | V | I | $ | Nle | A | L | D |
| SP-70 | Ac- | | F | I | D | E | Q | V | L | A | $ | L | V | I | $ | A | A | L | D |
| SP-71 | Ac- | | F | I | D | E | E | V | pL | Nle | $ | L | V | I | $ | Nle | A | L | D |
| SP-72 | Ac- | | F | I | D | E | E | V | L | Nle | $ | L | pL | I | $ | Nle | A | L | D |
| SP-73 | Ac- | | F | I | D | E | E | V | L | Nle | $ | L | V | Bpa | $ | Nle | A | L | D |
| SP-74 | Ac- | | F | I | D | E | E | V | L | Nle | $ | L | V | I | $ | Bpa | A | L | D |
| SP-75 | Ac- | | F | I | D | E | E | V | L | M | S | L | V | I | E | M | G | L | D |
| SP-76 | Ac- | | F | I | D | $ | E | V | L | $ | S | L | V | I | E | M | G | L | D |
| SP-77 | Ac- | | F | I | D | E | E | $ | L | M | S | $ | V | I | E | M | G | L | D |
| SP-78 | Ac- | | F | I | D | E | E | V | $ | M | S | L | $ | I | E | M | G | L | D |
| SP-79 | Ac- | | F | I | D | E | E | V | L | $ | S | L | V | $ | E | M | G | L | D |
| SP-80 | Ac- | | F | I | D | E | E | V | L | M | $ | L | V | I | E | $ | G | L | D |
| SP-81 | Ac- | | F | I | D | $r8 | E | V | L | M | S | L | $ | I | E | M | G | L | D |
| SP-82 | Ac- | | F | I | D | E | $r8 | V | L | M | S | L | V | $ | E | M | G | L | D |
| SP-83 | Ac- | | F | I | D | E | E | $r8 | L | M | S | L | V | I | $ | M | G | L | D |
| SP-84 | Ac- | | F | I | D | E | E | V | $r8 | M | S | L | V | I | E | $ | G | L | D |
| SP-85 | Ac- | | F | I | D | E | E | V | L | $r8 | S | L | V | I | E | M | $ | L | D |
| SP-86 | Ac- | | | I | D | E | E | V | L | M | $ | L | V | I | $ | M | G | L | D |
| SP-87 | Ac- | | | | D | E | E | V | L | M | $ | L | V | I | $ | M | G | L | D |
| SP-88 | Ac- | | | | | E | E | V | L | M | $ | L | V | I | $ | M | G | L | D |
| SP-89 | Ac- | | | | | | E | V | L | M | $ | L | V | I | $ | M | G | L | D |
| SP-90 | Ac- | | F | I | D | E | E | V | L | M | $ | L | V | I | $ | M | G | L | D |
| SP-91 | Ac- | | F | I | D | E | E | V | L | M | $ | L | V | I | $ | M | G | L | D |
| SP-92 | Ac- | | F | I | D | E | E | V | L | M | $ | L | V | I | $ | M | G | L | D |
| SP-93 | Ac- | | F | I | D | E | E | V | L | M | $ | L | V | I | $ | M | G | L | D |
| SP-94 | Ac- | | F | I | D | E | E | V | L | M | $ | L | V | I | $ | M | G | L | D |
| SP-95 | Ac- | | F | I | D | E | E | V | L | M | $ | L | V | I | $ | M | G | L | D |
| SP-96 | Ac- | | F | I | D | E | E | V | L | M | $ | L | V | I | $ | M | G | L | D |
| SP-97 | Ac- | | F | I | D | E | E | V | L | M | $ | L | V | I | $ | M | G | L | D |
| SP-98 | Ac- | | F | I | D | E | E | V | L | M | $ | L | V | I | $ | M | G | L | D |
| SP-99 | Ac- | | F | I | D | E | E | V | L | M | $ | L | V | I | $ | M | G | | | |
| SP-100 | Ac- | | F | I | D | E | E | V | L | M | $ | L | V | I | $ | M | A | L | D |
| SP-101 | Ac- | | F | I | D | E | E | V | L | M | $ | L | V | I | $ | M | A | L | D |
| SP-102 | Ac- | | F | I | D | E | E | V | L | M | $ | L | V | I | $ | M | A | | |
| SP-103 | Ac- | | F | I | D | E | E | V | L | M | $ | L | V | I | $ | M | A | A | |

| SP # | 23 | 24 | 25 | 26 | 27 | 28 | 29 | 30 | 31 | 32 | | observed masses | calculated mass (M + 2) | calculated mass (M + 3) |
|---|---|---|---|---|---|---|---|---|---|---|---|---|---|---|
| SP-1 | R | I | K | E | L | P | E | L | W | L | —NH2 | 1102.75 | 1653.42 | 1102.61 |
| SP-2 | R | I | K | E | L | P | E | L | W | L | —NH2 | 1091.23 | 1635.46 | 1090.64 |
| SP-3 | R | I | K | E | L | P | E | L | W | L | —NH2 | 1108.07 | 1660.43 | 1107.29 |
| SP-4 | R | I | K | E | L | P | E | L | W | L | —NH2 | 1095.67 | 1642.47 | 1095.32 |
| SP-5 | R | I | | | | | | | | | —NH2 | 1157.1 | 1156.14 | 771.1 |
| SP-6 | R | I | | | | | | | | | —NH2 | 1138.5 | 1138.19 | 759.13 |
| SP-7 | | | | | | | | | | | —NH2 | 964.5 | 964.04 | 643.03 |
| SP-8 | | | | | | | | | | | —NH2 | 946.56 | 946.08 | 631.06 |
| SP-9 | R | I | | | | | | | | | —NH2 | 1100.86 | 1100.17 | 733.78 |
| SP-10 | R | I | | | | | | | | | —NH2 | 1117.32 | 1117.19 | 745.11 |
| SP-11 | R | I | | | | | | | | | —NH2 | 1116.86 | 1116.19 | 744.46 |
| SP-12 | R | I | | | | | | | | | —NH2 | 1109.83 | 1109.19 | 739.79 |
| SP-13 | R | I | | | | | | | | | —NH2 | 1109.46 | 1109.19 | 739.79 |
| SP-14 | R | I | | | | | | | | | —NH2 | 1125 | 1124.17 | 749.78 |
| SP-15 | R | I | | | | | | | | | —NH2 | 1117.88 | 1117.16 | 745.11 |
| SP-16 | R | I | | | | | | | | | —NH2 | 1118.06 | 1117.16 | 745.11 |
| SP-17 | R | I | | | | | | | | | —NH2 | 1117.78 | 1117.16 | 745.11 |
| SP-18 | R | I | | | | | | | | | —NH2 | 1124.91 | 1124.17 | 749.78 |
| SP-19 | R | I | | | | | | | | | —NH2 | 1117.78 | 1117.16 | 745.11 |
| SP-20 | R | I | | | | | | | | | —NH2 | 1117.88 | 1117.16 | 745.11 |
| SP-21 | R | I | | | | | | | | | —NH2 | 1131.94 | 1131.18 | 754.46 |
| SP-22 | R | I | | | | | | | | | —NH2 | 1118.06 | 1117.16 | 745.11 |
| SP-23 | R | I | | | | | | | | | —NH2 | 1116.86 | 1116.19 | 744.46 |

TABLE 1a-continued

| | | | | | | | | | | | | | |
|---|---|---|---|---|---|---|---|---|---|---|---|---|---|
| SP-24 | A | I | | | | | | | | —NH2 | 1096.04 | 1095.66 | 730.77 |
| SP-25 | R | A | | | | | | | | —NH2 | 1117.78 | 1117.16 | 745.11 |
| SP-26 | R | I | | | | | | | | —NH2 | 1096.51 | 1096.14 | 731.1 |
| SP-27 | R | | | | | | | | | —NH2 | 1082.35 | 1081.65 | 721.43 |
| SP-28 | R | | | | | | | | | —NH2 | 1039.99 | 1039.6 | 693.4 |
| SP-29 | R | I | | | | | | | | —NH2 | 1196.5 | 1195.7 | 797.47 |
| SP-30 | R | I | | | | | | | | —NH2 | 1129.81 | 1129.18 | 753.12 |
| SP-31 | R | I | | | | | | | | —NH2 | 1146.64 | 1146.17 | 764.45 |
| SP-32 | R | I | | | | | | | | —NH2 | 1146.83 | 1146.17 | 764.45 |
| SP-33 | R | I | | | | | | | | —NH2 | 1146.83 | 1146.17 | 764.45 |
| SP-34 | R | I | | | | | | | | —NH2 | 1139.61 | 1139.16 | 759.77 |
| SP-35 | R | I | | | | | | | | —NH2 | 1139.98 | 1139.16 | 759.77 |
| SP-36 | R | I | | | | | | | | —NH2 | 1153.86 | 1153.18 | 769.12 |
| SP-37 | R | I | | | | | | | | —NH2 | 1147.11 | 1146.17 | 764.45 |
| SP-38 | R | I | | | | | | | | —NH2 | 1146.37 | 1146.17 | 764.45 |
| SP-39 | R | I | | | | | | | | —NH2 | 1167.27 | 1167.19 | 778.46 |
| SP-40 | R | I | | | | | | | | —NH2 | 1146.92 | 1146.17 | 764.45 |
| SP-41 | E | I | | | | | | | | —NH2 | 1125.55 | 1124.66 | 750.11 |
| SP-42 | R | E | | | | | | | | —NH2 | 1146.46 | 1146.17 | 764.45 |
| SP-43 | R | I | E | | | | | | | —NH2 | 1203.62 | 1202.71 | 802.14 |
| SP-44 | R | I | | | | | | | | —NH2 | 1108.72 | 1108.17 | 739.11 |
| SP-45 | R | I | | | | | | | | —NH2 | 1126.02 | 1125.16 | 750.44 |
| SP-46 | R | I | | | | | | | | —NH2 | 1124.72 | 1124.19 | 749.8 |
| SP-47 | R | I | | | | | | | | —NH2 | 1117.23 | 1117.18 | 745.12 |
| SP-48 | R | I | | | | | | | | —NH2 | 1133.05 | 1132.17 | 755.11 |
| SP-49 | R | I | | | | | | | | —NH2 | 1126.02 | 1125.16 | 750.44 |
| SP-50 | R | I | | | | | | | | —NH2 | 1125.65 | 1125.16 | 750.44 |
| SP-51 | R | I | | | | | | | | —NH2 | 1125.55 | 1125.16 | 750.44 |
| SP-52 | R | I | | | | | | | | —NH2 | 1132.49 | 1132.17 | 755.11 |
| SP-53 | R | I | | | | | | | | —NH2 | 1125.65 | 1125.16 | 750.44 |
| SP-54 | R | I | | | | | | | | —NH2 | 1125.83 | 1125.16 | 750.44 |
| SP-55 | R | I | | | | | | | | —NH2 | 1146.92 | 1146.19 | 764.46 |
| SP-56 | R | I | | | | | | | | —NH2 | 1126.11 | 1125.16 | 750.44 |
| SP-57 | R | I | | | | | | | | —NH2 | 1125 | 1124.67 | 749.8 |
| SP-58 | S | I | | | | | | | | —NH2 | 1104.19 | 1103.65 | 736.1 |
| SP-59 | R | S | | | | | | | | —NH2 | 1125.83 | 1125.16 | 750.44 |
| SP-60 | | | | | | | | | | —NH2 | 962.19 | 961.55 | 641.37 |
| SP-61 | R | I | | | | | | | | —NH2 | 1108.35 | 1107.68 | 738.79 |
| SP-62 | R | I | | | | | | | | —NH2 | 1124.07 | 1123.7 | 749.47 |
| SP-63 | R | I | | | | | | | | —NH2 | 1117.32 | 1116.69 | 744.8 |
| SP-64 | R | I | | | | | | | | —NH2 | 1132.49 | 1131.68 | 754.79 |
| SP-65 | R | I | | | | | | | | —NH2 | 1125 | 1124.67 | 750.11 |
| SP-66 | R | I | | | | | | | | —NH2 | 1125.46 | 1124.67 | 750.11 |
| SP-67 | Dpr | I | | | | | | | | —NH2 | 1103.91 | 1103.16 | 735.78 |
| SP-68 | Dpr | | | | | | | | | —NH2 | 1047.02 | 1046.62 | 698.08 |
| SP-69 | R | I | | | | | | | | —NH2 | 1138.6 | 1137.7 | 758.8 |
| SP-70 | R | I | | | | | | | | —NH2 | 1096.6 | 1095.65 | 730.77 |
| SP-71 | R | I | | | | | | | | —NH2 | 1145.16 | 1144.18 | 763.12 |
| SP-72 | R | I | | | | | | | | —NH2 | 1152.2 | 1151.18 | 767.79 |
| SP-73 | R | I | | | | | | | | —NH2 | 1208.07 | 1207.19 | 805.13 |
| SP-74 | R | I | | | | | | | | —NH2 | 1207.51 | 1207.19 | 805.13 |
| SP-75 | R | I | K | E | L | P | E | L | W | L | —NH2 | 1091.01 | 1636.37 | 1091.25 |
| SP-76 | R | I | K | E | L | P | E | L | W | L | —NH2 | 1088.14 | 1631.41 | 1087.94 |
| SP-77 | R | I | K | E | L | P | E | L | W | L | —NH2 | 1104.59 | 1655.38 | 1103.92 |
| SP-78 | R | I | K | E | L | P | E | L | W | L | —NH2 | 1104.13 | 1655.38 | 1103.92 |
| SP-79 | R | I | K | E | L | P | E | L | W | L | —NH2 | 1093.53 | 1639.39 | 1093.26 |
| SP-80 | R | I | K | E | L | P | E | L | W | L | —NH2 | 1093.73 | 1639.39 | 1093.26 |
| SP-81 | R | I | K | E | L | P | E | L | W | L | —NH2 | 1113.04 | 1668.42 | 1112.62 |
| SP-82 | R | I | K | E | L | P | E | L | W | L | —NH2 | 1108.81 | 1661.42 | 1107.95 |
| SP-83 | R | I | K | E | L | P | E | L | W | L | —NH2 | 1112.83 | 1668.42 | 1112.62 |
| SP-84 | R | I | K | E | L | P | E | L | W | L | —NH2 | 1108.44 | 1660.42 | 1107.28 |
| SP-85 | R | I | K | E | L | P | E | L | W | L | —NH2 | 1126.36 | 1688.45 | 1125.97 |
| SP-86 | R | I | K | E | L | P | E | L | W | L | —NH2 | 1053.82 | 1579.88 | 1053.59 |
| SP-87 | R | I | K | E | L | P | E | L | W | L | —NH2 | 1016.2 | 1523.34 | 1015.9 |
| SP-88 | R | I | K | E | L | P | E | L | W | L | —NH2 | 977.75 | 1465.83 | 977.55 |
| SP-89 | R | I | K | E | L | P | E | L | W | L | —NH2 | 934.71 | 1401.31 | 934.54 |
| SP-90 | R | I | K | E | L | P | E | L | W | | —NH2 | 1066.07 | 1596.88 | 1064.92 |
| SP-91 | R | I | K | E | L | P | E | L | | | —NH2 | 1003.11 | 1503.84 | 1002.89 |
| SP-92 | R | I | K | E | L | P | E | | | | —NH2 | 965.28 | 1447.3 | 965.2 |
| SP-93 | R | I | K | E | L | P | | | | | —NH2 | 1383.55 | 1382.77 | 922.18 |
| SP-94 | R | I | K | E | L | | | | | | —NH2 | 1334.71 | 1334.25 | 889.83 |
| SP-95 | R | I | K | E | | | | | | | —NH2 | 1277.66 | 1277.71 | 852.14 |
| SP-96 | R | I | K | | | | | | | | —NH2 | 1213.2 | 1213.18 | 809.12 |
| SP-97 | R | I | | | | | | | | | —NH2 | | | |
| SP-98 | | | | | | | | | | | —NH2 | | | |
| SP-99 | | | | | | | | | | | —NH2 | | | |

TABLE 1a-continued

|  |  |  |  |  |  |
|---|---|---|---|---|---|
| SP-100 | R | I | K | E | —NH2 |
| SP-101 |  |  |  |  | —NH2 |
| SP-102 |  |  |  |  | —NH2 |
| SP-103 |  |  |  |  | —NH2 |

(SEQ ID NOS 17-56, respectively, in order of appearance)

TABLE 1b

| SP # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| SP-104 | Ac- |  |  |  |  | F | I | D | E | $ | V | L | M | $ | L | V | I | E | M | G | L | D | R |
| SP-105 | Ac- |  |  |  |  | F | I | D | E | $ | V | L | Nle | $ | L | V | I | E | Nle | G | L | D | R |
| SP-106 | Ac- |  |  |  |  | F | I | D | E | $ | V | L | Nle | $ | L | V | I | E | Nle | A | L | D | R |
| SP-107 | Ac- |  |  |  |  | F | I | D | E | $ | V | L | M | $ | L | V | I | E | M | A | L | D | R |
| SP-108 | Ac- |  |  |  |  | F | I | D | E | $ | V | L | M | $ | L | V | I | E | M | A | L | D | R |
| SP-109 | Ac- |  |  |  |  | F | I | D | E | $ | V | L | Nle | $ | L | V | I | E | Nle | A | L | D | R |
| SP-110 | Ac- |  |  |  |  | F | I | D | E | $ | V | L | M | $ | L | V | I | E | M | A | L |  |  |
| SP-111 | Ac- |  |  |  |  | F | I | D | E | $ | V | L | Nle | $ | L | V | I | E | Nle | A | L |  |  |

| SP # | 24 | 25 | 26 | 27 | 28 | 29 | 30 | 31 | 32 |  | observed masses | calculated mass (M + 2) | calculated mass (M + 3) |
|---|---|---|---|---|---|---|---|---|---|---|---|---|---|
| SP-104 | I | K | E | L | P | E | L | W | L | —NH2 | 1102.75 | 1653.42 | 1102.61 |
| SP-105 | I | K | E | L | P | E | L | W | L | —NH2 | 1091.23 | 1635.46 | 1090.64 |
| SP-106 | I | K | E | L | P | E | L | W | L | —NH2 | 1095.86 | 1642.47 | 1095.32 |
| SP-107 | I | K | E | L | P | E | L | W | L | —NH2 | 1107.89 | 1660.43 | 1107.29 |
| SP-108 | I |  |  |  |  |  |  |  |  | —NH2 | 1156.4 | 1156.14 | 771.1 |
| SP-109 | I |  |  |  |  |  |  |  |  | —NH2 | 1138.87 | 1138.19 | 759.13 |
| SP-110 |  |  |  |  |  |  |  |  |  | —NH2 | 964.22 | 964.04 | 643.03 |
| SP-111 |  |  |  |  |  |  |  |  |  | —NH2 | 946 | 946.08 | 631.06 |

(SEQ ID NOS 120-127, respectively, in order of appearance)

TABLE 1c

| SP # |  | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|---|
| SP-112 | Ac- |  |  |  |  |  | F | I | D | E | $ | V | L | A | $ | L | V | I | E | M |
| SP-113 | Ac- |  |  |  |  |  | F | I | D | E | $ | V | L | M | $ | L | V | I | E | M |
| SP-114 | Ac- |  |  |  |  |  | F | I | D | E | $ | V | L | M | $ | L | V | I | E | M |
| SP-115 | Ac- |  |  |  |  |  | F | I | D | E | $ | V | L | M | $ | L | V | I | E | M |
| SP-116 | Ac- |  |  |  |  |  | F | I | D | E | $ | V | L | M | $ | L | V | I | E | M |
| SP-117 | Ac- |  |  |  |  |  | F | I | D | E | $ | V | L | M | $ | L | V | I | E | M |
| SP-118 | Ac- |  |  |  |  |  | F | I | D | E | $ | V | L | Nle | $ | L | V | I | E | M |
| SP-119 | Ac- |  |  |  |  |  | F | I | D | E | $ | V | L | M | $ | L | V | I | E | Nle |
| SP-120 | Ac- |  |  |  |  |  | F | I | A | E | $ | V | L | Nle | $ | L | V | I | E | Nle |
| SP-121 | Ac- |  |  |  |  |  | F | I | A | E | $ | V | L | Nle | $ | L | V | I | A | Nle |
| SP-122 | Ac- |  |  |  |  |  | F | I | D | E | $ | V | L | Nle | $ | L | V | I | A | Nle |
| SP-123 | Ac- |  |  |  |  |  | F | I | A | E | $ | V | L | Nle | $ | L | V | I | A | Nle |
| SP-124 | Ac- |  |  |  |  |  | F | I | D | E | $ | V | L | Nle | $ | L | V | I | L | Nle |
| SP-125 | Ac- |  |  |  |  |  | F | I | D | E | $ | V | L | Nle | $ | L | V | I | A | Nle |
| SP-126 | Ac- |  |  |  |  |  | F | I | D | E | $ | V | L | Nle | $ | L | V | I | L | Nle |
| SP-127 | Ac- |  |  |  |  |  | F | I | D | E | $ | V | L | Nle | $ | L | V | I | A | Nle |
| SP-128 | Ac- |  |  |  |  |  | F | I | D | E | $ | V | L | Nle | $ | L | V | I | L | Nle |
| SP-129 | Ac- |  |  |  |  |  | F | I | D | E | $ | V | L | Nle | $ | L | V | I | A | Nle |
| SP-130 | 5-FAM- |  |  | Ba |  |  | F | I | D | E | $ | V | L | Nle | $ | L | V | I | E | Nle |
| SP-131 | 5-FAM- |  |  | Ba |  |  | F | I | D | E | $ | V | L | Nle | $ | L | V | I | E | Nle |
| SP-132 | Ac- |  |  |  |  |  | F | I | D | E | $ | V | L | Nle | $ | L | V | I | E | Nle |
| SP-133 | Ac- |  |  |  |  |  | F | I | D | E | $ | V | L | Nle | $ | L | V | I | E | Nle |
| SP-134 | Ac- |  |  |  |  | K | F | I | D | E | $ | V | L | Nle | $ | L | V | I | E | Nle |
| SP-135 | Ac- |  |  |  |  | K | F | I | D | E | $ | V | L | Nle | $ | L | V | I | E | Nle |
| SP-136 | Ac- |  |  |  | K | K | F | I | D | E | $ | V | L | Nle | $ | L | V | I | E | Nle |
| SP-137 | Ac- |  |  |  | K | K | F | I | D | E | $ | V | L | Nle | $ | L | V | I | E | Nle |
| SP-138 | Ac- |  |  |  |  |  | F | I | D | E | $ | A | L | Nle | $ | L | V | I | E | Nle |
| SP-139 | Ac- |  |  |  |  |  | F | I | D | E | $ | T | L | Nle | $ | L | V | I | E | Nle |
| SP-140 | Ac- |  |  |  |  |  | F | I | D | E | $ | S | L | Nle | $ | L | V | I | E | Nle |
| SP-141 | Ac- |  |  |  |  |  | F | I | D | E | $ | N | L | Nle | $ | L | V | I | E | Nle |
| SP-142 | Ac- |  |  |  |  |  | F | I | D | E | $ | V | L | Nle | $ | A | V | I | E | Nle |
| SP-143 | Ac- |  |  |  |  |  | F | I | D | E | $ | V | L | Nle | $ | N | V | I | E | Nle |
| SP-144 | Ac- |  |  |  |  |  | F | I | D | E | $ | V | L | Nle | $ | S | V | I | E | Nle |
| SP-145 | Ac- |  |  |  |  |  | F | I | D | E | $ | V | L | Nle | $ | L | V | I | E | A |
| SP-146 | Ac- |  |  |  |  |  | F | I | D | E | $ | V | L | Nle | $ | L | V | I | E | Q |
| SP-147 | Ac- |  |  |  |  |  | F | I | D | E | $ | V | L | Nle | $ | L | V | I | E | S |
| SP-148 | Ac- |  |  |  |  |  | F | I | D | A | $ | V | L | Nle | $ | L | V | I | E | Nle |

TABLE 1c-continued

| | | | | | | | | | | | | | | | |
|---|---|---|---|---|---|---|---|---|---|---|---|---|---|---|---|
| SP-149 | Ac- | | | | F | I | D | A | $ | T | L | Nle | $ | L | V | I | E | Nle |
| SP-150 | Ac- | | | | F | I | D | A | $ | V | L | Nle | $ | N | V | I | E | Nle |
| SP-151 | Ac- | | | | F | I | D | A | $ | T | L | Nle | $ | N | V | I | E | Nle |
| SP-152 | Ac- | | | | F | I | D | E | $ | V | L | A | $ | L | V | I | E | Nle |
| SP-153 | Ac- | | | | F | T | D | E | $ | V | L | Nle | $ | L | V | I | E | Nle |
| SP-154 | Ac- | | | | F | S | D | E | $ | V | L | Nle | $ | L | V | I | E | Nle |
| SP-155 | Ac- | | | | F | I | R | E | $ | V | L | Nle | $ | L | V | I | E | Nle |
| SP-156 | Ac- | | | | F | I | D | R | $ | V | L | Nle | $ | L | V | I | E | Nle |
| SP-157 | Ac- | | | | F | I | D | E | $ | V | L | Nle | $ | L | V | I | R | Nle |
| SP-158 | Ac- | | | | | I | D | E | $ | V | F | Nle | $ | L | V | I | E | Nle |
| SP-159 | Ac- | | | | | | D | E | $ | V | F | Nle | $ | L | V | I | E | Nle |
| SP-160 | H- | | | | F | I | D | E | $ | V | F | Nle | $ | L | V | I | E | Nle |
| SP-161 | Ac- | | | | F | I | D | E | $ | V | F | A | $ | L | V | I | E | Nle |
| SP-162 | Ac- | | | | F | I | D | E | $ | V | F | A | $ | L | V | I | E | S |
| SP-163 | Ac- | | | | F | I | D | E | $ | V | F | Nle | $ | L | V | I | E | A |
| SP-164 | Ac- | | | | F | I | N | Q | $ | V | F | Nle | $ | L | V | I | Q | Nle |
| SP-165 | Ac- | | | | F | I | N | Q | $ | V | F | A | $ | L | V | I | Q | Nle |
| SP-166 | Ac- | | | | F | I | N | Q | $ | V | F | A | $ | L | V | I | Q | A |
| SP-167 | Ac- | | | | F | I | N | Q | $ | V | F | Nle | $ | L | V | I | Q | A |
| SP-168 | Ac- | | | | F | I | R | E | $ | V | F | Nle | $ | L | V | I | E | Nle |
| SP-169 | Ac- | | | | F | I | R | E | $ | V | F | A | $ | L | V | I | E | Nle |
| SP-170 | Ac- | | | | F | I | D | E | $ | V | F | A | $ | L | V | I | R | Nle |
| SP-171 | Ac- | | | | F | I | R | E | $ | V | F | Nle | $ | L | V | I | E | A |
| SP-172 | Ac- | | | | F | I | D | E | $ | V | F | Nle | $ | L | V | I | R | A |
| SP-173 | Dma ac- | | | | F | I | D | E | $ | V | F | Nle | $ | L | V | I | E | Nle |
| SP-174 | Ac- | | | | F | I | D | E | $r8 | V | L | M | S | L | V | $ | E | M |
| SP-175 | Ac- | | | | F | I | D | E | $r8 | V | L | M | S | L | V | $ | E | M |
| SP-176 | Ac- | | | | F | I | D | E | $r8 | V | L | M | S | L | V | $ | E | M |
| SP-177 | Ac- | | | | F | I | D | E | $r8 | V | L | M | S | L | V | $ | E | M |
| SP-178 | Ac- | | | | F | I | D | E | $r8 | V | L | M | S | L | V | $ | E | M |
| SP-179 | Ac- | | | | F | I | D | E | $r8 | V | L | M | S | L | V | $ | E | M |
| SP-180 | Ac- | | | | | L | T | E | $r8 | V | L | M | S | L | V | $ | S | M |
| SP-181 | Ac- | | | | | L | T | E | $r8 | V | L | M | S | L | V | $ | S | A |
| SP-182 | Ac- | | | | | L | T | F | $r8 | V | L | M | S | L | V | $ | S | A |
| SP-183 | Ac- | | | | F | I | D | E | $r8 | V | L | A | S | L | V | $ | E | M |
| SP-184 | Ac- | | | | F | I | D | E | $r8 | V | L | A | S | L | V | $ | E | M |
| SP-185 | Ac- | | | | F | I | D | E | $r8 | V | L | Nle | S | L | V | $ | E | M |
| SP-186 | Ac- | | | | F | I | D | E | $r8 | V | L | M | S | L | V | $ | E | Nle |
| SP-187 | Ac- | | | | F | I | D | E | $r8 | V | L | M | S | L | V | $ | E | M |
| SP-188 | Ac- | | | | F | I | D | E | $r8 | V | L | M | S | L | V | $ | E | M |
| SP-189 | Ac- | | | | F | I | D | E | $r8 | V | L | M | S | L | V | $ | E | M |
| SP-190 | Ac- | | | | F | I | D | E | $r8 | V | L | Nle | S | L | V | $ | E | Nle |
| SP-191 | Ac- | | | | F | I | D | E | $r8 | V | L | Nle | S | L | V | $ | A | Nle |
| SP-192 | Ac- | | | | F | I | A | E | $r8 | V | L | Nle | S | L | V | $ | E | Nle |
| SP-193 | Ac- | | | | F | I | A | E | $r8 | V | L | Nle | S | L | V | $ | A | Nle |
| SP-194 | Ac- | | | | F | I | A | E | $r8 | V | L | Nle | S | L | V | $ | A | Nle |
| SP-195 | Ac- | | | | F | I | D | E | $r8 | V | L | Nle | S | L | V | $ | E | Nle |
| SP-196 | Ac- | | | | F | I | D | E | $r8 | V | L | Nle | S | L | V | $ | A | Nle |
| SP-197 | Ac- | | | | F | I | A | E | $r8 | V | L | Nle | S | L | V | $ | E | Nle |
| SP-198 | Ac- | | | | F | I | A | E | $r8 | V | L | Nle | S | L | V | $ | A | Nle |
| SP-199 | Ac- | | | | F | I | D | E | E | $r8 | L | Nle | S | L | V | I | $ | Nle |
| SP-200 | Ac- | | | | F | I | D | E | E | $r8 | L | Nle | S | L | V | I | $ | Nle |
| SP-201 | Ac- | | | | F | I | D | E | $r5 | V | L | M | St | L | V | I | $ | M |
| SP-202 | Ac- | | | | F | I | D | E | $r5 | V | L | Nle | St | L | V | I | $ | Nle |
| SP-203 | Ac- | | | | F | I | D | E | $ | V | L | M | St | L | V | I | $r5 | M |
| SP-204 | Ac- | | | | F | I | D | E | $ | V | L | Nle | St | L | V | I | $r5 | Nle |
| SP-205 | Ac- | | | | F | I | D | E | $ | V | L | E | St | L | V | I | $r5 | Nle |
| SP-206 | Ac- | | | | F | I | D | E | $ | R | L | Nle | St | L | V | I | $r5 | Nle |
| SP-207 | Ac- | | | | F | I | D | E | $ | T | L | Nle | St | L | V | I | $r5 | Nle |
| SP-208 | Ac- | | | | F | I | D | E | $ | N | L | Nle | St | L | V | I | $r5 | Nle |
| SP-209 | Ac- | | | | F | I | D | E | $ | V | L | Nle | St | R | V | I | $r5 | Nle |
| SP-210 | Ac- | | | | F | I | D | E | $ | V | L | Nle | St | N | V | I | $r5 | Nle |
| SP-211 | Ac- | | | | F | I | D | E | $ | V | L | Nle | St | L | V | I | $r5 | A |
| SP-212 | Ac- | | | | F | I | D | E | $ | V | L | Nle | St | L | V | I | $r5 | Q |
| SP-213 | Ac- | | | | F | I | D | E | $ | V | L | Nle | St | L | V | I | $r5 | R |
| SP-214 | Ac- | | | | F | I | D | A | $ | T | L | Nle | St | S | V | I | $r5 | Nle |
| SP-215 | Ac- | | | | F | I | D | E | $5rn3 | V | L | Nle | Sta5 | L | V | I | $5n3 | Nle |
| SP-216 | Ac- | | | | F | I | D | E | Aib | V | L | M | $ | L | V | I | $ | M |
| SP-217 | Ac- | | | | A | I | D | E | E | V | L | M | $ | L | V | I | $ | M |
| SP-218 | Ac- | | | | F | I | D | A | E | V | L | M | $ | L | V | I | $ | M |
| SP-219 | Ac- | | | | F | I | D | E | E | V | L | Nle | $ | F | V | I | $ | Nle |
| SP-220 | Ac- | | | | F | I | D | E | E | V | L | Nle | $ | L | V | I | $ | Nle |
| SP-221 | Ac- | | | | F | I | A | E | E | V | L | Nle | $ | L | V | I | $ | Nle |
| SP-222 | Ac- | | | | F | I | A | E | A | V | L | Nle | $ | L | V | I | $ | Nle |
| SP-223 | Ac- | | | | F | I | A | E | A | V | L | Nle | $ | L | V | I | $ | Nle |
| SP-224 | Ac- | | | | F | I | D | E | E | V | L | Nle | $ | L | V | I | $ | M |
| SP-225 | Ac- | | | | F | I | D | E | E | V | L | M | $ | L | V | I | $ | Nle |
| SP-226 | Ac- | | | | F | I | D | E | E | V | L | M | $ | L | V | I | $ | M |
| SP-227 | Ac- | | | | F | I | D | E | E | V | L | M | $ | L | V | I | $ | M |

TABLE 1c-continued

| ID | | | | | | | | | | | | | | | | | | |
|---|---|---|---|---|---|---|---|---|---|---|---|---|---|---|---|---|---|---|
| SP-228 | Ac- | | | | | | | F | I | D | F4cooh | E | V | L | M | $ | L | V | I | $ | M |
| SP-229 | Ac- | | | | | | | F | I | D | E | E | V | L | M | $ | L | V | I | $ | M |
| SP-230 | Ac- | | | | | | | F | I | S | E | E | V | L | M | $ | L | V | I | $ | M |
| SP-231 | Ac- | | | | | | | F | I | T | E | E | V | L | M | $ | L | V | I | $ | M |
| SP-232 | Ac- | | | | | | | F | I | N | E | E | V | L | M | $ | L | V | I | $ | M |
| SP-233 | Ac- | | | | | | | F | I | D | Q | E | V | L | M | $ | L | V | I | $ | M |
| SP-234 | Ac- | | | | | | | F | I | D | E | Q | V | L | M | $ | L | V | I | $ | M |
| SP-235 | Ac- | | | | | | | F | I | D | E | N | V | L | M | $ | L | V | I | $ | M |
| SP-236 | Ac- | | | | | | | F | I | D | E | E | V | L | M | $ | F | V | I | $ | M |
| SP-237 | Ac- | | | | | | | F | I | D | E | E | V | L | M | $ | L | V | I | $ | M |
| SP-238 | Ac- | | | | | | | F | I | D | E | S | V | L | M | $ | L | V | I | $ | M |
| SP-239 | Ac- | | | | | | | F | I | D | E | T | V | L | M | $ | L | V | I | $ | M |
| SP-240 | 5-FAM- | Ba | | | | | | F | I | D | E | E | V | L | Nle | $ | L | V | I | $ | Nle |
| SP-241 | Ac- | | | | | | | F | I | D | E | E | V | L | Nle | $r5 | L | V | I | $r5 | Nle |
| SP-242 | Ac- | | | | | | | F | I | D | E | E | V | F | Nle | $ | L | V | I | $ | Nle |
| SP-243 | Ac- | | | | | | | | I | D | E | E | V | F | Nle | $ | L | V | I | $ | Nle |
| SP-244 | Ac- | | | | | | | | | D | E | E | V | F | Nle | $ | L | V | I | $ | Nle |
| SP-245 | H- | | | | | | | F | I | D | E | E | V | F | Nle | $ | L | V | I | $ | Nle |
| SP-246 | Ac- | | | | | | | F | I | D | E | E | V | F | A | $ | L | V | I | $ | Nle |
| SP-247 | Ac- | | | | | | | F | I | D | E | E | V | F | Nle | $ | L | V | I | $ | A |
| SP-248 | Ac- | | | | | | | F | I | N | Q | Q | V | F | Nle | $ | L | V | I | $ | Nle |
| SP-249 | Ac- | | | | | | | F | I | D | E | A | V | F | Nle | $ | L | V | I | $ | Nle |
| SP-250 | Ac- | | | | | | | F | I | D | Q | A | V | F | Nle | $ | L | V | I | $ | Nle |
| SP-251 | Ac- | | | | | | | F | I | D | Q | A | V | F | Nle | $ | N | V | I | $ | Nle |
| SP-252 | Ac- | | | | | | | F | I | D | Q | A | V | F | Nle | $ | S | V | I | $ | Nle |
| SP-253 | Ac- | | | | | | | F | I | D | Q | A | V | F | Nle | $ | R | V | I | $ | Nle |
| SP-254 | Ac- | | | | | | | F | I | D | Q | A | V | F | Nle | $ | H | V | I | $ | Nle |
| SP-255 | Ac- | | | | | | | F | I | D | Q | A | V | F | Nle | $ | L | V | I | $ | Q |
| SP-256 | Ac- | | | | | | | F | I | D | Q | A | V | F | Nle | $ | L | V | I | $ | R |
| SP-257 | Ac- | | | | | | | F | I | D | Q | A | V | F | Nle | $ | L | V | I | $ | S |
| SP-258 | Ac- | | | | | | | F | I | D | Q | A | V | F | Nle | $ | L | V | I | $ | H |
| SP-259 | Ac- | | | | | | | F | I | D | Q | A | V | F | Nle | $ | N | V | I | $ | H |
| SP-260 | Ac- | | | | | | | F | I | D | Q | A | V | F | Nle | $ | H | V | I | $ | Q |
| SP-261 | Ac- | | | | | | | F | I | D | Q | A | V | F | Nle | $ | S | V | I | $ | R |
| SP-262 | Ac- | | | | | | | F | I | D | Q | A | V | F | Nle | $ | R | V | I | $ | S |
| SP-263 | 5-FAM- | Ba | | | | | | F | I | D | E | E | V | L | Nle | $ | L | V | I | $ | Nle |
| SP-264 | Ac- | | | | | | | F | I | D | E | E | V | F | M | $ | L | V | I | $ | M |
| SP-265 | Ac- | | | | | | | F | I | D | E | E | V | F | Nle | $ | L | V | I | $ | Nle |
| SP-266 | Ac- | | | | | | | F | I | D | E | A | V | L | M | $ | L | V | I | $ | M |
| SP-267 | Ac- | | | | | | | F | I | D | Q | E | V | F | M | $ | L | V | I | $ | M |
| SP-268 | Ac- | | | | | | | F | I | D | Q | A | V | F | M | $ | L | V | I | $ | M |
| SP-269 | Ac- | | | | | | | F | I | D | Q | E | V | F | Nle | $ | L | V | I | $ | Nle |
| SP-270 | Ac- | | | | | | | F | I | D | Q | A | V | L | M | $ | L | V | I | $ | M |
| SP-271 | Ac- | | | | | | | F | I | N | Q | A | V | L | M | $ | L | V | I | $ | M |
| SP-272 | Ac- | | | | | | | F | I | N | Q | A | V | L | M | $ | L | V | I | $ | M |
| SP-273 | Ac- | | | | | | | F | I | D | Q | A | V | L | Nle | $ | L | V | I | $ | Nle |
| SP-274 | Ac- | | | | | | | F | I | D | E | E | F | L | M | $ | L | V | I | $ | M |
| SP-275 | Ac- | | | | | | | F | I | D | E | E | F | F | M | $ | L | V | I | $ | M |
| SP-276 | Ac- | | | | | | | F | I | D | E | E | V | F | M | $ | L | H | I | $ | M |
| SP-277 | Ac- | | | | | | | F | I | D | E | E | V | L | M | $ | Y | V | I | $ | M |
| SP-278 | Ac- | | | | | | | F | I | D | E | E | V | L | M | $ | L | H | I | $ | M |
| SP-279 | Ac- | | | | | | | F | I | D | E | E | V | L | M | $ | Y | V | I | $ | M |
| SP-280 | Ac- | | | | | | | F | I | D | E | E | V | I | M | $ | L | V | I | $ | M |
| SP-281 | Ac- | | | | | | | F | I | D | E | E | V | L | M | $ | L | V | I | $ | M |
| SP-282 | Ac- | | | | | | | F | I | D | E | Q | V | L | M | $ | L | V | I | $ | M |
| SP-283 | Ac- | | | | | | | F | I | D | E | K | V | L | M | $ | L | V | I | $ | M |
| SP-284 | Ac- | | | | | | | F | I | D | E | H | V | L | M | $ | L | V | I | $ | M |
| SP-285 | Ac- | | | | | | | F | I | N | E | K | V | L | M | $ | L | V | I | $ | M |
| SP-286 | Ac- | | | | | | | F | I | N | E | H | V | L | M | $ | L | V | I | $ | M |
| SP-287 | Ac- | | | | | | | F | I | D | E | E | V | L | M | $ | L | V | I | $ | M |
| SP-288 | Ac- | | | | | | | F | I | N | E | K | V | L | M | $ | L | V | I | $ | M |
| SP-289 | Ac- | | | | | | | F | I | N | Q | A | V | L | Nle | $ | L | V | I | $ | Nle |
| SP-290 | Ac- | | V | I | D | T | D | F | I | D | E | E | V | L | A | $ | L | V | I | $ | A |
| SP-291 | Ac- | | V | F | D | T | D | F | I | D | Q | E | V | L | A | $ | L | V | I | $ | A |
| SP-292 | Ac- | | V | I | D | T | D | F | I | D | Q | E | V | L | A | $ | L | V | I | $ | A |
| SP-293 | Ac- | | V | I | R | T | D | F | I | D | E | Q | V | L | A | $ | Y | V | I | $ | A |
| SP-294 | Ac- | | | | | | | F | I | D | E | E | V | L | Nle | $/ | L | V | I | $/ | Nle |
| SP-295 | Ac- | | | | | | | F | I | D | E | E | V | L | Nle | S | L | V | I | E | Nle |
| SP-296 | Ac- | | | | | | | F | I | D | E | E | V | L | Nle | $r5 | L | V | I | $r5 | Nle |
| SP-297 | 5-TAMRA- | Ba | | | | | | F | I | D | E | E | V | L | Nle | $ | L | V | I | $ | Nle |
| SP-298 | Ac- | | | | | | | F | I | D | E | E | V | L | MO | $ | L | V | I | $ | Nle |
| SP-299 | Ac- | | | | | | | F | I | D | E | E | V | L | Nle | $ | L | V | I | $ | MO |
| SP-300 | Ac- | | | | | | | F | I | D | E | E | V | L | MO2 | $ | L | V | I | $ | Nle |
| SP-301 | Ac- | | | | | | | F | I | D | E | E | V | L | Nle | $ | L | V | I | $ | MO2 |

TABLE 1c-continued

| SP # | 20 | 21 | 22 | 23 | 24 | 25 | 26 | 27 | 28 | 29 | 30 | 31 | 32 | | observed masses | calculated mass (M + 2) | calculated mass (M + 3) |
|---|---|---|---|---|---|---|---|---|---|---|---|---|---|---|---|---|---|
| SP-112 | A | L | D | R | I | K | E | L | P | E | L | W | L | —NH2 | 1087.49 | 1630.43 | 1087.29 |
| SP-113 | A | L | D | R | I | K | E | | | | | | | —NH2 | 1285.22 | 1284.71 | 856.81 |
| SP-114 | A | L | D | | | | | | | | | | | —NH2 | 1022.6 | 1021.55 | 681.37 |
| SP-115 | A | | | | | | | | | | | | | —NH2 | 908.54 | 907.5 | 605.33 |
| SP-116 | A | A | | | | | | | | | | | | —NH2 | 944.06 | 943.01 | 629.01 |
| SP-117 | A | A | A | | | | | | | | | | | —NH2 | 979.12 | 978.53 | 652.69 |
| SP-118 | A | L | D | R | I | | | | | | | | | —NH2 | 1147.61 | 1147.17 | 765.11 |
| SP-119 | A | L | D | R | I | | | | | | | | | —NH2 | 1147.05 | 1147.17 | 765.11 |
| SP-120 | A | L | D | A | I | | | | | | | | | —NH2 | 1073.81 | 1073.66 | 716.11 |
| SP-121 | A | L | D | A | I | | | | | | | | | —NH2 | 1044.77 | 1044.66 | 696.77 |
| SP-122 | A | L | | | | | | | | | | | | —NH2 | 917.05 | 917.08 | 611.72 |
| SP-123 | A | L | | | | | | | | | | | | —NH2 | 895.04 | 895.08 | 597.06 |
| SP-124 | A | L | A | A | Nle | | | | | | | | | —NH2 | 1065.8 | 1065.68 | 710.79 |
| SP-125 | A | L | D | R | Nle | | | | | | | | | —NH2 | 1109.04 | 1109.19 | 739.79 |
| SP-126 | A | Nle | A | A | Nle | | | | | | | | | —NH2 | 1065.85 | 1065.68 | 710.79 |
| SP-127 | A | L | A | A | I | | | | | | | | | —NH2 | 1044.77 | 1044.66 | 696.77 |
| SP-128 | A | L | S | S | I | | | | | | | | | —NH2 | 1082.04 | 1081.68 | 721.45 |
| SP-129 | A | L | S | S | I | | | | | | | | | —NH2 | 1060.49 | 1060.65 | 707.44 |
| SP-130 | A | L | | | | | | | | | | | | —NH2 | 1139.84 | 1139.62 | 760.08 |
| SP-131 | A | L | D | R | I | | | | | | | | | —NH2 | 888.11 | 1331.73 | 888.15 |
| SP-132 | A | L | K | | | | | | | | | | | —NH2 | 1009.99 | 1010.13 | 673.75 |
| SP-133 | A | L | K | K | | | | | | | | | | —NH2 | 1073.99 | 1074.18 | 716.45 |
| SP-134 | A | L | | | | | | | | | | | | —NH2 | 1009.99 | 1010.13 | 673.75 |
| SP-135 | A | L | | | | | | | | | | | | —NH2 | 1073.99 | 1074.18 | 716.45 |
| SP-136 | A | L | K | | | | | | | | | | | —NH2 | 1073.99 | 1074.18 | 716.45 |
| SP-137 | A | L | K | K | | | | | | | | | | —NH2 | 1201.99 | 1202.27 | 801.85 |
| SP-138 | A | L | | | | | | | | | | | | —NH2 | 931.94 | 932.07 | 621.71 |
| SP-139 | A | L | | | | | | | | | | | | —NH2 | 946.92 | 947.07 | 631.72 |
| SP-140 | A | L | | | | | | | | | | | | —NH2 | 939.89 | 940.06 | 627.04 |
| SP-141 | A | L | | | | | | | | | | | | —NH2 | 953.49 | 953.57 | 636.05 |
| SP-142 | A | L | | | | | | | | | | | | —NH2 | 924.91 | 925.06 | 617.04 |
| SP-143 | A | L | | | | | | | | | | | | —NH2 | 946.46 | 946.56 | 631.38 |
| SP-144 | A | L | | | | | | | | | | | | —NH2 | 932.96 | 933.06 | 622.37 |
| SP-145 | A | L | | | | | | | | | | | | —NH2 | 924.91 | 925.06 | 617.04 |
| SP-146 | A | L | | | | | | | | | | | | —NH2 | 953.4 | 953.57 | 636.05 |
| SP-147 | A | L | | | | | | | | | | | | —NH2 | 932.96 | 933.06 | 622.37 |
| SP-148 | A | L | | | | | | | | | | | | —NH2 | 917.79 | 917.08 | 611.72 |
| SP-149 | A | L | | | | | | | | | | | | —NH2 | 918.44 | 918.07 | 612.38 |
| SP-150 | A | L | | | | | | | | | | | | —NH2 | 917.80 | 917.56 | 612.04 |
| SP-151 | A | L | | | | | | | | | | | | —NH2 | 918.9 | 918.55 | 612.7 |
| SP-152 | A | L | | | | | | | | | | | | —NH2 | 925.01 | 925.06 | 617.04 |
| SP-153 | A | L | | | | | | | | | | | | —NH2 | 940.17 | 940.06 | 627.04 |
| SP-154 | A | L | | | | | | | | | | | | —NH2 | 933.14 | 933.06 | 622.37 |
| SP-155 | A | L | | | | | | | | | | | | —NH2 | 966.71 | 966.62 | 644.75 |
| SP-156 | A | L | | | | | | | | | | | | —NH2 | 959.5 | 959.61 | 640.08 |
| SP-157 | A | L | | | | | | | | | | | | —NH2 | 959.5 | 959.61 | 640.08 |
| SP-158 | A | L | | | | | | | | | | | | —NH2 | 889.85 | 889.54 | 593.36 |
| SP-159 | A | L | | | | | | | | | | | | —NH2 | 833.33 | 833 | 555.67 |
| SP-160 | A | L | | | | | | | | | | | | —NH2 | 942.39 | 942.07 | 628.38 |
| SP-161 | A | L | | | | | | | | | | | | —NH2 | 942.39 | 942.05 | 628.37 |
| SP-162 | A | L | | | | | | | | | | | | —NH2 | 929.44 | 929.02 | 619.68 |
| SP-163 | A | L | | | | | | | | | | | | —NH2 | 942.39 | 942.05 | 628.37 |
| SP-164 | A | L | | | | | | | | | | | | —NH2 | 961.91 | 961.6 | 641.4 |
| SP-165 | A | L | | | | | | | | | | | | —NH2 | 940.91 | 940.57 | 627.38 |
| SP-166 | A | L | | | | | | | | | | | | —NH2 | 919.92 | 919.55 | 613.37 |
| SP-167 | A | L | | | | | | | | | | | | —NH2 | 940.91 | 940.57 | 627.38 |
| SP-168 | A | L | | | | | | | | | | | | —NH2 | 983.94 | 983.61 | 656.08 |
| SP-169 | A | L | | | | | | | | | | | | —NH2 | 962.93 | 962.59 | 642.06 |
| SP-170 | A | L | | | | | | | | | | | | —NH2 | 955.9 | 955.58 | 637.39 |
| SP-171 | A | L | | | | | | | | | | | | —NH2 | 962.93 | 962.59 | 642.06 |
| SP-172 | A | L | | | | | | | | | | | | —NH2 | 955.99 | 955.58 | 637.39 |
| SP-173 | A | L | | | | | | | | | | | | —NH2 | 984.66 | 984.6 | 656.73 |
| SP-174 | A | L | D | R | I | K | E | | | | | | | —NH2 | 1293.63 | 1292.71 | 862.14 |
| SP-175 | A | L | D | R | I | | | | | | | | | —NH2 | 1164.07 | 1164.14 | 776.43 |
| SP-176 | A | L | D | | | | | | | | | | | —NH2 | 1030.27 | 1029.55 | 686.7 |
| SP-177 | A | L | | | | | | | | | | | | —NH2 | 972.17 | 972.04 | 648.36 |
| SP-178 | A | A | | | | | | | | | | | | —NH2 | 951.28 | 951.01 | 634.34 |
| SP-179 | A | A | A | | | | | | | | | | | —NH2 | 987.07 | 986.53 | 658.02 |
| SP-180 | A | | | | | | | | | | | | | —NH2 | 814.46 | 813.96 | 542.98 |
| SP-181 | A | | | | | | | | | | | | | —NH2 | 784.49 | 783.96 | 522.98 |
| SP-182 | A | | | | | | | | | | | | | —NH2 | 793.55 | 792.98 | 528.99 |
| SP-183 | G | L | D | R | I | K | E | L | P | E | L | W | L | —NH2 | 1088.14 | 1631.41 | 1087.94 |
| SP-184 | G | | | | | | | | | | | | | —NH2 | 879.31 | 878.48 | 585.99 |
| SP-185 | G | | | | | | | | | | | | | —NH2 | 900.4 | 899.51 | 600.01 |
| SP-186 | G | | | | | | | | | | | | | —NH2 | 900.49 | 899.51 | 600.01 |
| SP-187 | G | L | | | | | | | | | | | | —NH2 | 965.34 | 965.03 | 643.69 |
| SP-188 | G | L | D | | | | | | | | | | | —NH2 | 1023.06 | 1022.54 | 682.03 |

TABLE 1c-continued

| ID | | | | | | | | | | | | | | | | |
|---|---|---|---|---|---|---|---|---|---|---|---|---|---|---|---|---|
| SP-189 | G | L | D | R | | | | | | | | | —NH2 | 1101.04 | 1100.59 | 734.06 |
| SP-190 | A | L | D | R | I | | | | | | | | —NH2 | 1146.31 | 1146.19 | 764.46 |
| SP-191 | A | L | D | A | I | | | | | | | | —NH2 | 1074.55 | 1074.65 | 716.77 |
| SP-192 | A | L | D | A | I | | | | | | | | —NH2 | 1081.48 | 1081.66 | 721.44 |
| SP-193 | A | L | D | A | I | | | | | | | | —NH2 | 1052.54 | 1052.66 | 702.11 |
| SP-194 | A | L | A | A | I | | | | | | | | —NH2 | 1030.8 | 1030.66 | 687.44 |
| SP-195 | A | L | | | | | | | | | | | —NH2 | 954.04 | 954.08 | 636.39 |
| SP-196 | A | L | | | | | | | | | | | —NH2 | 925.01 | 925.08 | 617.05 |
| SP-197 | A | L | | | | | | | | | | | —NH2 | 932.31 | 932.08 | 621.72 |
| SP-198 | A | L | | | | | | | | | | | —NH2 | 903.27 | 903.08 | 602.39 |
| SP-199 | A | L | | | | | | | | | | | —NH2 | 960.98 | 961.09 | 641.06 |
| SP-200 | A | L | D | R | I | | | | | | | | —NH2 | 1152.97 | 1153.19 | 769.13 |
| SP-201 | G | L | D | R | I | K | E | L | P | E | L | W | L —NH2 | 1115.75 | 1671.46 | 1114.64 |
| SP-202 | A | L | | | | | | | | | | | —NH2 | 964.03 | 964.12 | 643.08 |
| SP-203 | A | | | | | | | | | | | | —NH2 | 926.02 | 925.53 | 617.36 |
| SP-204 | A | L | | | | | | | | | | | —NH2 | 964.12 | 964.12 | 643.08 |
| SP-205 | A | L | | | | | | | | | | | —NH2 | 971.99 | 972.1 | 648.4 |
| SP-206 | A | L | | | | | | | | | | | —NH2 | 992.42 | 992.63 | 662.09 |
| SP-207 | A | L | | | | | | | | | | | —NH2 | 965.23 | 965.11 | 643.74 |
| SP-208 | A | L | | | | | | | | | | | —NH2 | 971.52 | 971.61 | 648.07 |
| SP-209 | A | L | | | | | | | | | | | —NH2 | 985.49 | 985.63 | 657.42 |
| SP-210 | A | L | | | | | | | | | | | —NH2 | 964.59 | 964.6 | 643.4 |
| SP-211 | A | L | | | | | | | | | | | —NH2 | 943.32 | 943.09 | 629.06 |
| SP-212 | A | L | | | | | | | | | | | —NH2 | 971.43 | 971.61 | 648.07 |
| SP-213 | A | L | | | | | | | | | | | —NH2 | 985.49 | 985.63 | 657.42 |
| SP-214 | A | L | | | | | | | | | | | —NH2 | 923.9 | 923.08 | 615.72 |
| SP-215 | A | L | | | | | | | | | | | —NH2 | 1005.58 | 1005.12 | 670.41 |
| SP-216 | A | | | | | | | | | | | | —NH2 | 886.89 | 885.5 | 590.67 |
| SP-217 | A | L | | | | | | | | | | | —NH2 | 925.93 | 926.02 | 617.68 |
| SP-218 | A | L | | | | | | | | | | | —NH2 | 935.2 | 935.04 | 623.69 |
| SP-219 | A | L | | | | | | | | | | | —NH2 | 963.29 | 963.07 | 642.38 |
| SP-220 | A | F | | | | | | | | | | | —NH2 | 963.01 | 963.07 | 642.38 |
| SP-221 | A | L | D | A | I | | | | | | | | —NH2 | 1073.99 | 1073.66 | 716.11 |
| SP-222 | A | L | D | A | I | | | | | | | | —NH2 | 1044.95 | 1044.66 | 696.77 |
| SP-223 | A | L | A | A | I | | | | | | | | —NH2 | 1022.57 | 1022.66 | 682.11 |
| SP-224 | A | L | | | | | | | | | | | —NH2 | 954.97 | 955.06 | 637.04 |
| SP-225 | A | L | | | | | | | | | | | —NH2 | 955.34 | 955.06 | 637.04 |
| SP-226 | A | F | | | | | | | | | | | —NH2 | 980.86 | 981.03 | 654.36 |
| SP-227 | A | Nle | | | | | | | | | | | —NH2 | 964.22 | 964.04 | 643.03 |
| SP-228 | A | F | | | | | | | | | | | —NH2 | 1012.21 | 1012.04 | 675.03 |
| SP-229 | A | L | L | | | | | | | | | | —NH2 | 1020.44 | 1020.58 | 680.72 |
| SP-230 | A | L | | | | | | | | | | | —NH2 | 949.98 | 950.04 | 633.7 |
| SP-231 | A | L | | | | | | | | | | | —NH2 | 956.91 | 957.05 | 638.37 |
| SP-232 | A | L | | | | | | | | | | | —NH2 | 963.38 | 963.55 | 642.7 |
| SP-233 | A | L | | | | | | | | | | | —NH2 | 963.48 | 963.55 | 642.7 |
| SP-234 | A | L | | | | | | | | | | | —NH2 | 963.48 | 963.55 | 642.7 |
| SP-235 | A | L | | | | | | | | | | | —NH2 | 956.73 | 956.54 | 638.03 |
| SP-236 | A | L | | | | | | | | | | | —NH2 | 981.14 | 981.03 | 654.36 |
| SP-237 | A | Cba | | | | | | | | | | | —NH2 | 970.41 | 970.04 | 647.03 |
| SP-238 | A | L | | | | | | | | | | | —NH2 | 942.95 | 943.03 | 629.02 |
| SP-239 | A | L | | | | | | | | | | | —NH2 | 949.98 | 950.04 | 633.7 |
| SP-240 | A | L | | | | | | | | | | | —NH2 | 1139.84 | 1139.62 | 760.08 |
| SP-241 | A | L | | | | | | | | | | | —NH2 | 946.28 | 946.08 | 631.06 |
| SP-242 | A | L | L | | | | | | | | | | —NH2 | 1020.19 | 1019.62 | 680.08 |
| SP-243 | A | L | L | | | | | | | | | | —NH2 | 946.37 | 946.08 | 631.06 |
| SP-244 | A | L | L | | | | | | | | | | —NH2 | 889.85 | 889.54 | 593.36 |
| SP-245 | A | L | L | | | | | | | | | | —NH2 | 998.91 | 998.61 | 666.08 |
| SP-246 | A | L | L | | | | | | | | | | —NH2 | 998.91 | 998.59 | 666.06 |
| SP-247 | A | L | L | | | | | | | | | | —NH2 | 998.91 | 998.59 | 666.06 |
| SP-248 | A | L | L | | | | | | | | | | —NH2 | 1018.43 | 1018.14 | 679.1 |
| SP-249 | A | L | L | | | | | | | | | | —NH2 | 990.96 | 990.61 | 660.74 |
| SP-250 | A | L | L | | | | | | | | | | —NH2 | 990.4 | 990.12 | 660.42 |
| SP-251 | A | L | L | | | | | | | | | | —NH2 | 990.96 | 990.6 | 660.74 |
| SP-252 | A | L | L | | | | | | | | | | —NH2 | 977.36 | 977.1 | 651.73 |
| SP-253 | A | L | L | | | | | | | | | | —NH2 | 1011.96 | 1011.63 | 674.75 |
| SP-254 | A | L | L | | | | | | | | | | —NH2 | 1002.43 | 1002.11 | 668.41 |
| SP-255 | A | L | L | | | | | | | | | | —NH2 | 997.9 | 997.61 | 665.41 |
| SP-256 | A | L | L | | | | | | | | | | —NH2 | 1011.96 | 1011.63 | 674.75 |
| SP-257 | A | L | L | | | | | | | | | | —NH2 | 977.45 | 977.1 | 651.73 |
| SP-258 | A | L | L | | | | | | | | | | —NH2 | 1002.43 | 1002.11 | 668.41 |
| SP-259 | A | L | L | | | | | | | | | | —NH2 | 1002.89 | 1002.59 | 668.73 |
| SP-260 | A | L | L | | | | | | | | | | —NH2 | 1009.92 | 1009.6 | 673.4 |
| SP-261 | A | L | L | | | | | | | | | | —NH2 | 998.91 | 998.6 | 666.07 |
| SP-262 | A | L | L | | | | | | | | | | —NH2 | 998.91 | 998.6 | 666.07 |
| SP-263 | A | L | D | R | I | | | | | | | | —NH2 | 888.56 | 1331.73 | 888.15 |
| SP-264 | A | L | D | R | I | | | | | | | | —NH2 | 1173.66 | 1173.14 | 782.43 |
| SP-265 | A | L | D | R | I | | | | | | | | —NH2 | 1155.53 | 1155.18 | 770.46 |
| SP-266 | A | L | D | R | I | | | | | | | | —NH2 | 1127.87 | 1127.14 | 751.76 |
| SP-267 | A | L | D | R | I | | | | | | | | —NH2 | 1173.1 | 1172.64 | 782.1 |
| SP-268 | A | L | D | R | I | | | | | | | | —NH2 | 1144.24 | 1143.64 | 762.76 |

TABLE 1c-continued

| | | | | | | | | | | |
|---|---|---|---|---|---|---|---|---|---|---|
| SP-269 | A | L | D | R | I | | —NH2 | 1155.06 | 1154.69 | 770.13 |
| SP-270 | A | L | N | R | I | | —NH2 | 1126.48 | 1126.16 | 751.11 |
| SP-271 | A | L | D | R | I | | —NH2 | 1126.39 | 1126.16 | 751.11 |
| SP-272 | A | L | N | R | I | | —NH2 | 1126.2 | 1125.67 | 750.78 |
| SP-273 | A | L | N | R | I | | —NH2 | 1108.53 | 1108.2 | 739.14 |
| SP-274 | A | L | D | R | I | | —NH2 | 1180.69 | 1180.14 | 787.1 |
| SP-275 | A | L | D | R | I | | —NH2 | 1197.34 | 1197.14 | 798.43 |
| SP-276 | A | L | D | R | I | | —NH2 | 1192.8 | 1192.13 | 795.09 |
| SP-277 | A | L | D | R | I | | —NH2 | 1198.35 | 1198.13 | 799.09 |
| SP-278 | A | L | D | R | I | | —NH2 | 1175.6 | 1175.14 | 783.76 |
| SP-279 | A | L | D | R | I | | —NH2 | 1181.8 | 1181.13 | 787.76 |
| SP-280 | A | V | D | R | I | | —NH2 | 1149.33 | 1149.14 | 766.43 |
| SP-281 | A | L | D | R | | | —NH2 | 1099.84 | 1099.6 | 733.4 |
| SP-282 | A | L | D | R | I | | —NH2 | 1155.94 | 1155.65 | 770.77 |
| SP-283 | A | L | D | R | I | | —NH2 | 1156.12 | 1155.67 | 770.78 |
| SP-284 | A | L | D | R | I | | —NH2 | 1160.8 | 1160.15 | 773.77 |
| SP-285 | A | L | D | R | I | | —NH2 | 1155.85 | 1155.18 | 770.45 |
| SP-286 | A | L | D | R | I | | —NH2 | 1159.9 | 1159.66 | 773.44 |
| SP-287 | A | L | S | R | | | —NH2 | 1086.09 | 1085.6 | 724.07 |
| SP-288 | A | L | S | R | | | —NH2 | 1085.01 | 1084.64 | 723.43 |
| SP-289 | A | L | D | R | I | | —NH2 | 1108.44 | 1108.2 | 739.14 |
| SP-290 | A | L | D | R | I | | —NH2 | 1368.56 | 1367.77 | 912.18 |
| SP-291 | A | L | D | R | I | | —NH2 | 1385.12 | 1384.27 | 923.18 |
| SP-292 | A | L | D | A | | | —NH2 | 1269.12 | 1268.2 | 845.8 |
| SP-293 | A | L | D | A | | | —NH2 | 1314.63 | 1313.73 | 876.15 |
| SP-294 | A | L | D | R | I | | —NH2 | 1152.75 | 1152.2 | 768.47 |
| SP-295 | A | L | D | R | I | | —NH2 | 1121.48 | 1121.14 | 747.76 |
| SP-296 | A | L | D | R | I | | —NH2 | 1138.5 | 1138.19 | 759.13 |
| SP-297 | A | L | D | R | I | | —NH2 | 1358.94 | 1359.28 | 906.52 |
| SP-298 | A | L | D | R | I | | —NH2 | 1155.62 | 1155.16 | 770.45 |
| SP-299 | A | L | D | R | I | | —NH2 | 1155.62 | 1155.16 | 770.45 |
| SP-300 | A | L | D | R | I | | —NH2 | 1163.3 | 1163.16 | 775.78 |
| SP-301 | A | L | D | R | I | | —NH2 | 1164.04 | 1163.16 | 775.78 |

(SEQ ID NOS 128-165, respectively, in order of appearance)

TABLE 2

| SP # | | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|---|
| SP-302 | Ac- | L | L | Q | $ | E | E | L | $ | R | A | L | D | Q | V | N | I | D | E | E |
| SP-303 | Ac- | L | L | Q | G | E | $ | L | L | R | $ | L | D | Q | V | N | I | D | E | E |
| SP-304 | Ac- | L | L | Q | G | E | E | L | $ | R | A | L | $ | Q | V | N | I | D | E | E |
| SP-305 | Ac- | L | L | Q | G | E | $r8 | L | L | R | A | L | D | $ | V | N | I | D | E | E |
| SP-306 | Ac- | L | L | Q | $ | E | E | L | $ | R | A | L | D | Q | V | N | I | D | E | E |
| SP-307 | Ac- | L | L | Q | G | E | $ | L | L | R | $ | L | D | Q | V | N | I | D | E | E |
| SP-308 | Ac- | L | L | Q | G | E | E | L | $ | R | A | L | $ | Q | V | N | I | D | E | E |
| SP-309 | Ac- | L | L | Q | G | E | $r8 | L | L | R | A | L | D | $ | V | N | I | D | E | E |
| SP-310 | Ac- | L | L | Q | $ | E | E | L | $ | R | A | L | D | Q | V | N | I | D | E | $r8 |
| SP-311 | Ac- | L | L | Q | G | E | $ | L | L | R | $ | L | D | Q | V | N | I | D | E | $r8 |
| SP-312 | Ac- | L | L | Q | G | E | E | L | $ | R | A | L | $ | Q | V | N | I | D | E | $r8 |
| SP-313 | Ac- | L | L | Q | G | E | $r8 | L | L | R | A | L | D | $ | V | N | I | D | E | $r8 |
| SP-314 | Ac- | L | L | Q | G | E | E | L | $ | R | A | L | D | Q | V | N | I | D | E | E |
| SP-315 | Ac- | L | L | Q | G | E | $ | L | L | R | $ | L | D | Q | V | N | I | D | E | E |
| SP-316 | Ac- | L | L | Q | G | E | E | L | $ | R | A | L | $ | Q | V | N | I | D | E | E |
| SP-317 | Ac- | L | L | Q | G | E | $r8 | L | L | R | A | L | D | $ | V | N | I | D | E | E |
| SP-318 | Ac- | L | L | Q | G | E | E | L | L | R | A | L | D | Q | V | N | I | D | E | $ |
| SP-319 | Ac- | L | L | Q | G | E | E | L | L | R | A | L | D | Q | V | N | I | D | E | E |
| SP-320 | Ac- | L | L | Q | G | E | E | L | L | R | A | L | D | Q | V | N | I | D | E | $r8 |
| SP-321 | Ac- | | | | | | | | | | | | | | | F | I | D | E | E |
| SP-322 | Ac- | | | | | | | | | | | | | | | F | I | D | E | $ |
| SP-323 | Ac- | | | | | | | | | | | | | | | F | I | D | E | $r8 |
| SP-324 | Ac- | | | | | | | | | | | | | | | F | I | D | E | E |
| SP-325 | Ac- | L | L | Q | $ | E | E | L | $ | R | A | L | D | Q | V | N | I | D | E | $ |
| SP-326 | Ac- | L | L | Q | G | E | $ | L | L | R | $ | L | D | Q | V | N | I | D | E | $ |
| SP-327 | Ac- | L | L | Q | G | E | E | L | $ | R | A | L | $ | Q | V | N | I | D | E | $ |
| SP-328 | Ac- | L | L | Q | G | E | $r8 | L | L | R | A | L | D | $ | V | N | I | D | E | $ |
| SP-329 | Ac- | L | L | Q | $ | E | E | L | $ | R | A | L | D | Q | V | N | I | D | E | E |
| SP-330 | Ac- | L | L | Q | G | E | $ | L | L | R | $ | L | D | Q | V | N | I | D | E | E |
| SP-331 | Ac- | L | L | Q | G | E | E | L | $ | R | A | L | $ | Q | V | N | I | D | E | E |
| SP-332 | Ac- | L | L | Q | G | E | $r8 | L | L | R | A | L | D | $ | V | N | I | D | E | E |
| SP-333 | Ac- | L | L | Q | G | E | E | L | L | R | A | L | D | Q | V | N | I | D | E | E |
| SP-334 | Ac- | L | L | Q | G | E | E | L | L | R | A | L | D | Q | V | N | I | D | E | $ |
| SP-335 | Ac- | L | L | Q | G | E | E | L | L | R | A | L | D | Q | V | N | I | D | E | E |
| SP-336 | Ac- | L | L | Q | G | E | E | L | L | R | A | L | D | Q | V | N | I | D | E | $r8 |
| SP-337 | Ac- | L | L | Q | G | E | E | L | L | R | A | L | D | Q | V | N | I | D | E | E |
| SP-338 | Ac- | L | L | Q | G | $ | E | L | L | $ | A | L | D | Q | V | N | I | D | E | E |
| SP-339 | Ac- | L | L | Q | G | E | E | $ | L | R | A | $ | D | Q | V | N | I | D | E | E |

TABLE 2-continued

| SP # | | | | | | | | | | | | | | | | | | | |
|---|---|---|---|---|---|---|---|---|---|---|---|---|---|---|---|---|---|---|---|
| SP-340 | Ac- | | L | L | Q | G | E | E | L | L | $ | A | L | D | $ | V | N | I | D | E | E |
| SP-341 | Ac- | | L | L | Q | $r8 | E | E | L | L | R | A | $ | D | Q | V | N | I | D | E | E |
| SP-342 | Ac- | | L | L | Q | G | $r8 | E | L | L | R | A | L | $ | Q | V | N | I | D | E | E |
| SP-343 | Ac- | | L | L | Q | G | $ | E | L | L | R | A | $ | D | Q | V | N | I | D | E | $r8 |
| SP-344 | Ac- | | L | L | Q | G | E | E | $ | L | R | A | $ | D | Q | V | N | I | D | E | $r8 |
| SP-345 | Ac- | | L | L | Q | $r8 | E | E | L | L | R | A | $ | D | Q | V | N | I | D | E | $r8 |
| SP-346 | Ac- | | L | L | Q | G | E | $r8 | L | L | R | A | L | D | $ | V | N | I | D | A | E |
| SP-347 | Ac- | | L | L | Q | G | E | $r8 | L | L | R | A | L | D | $ | V | N | I | D | E | A |
| SP-348 | Ac- | | L | L | Q | G | A | $r8 | L | L | R | A | L | A | $ | V | N | I | A | A | A |
| SP-349 | Ac- | | L | L | Q | G | E | $r8 | L | L | R | A | L | D | $ | V | N | I | A | E | E |
| SP-350 | Ac- | | L | L | Q | A | E | $r8 | L | L | R | A | L | D | $ | V | N | I | D | E | E |
| SP-351 | Ac- | | | | | | E | $r8 | L | L | R | A | L | D | $ | V | N | I | D | E | E |
| SP-352 | Ac- | | L | L | Q | G | E | $r8 | L | L | R | A | L | D | $ | A | A | A | A | E | $r8 |
| SP-353 | Ac- | | L | L | Q | G | A | $r8 | L | L | R | A | L | D | $ | V | N | I | D | E | $r8 |
| SP-354 | Ac- | | L | L | Q | G | E | $r8 | L | L | R | A | L | A | $ | V | N | I | D | E | $r8 |
| SP-355 | Ac- | | L | L | Q | G | E | $r8 | L | L | R | A | L | D | $ | V | N | I | A | E | $r8 |
| SP-356 | Ac- | | L | L | Q | G | A | $r8 | L | L | R | A | L | A | $ | V | N | I | A | A | $r8 |
| SP-357 | Ac- | | L | L | Q | A | E | $r8 | L | L | R | A | L | D | $ | V | N | I | D | E | $r8 |
| SP-358 | Ac- | | | | | | E | $r8 | L | L | R | A | L | D | $ | V | N | I | D | E | $r8 |
| SP-359 | Ac- | | L | L | Q | G | E | E | L | $ | R | A | L | $ | Q | A | A | A | A | E | $r8 |
| SP-360 | Ac- | | L | L | Q | G | A | E | L | $ | R | A | L | $ | Q | V | N | I | D | E | $r8 |
| SP-361 | Ac- | | L | L | Q | G | E | A | L | $ | R | A | L | $ | Q | V | N | I | D | E | $r8 |
| SP-362 | Ac- | | L | L | Q | G | E | E | L | $ | R | A | L | $ | Q | V | N | I | D | A | $r8 |
| SP-363 | Ac- | | L | L | Q | G | E | E | L | $ | R | A | L | $ | Q | V | N | I | D | E | $r8 |
| SP-364 | Ac- | | L | L | Q | G | A | A | L | $ | R | A | L | $ | Q | V | N | I | A | A | $r8 |
| SP-365 | Ac- | | L | L | Q | G | E | E | L | $ | R | A | L | $ | Q | V | N | I | A | E | $r8 |
| SP-366 | Ac- | | | | | | E | E | L | $ | R | A | L | $ | Q | V | N | I | D | E | $r8 |
| SP-367 | Ac- | | L | L | Q | A | E | E | L | $ | R | A | L | $ | Q | V | N | I | D | E | $r8 |
| SP-368 | 5-FAM- | Ba | L | L | Q | G | E | $r8 | L | L | R | A | L | D | $ | V | N | I | D | E | E |
| SP-369 | Ac- | | L | L | Q | G | E | $r8 | L | L | R | A | L | D | $ | V | N | I | D | E | E |
| SP-370 | Ac- | | L | L | Q | $ | E | E | L | $ | R | A | L | D | Q | V | N | I | D | E | E |
| SP-371 | Ac- | | L | L | Q | G | E | E | L | $ | R | A | L | $ | Q | V | N | I | D | E | E |
| SP-372 | Ac- | | L | L | Q | G | E | $r8 | L | L | R | A | L | D | $ | V | N | I | D | E | E |
| SP-373 | Ac- | | L | L | Q | G | E | $r8 | L | L | R | A | L | D | $ | V | N | I | D | E | $r8 |

| SP # | 20 | 21 | 22 | 23 | 24 | 25 | 26 | 27 | 28 | 29 | 30 | 31 | 32 | 33 | 34 | 35 | 36 |
|---|---|---|---|---|---|---|---|---|---|---|---|---|---|---|---|---|---|
| SP-302 | V | $ | Nle | S | L | $ | I | E | Nle | G | | | | | | | |
| SP-303 | V | $ | Nle | S | L | $ | I | E | Nle | G | | | | | | | |
| SP-304 | V | $ | Nle | S | L | $ | I | E | Nle | G | | | | | | | |
| SP-305 | V | $ | Nle | S | L | $ | I | E | Nle | G | | | | | | | |
| SP-306 | V | L | Nle | $ | L | V | I | $ | Nle | G | | | | | | | |
| SP-307 | V | L | Nle | $ | L | V | I | $ | Nle | G | | | | | | | |
| SP-308 | V | L | Nle | $ | L | V | I | $ | Nle | G | | | | | | | |
| SP-309 | V | L | Nle | $ | L | V | I | $ | Nle | G | | | | | | | |
| SP-310 | V | L | Nle | S | L | V | $ | E | Nle | G | | | | | | | |
| SP-311 | V | L | Nle | S | L | V | $ | E | Nle | G | | | | | | | |
| SP-312 | V | L | Nle | S | L | V | $ | E | Nle | G | | | | | | | |
| SP-313 | V | L | Nle | S | L | V | $ | E | Nle | G | | | | | | | |
| SP-314 | V | $r8 | Nle | S | L | V | I | E | $ | G | | | | | | | |
| SP-315 | V | $r8 | Nle | S | L | V | I | E | $ | G | | | | | | | |
| SP-316 | V | $r8 | Nle | S | L | V | I | E | $ | G | | | | | | | |
| SP-317 | V | $r8 | Nle | S | L | V | I | E | $ | G | | | | | | | |
| SP-318 | V | L | M | S | L | V | I | E | M | | | | | | | | |
| SP-319 | V | L | M | S | L | V | I | $ | M | | | | | | | | |
| SP-320 | V | L | M | $ | L | V | $ | E | M | | | | | | | | |
| SP-321 | V | L | M | $ | L | V | I | $ | M | G | L | D | R | I | K | E | L |
| SP-322 | V | L | M | S | L | V | I | $ | M | G | L | D | R | I | K | E | L |
| SP-323 | V | L | M | S | L | V | $ | E | M | G | L | D | R | I | K | E | L |
| SP-324 | $r8 | L | M | $ | L | V | I | $ | M | G | L | D | R | I | K | E | L |
| SP-325 | V | L | Nle | $ | L | V | I | E | Nle | G | | | | | | | |
| SP-326 | V | L | Nle | $ | L | V | I | E | Nle | G | | | | | | | |
| SP-327 | V | L | Nle | $ | L | V | I | E | Nle | G | | | | | | | |
| SP-328 | V | L | Nle | $ | L | V | I | E | Nle | G | | | | | | | |
| SP-329 | $r8 | L | Nle | S | L | V | I | $ | Nle | G | | | | | | | |
| SP-330 | $r8 | L | Nle | S | L | V | I | $ | Nle | G | | | | | | | |
| SP-331 | $r8 | L | Nle | S | L | V | I | $ | Nle | G | | | | | | | |
| SP-332 | $r8 | L | Nle | S | L | V | I | $ | Nle | G | | | | | | | |
| SP-333 | V | L | Nle | $ | L | V | I | E | Nle | | | | | | | | |
| SP-334 | V | L | Nle | $ | L | V | I | E | Nle | | | | | | | | |
| SP-335 | V | L | Nle | S | L | V | I | $ | Nle | | | | | | | | |
| SP-336 | V | L | Nle | S | L | V | $ | E | Nle | | | | | | | | |
| SP-337 | $r8 | L | Nle | S | L | V | I | $ | Nle | | | | | | | | |
| SP-338 | V | L | Nle | $ | L | V | I | $ | Nle | G | | | | | | | |
| SP-339 | V | L | Nle | $ | L | V | I | $ | Nle | G | | | | | | | |
| SP-340 | V | L | Nle | $ | L | V | I | $ | Nle | G | | | | | | | |
| SP-341 | V | L | Nle | $ | L | V | I | $ | Nle | G | | | | | | | |
| SP-342 | V | L | Nle | $ | L | V | I | $ | Nle | G | | | | | | | |
| SP-343 | V | L | Nle | S | L | V | $ | E | Nle | G | | | | | | | |
| SP-344 | V | L | Nle | S | L | V | $ | E | Nle | G | | | | | | | |

TABLE 2-continued

| SP- | | | | | | | | | | | |
|---|---|---|---|---|---|---|---|---|---|---|---|
| SP-345 | V | L | Nle | $ | L | V | $ | E | Nle | G | |
| SP-346 | V | L | Nle | $ | L | V | I | $ | Nle | | |
| SP-347 | V | L | Nle | $ | L | V | I | $ | Nle | | |
| SP-348 | V | L | Nle | $ | L | V | I | $ | Nle | | |
| SP-349 | V | L | Nle | $ | L | V | I | $ | Nle | | |
| SP-350 | V | L | Nle | $ | L | V | I | $ | Nle | | |
| SP-351 | V | L | Nle | S | L | V | I | $ | Nle | | |
| SP-352 | V | L | Nle | S | L | V | $ | E | Nle | | |
| SP-353 | V | L | Nle | S | L | V | $ | E | Nle | | |
| SP-354 | V | L | Nle | S | L | V | $ | E | Nle | | |
| SP-355 | V | L | Nle | S | L | V | $ | E | Nle | | |
| SP-356 | V | L | Nle | S | L | V | $ | E | Nle | | |
| SP-357 | V | L | Nle | S | L | V | $ | E | Nle | | |
| SP-358 | V | L | Nle | S | L | V | $ | E | Nle | | |
| SP-359 | V | L | Nle | S | L | V | $ | E | Nle | | |
| SP-360 | V | L | Nle | S | L | V | $ | E | Nle | | |
| SP-361 | V | L | Nle | S | L | V | $ | E | Nle | | |
| SP-362 | V | L | Nle | S | L | V | $ | E | Nle | | |
| SP-363 | V | L | Nle | S | L | V | $ | A | Nle | | |
| SP-364 | V | L | Nle | S | L | V | $ | A | Nle | | |
| SP-365 | V | L | Nle | S | L | V | $ | E | Nle | | |
| SP-366 | V | L | Nle | S | L | V | $ | E | Nle | | |
| SP-367 | V | L | Nle | S | L | V | $ | E | Nle | | |
| SP-368 | V | L | Nle | $ | L | V | I | $ | Nle | A | L |
| SP-369 | V | $ | Nle | S | L | $ | I | E | Nle | A | L |
| SP-370 | V | L | Nle | $ | L | V | I | $ | Nle | A | L |
| SP-371 | V | L | Nle | $ | L | V | I | $ | Nle | A | L |
| SP-372 | V | L | Nle | $ | L | V | I | $ | Nle | A | L |
| SP-373 | V | L | Nle | S | L | V | $ | E | Nle | A | L |

| SP # | 37 | 38 | 39 | 40 | 41 | 42 | 43 | 44 | 45 | 46 | 47 | 48 | | observed masses | calculated mass (M + 2) | calculated mass |
|---|---|---|---|---|---|---|---|---|---|---|---|---|---|---|---|---|
| SP-302 | | | | | | | | | | | | | —NH2 | 1132.35 | 1697 | 1131.6 |
| SP-303 | | | | | | | | | | | | | —NH2 | 1122.36 | 1682 | 1121.6 |
| SP-304 | | | | | | | | | | | | | —NH2 | 1112.93 | 1668 | 1112.3 |
| SP-305 | | | | | | | | | | | | | —NH2 | 1117 | 1674.5 | 1116.7 |
| SP-306 | | | | | | | | | | | | | —NH2 | 1131.05 | 1695 | 1130.3 |
| SP-307 | | | | | | | | | | | | | —NH2 | 1120.84 | 1680 | 1120.3 |
| SP-308 | | | | | | | | | | | | | —NH2 | 1111.63 | 1666 | 1111 |
| SP-309 | | | | | | | | | | | | | —NH2 | 1116.21 | 1672.5 | 1115.4 |
| SP-310 | | | | | | | | | | | | | —NH2 | 1136.05 | 1703 | 1135.7 |
| SP-311 | | | | | | | | | | | | | —NH2 | 1126.43 | 1688 | 1125.7 |
| SP-312 | | | | | | | | | | | | | —NH2 | 1116.26 | 1674 | 1116.3 |
| SP-313 | | | | | | | | | | | | | —NH2 | 1121.34 | 1680.5 | 1120.7 |
| SP-314 | | | | | | | | | | | | | —NH2 | 1141.69 | 1711 | 1141 |
| SP-315 | | | | | | | | | | | | | —NH2 | 1131.33 | 1696 | 1131 |
| SP-316 | | | | | | | | | | | | | —NH2 | 1122.08 | 1682 | 1121.6 |
| SP-317 | | | | | | | | | | | | | —NH2 | 1126.61 | 1688.5 | 1126 |
| SP-318 | | | | | | | | | | | | | —NH2 | 1097.52 | 1644.4 | 1096.6 |
| SP-319 | | | | | | | | | | | | | —NH2 | 1097.8 | 1644.4 | 1096.6 |
| SP-320 | | | | | | | | | | | | | —NH2 | 1103.17 | 1652.4 | 1101.9 |
| SP-321 | P | Q | L | T | $ | Y | D | Abu | $ | V | N | A | —NH2 | 1336.37 | 2002.6 | 1335.4 |
| SP-322 | P | Q | L | T | $ | Y | D | Abu | $ | V | N | A | —NH2 | 1336.83 | 2002.6 | 1335.4 |
| SP-323 | P | Q | L | T | $ | Y | D | Abu | $ | V | N | A | —NH2 | 1341.83 | 2010.6 | 1340.7 |
| SP-324 | P | Q | L | T | $ | Y | D | Abu | $ | V | N | A | —NH2 | 1346.82 | 2017.6 | 1345.4 |
| SP-325 | | | | | | | | | | | | | —NH2 | 1131.38 | 1695 | 1130.3 |
| SP-326 | | | | | | | | | | | | | —NH2 | 1121.11 | 1680 | 1120.3 |
| SP-327 | | | | | | | | | | | | | —NH2 | 1111.77 | 1666 | 1111 |
| SP-328 | | | | | | | | | | | | | —NH2 | 1115.52 | 1672.5 | 1115.4 |
| SP-329 | | | | | | | | | | | | | —NH2 | 1140.58 | 1710 | 1140.3 |
| SP-330 | | | | | | | | | | | | | —NH2 | 1130.87 | 1695 | 1130.3 |
| SP-331 | | | | | | | | | | | | | —NH2 | 1121.53 | 1681 | 1121 |
| SP-332 | | | | | | | | | | | | | —NH2 | 1125.74 | 1687.5 | 1125.4 |
| SP-333 | | | | | | | | | | | | | —NH2 | 1073.44 | 1609.4 | 1073.3 |
| SP-334 | | | | | | | | | | | | | —NH2 | 1084.72 | 1626.5 | 1084.6 |
| SP-335 | | | | | | | | | | | | | —NH2 | 1084.81 | 1626.5 | 1084.6 |
| SP-336 | | | | | | | | | | | | | —NH2 | 1090.08 | 1634.5 | 1090 |
| SP-337 | | | | | | | | | | | | | —NH2 | 1094.71 | 1641.5 | 1094.6 |
| SP-338 | | | | | | | | | | | | | —NH2 | 1092.03 | 1637.5 | 1092 |
| SP-339 | | | | | | | | | | | | | —NH2 | 1111.72 | 1667 | 1111.6 |
| SP-340 | | | | | | | | | | | | | —NH2 | 1092.21 | 1638 | 1092.3 |
| SP-341 | | | | | | | | | | | | | —NH2 | 1144.46 | 1716 | 1144.3 |
| SP-342 | | | | | | | | | | | | | —NH2 | 1119.77 | 1679 | 1119.7 |
| SP-343 | | | | | | | | | | | | | —NH2 | 1097.48 | 1645.5 | 1097.3 |
| SP-344 | | | | | | | | | | | | | —NH2 | 1117.09 | 1675 | 1117 |

TABLE 2-continued

| | | | | |
|---|---|---|---|---|
| SP-345 | | —NH2 | 1149.92 | 1724 | 1149.7 |
| SP-346 | | —NH2 | 1077.73 | 1615 | 1077 |
| SP-347 | | —NH2 | 1077.54 | 1615 | 1077 |
| SP-348 | | —NH2 | 1010.2 | 1513 | 1009 |
| SP-349 | | —NH2 | 1082.17 | 1622 | 1081.7 |
| SP-350 | | —NH2 | 1101.87 | 1651 | 1101 |
| SP-351 | | —NH2 | 960.06 | 1438.4 | 959.26 |
| SP-352 | | —NH2 | 1049.89 | 1573.5 | 1049.3 |
| SP-353 | | —NH2 | 1083.46 | 1623 | 1082.3 |
| SP-354 | | —NH2 | 1087.53 | 1630 | 1087 |
| SP-355 | | —NH2 | 1087.9 | 1630 | 1087 |
| SP-356 | | —NH2 | 1034.81 | 1550 | 1033.7 |
| SP-357 | | —NH2 | 1107.42 | 1659 | 1106.3 |
| SP-358 | | —NH2 | 965.52 | 1446.4 | 964.59 |
| SP-359 | | —NH2 | 1045.81 | 1566.9 | 1045 |
| SP-360 | | —NH2 | 1078.93 | 1616.5 | 1078 |
| SP-361 | | —NH2 | 1078.47 | 1616.5 | 1078 |
| SP-362 | | —NH2 | 1078.84 | 1616.5 | 1078 |
| SP-363 | | —NH2 | 1078.56 | 1616.5 | 1078 |
| SP-364 | | —NH2 | 1005.85 | 1507.5 | 1005.3 |
| SP-365 | | —NH2 | 1083.83 | 1623.5 | 1082.7 |
| SP-366 | | —NH2 | 961.08 | 1439.9 | 960.23 |
| SP-367 | | —NH2 | 1103.17 | 1652.5 | 1102 |
| SP-368 | | —NH2 | 1286.71 | 1929.6 | 1286.7 |
| SP-369 | | —NH2 | 1159.72 | 1738 | 1159 |
| SP-370 | | —NH2 | 1172.86 | 1758.5 | 1172.7 |
| SP-371 | | —NH2 | 1153.44 | 1729.5 | 1153.4 |
| SP-372 | | —NH2 | 1157.88 | 1736.1 | 1157.7 |
| SP-373 | | —NH2 | 1163.05 | 1744.1 | 1163 |

(SEQ ID NOS 318-389, respectively, in order of appearance)

In the sequences shown above and elsewhere, the following abbreviations are used: amino acids represented as "$" are alpha-Me S5-pentenyl-alanine olefin amino acids connected by an all-carbon i to i+4 crosslinker comprising one double bond. Amino acids represented as "$r8" are alpha-Me R8-octenyl-alanine olefin amino acids connected by an all-carbon i to i+7 crosslinker comprising one double bond. "Nle" represents norleucine. "Aib" represents 2-aminoisobutyric acid. "Ac" represents acetyl. Amino acids represented as "Ba" are beta-alanine. Amino acids designated as "Cba" represent cyclobutyl alanine. Amino acids designated as "F4cooh" represent 4-carboxy phenylalanine. Amino acids represented as "$/" are alpha-Me S5-pentenyl-alanine olefin amino acids that are not connected by any crosslinker. "$r5" are alpha-Me R5-pentenyl-alanine olefin amino acids connected by an all-carbon comprising one double bond. Amino acids represented as "$/r5" are alpha-Me R5-pentenyl-alanine olefin amino acids that are not connected by any crosslinker. Amino acids represented as "St" are amino acids comprising two pentenyl-alanine olefin side chains, each of which is crosslinked to another amino acid as indicated. Amino acids represented as "Sta5" are amino acids comprising two R5-pentenyl-alanine olefin side chains, each of which is crosslinked to another amino acid as indicated. Other amino acids are described below.

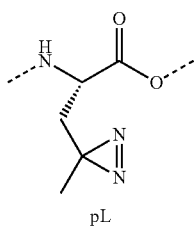

pL

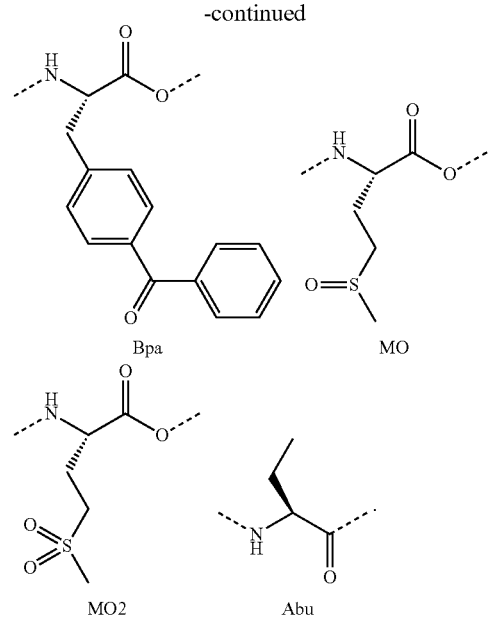

Bpa  MO

MO2  Abu

Additionally, "Bpa" represents 4-benzoyyl-phenylalanine, a photoreactive amino acid analog useful in making photoreactive stapled peptides that covalently capture their physiologic targets, as described for example Braun et al. Chem Biol. 2010 Dec. 22; 17(12):1325-33 and Leshchiner et al. Proc Nat Acad Sci USA. 2013 Feb. 12.

Amino acids which are used in the formation of triazole cross-linkers are represented according to the legend indicated below. Stereochemistry at the alpha position of each amino acid is S unless otherwise indicated. For azide amino acids, the number of carbon atoms indicated refers to the number of methylene units between the alpha carbon and the terminal azide. For alkyne amino acids, the number of carbon atoms indicated is the number of methylene units between the alpha position and the triazole moiety plus the two carbon atoms within the triazole group derived from the alkyne.

$5rn3 Alpha-Me R-azide 1,5 triazole (3 carbon)
$5a5 Alpha-Me alkyne 1,5 triazole (5 carbon)
$5n3 Alpha-Me azide 1,5 triazole (3 carbon)
$4rn6 Alpha-Me R-azide 1,4 triazole (6 carbon)
$4a5 Alpha-Me alkyne 1,4 triazole (5 carbon)

In some embodiments, the present invention provides a peptidomimetic macrocycle comprising an amino acid sequence which is at least about 60% identical to an amino acid sequence selected from the group consisting of the amino acid sequences in Tables 1a, 1b and 1c, further comprising at least one macrocycle-forming linker, wherein the macrocycle-forming linker connects a first amino acid to a second amino acid. In some embodiments, the peptidomimetic macrocycle comprises an amino acid sequence which is at least about 65%, 70%, 75%, 80%, 85%, 90% or 95% an amino acid sequence identical to selected from the group consisting of the amino acid sequences in Tables 1a, 1b and 1c. In some embodiments, the peptidomimetic macrocycle comprises an amino acid sequence selected from the group consisting of the amino acid sequences in Tables 1a, 1b and 1c. In some embodiments, a macrocycle-forming linker of the peptidomimetic macrocycle of the invention connects one of the following pairs of amino acids: 9 and 13, 9 and 16, 10 and 14, 10 and 17, 11 and 15, 11 and 18, 12 and 16, 12 and 19, 13 and 17, 13 and 20, 14 and 18, and 15 and 19. In some embodiments, the macrocycle-forming linker connects amino acids 10 and 14. In some embodiments, the macrocycle-forming linker connects amino acids 14 and 18.

In some embodiments, the present invention provides a peptidomimetic macrocycle comprising an amino acid sequence which is at least about 60% identical to an amino acid sequence selected from the group consisting of the amino acid sequences in Table 2, further comprising at least one macrocycle-forming linker, wherein the macrocycle-forming linker connects a first amino acid to a second amino acid. In some embodiments, the peptidomimetic macrocycle comprises an amino acid sequence which is at least about 65%, 70%, 75%, 80%, 85%, 90% or 95% identical to an amino acid sequence selected from the group consisting of the amino acid sequences in Table 2. In some embodiments, the peptidomimetic macrocycle comprises an amino acid sequence selected from the group consisting of the amino acid sequences in Table 2. In some embodiments, one or more macrocycle-forming linkers of the peptidomimetic macrocycle of the invention connect one or more of the following pairs of amino acids: 4 and 8, 4 and 11, 5 and 9, 5 and 12, 6 and 10, 6 and 13, 7 and 11, 8 and 12, 9 and 13, 19 and 23, 19 and 26, 20 and 27, 21 and 25, 21 and 28, 23 and 27, and 41 and 45. In some embodiments, the peptidomimetic macrocycle comprise two macrocycle-forming linkers. In some embodiments, the macrocycle-forming linkers connect amino acids 6 and 13 and amino acids 23 and 27. In some embodiments, the macrocycle-forming linkers connect amino acids 8 and 12 and amino acids 19 and 26. In some embodiments, the macrocycle-forming linkers connect amino acids 8 and 12 and amino acids 23 and 27. In some embodiments, the macrocycle-forming linkers connect amino acids 23 and 27 and amino acids 41 and 45.

In some embodiments, a peptidomimetic macrocycle of the invention comprises a helix, for example an α-helix. In some embodiments, a peptidomimetic macrocycle of the invention comprises an α,α-disubstituted amino acid. In some embodiments, each amino acid connected by the macrocycle-forming linker is an α,α-di substituted amino acid.

In some embodiments, a peptidomimetic macrocycle of the invention has Formula (I):

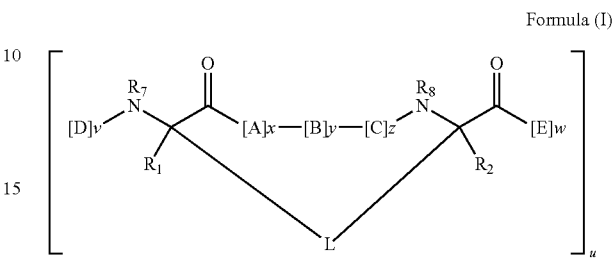

Formula (I)

wherein:

each A, C, D, and E is independently an amino acid (including natural or non-natural amino acids and amino acid analogs) and the terminal D and E independently optionally include a capping group, B is an amino acid (including natural or non-natural amino acids and amino acid analogs),

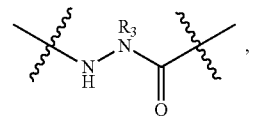

[—NH-$L_3$-CO—], [—NH-$L_3$-$SO_2$—], or [—NH-$L_3$-], wherein A, B C, D, and E, taken together with the cross-linked amino acids connected by the macrocycle-forming linker L, form the amino acid sequence of the peptidomimetic macrocycle;

L is a macrocycle-forming linker of the formula -$L_1$-$L_2$- or the formula

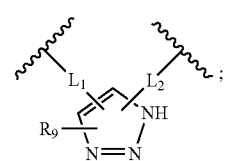

$R_1$ and $R_2$ are independently —H, alkyl, alkenyl, alkynyl, arylalkyl, cycloalkyl, cycloalkylalkyl, heteroalkyl, or heterocycloalkyl, unsubstituted or substituted with halo-;

$R_3$ is hydrogen, alkyl, alkenyl, alkynyl, arylalkyl, heteroalkyl, cycloalkyl, heterocycloalkyl, cycloalkylalkyl, cycloaryl, or heterocycloaryl, optionally substituted with $R_5$;

$L_1$, $L_2$ and $L_3$ are independently alkylene, alkenylene, alkynylene, heteroalkylene, cycloalkylene, heterocycloalkylene, cycloarylene, heterocycloarylene, or [—$R_4$—K—$R_4$—]$_n$, each being optionally substituted with $R_5$;

each is alkylene, alkenylene, alkynylene, heteroalkylene, cycloalkylene, heterocycloalkylene, arylene, or heteroarylene;

each K is O, S, SO, $SO_2$, CO $CO_2$ or $CONR_3$;
each $R_5$ is independently halogen, alkyl, $-OR_6$, $-N(R_6)_2$, $-SR_6$, $-SOR_6$, $-SO_2R_6$, $-CO_2R_6$, a fluorescent moiety, a radioisotope or a therapeutic agent;
each is independently —H, alkyl, alkenyl, alkynyl, arylalkyl, cycloalkylalkyl, heterocycloalkyl, a fluorescent moiety, a radioisotope or a therapeutic agent;
$R_8$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$, or part of a cyclic structure with a D residue;
$R_8$ is —H, alkyl, alkenyl, alkynyl, arylalkyl, cycloalkyl, heteroalkyl, cycloalkylalkyl, heterocycloalkyl, cycloakyl, or heterocycloaryl, optionally substituted with $R_5$, or part of a cyclic structure with an E residue;
$R_9$ is alkyl, alkenyl, alkynyl, aryl, cycloalkyl, cycloalkenyl, heteroaryl, or heterocyclyl group, unsubstituted or optionally substituted with $R_a$ and/or $R_b$;
$R_a$ and $R_b$ are independently alkyl, $OCH_3$, $CF_3$, $NH_2$, $CH_2NH_2$, F, Br, I,

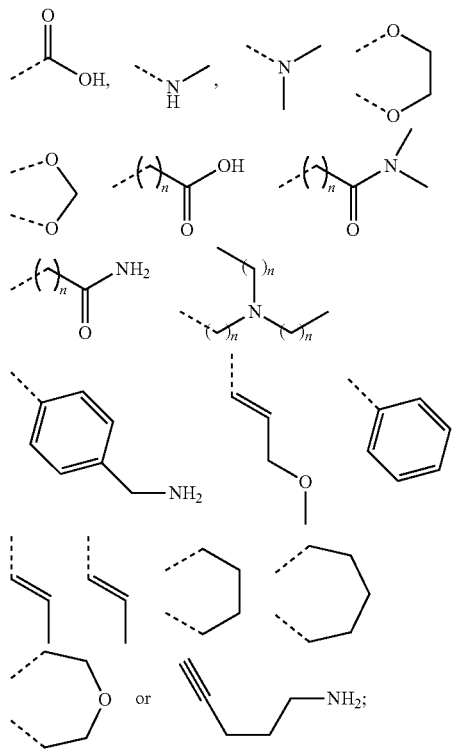

v and w are independently integers from 1-1000, for example 1-500, 1-200, 1-100, 1-50, 1-40, 1-25, 1-20, 1 to 15, or 1 to 10;

u, x, y and z are independently integers from 0-10, for example u is 1, 2, or 3; and is an integer from 1-5, for example 1.

In some embodiments, u is 1.
In some embodiments, the sum of x+y+z is 2, 3 or 6, for example 3 or 6.
In some embodiments, $L_1$ and $L_2$ are independently alkylene, alkenylene or alkynylene. In some embodiments, $L_1$ and $L_2$ are independently $C_3$-$C_{10}$ alkylene or alkenylene, for example $C_3$-$C_6$ alkylene or alkenylene.
In some embodiments, $R_1$ and $R_2$ are H. In some embodiments, $R_1$ and $R_2$ are independently alkyl, for example methyl.
In some embodiments, A, B, C, D, and E, taken together with the crosslinked amino acids connected by the macrocycle-forming linker L, form the amino acid sequence of the peptidomimetic macrocycle which is at least about 60%, 65%, 70%, 75%, 80%, 85%, 90%, 95%, 96%, 97%, 98%, or 99% identical to an amino acid sequence chosen from the group consisting of the amino acid sequences in Tables 1a, 1b, 1c and 2.
In some embodiments, the present invention provides a peptidomimetic macrocycle having the formula

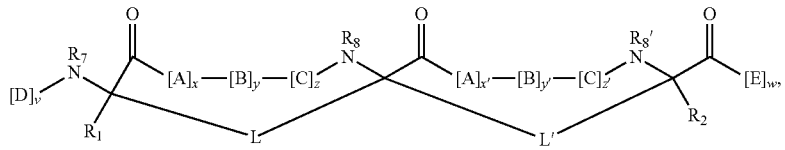

wherein:
L' is a macrocycle-forming linker of the formula -$L_1$'-$L_2$'- or the formula

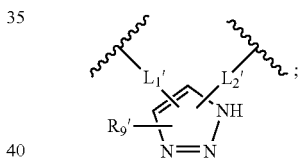

$L_1$' and $L_2$' are independently alkylene, alkenylene, alkynylene, heteroalkylene, cycloalkylene, heterocycloalkylene, cycloarylene, heterocycloarylene, or $[-R_4-K-R_4-]_n$, each being optionally substituted with $R_5$;
$R_8$' is —H, alkyl, alkenyl, alkynyl, arylalkyl, cycloalkyl, heteroalkyl, cycloalkylalkyl, heterocycloalkyl, cycloaryl, or heterocycloaryl, each of which except for —H is optionally substituted with $R_5$, or part of a cyclic structure with an E residue;
$R_9$ is alkyl, alkenyl, alkynyl, aryl, cycloalkyl, cycloalkenyl, heteroaryl, or heterocyclyl group, unsubstituted or optionally substituted with $R_a$' and/or $R_b$';
$R_a$' and $R_b$' are independently alkyl, $OCH_3$, $CF_3$, $NH_2$, $CH_2NH_2$, F, Br, I,

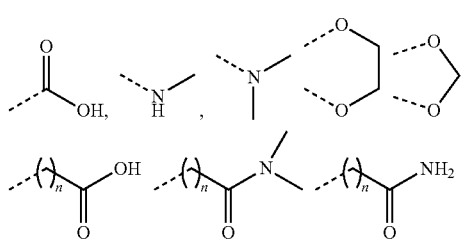

-continued

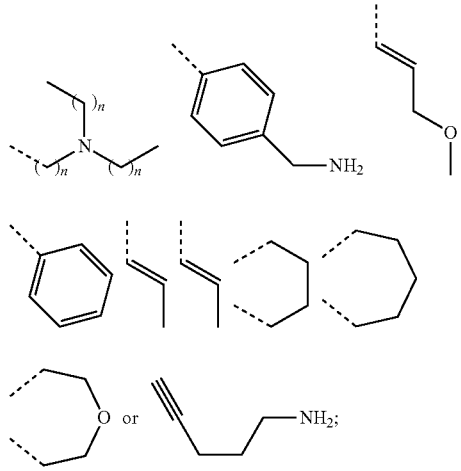

and x', y', and z' are independently integers from 0-10.

In some embodiments, the sum of x+y+z and the sum of x'+y'+z' are independently 2, 3 or 6, for example 3.

In some embodiments, each of v, w, v' and w' is independently an integer from 1 to 10, 1 to 15, 1 to 20, or 1 to 25.

In some embodiments, each of v, w, v' and w' is independently an integer from 1 to 15.

In some embodiments, $L_1$, $L_2$, $L_1'$, and $L_2'$ are independently alkylene, alkenylene or alkynylene. In some embodiments, $L_1$, $L_2$, $L_1'$, and $L_2'$ are independently $C_3$-$C_{10}$ alkylene or alkenylene, for example $C_3$-$C_6$ alkylene or alkenylene. In some embodiments, L and L' are both

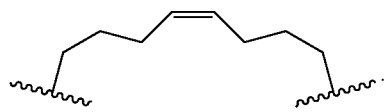 [SMILES: *CCC/C=C\CCC*]

In some embodiments, L is

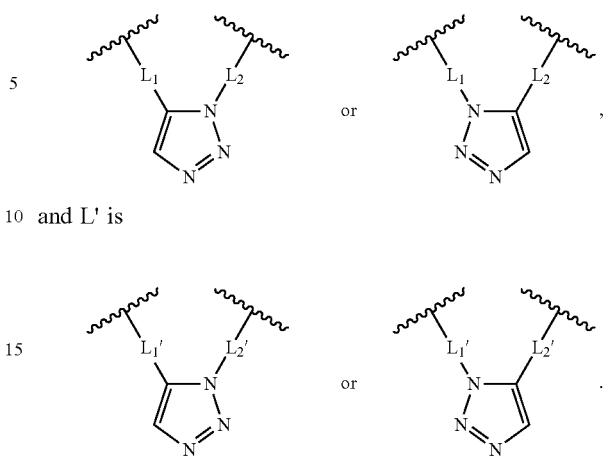

and L' is

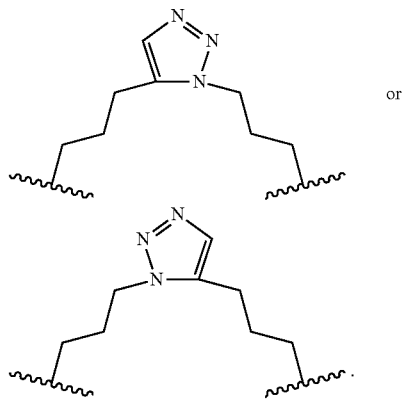

For example, L and L' are independently

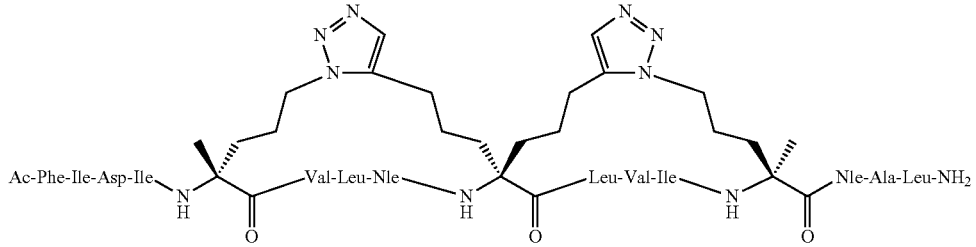

In some embodiments, $R_1$ and $R_2$ are H. In some embodiments, $R_1$ and $R_2$ are independently alkyl for example methyl.

In some embodiments, the peptidomimetic macrocycle is (SEQ ID NO: 1)

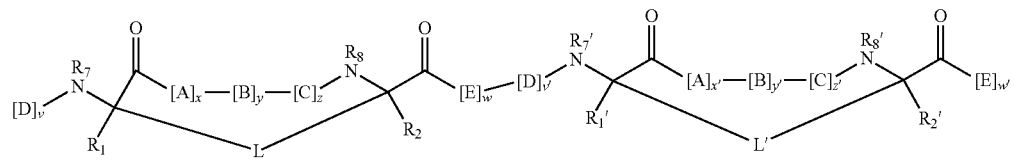

or a pharmaceutically acceptable salt thereof.

In some embodiments, u is 2.

In some embodiments, the peptidomimetic macrocycle of Formula (I) has the Formula:

wherein each A, C, D, and E is independently an amino acid; B is an amino acid,

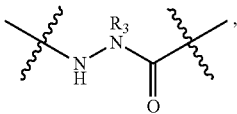

[—NH-L$_3$-CO—], [—NH-L$_3$-SO$_2$—], or [—NH-L$_3$-]; L' is a macrocycle-forming linker of the formula -L$_1$'-L$_2$'- or the formula

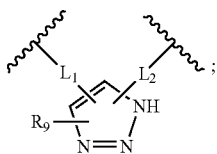

and wherein A, B, C, D, and E, taken together with the crosslinked amino acids connected by the macrocycle-forming linkers L and L', form the amino acid sequence of the peptidomimetic macrocycle;
R$_1$' and R$_2$' are independently —H, alkyl, alkenyl, alkynyl, arylalkyl, cycloalkyl, cycloalkylalkyl, heteroalkyl, or heterocycloalkyl, unsubstituted or substituted with halo-;
L$_1$' and L$_2$' are independently alkylene, alkenylene, alkynylene, heteroalkylene, cycloalkylene, heterocycloalkylene, cycloarylene, heterocycloarylene, or [—R$_4$—K—R$_4$—]$_n$, each being optionally substituted with R$_5$;
each K is independently O, S, SO, SO$_2$, CO, CO$_2$, or CONR$_3$;
R$_7$' is —H, alkyl, alkenyl, alkynyl, arylalkyl, cycloalkyl, heteroalkyl, cycloalkylalkyl, heterocycloalkyl, cycloaryl, or heterocycloaryl, optionally substituted with R$_5$, or part of a cyclic structure with a D residue;
R$_8$' is —H, alkyl, alkenyl, alkynyl, arylalkyl, cycloalkyl, heteroalkyl, cycloalkylalkyl, heterocycloalkyl, cycloaryl, or heterocycloaryl, optionally substituted with R$_5$, or part of a cyclic structure with an E residue;
v' and w' are independently integers from 1-1000, for example 1-500, 1-200, 1-100, 1-50, 1-40, 1-25, 1-20, 1 to 15, or 1 to 10;
x', y' and z' are independently integers from 0-10; and n is an integer from 1-5. In some embodiments, the sum of x'+y'+z' is 2, 3 or 6, for example 3 or 6.

In some embodiments of any of the peptidomimetic macrocycles described herein, each K is O, S, SO, SO$_2$, CO, or CO$_2$.

In one example, at least one of R$_1$ and R$_2$ is alkyl, unsubstituted or substituted with halo-. In another example, both R$_1$ and R$_2$ are independently alkyl, unsubstituted or substituted with halo-. In some embodiments, at least one of R$_1$ and R$_2$ is methyl. In other embodiments, R$_1$ and R$_2$ are methyl.

In some embodiments of the invention, the sum of the sum of x+y+z is at least 3, and/or the sum of x'+y'+z is at least 3. In other embodiments of the invention, the sum of the sum of x+y+z is 1, 2, 3, 4, 5, 6, 7, 8, 9 or 10 (for example 2, 3 or 6) and/or the sum of x'+y'+z' is 1, 2, 3, 4, 5, 6, 7, 8, 9 or 10 (for example 2, 3 or 6).

Each occurrence of A, B, C, D or E in a macrocycle or macrocycle precursor of the invention is independently selected. For example, a sequence represented by the formula [A]$_x$, when x is 3, encompasses embodiments where the amino acids are not identical, e.g. Gln-Asp-Ala as well as embodiments where the amino acids are identical, e.g. Gln-Gln-Gln. This applies for any value of x, y, or z in the indicated ranges. Similarly, when u is greater than 1, each compound of the invention may encompass peptidomimetic macrocycles which are the same or different. For example, a compound of the invention may comprise peptidomimetic macrocycles comprising different linker lengths or chemical compositions.

In some embodiments, the peptidomimetic macrocycle of the invention comprises a secondary structure which is an α-helix and R$_8$ is —H, allowing intrahelical hydrogen bonding. In some embodiments, at least one of A, B, C, D or E is an α,α-disubstituted amino acid. In one example, B is an α,α-disubstituted amino acid. For instance, at least one of A, B, C, D or E is 2-aminoisobutyric acid. In other embodiments, at least one of A, B, C, D or E is

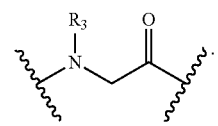

In other embodiments, the length of the macrocycle-forming linker L as measured from a first Cα to a second Cα is selected to stabilize a desired secondary peptide structure, such as an α-helix formed by residues of the peptidomimetic macrocycle including, but not necessarily limited to those between the first Cα to a second Cα.

In one embodiment, the peptidomimetic macrocycle of Formula (I) is:

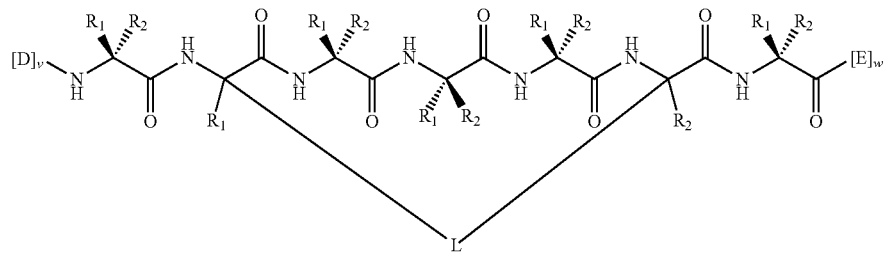

wherein each $R_1$ and $R_2$ is independently —H, alkyl, alkenyl, alkynyl, arylalkyl, cycloalkyl, cycloalkylalkyl, heteroalkyl, or heterocycloalkyl, unsubstituted or substituted with halo-.

In related embodiments, the peptidomimetic macrocycle comprises a structure of Formula (I) which is:

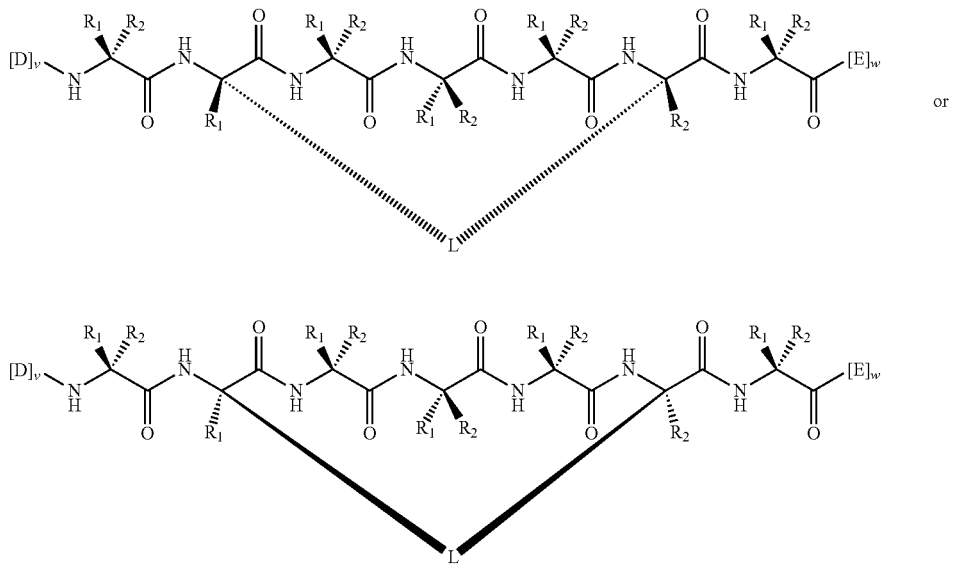

or

In other embodiments, the peptidomimetic macrocycle of Formula (I) is a compound of any of the formulas shown below:

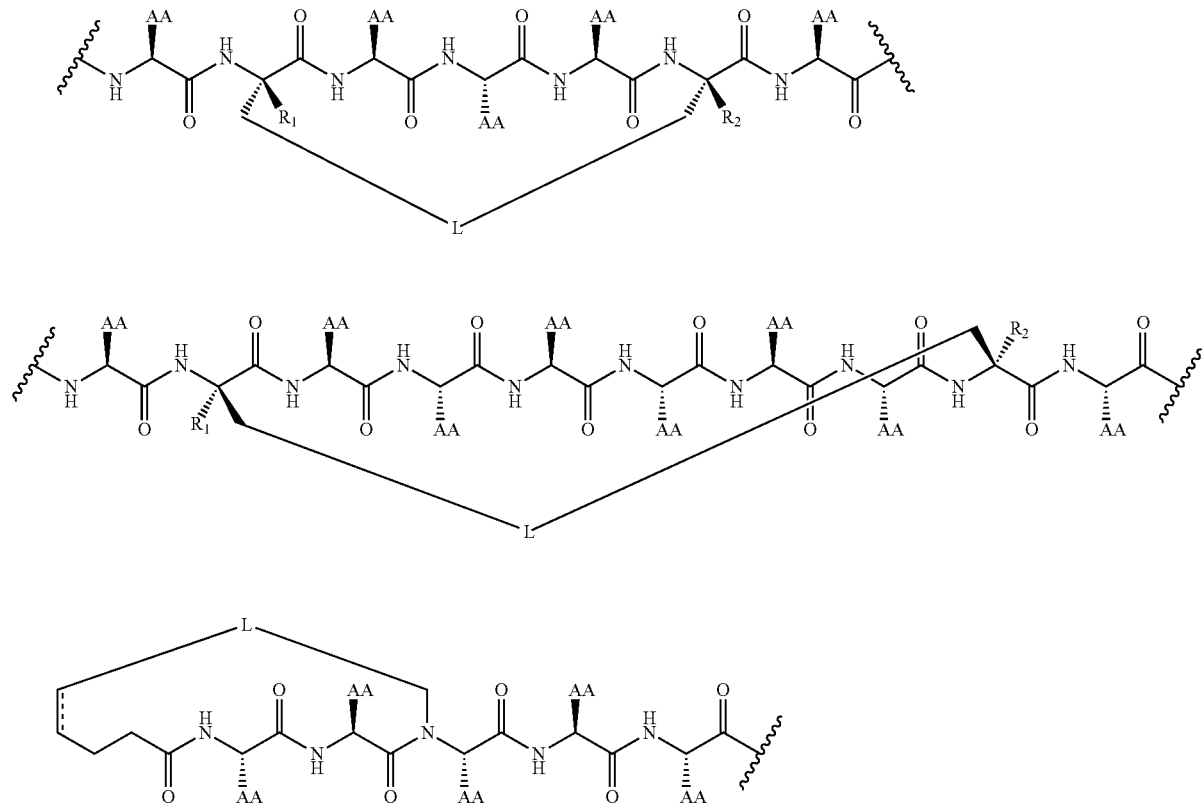

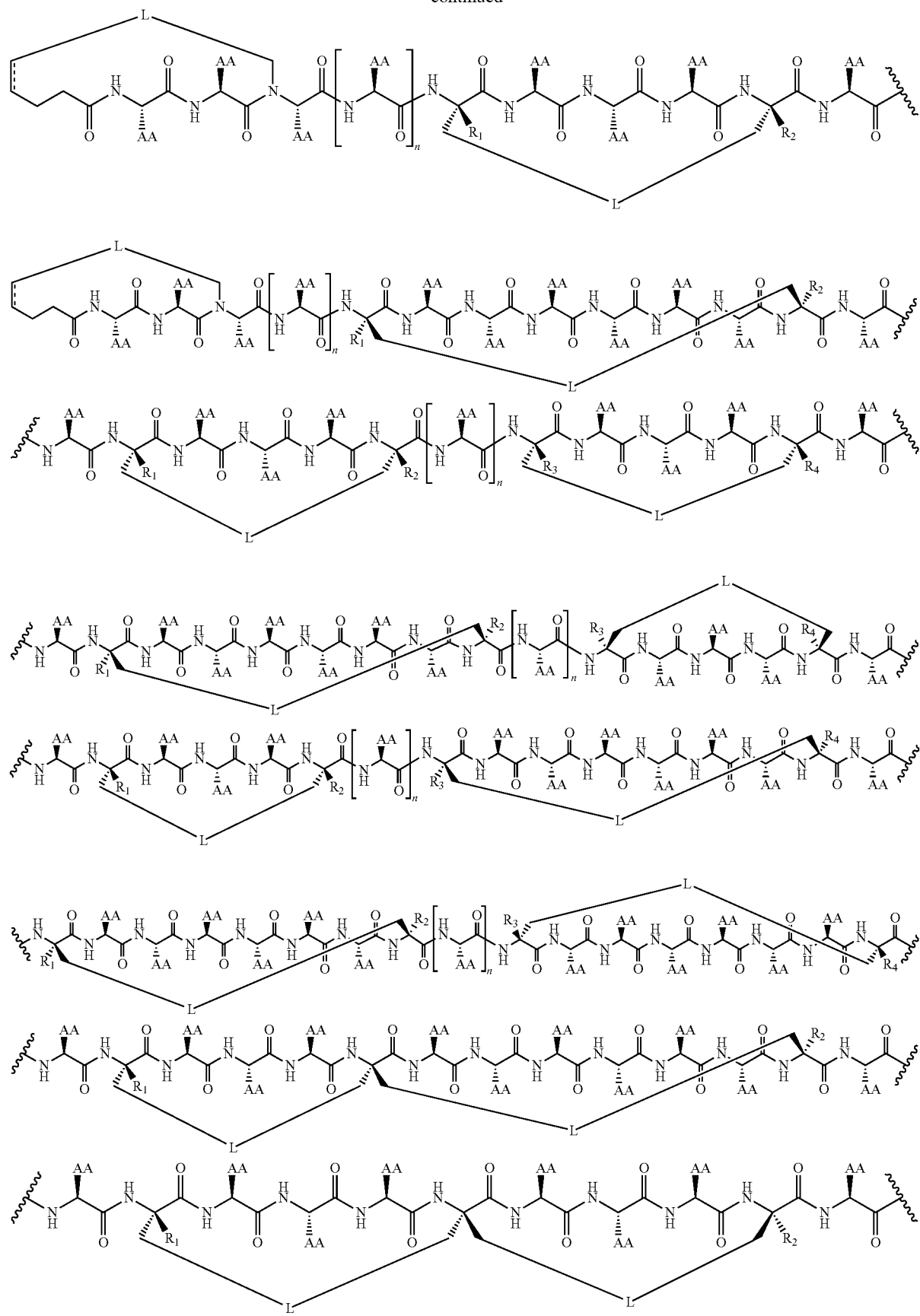

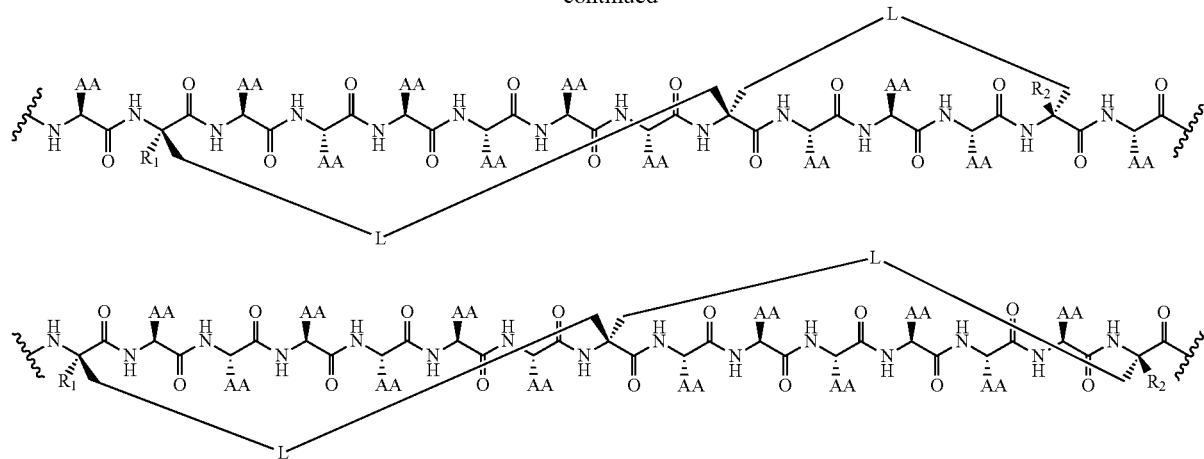

wherein "AA" represents any natural or non-natural amino acid side chain and " ⌇ " is [D]$_v$, [E]$_w$ as defined above, and n is an integer between 0 and 20, 50, 100, 200, 300, 400 or 500. In some embodiments, the substituent "n" shown in the preceding paragraph is 0. In other embodiments, the substituent "n" shown in the preceding paragraph is less than 50, 40, 30, 20, 10, or 5.

Exemplary embodiments of the macrocycle-forming linker L are shown below.

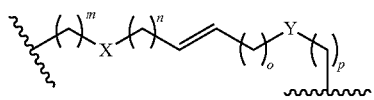

where X, Y = —CH$_2$—, O, S, or NH m, n, o, p = 0-10

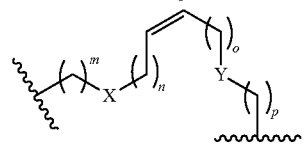

where X, Y = —CH$_2$—, O, S, or NH m, n, o, p = 0-10

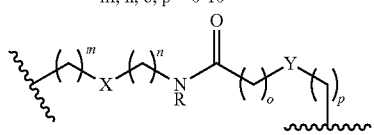

where X, Y = —CH$_2$—, O, S, or NH m, n, o, p = 0-10

R = H, alkyl, other substituent

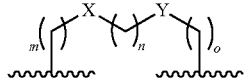

where X, Y = —CH$_2$—, O, S, or NH m, n, o, = 0-10

In other embodiments, D and/or E in the compound of Formula I are further modified in order to facilitate cellular uptake. In some embodiments, lipidating or PEGylating a peptidomimetic macrocycle facilitates cellular uptake, increases bioavailability, increases blood circulation, alters pharmacokinetics, decreases immunogenicity and/or decreases the needed frequency of administration.

In other embodiments, at least one of [D] and [E] in the compound of Formula I represents a moiety comprising an additional macrocycle-forming linker such that the peptidomimetic macrocycle comprises at least two macrocycle-forming linkers. In a specific embodiment, a peptidomimetic macrocycle comprises two macrocycle-forming linkers.

In the peptidomimetic macrocycles of the invention, any of the macrocycle-forming linkers described herein may be used in any combination with any of the sequences shown in Tables 1a, 1b c, and 2 and also with any of the R— substituents indicated herein.

In some embodiments, the peptidomimetic macrocycle comprises at least one α-helix motif. For example, A, B and/or C in the compound of Formula I include one or more α-helices. As a general matter, α-helices include between 3 and 4 amino acid residues per turn. In some embodiments, the α-helix of the peptidomimetic macrocycle includes 1 to 5 turns and, therefore, 3 to 20 amino acid residues. In specific embodiments, the α-helix includes 1 turn, 2 turns, 3 turns, 4 turns, or 5 turns. In some embodiments, the macrocycle-forming linker stabilizes an α-helix motif included within the peptidomimetic macrocycle. Thus, in some embodiments, the length of the macrocycle-forming linker L from a first Cα to a second Cα is selected to increase the stability of an α-helix. In some embodiments, the macrocycle-forming linker spans from 1 turn to 5 turns of the α-helix. In some embodiments, the macrocycle-forming linker spans approximately 1 turn, 2 turns, 3 turns, 4 turns, or 5 turns of the α-helix. In some embodiments, the length of the macrocycle-forming linker is approximately 5 Å to 9 Å per turn of the α-helix, or approximately 6 Å to 8 Å per turn of the α-helix. Where the macrocycle-forming linker spans approximately 1 turn of an α-helix, the length is equal to approximately 5 carbon-carbon bonds to 13 carbon-carbon bonds, approximately 7 carbon-carbon bonds to 11 carbon-carbon bonds, or approximately 9 carbon-carbon bonds. Where the macrocycle-forming linker spans approximately 2 turns of an α-helix, the length is equal to approximately 8 carbon-carbon bonds to 16 carbon-carbon bonds, approximately 10 carbon-carbon bonds to 14 carbon-carbon bonds, or approximately 12 carbon-carbon bonds. Where the macrocycle-forming linker spans approximately 3 turns of an α-helix, the length is equal to approximately 14 carbon-carbon bonds to 22 carbon-carbon bonds, approximately 16 carbon-carbon bonds to 20 carbon-carbon bonds, or approximately 18 carbon-carbon bonds. Where the macrocycle-forming linker spans approximately 4 turns of an α-helix, the length is equal to approximately 20 carbon-carbon bonds to 28 carbon-carbon bonds, approximately 22 carbon-carbon bonds to 26 carbon-carbon bonds, or approximately 24 carbon-carbon bonds. Where the macrocycle-forming linker spans approximately 5 turns of an α-helix, the length is equal to approximately 26 carbon-carbon bonds to 34 carbon-carbon bonds, approximately 28 carbon-carbon bonds to 32 carbon-carbon bonds, or approximately 30 carbon-carbon bonds. Where the macrocycle-forming linker spans approximately 1 turn of an α-helix, the linkage contains approximately 4 atoms to 12 atoms, approximately 6 atoms to 10 atoms, or approximately 8 atoms. Where the macrocycle-forming linker spans approximately 2 turns of the α-helix, the linkage contains approximately 7 atoms to 15 atoms, approximately 9 atoms to 13 atoms, or approximately 11 atoms. Where the macrocycle-forming linker spans approximately 3 turns of the α-helix, the linkage contains approximately 13 atoms to 21 atoms, approximately 15 atoms to 19 atoms, or approximately 17 atoms. Where the macrocycle-forming linker spans approximately 4 turns of the α-helix, the linkage contains approximately 19 atoms to 27 atoms, approximately 21 atoms to 25 atoms, or approximately 23 atoms. Where the macrocycle-forming linker spans approximately 5 turns of the α-helix, the linkage contains approximately 25 atoms to 33 atoms, approximately 27 atoms to 31 atoms, or approximately 29 atoms. Where the macrocycle-forming linker spans approximately 1 turn of the α-helix, the resulting macrocycle forms a ring containing approximately 17 members to 25 members, approximately 19 members to 23 members, or approximately 21 members. Where the macrocycle-forming linker spans approximately 2 turns of the α-helix, the resulting macrocycle forms a ring containing approximately 29 members to 37 members, approximately 31 members to 35 members, or approximately 33 members. Where the macrocycle-forming linker spans approximately 3 turns of the α-helix, the resulting macrocycle forms a ring containing approximately 44 members to 52 members, approximately 46 members to 50 members, or approximately 48 members. Where the macrocycle-forming linker spans approximately 4 turns of the α-helix, the resulting macrocycle forms a ring containing approximately 59 members to 67 members, approximately 61 members to 65 members, or approximately 63 members. Where the macrocycle-forming linker spans approximately 5 turns of the α-helix, the resulting macrocycle forms a ring containing approximately 74 members to 82 members, approximately 76 members to 80 members, or approximately 78 members.

In some embodiments, L is a macrocycle-forming linker of the formula

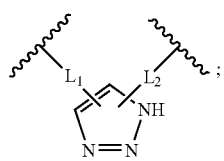

Exemplary embodiments of such macrocycle-forming linkers L are shown below.

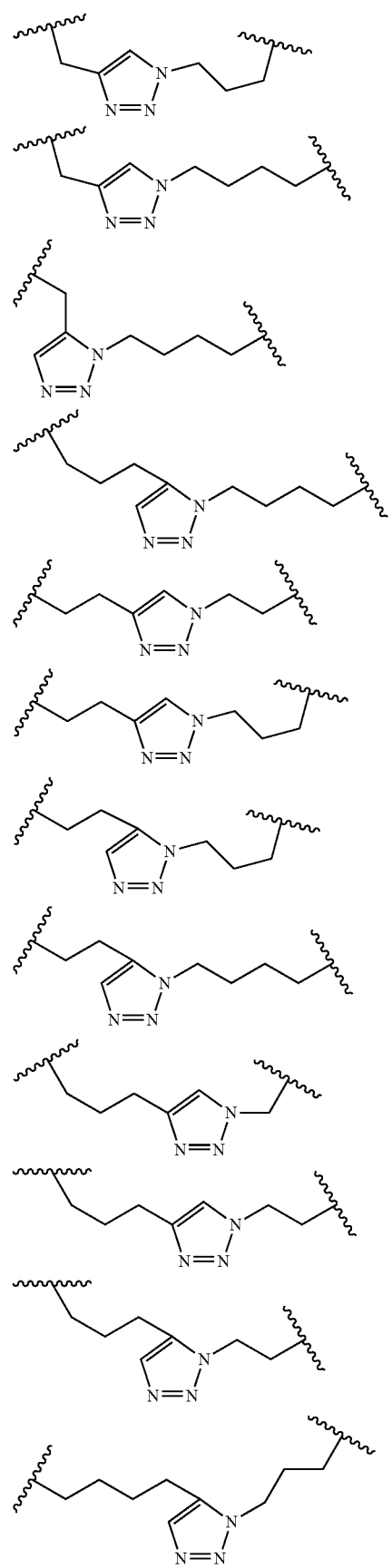

-continued
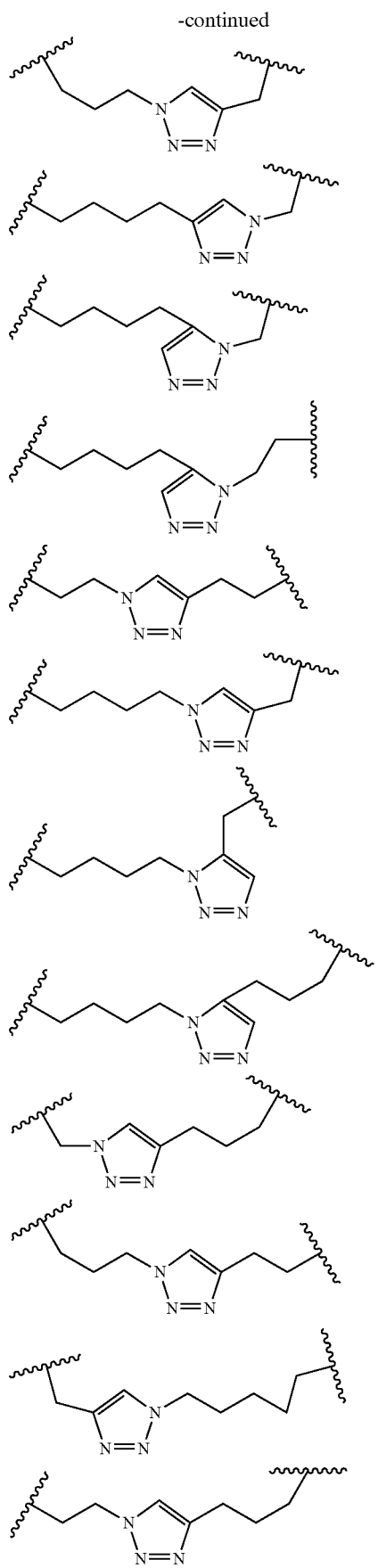
-continued
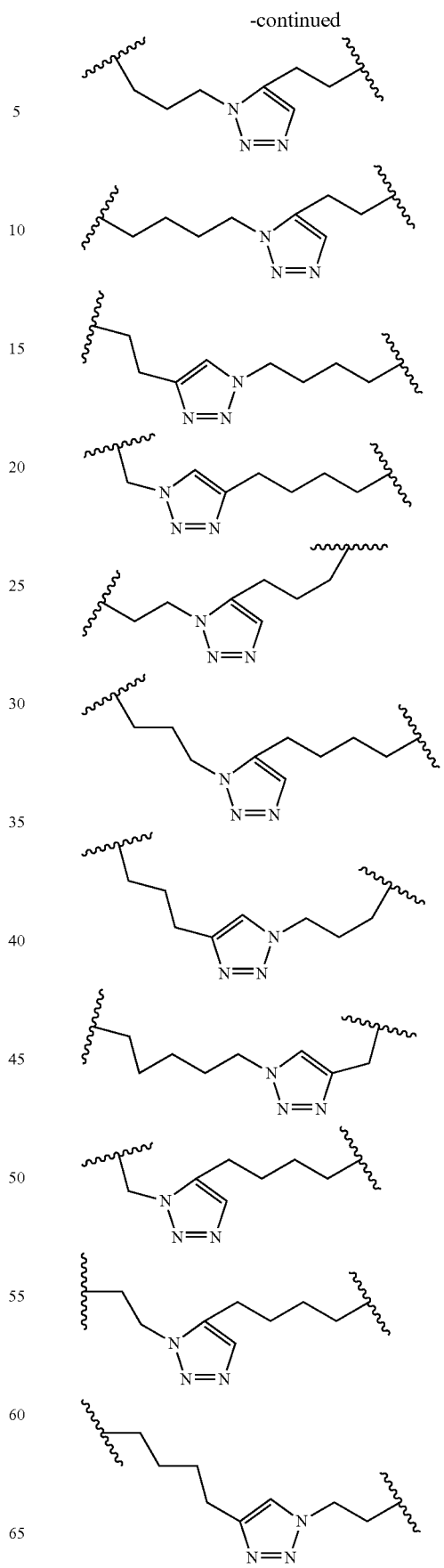

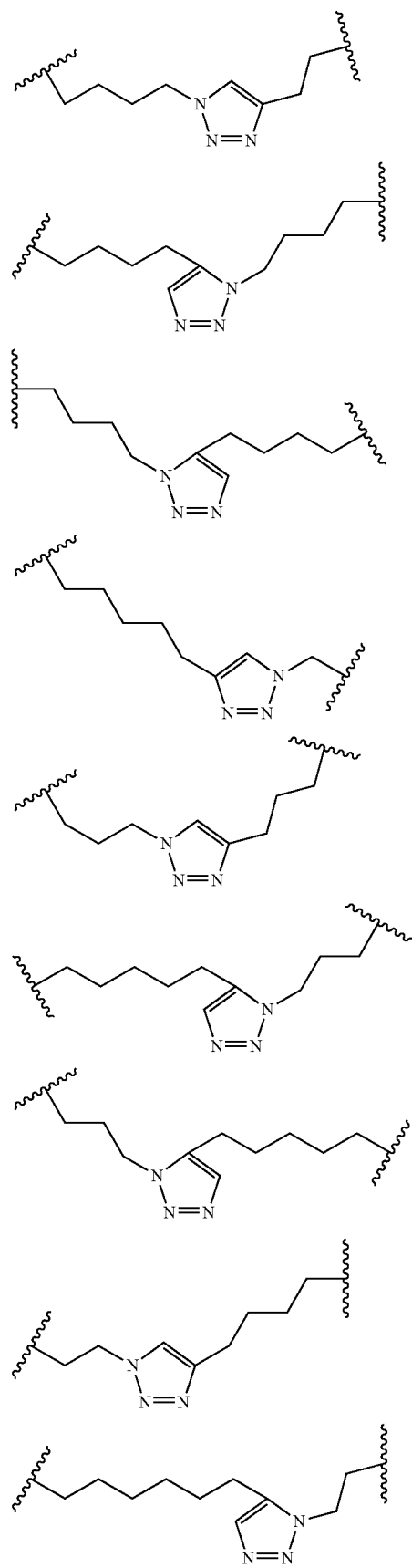
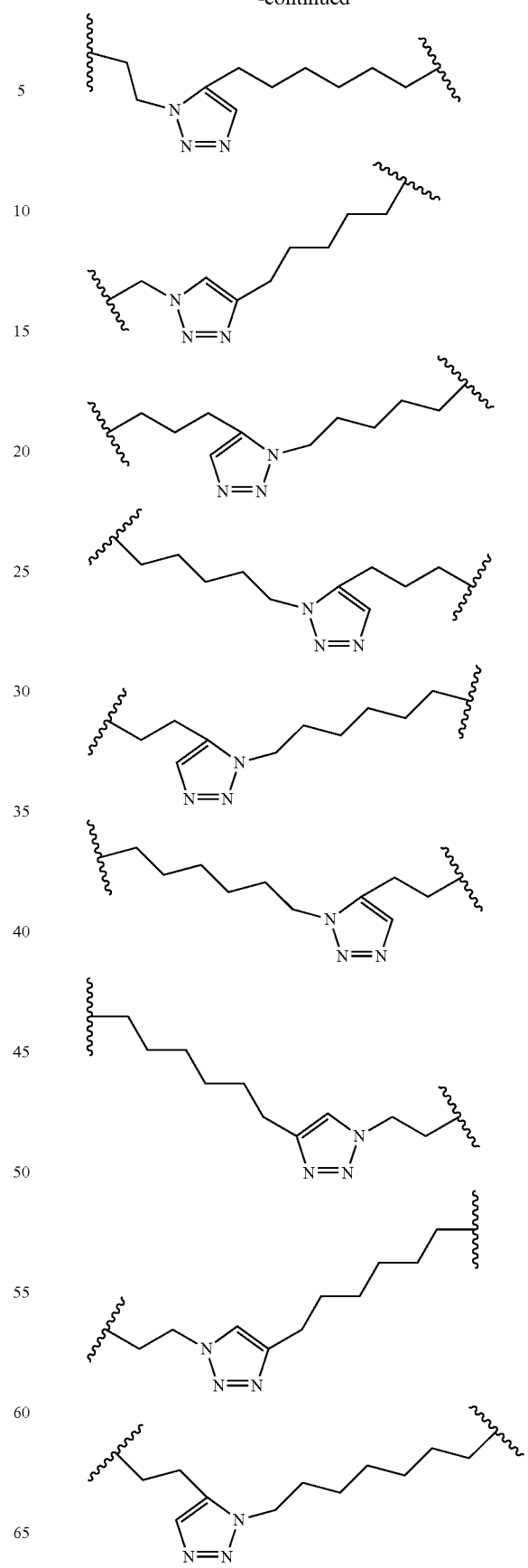

83
-continued
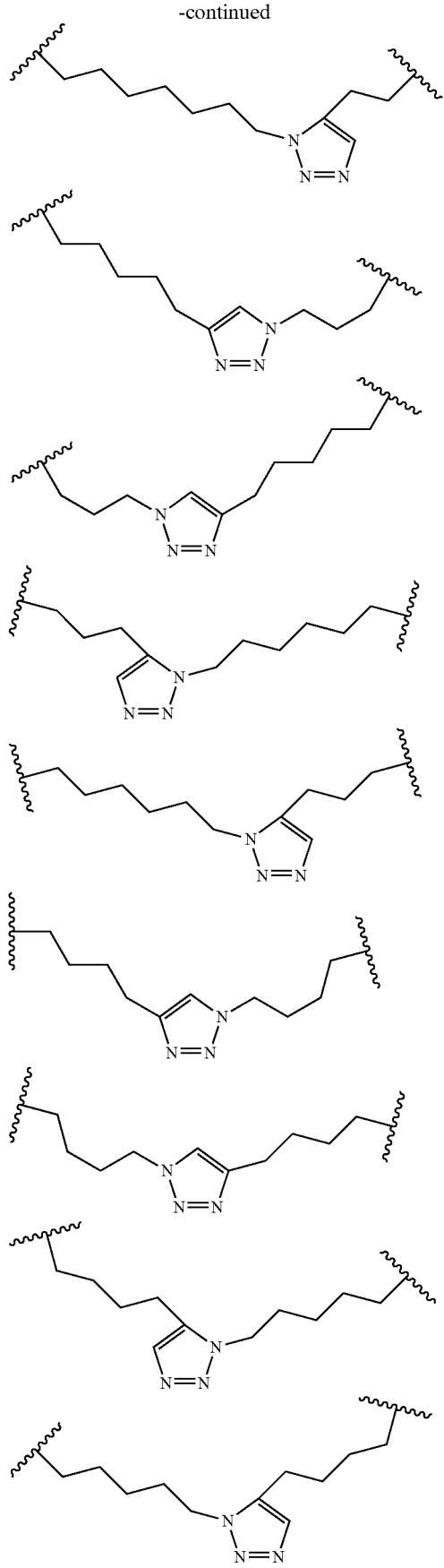
84
-continued
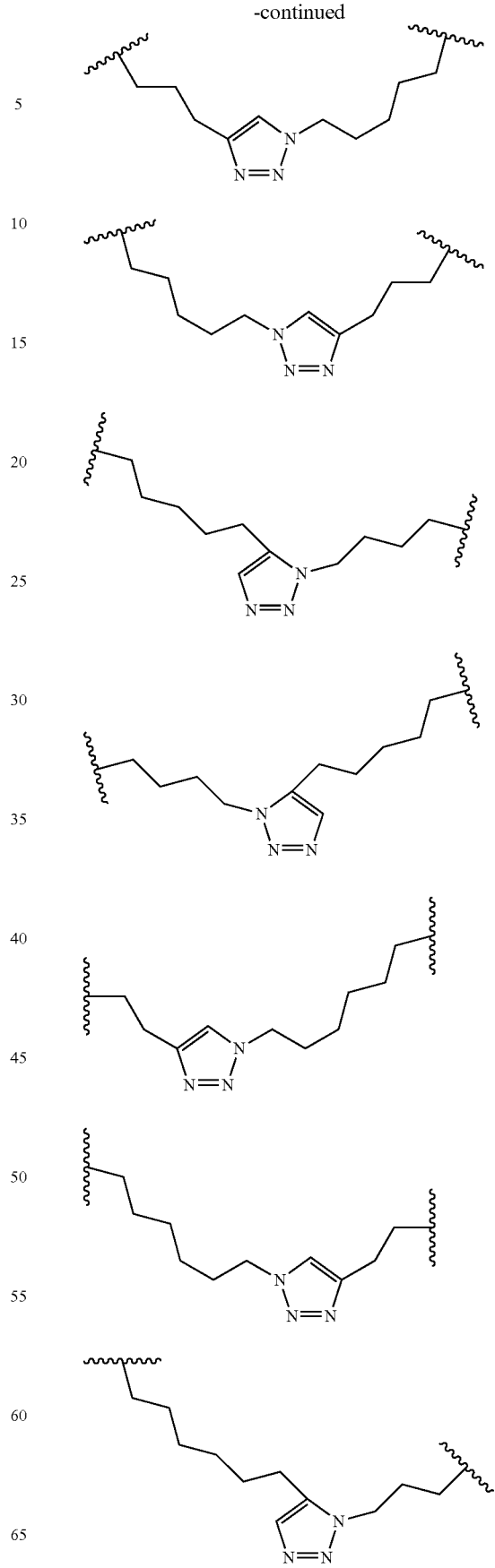

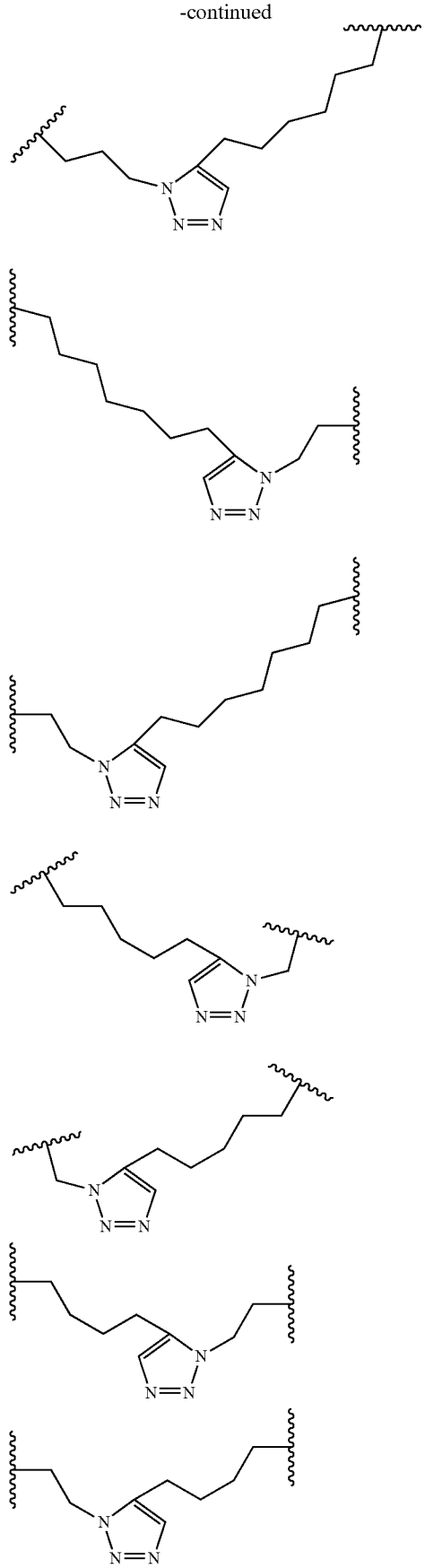
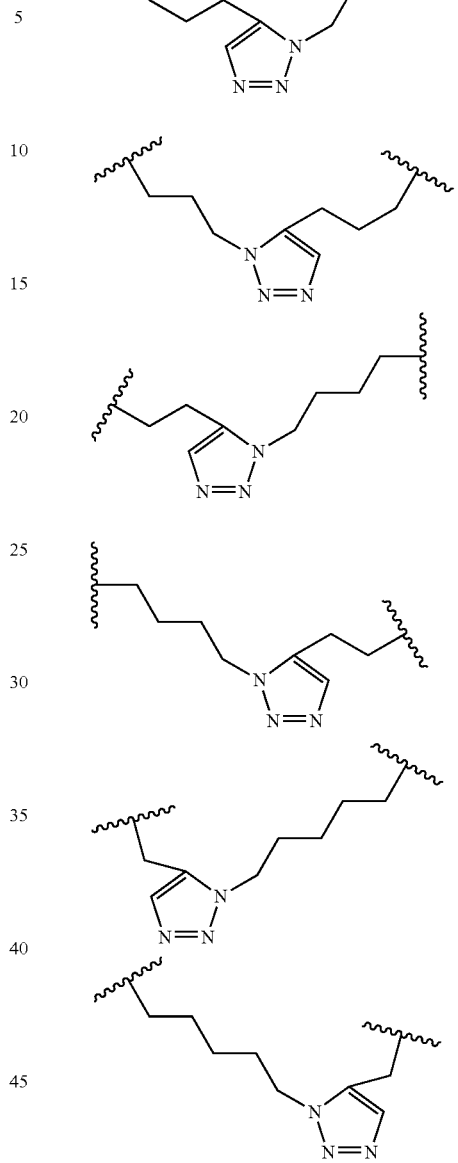
In some embodiments, a peptidomimetic macrocycle of the invention comprises a macrocycle-forming linker connecting a backbone amino group of a first amino acid to a second amino acid within the peptidomimetic macrocycle.
In other embodiments, the invention provides peptidomimetic macrocycles of Formula (II) or (IIa):
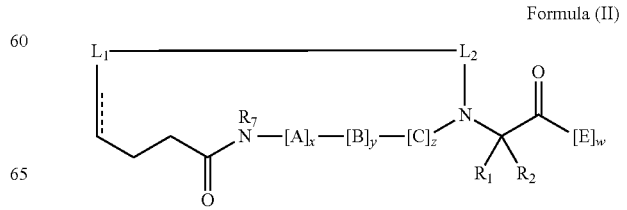
Formula (II)

Formula (IIa)

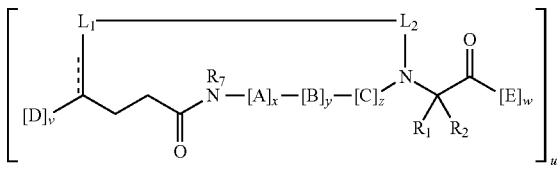

wherein:
each A, C, D, and E is independently an amino acid;
B is an amino acid

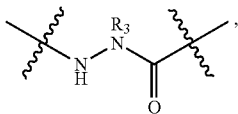

[—NH-L$_3$-CO—], [—NH-L$_3$-SO$_2$—], or [—NH-L$_3$-];
R$_1$ and R$_2$ are independently —H, alkyl, alkenyl, alkynyl, arylalkyl, cycloalkyl, cycloalkylalkyl, heteroalkyl, or heterocycloalkyl, unsubstituted or substituted with halo-, or part of a cyclic structure with an E residue;
R$_3$ is hydrogen, alkyl, alkenyl, alkynyl, arylalkyl, heteroalkyl, cycloalkyl, heterocycloalkyl, cycloalkylalkyl, cycloaryl, or heterocycloaryl, optionally substituted with R$_5$;
L$_1$, L$_2$ and L$_3$ are independently alkylene, alkenylene, alkynylene, heteroalkylene, cycloalkylene, heterocycloalkylene, cycloarylene, heterocycloarylene, or [—R$_4$—K—R$_4$—]$_n$, each being optionally substituted with R$_5$;
and wherein A, B, C, D, and E, taken together with the crosslinked amino acids connected by the macrocycle-forming linker -L$_1$-L$_2$-, form the amino acid sequence of the peptidomimetic macrocycle which is at least about 60%, 65%, 70, 75%, 80%, 85%, 90%, 95%, 96%, 97%, 98%, or 99% identical to an amino acid sequence chosen from the group consisting of the amino acid sequences in Tables 1a, 1b, 1c and 2;
each R$_4$ is alkylene, alkenylene, alkynylene, heteroalkylene, cycloalkylene, heterocycloalkylene, arylene, or heteroarylene;
each K is O, S, SO, SO$_2$, CO C$_2$ or CONR$_3$;
each R$_5$ is independently halogen, alkyl, —OR$_6$, —N(R$_6$)$_2$, —SR$_6$, —SOR$_6$, —SO$_2$R$_6$, —CO$_2$R$_6$, a fluorescent moiety, a radioisotope or a therapeutic agent;
each R$_6$ is independently —H, alkyl, alkenyl, alkynyl, arylalkyl, cycloalkylalkyl, heterocycloalkyl, a fluorescent moiety, a radioisotope or a therapeutic agent;
R$_7$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with R$_5$;
v and w are independently integers from 1-1000, for example 1-100;
u, x, y and z are independently integers from 0-10, for example u is 1-3; and
n is an integer from 1-5.1.
In some embodiments, u is 1.
In some embodiments, the sum of x+y+z is 2, 3 or 6, for example 3.
In some embodiments, each of v and w is independently an integer from 1 to 10, 1 to 15, 1 to 20, or 1 to 25, for example from 1 to 15.
In some embodiments, L$_1$ and L$_2$ are independently alkylene, alkenylene or alkynylene. In some embodiments, L$_1$ and L$_2$ are independently C$_3$-C$_{10}$ alkylene or alkenylene, for example C$_3$-C$_6$ alkylene or alkenylene.
In some embodiments, R$_1$ and R$_2$ are H.
In some embodiments, at least one of R$_1$ and R$_2$ is alkyl, unsubstituted or substituted with halo-. In another example, both R$_1$ and R$_2$ are independently alkyl, unsubstituted or substituted with halo-. In some embodiments, at least one of R$_1$ and R$_2$ is methyl. In other embodiments, R$_1$ and R$_2$ are methyl.
In some embodiments of the invention, the sum of x+y+z is at least 1. In other embodiments of the invention, the sum of x+y+z is at least 2. In other embodiments of the invention, the sum of x+y+z is 1, 2, 3, 4, 5, 6, 7, 8, 9 or 10. Each occurrence of A, B, C, D or E in a macrocycle or macrocycle precursor of the invention is independently selected. For example, a sequence represented by the formula [A], when x is 3, encompasses embodiments where the amino acids are not identical, e.g. Gln-Asp-Ala as well as embodiments where the amino acids are identical, e.g. Gln-Gln-Gln. This applies for any value of x, y, or z in the indicated ranges.
In some embodiments, the peptidomimetic macrocycle of the invention comprises a secondary structure which is an α-helix and R$_8$ is —H, allowing intrahelical hydrogen bonding. In some embodiments, at least one of A, B, C, D or E is an α,α-disubstituted amino acid. In one example, B is an α,α-disubstituted amino acid. For instance, at least one of A, B, C, D or E is 2-aminoisobutyric acid. In other embodiments, at least one of A, B, C, D or E is

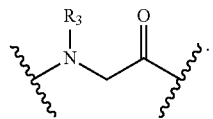

In some embodiments, the present invention provides a peptidomimetic macrocycle comprising an amino acid sequence of the formula:

X1-X2-X3-X4-X5-X6-X7-X8-X9-X10-X11-X12-X13-X14-X15-X16-X17-X18-X19-X20-X21-X22-X23-X24-X25-X26-X27-X28-X29-X30-X31-X32     (SEQ ID NO: 2)

wherein:
X1 is a hydrophobic amino acid, or absent;
X2 is a hydrophobic amino acid, or absent;
X3 is a negatively charged amino acid, a positively charged amino acid, or absent;
X4 is an uncharged polar amino acid, or absent;
X5 is a negatively charged amino acid, or absent;
X6 is a hydrophobic amino acid, a negatively charged amino acid, a positively charged amino acid, an uncharged polar amino acid, or absent;
X7 is a hydrophobic amino acid, a negatively charged amino acid, or absent;
X8 is a negatively charged amino acid, a positively charged amino acid, or absent;
X9 is a negatively charged amino acid, absent, or a cross-linked amino acid;
X10 is a negatively charged amino acid, a positively charged amino acid, an uncharged polar amino acid, or a cross-linked amino acid;
X11 is a hydrophobic amino acid, a negatively charged amino acid, a positively charged amino acid, or a cross-linked amino acid;
X12 is a hydrophobic amino acid, a negatively charged amino acid, or a cross-linked amino acid;

X13 is a hydrophobic amino acid, a hydrophobic amino acid, a negatively charged amino acid, or a cross-linked amino acid;
X14 is a cross-linked amino acid;
X15 is a hydrophobic amino acid, a negatively charged amino acid, or a cross-linked amino acid;
X16 is a hydrophobic amino acid, a negatively charged amino acid, or a cross-linked amino acid;
X17 is a hydrophobic amino acid, a negatively charged amino acid, a positively charged amino acid, or a cross-linked amino acid;
X18 is a cross-linked amino acid;
X19 is a hydrophobic amino acid, a negatively charged amino acid, a positively charged amino acid, or a cross-linked amino acid;
X20 is a negatively charged amino acid, a hydrophobic amino acid, or a cross-linked amino acid;
X21 is a hydrophobic amino acid, or a negatively charged amino acid;
X22 is a negatively charged amino acid, or absent;
X23 is a positively charged amino acid, a negatively charged amino acid, or absent;
X24 is a hydrophobic amino acid, a negatively charged amino acid, or absent;
X25 is a hydrophobic amino acid, a negatively charged amino acid, or absent;
X26 is a negatively charged amino acid, or absent;
X27 is a hydrophobic amino acid, or absent;
X28 is a hydrophobic amino acid, or absent; absent;
X29 is a negatively charged amino acid, an uncharged polar amino acid, or absent;
X30 is a hydrophobic amino acid, or absent;
X31 is a hydrophobic amino acid, or absent; and
X32 is a hydrophobic amino acid, or absent;
wherein the peptidomimetic macrocycle comprises at least one macrocycle-forming linker connecting at least one pair of amino acids selected from X1-X28;
L is a macrocycle-forming linker of the formula -$L_1$-$L_2$- or the formula

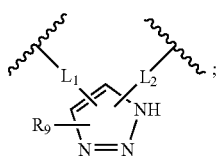

$L_1$ and $L_2$ are independently alkylene, alkenylene, alkynylene, heteroalkylene, cycloalkylene, heterocycloalkylene, cycloarylene, heterocycloarylene, or [—$R_4$—K—$R_4$—]$_n$, each being optionally substituted with $R_5$;
each the cross-linked amino acid is optionally substituted at the alpha carbon position with $R_1$ or $R_2$, wherein $R_1$ and $R_2$ are independently alkyl, alkenyl, alkynyl, arylalkyl, cycloalkyl, cycloalkylalkyl, heteroalkyl, or heterocycloalkyl, each being optionally substituted with halo-;
each $R_4$ is alkylene, alkenylene, alkynylene, heteroalkylene, cycloalkylene, heterocycloalkylene, arylene, or heteroarylene;
each K is O, S, SO, $SO_2$, CO, or $CO_2$;
each $R_5$ is independently halogen, alkyl, —$OR_6$, —$N(R_6)_2$, —$SR_6$, —$SOR_6$, —$SO_2R_6$, —$CO_2R_6$, a fluorescent moiety, a radioisotope, or a therapeutic agent;
each $R_6$ is independently —H, alkyl, alkenyl, alkynyl, arylalkyl, cycloalkylalkyl, heterocycloalkyl, a fluorescent moiety, a radioisotope, or a therapeutic agent;

$R_9$ is alkyl, alkenyl, alkynyl, aryl, cycloalkyl, cycloalkenyl, heteroaryl, or heterocyclyl group, unsubstituted or optionally substituted with $R_a$ and/or $R_b$; and
$R_a$ and $R_b$ are independently alkyl, $OCH_3$, $CF_3$, $NH_2$, $CH_2NH_2$, F, Br, I,

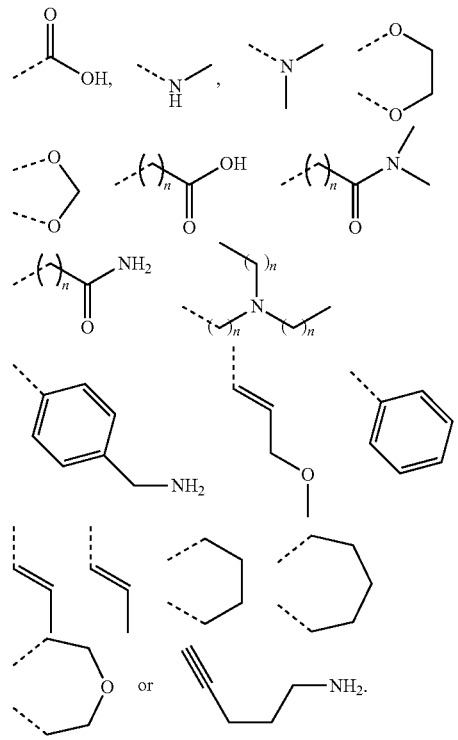

In some embodiments, the present invention provides a peptidomimetic macrocycle comprising an amino acid sequence of the formula:

X1-X2-X3-X4-X5-X6-X7-X8-X9-X10-X11-X12-X13-X14-X15-X16-X17-X18-X19-X20-X21-X22-X23-X24-X25-X26-X27-X28-X29-X30-X31-X32 (SEQ ID NO:3)

wherein:
X1 is Val or absent;
X2 is Ile, Phe, or absent;
X3 is Asp, Arg, or absent;
X4 is Thr or absent;
X5 is Asp or absent;
X6 is Phe, Ala, Glu, Ser, Dpr, Asn, or absent;
X7 is Ile, Ala, Glu, Ser, or absent;
X8 is Asp, Ala, Ser, Dpr, or absent;
X9 is Glu, Ala, absent, or a cross-linked amino acid;
X10 is Glu, Ala, Ser Dpr, Gln, or a cross-linked amino acid;
X11 is Vat, Ala, Asp, Ser, Dpr, or a cross-linked amino acid;
X12 is Leu, Ala, Glu, Ser, pL, or a cross-linked amino acid;
X13 is Met, Nle, Ala, Asp, or a cross-linked amino acid;
X14 is Ser or a cross-linked amino acid;
X5 is Leu, Ala, Asp, Ser, or a cross-linked amino acid;
X16 is Val, Ala, Glu, Ser, pL, or a cross-linked amino acid;
X17 is Ile, Ala, Glu, Ser, Dpr, Bpa, or a cross-linked amino acid;
X18 is Glu or a cross-linked amino acid;
X19 is Met, Nle, Ala, Glu, Ser, Dpr, Bpa, or a cross-linked amino acid;
X20 is Gly, Ala, Glu, Ser, or a cross-linked amino acid;

X21 is Leu, Ala, Glu, or Ser;
X22 is Asp, Ala, Ser, or absent;
X23 is Arg, Ala, Glu, Ser, Dpr, or absent;
X24 is Ile, Ala, Glu, Ser, or absent;
X25 is Lys, Glu, or absent;
X26 is Glu or absent;
X27 is Leu or absent;
X28 is Pro or absent;
X29 is Glu, Gln, or absent;
X30 is Leu or absent;
X31 is Trp or absent; and
X32 is Leu or absent;
wherein the peptidomimetic macrocycle comprises at least one macrocycle-forming linker connecting at least one pair of amino acids selected from X1-X28;
L is a macrocycle-forming linker of the formula -$L_1$-$L_2$- or the formula

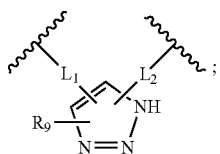

$L_1$ and $L_2$ are independently alkylene, alkenylene, alkynylene, heteroalkylene, cycloalkylene, heterocycloalkylene, cycloarylene, heterocycloarylene, or [—$R_4$—K—$R_4$—]$_n$, each being optionally substituted with $R_5$;
each the cross-linked amino acid is optionally substituted at the alpha carbon position with $R_1$ or $R_2$, wherein $R_1$ and $R_2$ are independently alkyl, alkenyl, alkynyl, arylalkyl, cycloalkyl, cycloalkylalkyl, heteroalkyl, or heterocycloalkyl, each being optionally substituted with halo-;
each $R_4$ is alkylene, alkenylene, alkynylene, heteroalkylene, cycloalkylene, heterocycloalkylene, arylene, or heteroarylene;
each K is O, S, SO, $SO_2$, CO, or $CO_2$;
each $R_5$ is independently halogen, alkyl, —$OR_6$, —$N(R_6)_2$, —$SR_6$, —$SOR_6$, —$SO_2R_6$, —$CO_2R_6$, a fluorescent moiety, a radioisotope, or a therapeutic agent;
each $R_6$ is independently —H, alkyl, alkenyl, alkynyl, arylalkyl, cycloalkylalkyl, heterocycloalkyl, a fluorescent moiety, a radioisotope, or a therapeutic agent;
$R_9$ is alkyl, alkenyl, alkynyl, aryl, cycloalkyl, cycloalkenyl, heteroaryl, or heterocyclyl group, unsubstituted or optionally substituted with $R_a$ and/or $R_b$; and
$R_a$ and $R_b$ are independently alkyl, $OCH_3$, $CF_3$, $NH_2$, $CH_2NH_2$, F, Br, I,

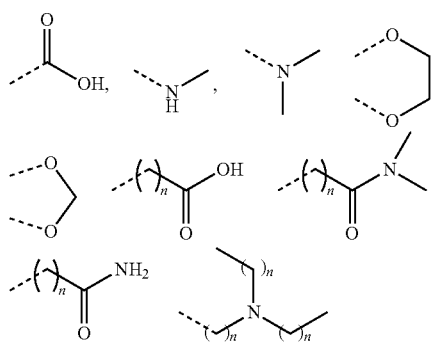

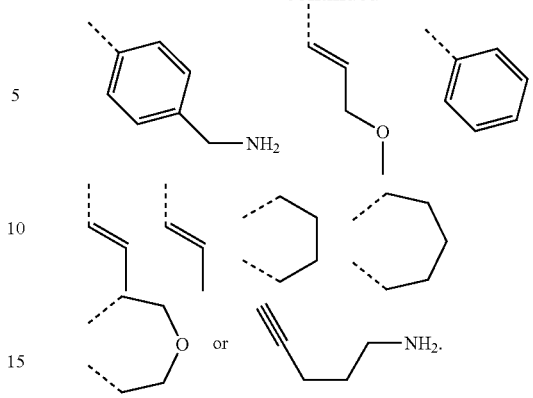

A peptidomimetic macrocycle comprising an amino acid sequence of the formula:

X1-X2-X3-X4-X5-X6-X7-X8-X9-X10-X11-X12-
X13-X14-X15-X16-X17-X18-X19-X20-X21-
X22-X23-X24-X25-X26-X27-X28-X29-X30-
X31-X32    (SEQ ID NO: 4)

wherein:
X1 is Val or absent;
X2 is Ile, Phe, or absent;
X3 is Asp, Arg, or absent;
X4 is Thr or absent;
X5 is Asp or absent;
X6 is Phe, Ala, Glu, Ser, Dpr, Asn, or absent;
X7 is Ile, Ala, Glu, Ser, or absent;
X8 is Asp, Ala, Ser, Dpr, or absent;
X9 is Glu, Ala, absent, or a cross-linked amino acid;
X10 is Glu, Ala, Ser, Dpr, Gln, or a cross-linked amino acid;
X11 is Val, Ala, Asp, Ser, Dpr, or a cross-linked amino acid;
X12 is Leu, Ala, Glu, Ser, pL, or a cross-linked amino acid;
X13 is Met, e, Ala, Asp, or a cross-linked amino acid;
X14 is Ser or a cross-linked amino acid;
X5 is Leu, Ala, Asp, Ser, or a cross-linked amino acid;
X16 is Val, Ala, Glu, Ser, pL, or a cross-linked amino acid;
X17 is Ile, Ala, Glu, Ser, Dpr, Bpa, or a cross-linked amino acid;
X18 is Glu or a cross-linked amino acid;
X19 is Met, Nle, Ala, Glu, Ser, Dpr, Bpa, or a cross-linked amino acid;
X20 is Gly, Ala, Glu, Ser, or a cross-linked amino acid;
X21 is Leu, Ala, Glu, or Ser;
X22 is Asp, Ala, Ser, or absent;
X23 is Arg, Ala, Glu, Ser, Dpr, or absent;
X24 is Ile, Ala, Glu, Ser, or absent;
X25 is Lys, Glu, or absent;
X26 is Glu or absent;
X27 is Leu or absent;
X28 is Pro or absent;
X29 is Glu, Gln, or absent;
X30 is Leu or absent;
X31 is Trp or absent; and
X32 is Leu or absent;
wherein the peptidomimetic macrocycle comprises at least one macrocycle-forming linker connecting at least one pair of amino acids selected from X1-X28;
L is a macrocycle-forming linker of the formula -$L_1$-$L_2$- or the formula

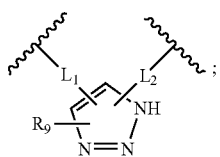

$L_1$ and $L_2$ are independently alkylene, alkenylene, alkynylene, heteroalkylene, cycloalkylene, heterocycloalkylene, cycloarylene, heterocycloarylene, or [—$R_4$—K—$R_4$—]$_n$, each being optionally substituted with $R_5$;

each the cross-linked amino acid is optionally substituted at the alpha carbon position with $R_1$ or $R_2$, wherein $R_1$ and $R_2$ are independently alkyl, alkenyl, alkynyl, arylalkyl, cycloalkyl, cycloalkylalkyl, heteroalkyl, or heterocycloalkyl, each being optionally substituted with halo-;

each $R_4$ is alkylene, alkenylene, alkynylene, heteroalkylene, cycloalkylene, heterocycloalkylene, arylene, or heteroarylene;

each K is O, S, SO, $SO_2$, CO, or $CO_2$;

each $R_5$ is independently halogen, alkyl, —$OR_6$, —$N(R)_2$, —$SR_6$, —$SOR_6$, —$SO_2R_6$, —$CO_2R_6$, a fluorescent moiety, a radioisotope, or a therapeutic agent;

each $R_6$ is independently —H, alkyl, alkenyl, alkynyl, arylalkyl, cycloalkylalkyl, heterocycloalkyl, a fluorescent moiety, a radioisotope, or a therapeutic agent;

$R_9$ is alkyl, alkenyl, alkynyl, aryl, cycloalkyl, cycloalkenyl, heteroaryl, or heterocyclyl group, unsubstituted or optionally substituted with $R_a$ and/or $R_b$; and $R_a$ and $R_b$ are independently alkyl, $OCH_3$, $CF_3$, $NH_2$, $CH_2NH_2$, F, Br, I,

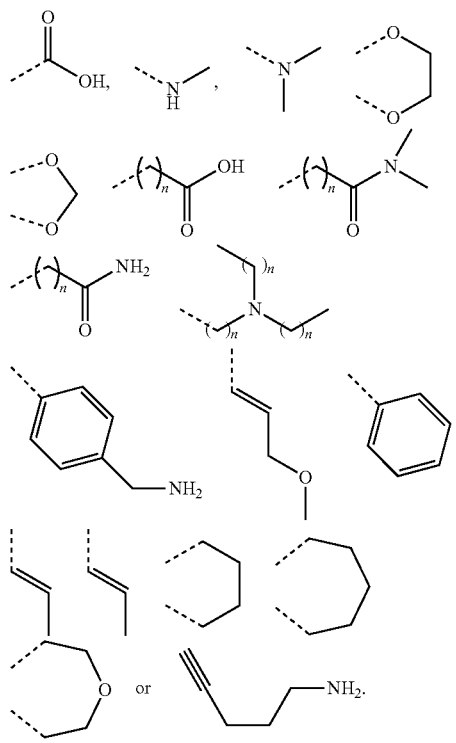

In some embodiments, the peptidomimetic macrocycle of the invention comprises one macrocycle-forming linker.

In some embodiments, the macrocycle-forming linker of the peptidomimetic macrocycle of the invention connects one of the following pairs of amino acids: X9 and X14, X9 and X16, X10 and X14, X10 and X17, X11 and X15, X11 and X18, X12 and X16, X12 and X19, X13 and X17, X13 and X20, X14 and X18, and X14 and X19. In some embodiments, the macrocycle-forming linker connects amino acids: X10 and X14. In some embodiments, the macrocycle-forming linker connects amino acids: X14 and X18.

In some embodiments, X9 is Glu. In some embodiments, X12 is Leu. In some embodiments, X13 is e or Met. In some embodiments, X16 is Val. In some embodiments, X18 is Glu. In some embodiments, X19 is Nle or Met. In some embodiments, X20 is Ala. In some embodiments, X21 is Leu. In some embodiments, X22 is Asp. In some embodiments, X24 is Ile. In some embodiments, X30 is Leu. In some embodiments, X31 is Trp.

In some embodiments, $L_1$ and $L_2$ are independently alkylene, alkenylene or alkynylene. In some embodiments, $L_1$ and $L_2$ are independently $C_3$-$C_{10}$ alkylene or alkenylene, for example $C_3$-$C_6$ alkylene or alkenylene. For example, L is

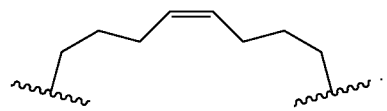

In some embodiments, L is

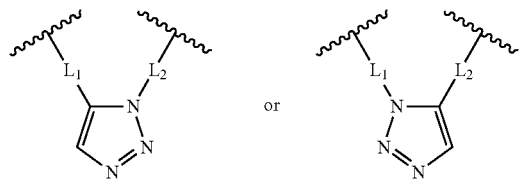

for example

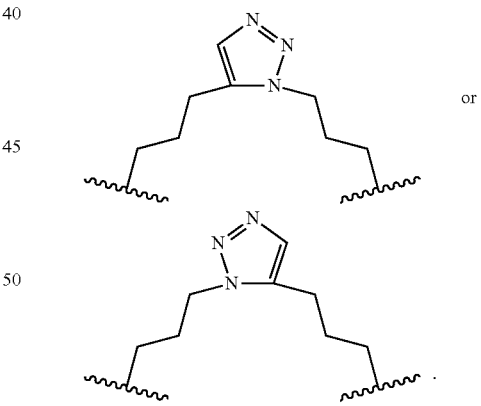

In some embodiments, $R_1$ and $R_2$ are H. In some embodiments, $R_1$ and $R_2$ are independently alkyl, for example methyl.

In some embodiments, the present invention provides a peptidomimetic macrocycle comprising an amino acid sequence which is about 60%, 65%, 70%, 75%, 800%, 85%, 90%, or 95% identical to an amino acid sequence of FIDEEVLMSLVIEMALDRI (SEQ ID NO: 5), for example an amino acid sequence of FIDEEVLM-Z-LVI-Z-MALDRI (SEQ ID NO: 6), wherein each Z is independently a cross-linked amino acid. In some embodiments, the peptidomimetic macrocycle is (SEQ ID NO: 6)

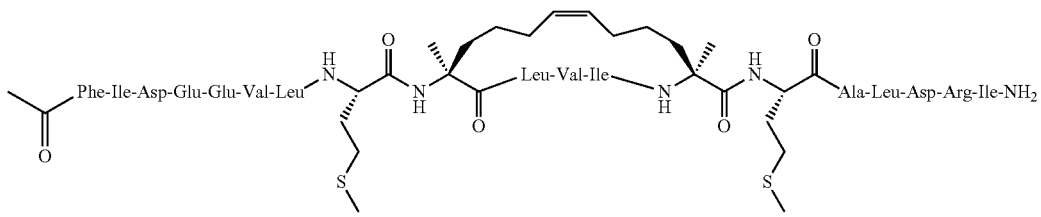

or a pharmaceutically acceptable salt thereof.

In some embodiments, the present invention provides a peptidomimetic macrocycle comprising an amino acid sequence which is about 60%, 65%, 70%, 750%, 80%, 85%, 90%, or 95% identical to an amino acid sequence of FIDEEVLNleSLVIENleALDRI (SEQ ID NO: 7), for example an amino acid sequence of FIDEEVLNle-Z-LVI-Z-NleALDRI (SEQ ID NO: 8), wherein each Z is independently a cross-linked amino acid. In some embodiments, the peptidomimetic macrocycle is some embodiments, the peptidomimetic macrocycle comprises an amino acid sequence of LLQGE-Z-LLRALD-Z-V (SEQ ID NO: 14), wherein each Z is independently a cross-linked amino acid. In some embodiments, X6 is linked to the amino acid sequence of LLQGEEL-Z-RAL-Z-QV (SEQ ID NO: 13).

In some embodiments, a peptidomimetic macrocycle of the invention further comprises an amino acid sequence which is about 60%, 65%, 70%, 75%, 80%, 85%, 90%, or 95% identical to an amino acid sequence of QLTSYD- (SEQ ID NO: 8)

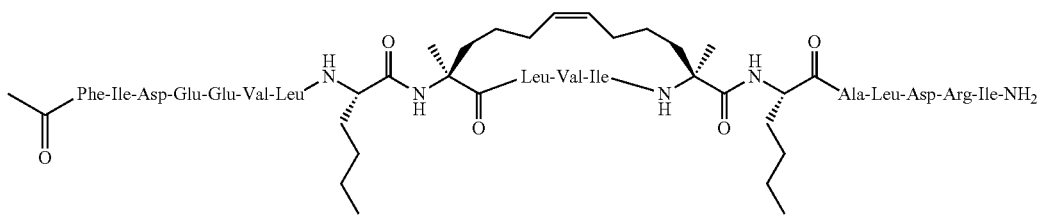

or a pharmaceutically acceptable salt thereof.

In some embodiments, the present invention provides a peptidomimetic macrocycle comprising an amino acid sequence which is about 60%, 65%, 70%, 75%, 80%, 85%, 90%, or 95% identical to an amino acid sequence of FIDEEVLMSLVIEMGLDRIKELPELWL (SEQ ID NO: 9), for example an amino acid sequence of FIDEEVLM-Z-LVI-Z-MGLDRIKELPELWL (SEQ ID NO: 10), wherein each Z is independently a cross-linked amino acid.

In some embodiments, a peptidomimetic macrocycle of the invention has a formula X6-X7-X8-X9-X10-X11-X12-X13-X14-X15-X16-X17-X18-X19-X20-X21-X22-X23-X24-X25-X26-X27-X28 (SEQ ID NO: 11). In some embodiments, a macrocycle-forming linker of the peptidomimetic macrocycle of the invention connects one of the following pairs of amino acids: X10 and X14, X10 and X17, X11 and X18, X12 and X16, X12 and X19, and X14 and X18, for example X14 and X18. In some embodiments, X13 is Nle. In some embodiments, X19 is Nle. In some embodiments, X20 is Ala.

In some embodiments, a peptidomimetic macrocycle of the invention further comprises an amino acid sequence which is about 60%, 65%, 70%, 75%, 80%, 85%, 90%, or 95% identical to an amino acid sequence of LLQGEELL-RALDQV (SEQ ID NO: 12) In some embodiments, the peptidomimetic macrocycle comprises an amino acid sequence of LLQGEEL-Z-RAL-Z-QV (SEQ ID NO: 13), wherein each Z is independently a cross-linked amino acid. In some embodiments, X6 is linked to the amino acid sequence of LLQGEEL-Z-RAL-Z-QV (SEQ ID NO: 13). In CEVNA (SEQ ID NO: 15), for example an amino acid sequence of QLT-Z-YDAbu-Z-VNA (SEQ ID NO: 16), wherein each Z is independently a cross-linked amino acid. In some embodiments, X28 is linked to the amino acid sequence of QLT-Z-YDAbu-Z-VNA (SEQ ID NO: 16).

In other embodiments, the length of the macrocycle-forming linker -L$_1$-L$_2$-as measured from a first Cα to a second Cα is selected to stabilize a desired secondary peptide structure, such as an α-helix formed by residues of the peptidomimetic macrocycle including, but not necessarily limited to, those between the first Cα to a second Ca.

Exemplary embodiments of the macrocycle-forming linker -L$_1$-L$_2$-are shown below.

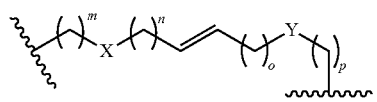

where X, Y = —CH$_2$—, O, S, or NH m, n, o, p = 0-10

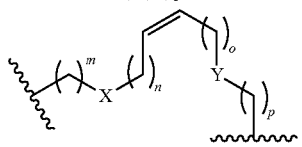

where X, Y = —CH$_2$—, O, S, or NH m, n, o, p = 0-10

-continued

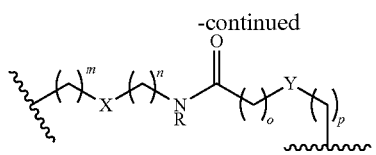

where X, Y = —CH$_2$—, O, S, or NH m, n, o, p = 0-10

R = H, alkyl, other substituent

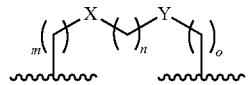

where X, Y = —CH$_2$—, O, S, or NH m, n, o, = 0-10

Preparation of Peptidomimetic Macrocycles

Peptidomimetic macrocycles of the invention may be prepared by any of a variety of methods known in the art. For example, any of the cross-linked amino acids in Tables 1a, 1b, 1c and 2 may be substituted with a residue capable of forming a crosslinker with a second residue in the same molecule or a precursor of such a residue.

Various methods to effect formation of peptidomimetic macrocycles are known in the art. For example, the preparation of peptidomimetic macrocycles of Formula (I) is described in Schafeister et al., J. Am. Chem. Soc. 122:5891-5892 (2000); Schafmineister & Verdine, J. Am. Chem. Soc. 122:5891 (2005); Walensky et al., Science 305:1466-1470 (2004); U.S. Pat. No. 7,192,713 and PCT application WO 2008/121767. The α,α-disubstituted amino acids and amino acid precursors disclosed in the cited references may be employed in synthesis of the peptidomimetic macrocycle precursor polypeptides. For example, the "S5-olefin amino acid" is (S)-α-(2'-pentenyl) alanine and the "R8 olefin amino acid" is (R)-α-(2'-octenyl) alanine. Following incorporation of such amino acids into precursor polypeptides, the terminal olefins are reacted with a metathesis catalyst, leading to the formation of the peptidomimetic macrocycle. In various embodiments, the following amino acids may be employed in the synthesis of the peptidomimetic macrocycle:

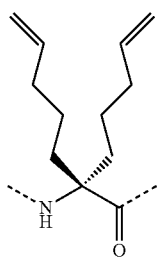

S$t$//

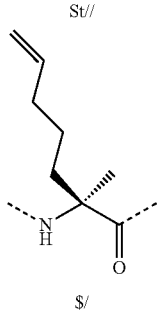

$/

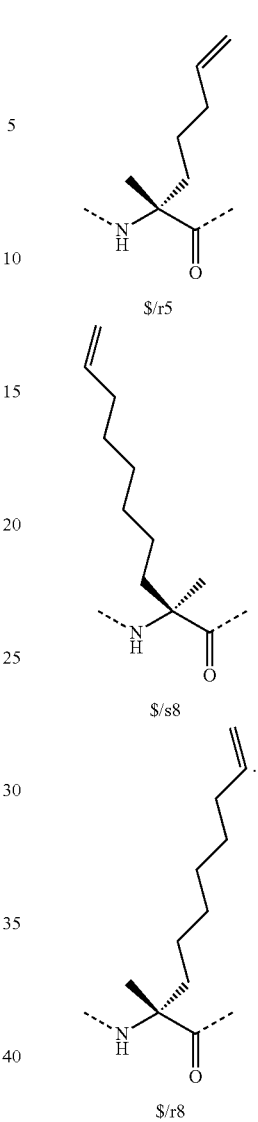

$/r5

$/s8

$/r8

In some embodiments, x+y+z is 3, and A, B and C are independently natural or non-natural amino acids. In other embodiments, x+y+z is 6, and A, B and C are independently natural or non-natural amino acids.

In some embodiments, the contacting step is performed in a solvent selected from the group consisting of protic solvent, aqueous solvent, organic solvent, and mixtures thereof. For example, the solvent may be chosen from the group consisting of H$_2$O, THF, THF/H$_2$O, tBuOH/H$_2$O, DMF, DPEA, CH$_3$CN or CH$_2$Cl$_2$, ClCH$_2$CH$_2$Cl or a mixture thereof. The solvent may be a solvent which favors helix formation.

Alternative but equivalent protecting groups, leaving groups or reagents are substituted, and certain of the synthetic steps are performed in alternative sequences or orders to produce the desired compounds. Synthetic chemistry transformations and protecting group methodologies (protection and deprotection) useful in synthesizing the compounds described herein include, for example, those such as described in Larock, *Comprehensive Organic Transformations*, VCH Publishers (1989); Greene and Wuts, *Protective Groups in Organic Synthesis*, 2d. Ed., John Wiley and Sons (1991); Fieser and Fieser, *Fieser and Fieser's Reagents for*

*Organic Synthesis*, John Wiley and Sons (1994); and Paquette, ed., *Encyclopedia of Reagents for Organic Synthesis*, John Wiley and Sons (1995), and subsequent editions thereof.

The peptidomimetic macrocycles disclosed herein are made, for example, by chemical synthesis methods, such as described in Fields et al., Chapter 3 in *Synthetic Peptides: A User's Guide*, ed. Grant, W. H. Freeman & Co., New York, N.Y., 1992, p. 77. Hence, for example, peptides are synthesized using the automated Merrifield techniques of solid phase synthesis with the amine protected by either tBoc or Fmoc chemistry using side chain protected amino acids on, for example, an automated peptide synthesizer (e.g., Applied Biosystems (Foster City, Calif.), Model 430A, 431, or 433).

One manner of producing the peptidomimetic precursors and peptidomimetic macrocycles described herein uses solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Side chain functional groups are protected as necessary with base stable, acid labile groups.

Longer peptidomimetic precursors are produced, for example, by conjoining individual synthetic peptides using native chemical ligation. Alternatively, the longer synthetic peptides are biosynthesized by well known recombinant DNA and protein expression techniques. Such techniques are provided in well-known standard manuals with detailed protocols. To construct a gene encoding a peptidomimetic precursor of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The peptidomimetic precursors are made, for example, in a high-throughput, combinatorial fashion using, for example, a high-throughput polychannel combinatorial synthesizer (e.g., Thuramed TETRAS multichannel peptide synthesizer from CreoSalus, Louisville, Ky. or Model Apex 396 multichannel peptide synthesizer from AAPPTEC, Inc., Louisville, Ky.).

In some embodiments, the peptidomimetic macrocycles of the invention comprise triazole macrocycle-forming linkers. For example, the synthesis of such peptidomimetic macrocycles involves a multi-step process that features the synthesis of a peptidomimetic precursor containing an azide moiety and an alkyne moiety; followed by contacting the peptidomimetic precursor with a macrocyclization reagent to generate a triazole-linked peptidomimetic macrocycle. Such a process is described, for example, in U.S. application Ser. No. 12/037,041, filed on Feb. 25, 2008. Macrocycles or macrocycle precursors are synthesized, for example, by solution phase or solid-phase methods, and can contain both naturally-occurring and non-naturally-occurring amino acids. See, for example, Hunt, "The Non-Protein Amino Acids" in *Chemistry and Biochemistry of the Amino Acids*, edited by G. C. Barrett, Chapman and Hall, 1985.

In some embodiments, an azide is linked to the α-carbon of a residue and an alkyne is attached to the α-carbon of another residue. In some embodiments, the azide moieties are azido-analogs of amino acids L-lysine, D-lysine, alpha-methyl-L-lysine, alpha-methyl-D-lysine, L-ornithine, D-ornithine, alpha-methyl-L-ornithine or alpha-methyl-D-ornithine. In another embodiment, the alkyne moiety is L-propargylglycine. In yet other embodiments, the alkyne moiety is an amino acid selected from the group consisting of L-propargylglycine, D-propargylglycine, (S)-2-amino-2-methyl-4-pentynoic acid, (R)-2-amino-2-methyl-4-pentynoic acid, (S)-2-amino-2-methyl-5-hexynoic acid, (R)-2-amino-2-methyl-5-hexynoic acid, (S)-2-amino-2-methyl-6-heptynoic acid, (R)-2-amino-2-methyl-6-heptynoic acid, (S)-2-amino-2-methyl-7-octynoic acid, (R)-2-amino-2-methyl-7-octynoic acid, (S)-2-amino-2-methyl-8-nonynoic acid and (R)-2-amino-2-methyl-8-nonynoic acid.

The following synthetic schemes are provided solely to illustrate the present invention and are not intended to limit the scope of the invention, as described herein. To simplify the drawings, the illustrative schemes depict azido amino acid analogs ε-azido-α-methyl-L-lysine and ε-azido-α-methyl-D-lysine, and alkyne amino acid analogs L-propargylglycine, (S)-2-amino-2-methyl-4-pentynoic acid, and (S)-2-amino-2-methyl-6-heptynoic acid. Thus, in the following synthetic schemes, each $R_1$, $R_2$, $R_7$ and $R_8$ is —H; each $L_1$ is —$(CH_2)_4$—; and each $L_2$ is —$(CH_2)$—. However, as noted throughout the detailed description above, many other amino acid analogs can be employed in which $R_1$, $R_2$, $R_7$, $R_8$, $L_1$ and $L_2$ can be independently selected from the various structures disclosed herein.

Synthetic Scheme 1:

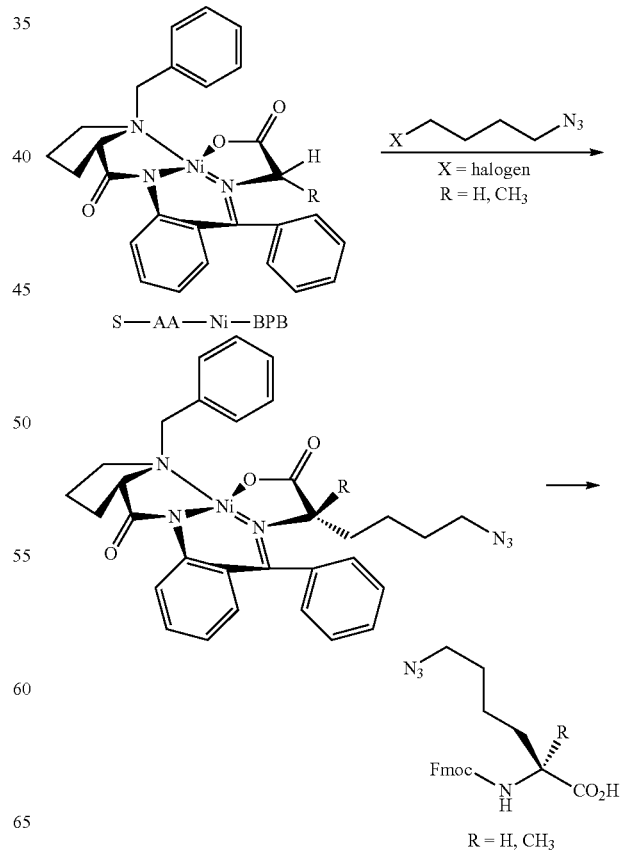

101

-continued

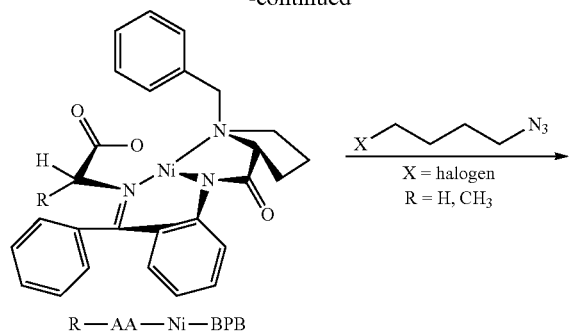

102

-continued

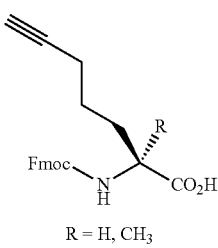

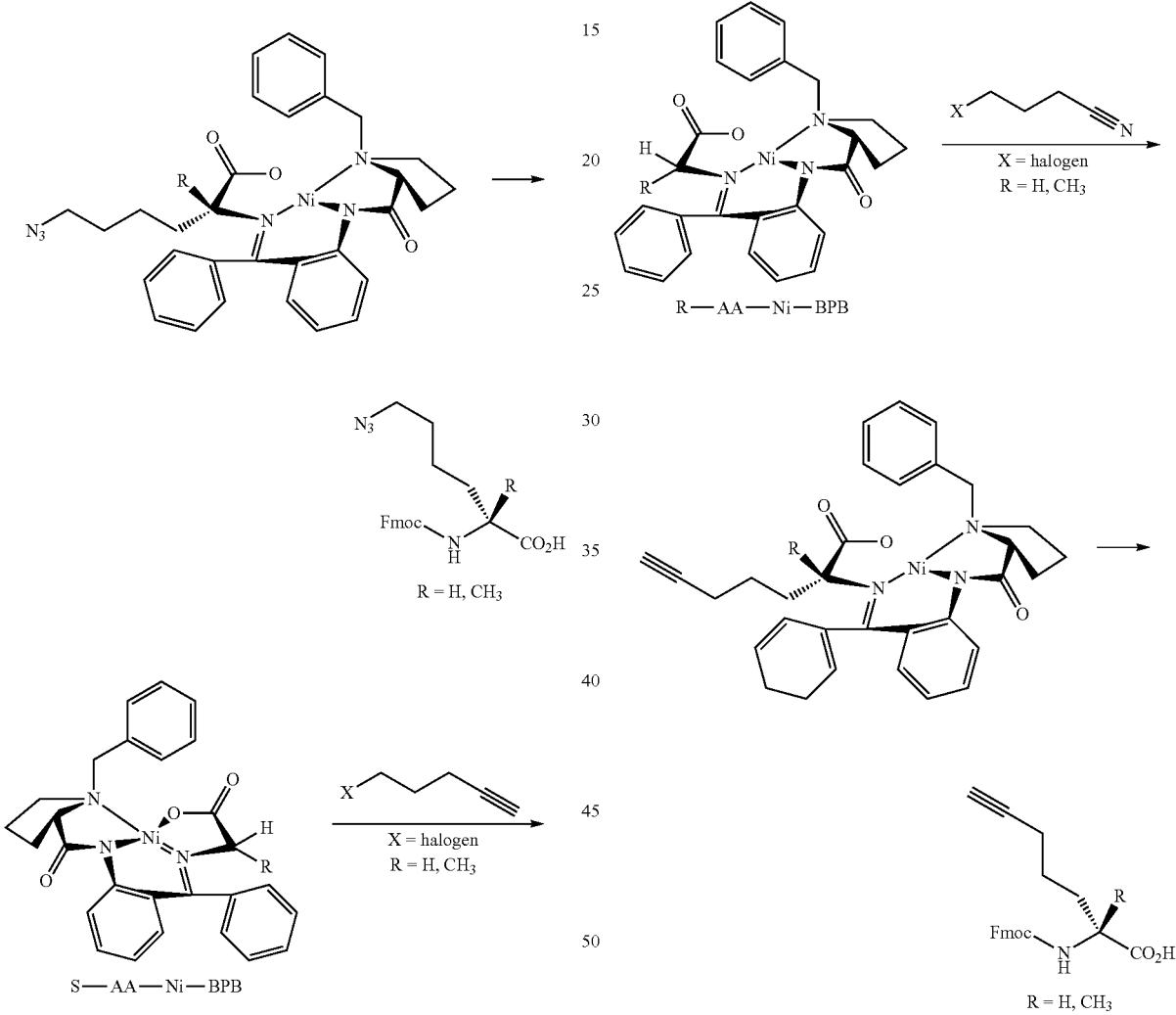

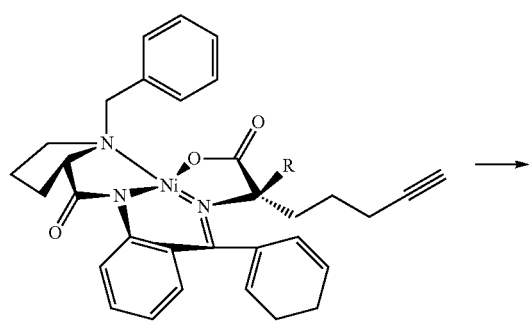

Synthetic Scheme 1 describes the preparation of several compounds of the invention. Ni(II) complexes of Schiff bases derived from the chiral auxiliary (S)-2-[N—(N'-benzylprolyl)amino]benzophenone (BPB) and amino acids such as glycine or alanine are prepared as described in Belokon et al. (1998), *Tetrahedron Asymm.* 9:4249-4252. The resulting complexes are subsequently reacted with alkylating reagents comprising an azido or alkynyl moiety to yield enantiomerically enriched compounds of the invention. If desired, the resulting compounds can be protected for use in peptide synthesis.

Synthetic Scheme 2:

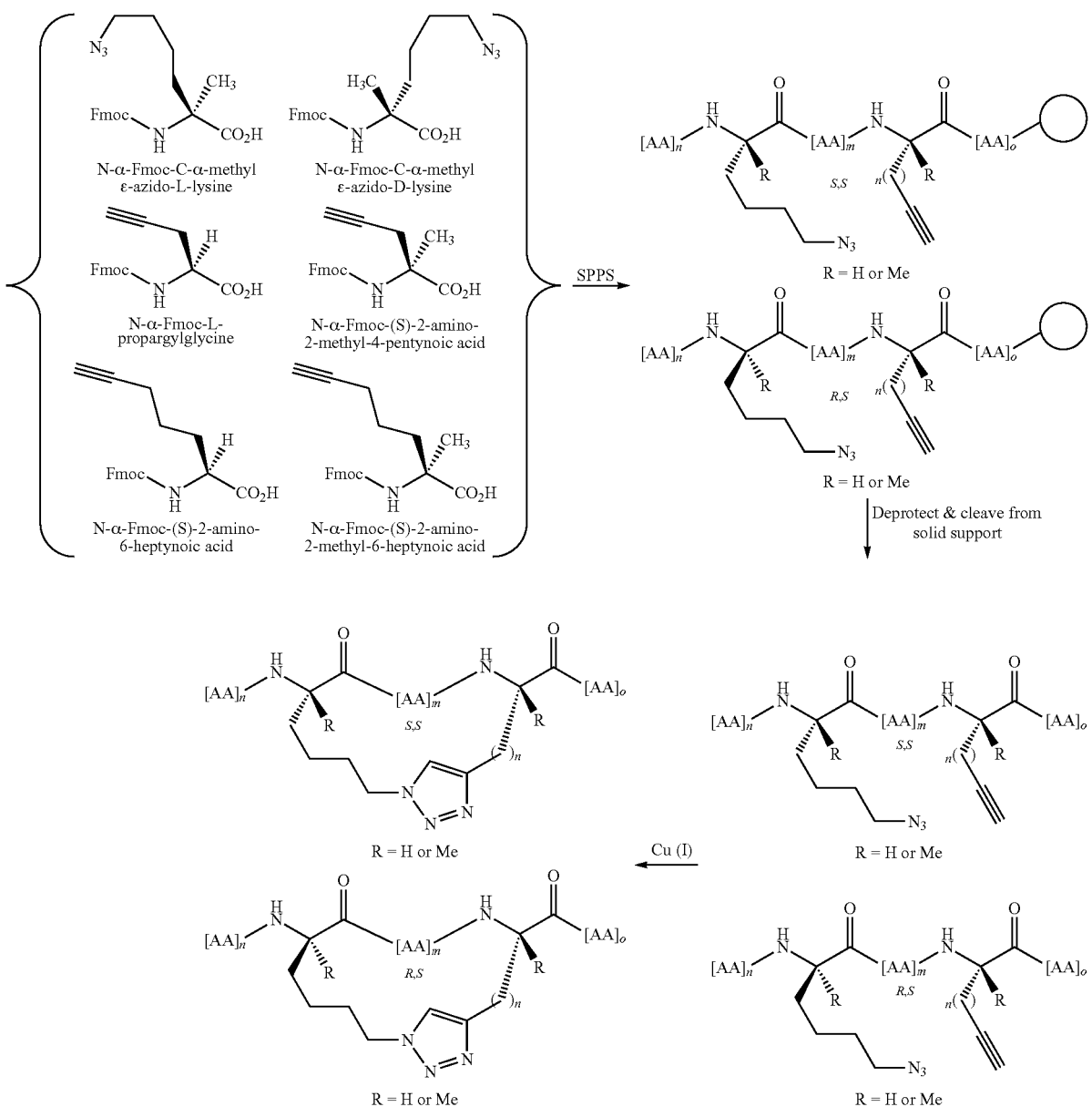

In the general method for the synthesis of peptidomimetic macrocycles shown in Synthetic Scheme 2 the peptidomimetic precursor contains an azide moiety and an alkyne moiety and is synthesized by solution-phase or solid-phase peptide synthesis (SPPS) using the commercially available amino acid N-α-Fmoc-L-propargylglycine and the N-α-Fmoc-protected forms of the amino acids (S)-2-amino-2-methyl-4-pentynoic acid, (S)-2-amino-6-heptynoic acid, (S)-2-amino-2-methyl-6-heptynoic acid, N-methyl-ε-azido-L-lysine, and N-methyl-ε-azido-D-lysine. The peptidomimetic precursor is then deprotected and cleaved from the solid-phase resin by standard conditions (e.g., strong acid such as 95% TFA). The peptidomimetic precursor is reacted as a crude mixture or is purified prior to reaction with a macrocyclization reagent such as a Cu(I) in organic or aqueous solutions (Rostovtsev et al. (2002), Angew. Chem. Int. F. 41:2596-2599; Tornoe et. (2002), J. Org. Chem. 67:3057-3064; Deiters et al. (2003), J. Am. Chem. Soc. 125:11782-11783; Punna e al. (2005), Angew. Chem. Int. Ed. 44:2215-2220). In one embodiment, the triazole forming reaction is performed under conditions that favor α-helix formation. In one embodiment, the macrocyclization step is performed in a solvent chosen from the group consisting of $H_2$, THF, $CH_3CN$, DMF, DIPEA, tBuOH or a mixture thereof. In another embodiment, the macrocyclization step is performed in DMF. In some embodiments, the macrocyclization step is performed in a buffered aqueous or partially aqueous solvent.

Synthetic Scheme 3:

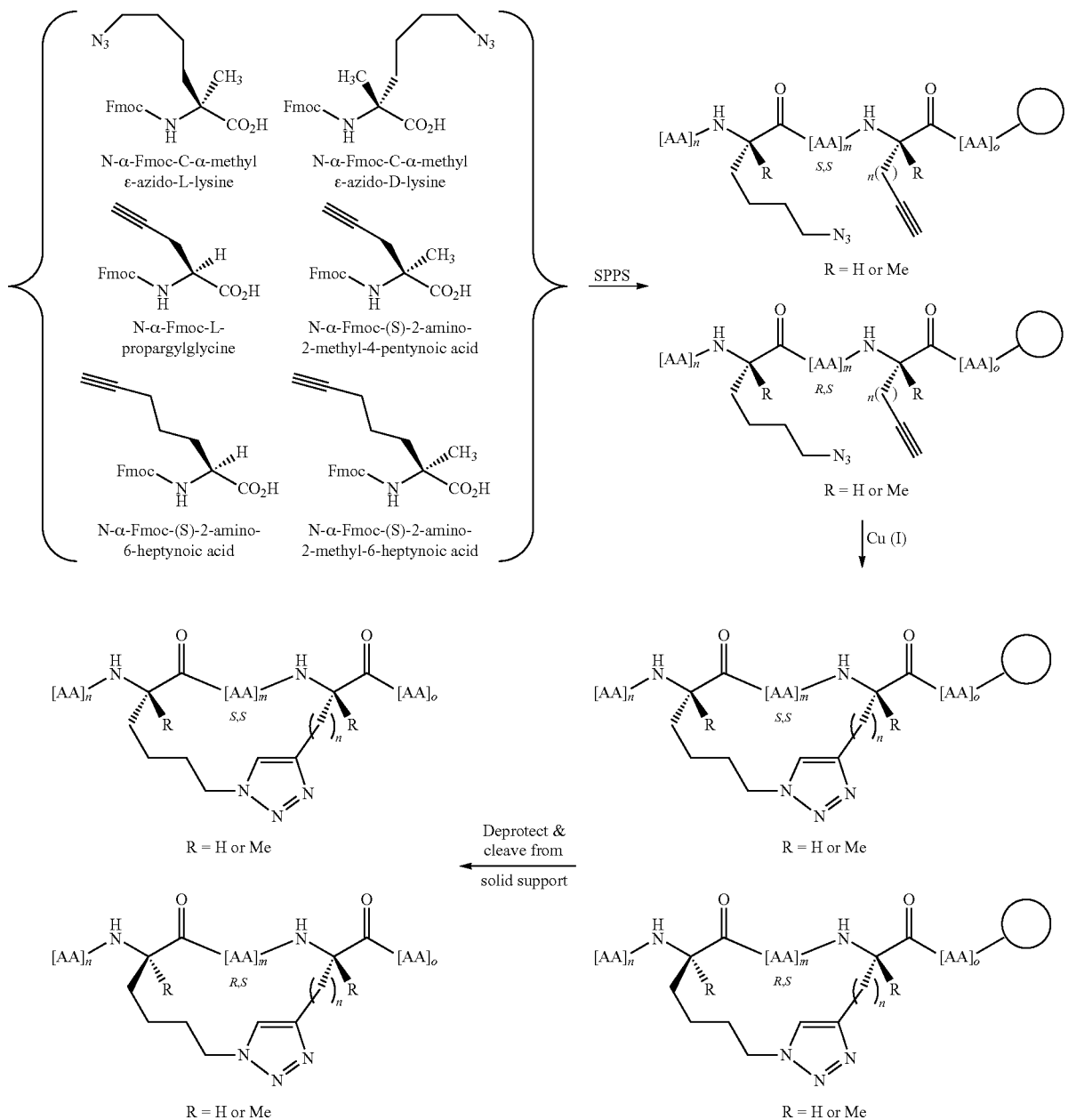

In the general method for the synthesis of peptidomimetic macrocycles shown in Synthetic Scheme 3, the peptidomimetic precursor contains an azide moiety and an alkyne moiety and is synthesized by solid-phase peptide synthesis (SPPS) using the commercially available amino acid N-α-Fmoc-L-propargylglycine and the N-α-Fmoc-protected forms of the amino acids (S)-2-amino-2-methyl-4-pentynoic acid, (S)-2-amino-6-heptynoic acid, (S)-2-amino-2-methyl-6-heptynoic acid, N-methyl-ε-azido-L-lysine, and N-methyl-ε-azido-D-lysine. The peptidomimetic precursor is reacted with a macrocyclization reagent such as a Cu(I) reagent on the resin as a crude mixture (Rostovtsev et al. (2002), *Angew. Chem. Int. Ed* 41:2596-2599; Tornoe et al. (2002), *J. Org. Chem.* 67:3057-3064; Deiters et al. (2003), *J Am. Chem. Soc.* 125:11782-11783; Punna et al. (2005), *Angew. Chem. Int. Ed* 44:2215-2220). The resultant triazole-containing peptidomimetic macrocycle is then deprotected and cleaved from the solid-phase resin by standard conditions (e.g., strong acid such as 95% TFA). In some embodiments, the macrocyclization step is performed in a solvent chosen from the group consisting of $CH_2Cl_2$, $ClCH_2CH_2Cl$, DMF, THF, NMP, DIPEA, 2,6-lutidine, pyridine, DMSO, $H_2$ or a mixture thereof. In some embodiments, the macrocyclization step is performed in a buffered aqueous or partially aqueous solvent.

Synthetic Scheme 4:

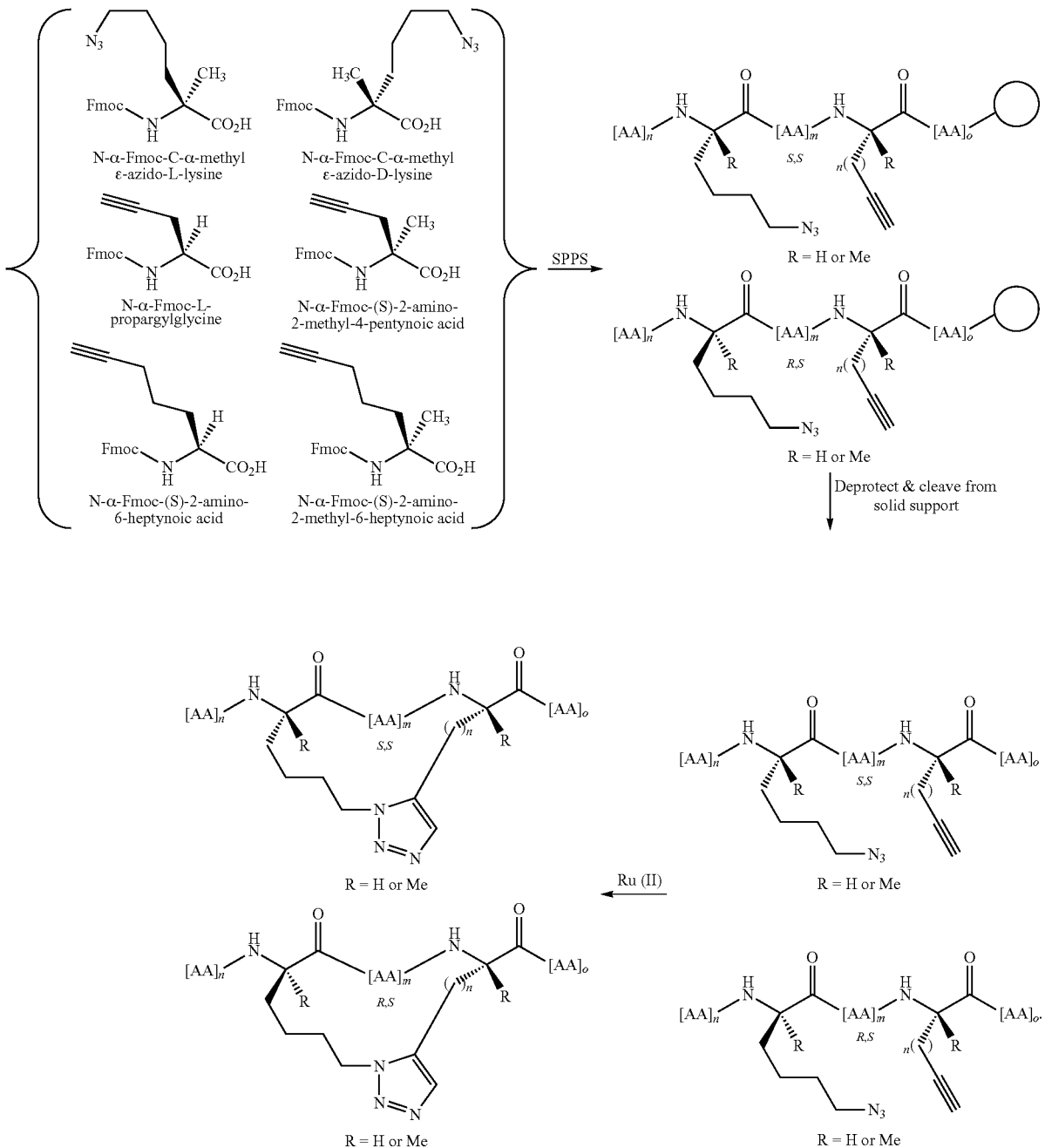

In the general method for the synthesis of peptidomimetic macrocycles shown in Synthetic Scheme 4, the peptidomimetic precursor contains an azide moiety and an alkyne moiety and is synthesized by solution-phase or solid-phase peptide synthesis (SPPS) using the commercially available amino acid N-α-Fmoc-L-propargylglycine and the N-α-Fmoc-protected forms of the amino acids (S)-2-amino-2-methyl-4-pentynoic acid, (S)-2-amino-6-heptynoic acid, (S)-2-amino-2-methyl-6-heptynoic acid, N-methyl-ε-azido-L-lysine, and N-methyl-ε-azido-D-lysine. The peptidomimetic precursor is then deprotected and cleaved from the solid-phase resin by standard conditions (e.g., strong acid such as 95% TFA). The peptidomimetic precursor is reacted as a crude mixture or is purified prior to reaction with a macrocyclization reagent such as a Ru(II) reagents, for example Cp*RuC(PPh$_3$)$_2$ or [Cp*RuCl]$_4$ (Rasmussen et al. (2007), Org. Lett. 9:5337-5339; Zhang et al. (2005) J. Am. Chem. Soc. 127:15998-15999). In some embodiments, the macrocyclization step is performed in a solvent chosen from the group consisting of DMF, CH$_3$CN and THF.

Synthetic Scheme 5:

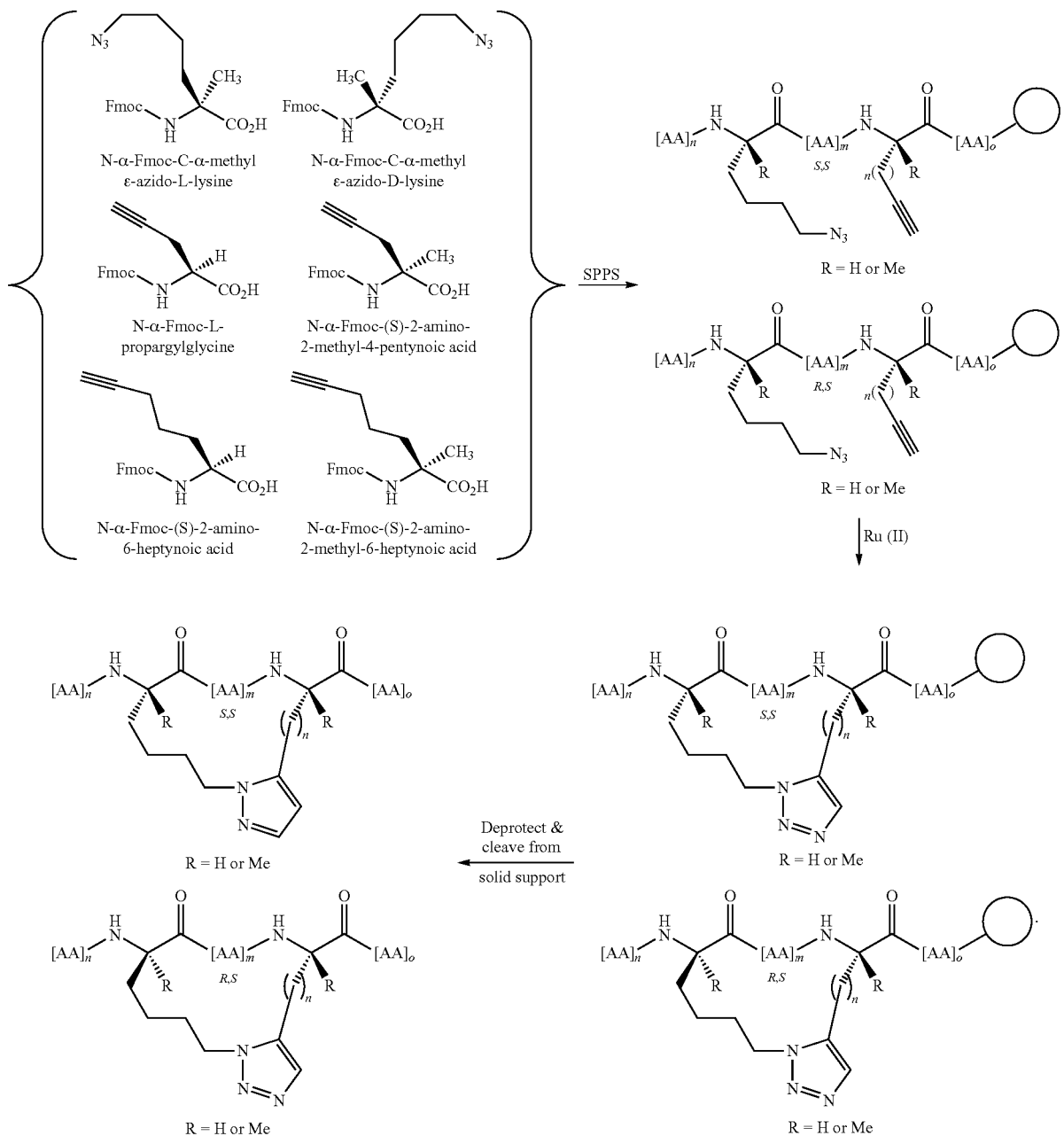

In the general method for the synthesis of peptidomimetic macrocycles shown in Synthetic Scheme 5, the peptidomimetic precursor contains an azide moiety and an alkyne moiety and is synthesized by solid-phase peptide synthesis (SPPS) using the commercially available amino acid N-α-Fmoc-L-propargylglycine and the N-α-Fmoc-protected forms of the amino acids (S)-2-amino-2-methyl-4-pentynoic acid, (S)-2-amino-6-heptynoic acid, (S)-2-amino-2-methyl-6-heptynoic acid, N-methyl-ε-azido-L-lysine, and N-methyl-ε-azido-D-lysine. The peptidomimetic precursor is reacted with a macrocyclization reagent such as a Ru(II) reagent on the resin as a crude mixture. For example, the reagent can be Cp*RuC(PPh$_3$)$_2$ or [Cp*RuCl]$_4$ (Rasmussen et al. (2007), Org. Lett. 9:5337-5339; Zhangea (2005), J. Am. Chem. Soc. 127:15998-15999). In some embodiments, the macrocyclization step is performed in a solvent chosen from the group consisting of $CH_2Cl_2$, $ClCH_2CH_2Cl$, $CH_3CN$, DMF, and THF.

In some embodiments, a peptidomimetic macrocycle of Formula I comprises a halogen group substitution on a triazole moiety, for example an iodo substitution. Such peptidomimetic macrocycles may be prepared from a precursor having the partial structure and using the cross-linking methods taught herein. Crosslinkers of any length, as described herein, may be prepared comprising such substitutions. In one embodiment, the peptidomimetic macrocycle is prepared according to the scheme shown below. The reaction is performed, for example, in the presence of CuI and an amine ligand such as TEA or TTTA. See, e.g., Hein et al. Angew. Chem., Int. Ed. 2009, 48, 8018-8021.

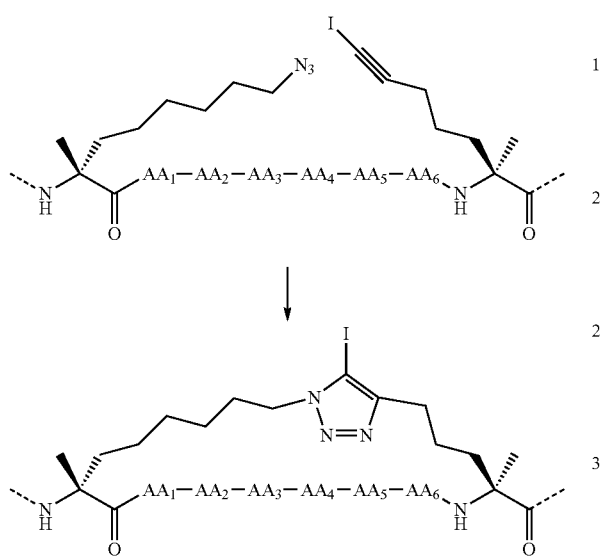

In other embodiments, an iodo-substituted triazole is generated according to the scheme shown below. For example, the second step in the reaction scheme below is performed using, for example, Cu and N-bromosuccinimide (NBS) in the presence of THF (see, e.g. Zhang et al., J. Org. Chem. 2008, 73, 3630-3633). In other embodiments, the second step in the reaction scheme shown below is performed, for example, using CuI and an iodinating agent such as ICl (see, e.g. Wu et al., Synthesis 2005, 1314-1318.)

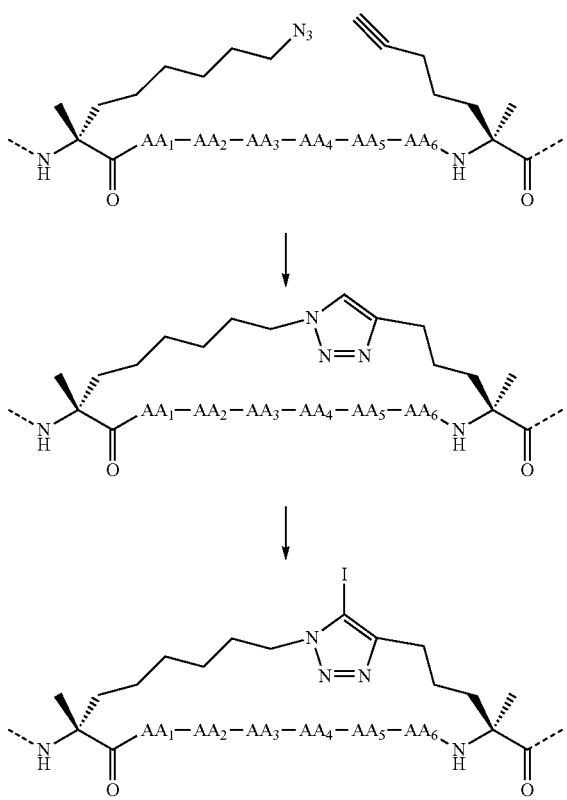

In some embodiments, an iodo-substituted triazole moiety is used in a cross-coupling reaction, such as a Suzuki or Sonogashira coupling, to afford a peptidomimetic macrocycle comprising a substituted crosslinker. Sonogashira couplings using an alkyne as shown below may be performed, for example, in the presence of a palladium catalyst such as $Pd(PPh_3)_2Cl_2$, CuI, and in the presence of a base such as triethylamine. Suzuki couplings using an arylboronic or substituted alkenyl boronic acid as shown below may be performed, for example, in the presence of a catalyst such as $Pd(PPh_3)_4$, and in the presence of a base such as $K_2CO_3$.

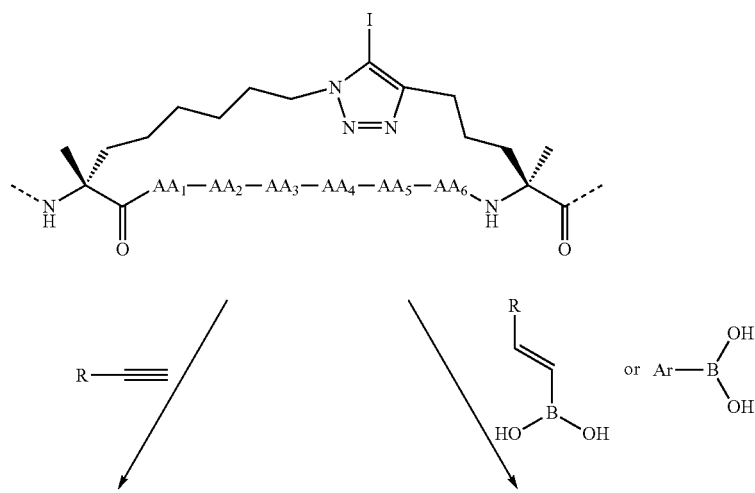

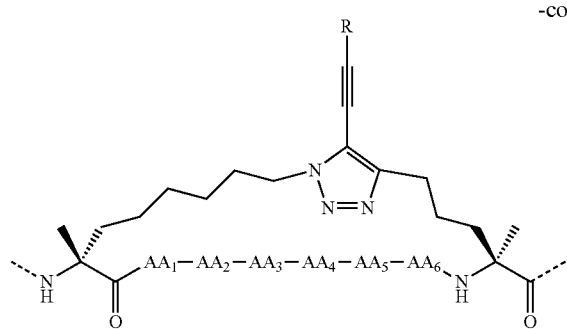

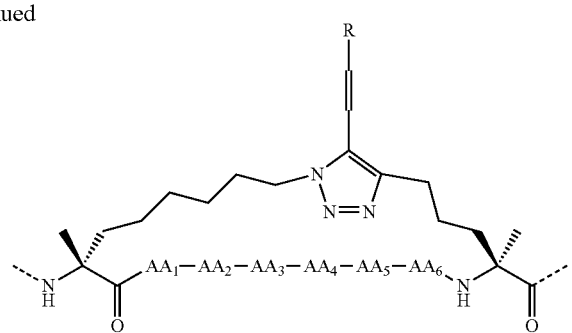

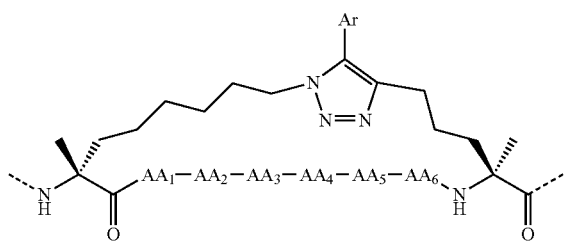

Any suitable triazole substituent groups which reacts with the iodo-substituted triazole can be used in Suzuki couplings described herein. Example triazole substituents for use in Suzuki couplings are shown below:

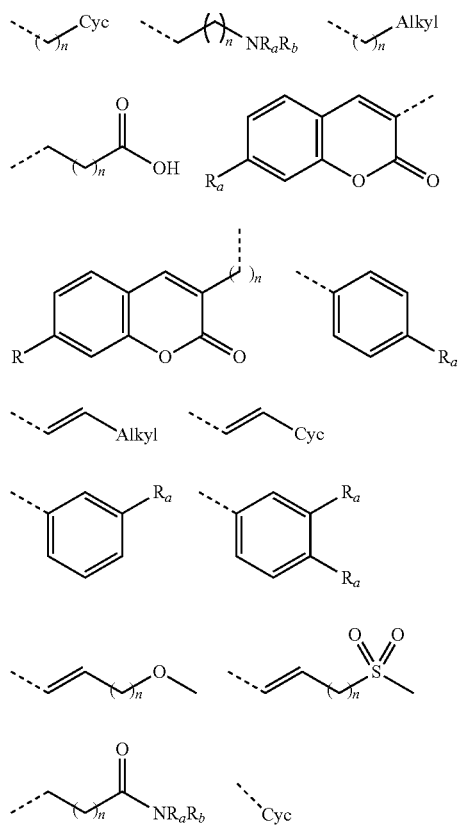

wherein "Cyc" is a suitable aryl, cycloalkyl, cycloalkenyl, heteroaryl, or heterocyclyl group, unsubstituted or optionally substituted with an $R_a$ or $R_b$ group as described below.

In some embodiments, the substituent is:

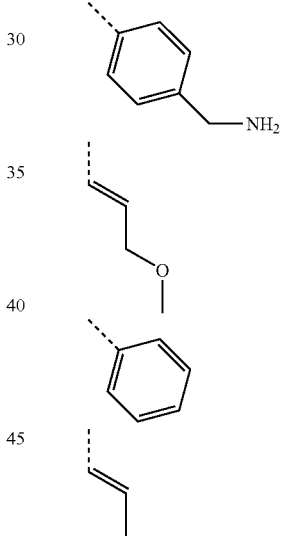

Any suitable substituent group which reacts with the iodo-substituted triazole can be used in Sonogashira couplings described herein. Example triazole substituents for use in Sonogashira couplings are shown below:

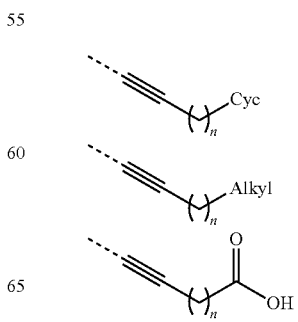

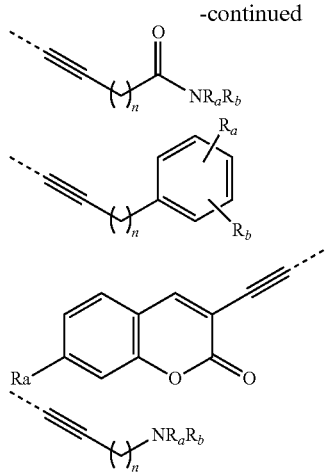

wherein "Cyc" is a suitable aryl, cycloalkyl, cycloalkenyl, heteroaryl, or heterocyclyl group, unsubstituted or optionally substituted with an $R_a$ or $R_b$ group as described below.

In some embodiments, the triazole substituent is:

In some embodiments, the Cyc group shown above is further substituted by at least one $R_a$ or $R_b$ substituent. In some embodiments, at least one of $R_a$ and $R_b$ is independently:

$R_a$ or $R_b$ = H, OCH$_3$, CF$_3$, NH$_2$, CH$_2$NH$_2$, F, Br, I

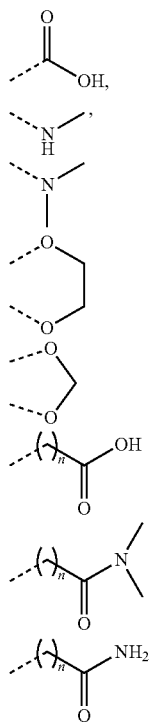

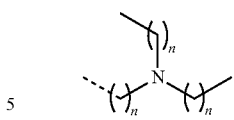

In other embodiments, the triazole substituent is

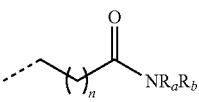

and at least one of $R_a$ and $R_b$ is alkyl (including hydrogen, methyl, or ethyl), or:

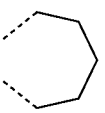

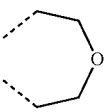

The present invention contemplates the use of non-naturally-occurring amino acids and amino acid analogs in the synthesis of the peptidomimetic macrocycles described herein. Any amino acid or amino acid analog amenable to the synthetic methods employed for the synthesis of stable triazole containing peptidomimetic macrocycles can be used in the present invention. For example, L-propargylglycine is contemplated as a useful amino acid in the present invention. However, other alkyne-containing amino acids that contain a different amino acid side chain are also useful in the invention. For example, L-propargylglycine contains one methylene unit between the α-carbon of the amino acid and the alkyne of the amino acid side chain. The invention also contemplates the use of amino acids with multiple methylene units between the α-carbon and the alkyne. Also, the azido-analogs of amino acids L-lysine, alpha-methyl-L-lysine, and alpha-methyl-D-lysine are contemplated as useful amino acids in the present invention. However, other terminal azide amino acids that contain a different amino acid side chain are also useful in the invention. For example, the azido-analog of L-lysine contains four methylene units between the α-carbon of the amino acid and the terminal azide of the amino acid side chain. The invention also contemplates the use of amino acids with fewer than or greater than four methylene units between the α-carbon and the terminal azide. Table 3 shows some amino acids useful in the preparation of peptidomimetic macrocycles disclosed herein.

TABLE 3

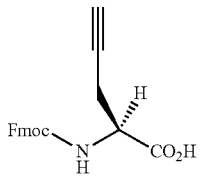

N-α-Fmoc-L-propargyl glycine

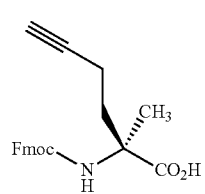

N-α-Fmoc-D-propargyl glycine

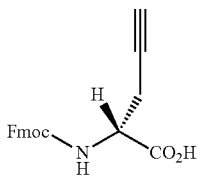

N-α-Fmoc-(S)-2-amino-2-methyl-4-pentynoic acid

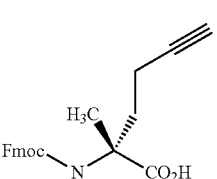

N-α-Fmoc-(R)-2-amino-2-methyl-4-pentynoic acid

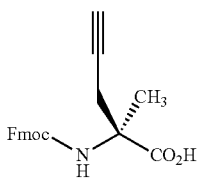

N-α-Fmoc-ε-azido-L-lysine

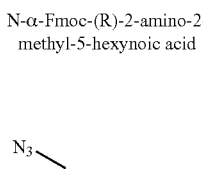

N-α-Fmoc-ε-azido-D-lysine

TABLE 3-continued

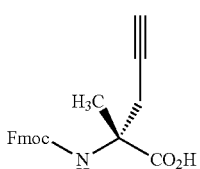

N-α-Fmoc-(S)-2-amino-2-methyl-5-hexynoic acid

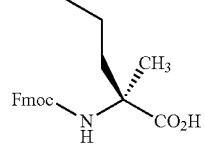

N-α-Fmoc-(R)-2-amino-2-methyl-5-hexynoic acid

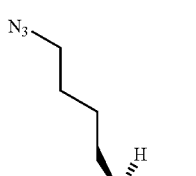

N-α-Fmoc-ε-azido-α-methyl-L-lysine

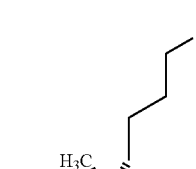

N-α-Fmoc-ε-azido-α-methyl-D-lysine

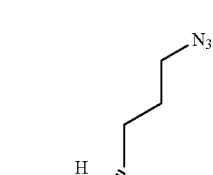

N-α-Fmoc-(S)-2-amino-2-methyl-6-heptynoic acid

TABLE 3-continued

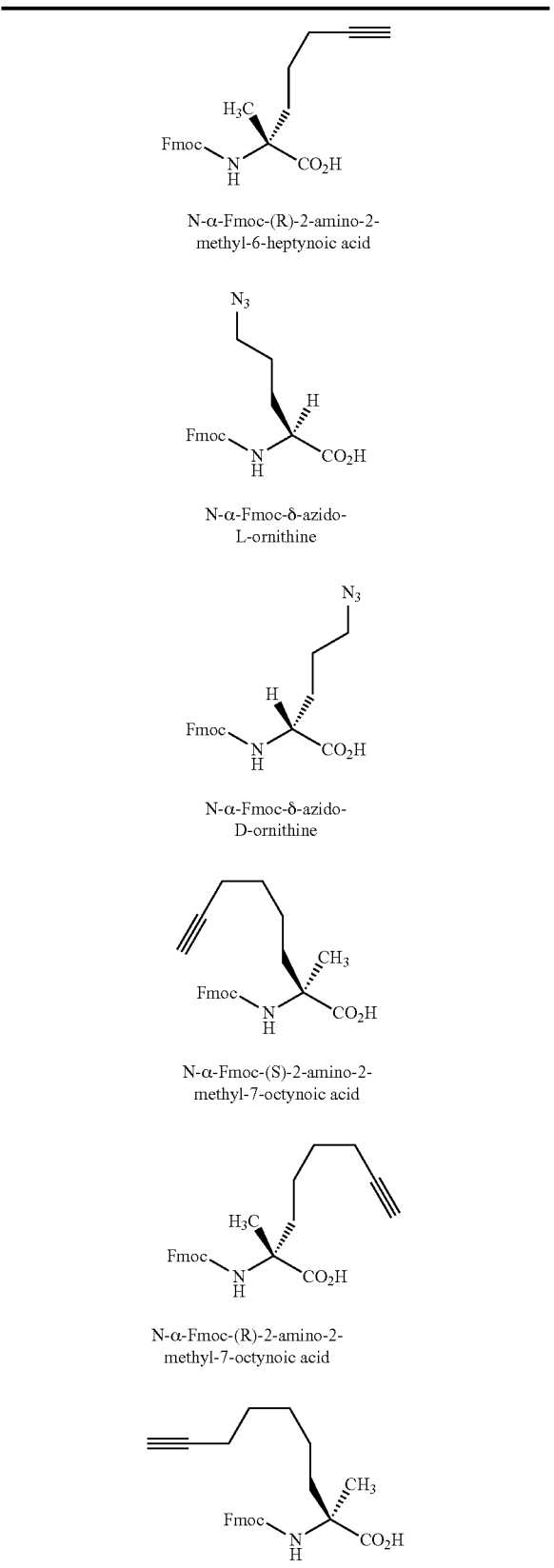

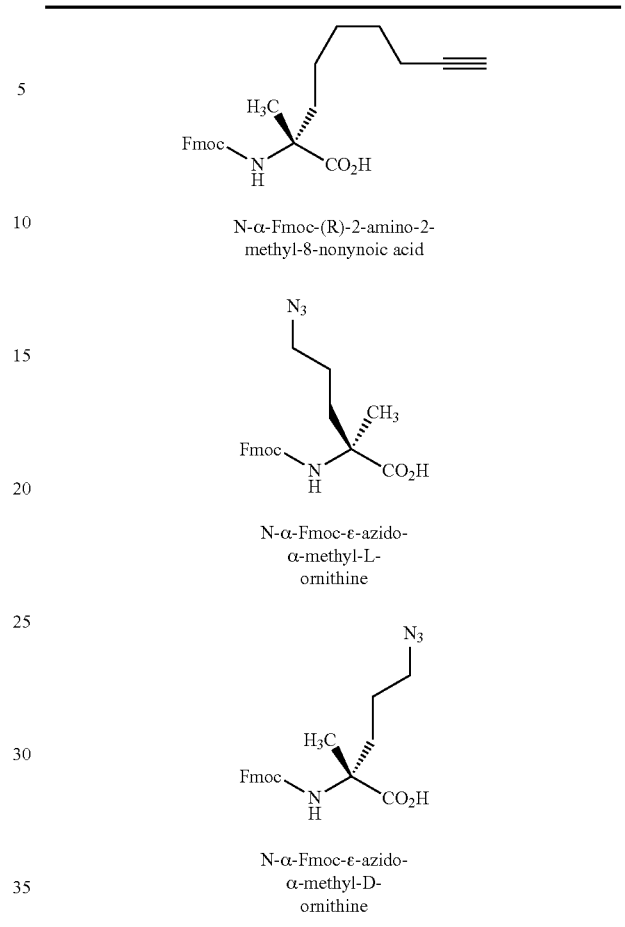

Table 3 shows exemplary amino acids useful in the preparation of peptidomimetic macrocycles disclosed herein.

In some embodiments the amino acids and amino acid analogs are of the D-configuration. In other embodiments they are of the L-configuration. In some embodiments, some of the amino acids and amino acid analogs contained in the peptidomimetic are of the D-configuration while some of the amino acids and amino acid analogs are of the L-configuration. In some embodiments the amino acid analogs are α,α-disubstituted, such as α-methyl-L-propargyglycine, α-methyl-D-propargylglycine, ε-azido-alpha-methyl-L-lysine, and ε-azido-alpha-methyl-D-lysine. In some embodiments the amino acid analogs are N-alkylated, e.g., N-methyl-L-propargyglycine, N-methyl-D-propargylglycine, N-methyl-ε-azido-L-lysine, and N-methyl-ε-azido-D-lysine.

In some embodiments, the —NH moiety of the amino acid is protected using a protecting group, including without limitation -Fmoc and -Boc. In other embodiments, the amino acid is not protected prior to synthesis of the peptidomimetic macrocycle.

Additional methods of forming peptidomimetic macrocycles which are envisioned as suitable to perform the present invention include those disclosed by Mustapa, M. Firouz Mohd et al., J. Org. Chem (2003), 68, pp. 8193-8198; Yang, Bin et al. Bioorg Med. Chem. Lett. (2004), 14, pp. 1403-1406; U.S. Pat. Nos. 5,364,851; 5,446,128; 5,824,483; 6,713,280; and 7,202,332. In such embodiments, amino acid precursors are used containing an additional substituent R— at the alpha position. Such amino acids are incorporated into the macrcycle precursor at the desired positions, which may be at the positions where the crosslinker is substituted or, alternatively, elsewhere in the sequence of the macrocycle precursor. Cyclization of the precursor is then performed according to the indicated method.

For example, a peptidomimetic macrocycle of Formula (II) is prepared as indicated:

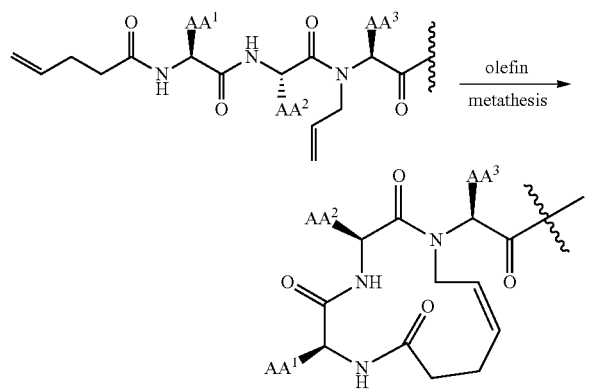

wherein each $AA_1$, $AA_2$, $AA_3$ is independently an amino acid side chain.

In other embodiments, a peptidomimetic macrocycle of Formula (II) is prepared as indicated:

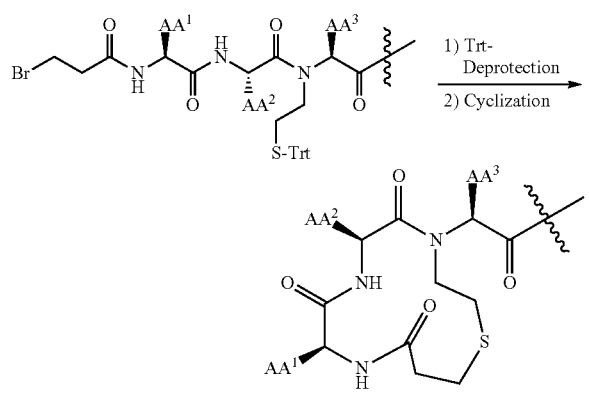

wherein each $AA_1$, $AA_2$, $AA_3$ is independently an amino acid side chain.

In some embodiments, a peptidomimetic macrocycle is obtained in more than one isomer, for example due to the configuration of a double bond within the structure of the crosslinker (E vs Z). Such isomers can or can not be separable by conventional chromatographic methods. In some embodiments, one isomer has improved biological properties relative to the other isomer. In one embodiment, an E crosslinker olefin isomer of a peptidomimetic macrocycle has better solubility, better target affinity, better in vivo or in vitro efficacy, higher helicity, or improved cell permeability relative to its Z counterpart. In another embodiment, a Z crosslinker olefin isomer of a peptidomimetic macrocycle has better solubility, better target affinity, better in vivo or in vitro efficacy, higher helicity, or improved cell permeability relative to its E counterpart.

Assays

The properties of the peptidomimetic macrocycles of the invention are assayed, for example, by using the methods described below. In some embodiments, a peptidomimetic macrocycle of the invention has improved biological properties relative to a corresponding polypeptide lacking the substituents described herein.

Assay to Determine α-Helicity.

In solution, the secondary structure of polypeptides with α-helical domains will reach a dynamic equilibrium between random coil structures and α-helical structures, often expressed as a "percent helicity". Thus, for example, alpha-helical domains are predominantly random coils in solution, with α-helical content usually under 25%. Peptidomimetic macrocycles with optimized linkers, on the other hand, possess, for example, an alpha-helicity that is at least two-fold greater than that of a corresponding uncrosslinked polypeptide. In some embodiments, macrocycles of the invention will possess an alpha-helicity of greater than 50%. To assay the helicity of peptidomimetic macrocycles of the invention, the compounds are dissolved in an aqueous solution (e.g. 50 mM potassium phosphate solution at pH 7, or distilled $H_2O$, to concentrations of 25-50 μM). Circular dichroism (CD) spectra are obtained on a spectropolarimeter (e.g., Jasco J-710) using standard measurement parameters (e.g. temperature, 20° C.; wavelength, 190-260 nm; step resolution, 0.5 nm; speed, 20 nm/sec; accumulations, 10; response, 1 sec; bandwidth, 1 nm; path length, 0.1 cm). The α-helical content of each peptide is calculated by dividing the mean residue ellipticity (e.g. [Φ]222obs) by the reported value for a model helical decapeptide (Yang et al. (1986), *Methods Enzymol.* 130:208)).

Assay to Determine Melting Temperature (Tm).

A peptidomimetic macrocycle of the invention comprising a secondary structure such as an α-helix exhibits, for example, a higher melting temperature than a corresponding uncrosslinked polypeptide. Typically peptidomimetic macrocycles of the invention exhibit Tm of >60° C. representing a highly stable structure in aqueous solutions. To assay the effect of macrocycle formation on melting temperature, peptidomimetic macrocycles or unmodified peptides are dissolved in distilled $H_2$ (e.g. at a final concentration of 50 μM) and the Tm is determined by measuring the change in ellipticity over a temperature range (e.g. 4 to 95° C.) on a spectropolarimeter (e.g., Jasco J-710) using standard parameters (e.g. wavelength 222 nm; step resolution, 0.5 nm; speed, 20 nm/sec; accumulations, 10; response, 1 sec; bandwidth, 1 nm; temperature increase rate: 1° C./min; path length, 0.1 cm).

Protease Resistance Assay.

The amide bond of the peptide backbone is susceptible to hydrolysis by proteases, thereby rendering peptidic compounds vulnerable to rapid degradation in vivo. Peptide helix formation, however, typically buries the amide backbone and therefore may shield it from proteolytic cleavage. The peptidomimetic macrocycles of the present invention may be subjected to in vitro trypsin proteolysis to assess for any change in degradation rate compared to a corresponding uncrosslinked polypeptide. For example, the peptidomimetic macrocycle and a corresponding uncrosslinked polypeptide are incubated with trypsin agarose and the reactions quenched at various time points by centrifugation and subsequent HPLC injection to quantitate the residual substrate by ultraviolet absorption at 280 nm. Briefly, the peptidomimetic macrocycle and peptidomimetic precursor (5 mcg) are incubated with trypsin agarose (Pierce) (S/E~125) for 0, 10, 20, 90, and 180 minutes. Reactions are quenched by tabletop centrifugation at high speed; remaining substrate in the isolated supernatant is quantified by IPLC-based peak detection at 280 nm. The proteolytic reaction displays first order kinetics and the rate constant, k, is determined from a plot of ln[S] versus time (k=−1×slope).

Ex Vivo Stability Assay.

Peptidomimetic macrocycles with optimized linkers possess, for example, an ex vivo half-life that is at least two-fold greater than that of a corresponding uncrosslinked polypeptide, and possess an ex vivo half-life of 12 hours or more. For ex vivo serum stability studies, a variety of assays may be used. For example, a peptidomimetic macrocycle and a corresponding uncrosslinked polypeptide (2 mcg) are incubated with fresh mouse, rat and/or human serum (2 mL) at 37° C. for 0, 1, 2, 4, 8, and 24 hours. To determine the level of intact compound, the following procedure may be used: The samples are extracted by transferring 100 μl of sera to 2 ml centrifuge tubes followed by the addition of 10 μL of 50 formic acid and 500 μL acetonitrile and centrifugation at 14,000 RPM for 10 min at 4±2° C. The supernatants are then transferred to fresh 2 ml tubes and evaporated on Turbovap under $N_2$<10 psi, 37° C. The samples are reconstituted in 100 μL of 50:50 acetonitrile:water and submitted to LC-MS/MS analysis.

In Vitro Binding Assays.

To assess the binding and affinity of peptidomimetic macrocycles and peptidomimetic precursors to acceptor proteins, a fluorescence polarization assay (FPA) is used, for example. The FPA technique measures the molecular orientation and mobility using polarized light and fluorescent tracer. When excited with polarized light, fluorescent tracers (e.g., FITC) attached to molecules with high apparent molecular weights (e.g. FITC-labeled peptides bound to a large protein) emit higher levels of polarized fluorescence due to their slower rates of rotation as compared to fluorescent tracers attached to smaller molecules (e.g. FITC-labeled peptides that are free in solution).

For example, fluoresceinated peptidomimetic macrocycles (25 nM) are incubated with the acceptor protein (25-1000 nM) in binding buffer (140 mM NaCl, 50 mM Tris-HCL, pH 7.4) for 30 minutes at room temperature. Binding activity is measured, for example, by fluorescence polarization on a luminescence spectrophotometer (e.g. Perkin-Elmer LS50B). Kd values may be determined by nonlinear regression analysis using, for example, Graphpad Prism software (GraphPad Software, Inc., San Diego, Calif.). A peptidomimetic macrocycle of the invention shows, in some instances, similar or lower Kd than a corresponding uncrosslinked polypeptide.

In Vitro Displacement Assays to Characterize Antagonists of Peptide-Protein Interactions.

To assess the binding and affinity of compounds that antagonize the interaction between a peptide and an acceptor protein, a fluorescence polarization assay (FPA) utilizing a fluoresceinated peptidomimetic macrocycle derived from a peptidomimetic precursor sequence is used, for example. The FPA technique measures the molecular orientation and mobility using polarized light and fluorescent tracer. When excited with polarized light, fluorescent tracers (e.g., FITC) attached to molecules with high apparent molecular weights (e.g. FITC-labeled peptides bound to a large protein) emit higher levels of polarized fluorescence due to their slower rates of rotation as compared to fluorescent tracers attached to smaller molecules (e.g. FITC-labeled peptides that are free in solution). A compound that antagonizes the interaction between the fluoresceinated peptidomimetic macrocycle and an acceptor protein will be detected in a competitive binding FPA experiment.

For example, putative antagonist compounds (1 nM to 1 mM) and a fluoresceinated peptidomimetic macrocycle (25 nM) are incubated with the acceptor protein (50 nM) in binding buffer (140 mM NaCl, 50 mM Tris-HCL, pH 7.4) for 30 minutes at room temperature. Antagonist binding activity is measured, for example, by fluorescence polarization on a luminescence spectrophotometer (e.g. Perkin-Elmer LS50B). Kd values may be determined by nonlinear regression analysis using, for example, Graphpad Prism software (GraphPad Software, Inc., San Diego, Calif.).

Any class of molecule, such as small organic molecules, peptides, oligonucleotides or proteins can be examined as putative antagonists in this assay.

Assay for Protein-Ligand Binding by Affinity Selection-Mass Spectrometry

To assess the binding and affinity of test compounds for proteins, an affinity-selection mass spectrometry assay is used, for example. Protein-ligand binding experiments are conducted according to the following representative procedure outlined for a system-wide control experiment using 1 μM peptidomimetic macrocycle plus 5 μM target protein. A 1 μL DMSO aliquot of a 40 μM stock solution of peptidomimetic macrocycle is dissolved in 19 μL of PBS (Phosphate-buffered saline: 50 mM, pH 7.5 Phosphate buffer containing 150 mM NaCl). The resulting solution is mixed by repeated pipetting and clarified by centrifugation at 10 000 g for 10 min. To a 4 μL aliquot of the resulting supernatant is added 4 μL of 10 μM target protein in PBS. Each 8.0 μL experimental sample thus contains 40 pmol (1.5 μg) of protein at 5.0 μM concentration in PBS plus 1 μM peptidomimetic macrocycle and 2.5% DMSO. Duplicate samples thus prepared for each concentration point are incubated for 60 min at room temperature, and then chilled to 4° C. prior to size-exclusion chromatography-LC-MS analysis of 5.0 μL injections. Samples containing a target protein, protein-ligand complexes, and unbound compounds are injected onto an SEC column, where the complexes are separated from non-binding component by a rapid SEC step. The SEC column eluate is monitored using UV detectors to confirm that the early-eluting protein fraction, which elutes in the void volume of the SEC column, is well resolved from unbound components that are retained on the column. After the peak containing the protein and protein-ligand complexes elutes from the primary UV detector, it enters a sample loop where it is excised from the flow stream of the SEC stage and transferred directly to the LC-MS via a valving mechanism. The $(M+3H)^{3+}$ ion of the peptidomimetic macrocycle is observed by ESI-MS at the expected m/z, confirming the detection of the protein-ligand complex.

Assay for Protein-Ligand Kd Titration Experiments.

To assess the binding and affinity of test compounds for proteins, a protein-ligand Kd titration experiment is performed. Protein-ligand $K_d$ titrations experiments are conducted as follows: 2 μL DMSO aliquots of a serially diluted stock solution of titrant peptidomimetic macrocycle (5, 2.5, . . . , 0.098 mM) are prepared then dissolved in 38 μL of PBS. The resulting solutions are mixed by repeated pipetting and clarified by centrifugation at 10 000 g for 10 min. To 4.0 μL aliquots of the resulting supernatants is added 4.0 μL of 10 μM target protein in PBS. Each 8.0 μL experimental sample thus contains 40 pmol (1.5 μg) of protein at 5.0 μM concentration in PBS, varying concentrations (125, 62.5, . . . , 0.24 μM) of the titrant peptide, and 2.5% DMSO. Duplicate samples thus prepared for each concentration point are incubated at room temperature for 30 min, then chilled to 4° C. prior to SEC-LC-MS analysis of 2.0 µL injections. The $(M+H)^{1+}$, $(M+2H)^{2+}$, $(M+3H)^{3+}$, and/or $(M+Na)^{1+}$ ion is observed by ESI-MS; extracted ion chromatograms are quantified, then fit to equations to derive the binding affinity $K_d$ as described in "*A General Technique to Rank Protein-Ligand Binding Affinities and Determine Allosteric vs. Direct Binding Site Competition in Compound Mixtures*." Annis, D. A.; Nazef, N.; Chuang, C. C.; Scott, M. P.; Nash, H. M. *J. Am. Chem. Soc.* 2004, 126, 15495-15503; also in "*ALIS: An Affinity Selection-Mass Spectrometry System for the Discovery and Characterization of Protein-Ligand Interactions*" D. A. Annis, C.-C. Chuang, and N. Nazef. In Mass Spectrometry in Medicinal Chemistry. Edited by Wanner K, Höfner G: Wiley-VCH; 2007:121-184. Mannhold R, Kubinyi H, Folkers G (Series Editors): Methods and Principles in Medicinal Chemistry.

Assay for Competitive Binding Experiments by Affinity Selection-Mass Spectrometry To determine the ability of test compounds to bind competitively to proteins, an affinity selection mass spectrometry assay is performed, for example. A mixture of ligands at 40 µM per component is prepared by combining 2 µL aliquots of 400 µM stocks of each of the three compounds with 14 µL of DMSO. Then, 1 µL aliquots of this 40 µM per component mixture are combined with 1 µL DMSO aliquots of a serially diluted stock solution of titrant peptidomimetic macrocycle (10, 5, 2.5, . . . , 0.078 mM). These 2 µL samples are dissolved in 38 µL of PBS. The resulting solutions were mixed by repeated pipetting and clarified by centrifugation at 10 000 g for 10 min. To 4.0 µL aliquots of the resulting supernatants is added 4.0 µL of 10 µM target protein in PBS. Each 8.0 µL experimental sample thus contains 40 pmol (1.5 µg) of protein at 5.0 µM concentration in PBS plus 0.5 M ligand, 2.5% DMSO, and varying concentrations (125, 62.5, . . . , 0.98 M) of the titrant peptidomimetic macrocycle. Duplicate samples thus prepared for each concentration point are incubated at room temperature for 60 min, then chilled to 4° C. prior to SEC-LC-MS analysis of 2.0 µL injections. Additional details on these and other methods are provided in "*A General Technique to Rank Protein-Ligand Binding Affinities and Determine Allosteric vs. Direct Binding Site Competition in Compound Mixtures*." Annis, D. A.; Nazef, N.; Chuang, C. C.; Scott, M. P.; Nash, H. M. *J. Am. Chem. Soc.* 2004, 126, 15495-15503; also in "*ALIS: An Affinity Selection-Mass Spectrometry System for the Discovery and Characterization of Protein-Ligand Interactions*" D. A. Annis, C.-C. Chuang, and N. Nazef. In Mass Spectrometry in Medicinal Chemistry. Edited by Wanner K, Hofner G: Wiley-VCH; 2007:121-184. Mannhold R, Kubinyi H, Folkers G (Series Editors): Methods and Principles in Medicinal Chemistry.

Binding Assays in Intact Cells.

It is possible to measure binding of peptides or peptidomimetic macrocycles to their natural acceptors in intact cells by immunoprecipitation experiments. For example, intact cells are incubated with fluoresceinated (FITC-labeled) compounds for 4 hrs in the absence of serum, followed by serum replacement and further incubation that ranges from 4-18 hrs. Cells are then pelleted and incubated in lysis buffer (50 mM Tris [pH 7.6], 150 mM NaCl, 1% CHAPS and protease inhibitor cocktail) for 10 minutes at 4° C. Extracts are centrifuged at 14,000 rpm for 15 minutes and supernatants collected and incubated with 10 µl goat anti-FITC antibody for 2 hrs, rotating at 4° C. followed by further 2 hrs incubation at 4° C. with protein A/G Sepharose (50 µl of 50% bead slurry). After quick centrifugation, the pellets are washed in lysis buffer containing increasing salt concentration (e.g., 150, 300, 500 mM). The beads are then re-equilibrated at 150 mM NaCl before addition of SDS-containing sample buffer and boiling. After centrifugation, the supernatants are optionally electrophoresed using 4%-12% gradient Bis-Tris gels followed by transfer into Immobilon-P membranes. After blocking, blots are optionally incubated with an antibody that detects FITC and also with one or more antibodies that detect proteins that bind to the peptidomimetic macrocycle.

Cellular Penetrability Assays.

To measure the cell penetrability of peptidomimetic macrocycles and corresponding uncrosslinked macrocycle intact cells are incubated with fluoresceinated peptidomimetic macrocycles or corresponding uncrosslinked macrocycle (10 µM) for 4 hrs in serum free media at 37° C., washed twice with media and incubated with trypsin (0.25%) for 10 min at 37° C. The cells are washed again and resuspended in PBS. Cellular fluorescence is analyzed, for example, by using either a FACSCalibur flow cytometer or Cellomics' KineticScan® HCS Reader.

In Vivo Stability Assay.

To investigate the in vivo stability of the peptidomimetic macrocycles, the compounds are, for example, administered to mice and/or rats by IV, IP, PO or inhalation routes at concentrations ranging from 0.1 to 50 mg/kg and blood specimens withdrawn at 0', 5', 15', 30', 1 hr, 4 hrs, 8 hrs and 24 hours post-injection. Levels of intact compound in 25 µL of fresh serum are then measured by LC-MS/MS as above.

Clinical Trials.

To determine the suitability of the peptidomimetic macrocycles of the invention for treatment of humans, clinical trials are performed. For example, patients diagnosed with a muscle wasting disease or lipodystrophy and in need of treatment are selected and separated in treatment and one or more control groups, wherein the treatment group is administered a peptidomimetic macrcycle of the invention, while the control groups receive a placebo or a known HIF drug. The treatment safety and efficacy of the peptidomimetic macrocycles of the invention can thus be evaluated by performing comparisons of the patient groups with respect to factors such as survival and quality-of-life. In this example, the patient group treated with a peptidomimetic macrocycle show improved long-term survival compared to a patient control group treated with a placebo.

Pharmaceutical Compositions and Routes of Administration

In some embodiments, the present invention provides a pharmaceutical composition comprising a peptidomimetic macrcycle of the invention and a pharmaceutically acceptable carrier.

The peptidomimetic macrocycles of the invention also include pharmaceutically acceptable derivatives or prodrugs thereof. A "pharmaceutically acceptable derivative" means any pharmaceutically acceptable salt, ester, salt of an ester, pro-drug or other derivative of a compound of this invention which, upon administration to a recipient, is capable of providing (directly or indirectly) a compound of this invention. Particularly favored pharmaceutically acceptable derivatives are those that increase the bioavailability of the compounds of the invention when administered to a mammal (e.g., by increasing absorption into the blood of an orally administered compound) or which increases delivery of the active compound to a biological compartment (e.g., the brain or lymphatic system) relative to the parent species. Some pharmaceutically acceptable derivatives include a chemical group which increases aqueous solubility or active transport across the gastrointestinal mucosa.

In some embodiments, the peptidomimetic macrocycles of the invention are modified by covalently or non-covalently joining appropriate functional groups to enhance selective biological properties. Such modifications include those which increase biological penetration into a given biological compartment (e.g., blood, lymphatic system, central nervous system), increase oral availability, increase solubility to allow administration by injection, alter metabolism, and alter rate of excretion.

Pharmaceutically acceptable salts of the compounds of this invention include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate nitrate, palmoate, phosphate, picrate, pivalate, propionate, salicylate, succinate, sulfate, tartrate, tosylate and undecanoate. Salts derived from appropriate bases include alkali metal (e.g., sodium), alkaline earth metal (e.g., magnesium), ammonium and N-(alkyl)$_4^+$ salts.

For preparing pharmaceutical compositions from the compounds of the present invention, pharmaceutically acceptable carriers include either solid or liquid carriers. Solid form preparations include powders, tablets, pills, capsules, cachets, suppositories, and dispersible granules. A solid carrier can be one or more substances, which also acts as diluents, flavoring agents, binders, preservatives, tablet disintegrating agents, or an encapsulating material. Details on techniques for formulation and administration are well described in the scientific and patent literature, see, e.g., the latest edition of *Remington's Pharmaceutical Sciences*, Maack Publishing Co, Easton Pa.

In powders, the carrier is a finely divided solid, which is in a mixture with the finely divided active component. In tablets, the active component is mixed with the carrier having the necessary binding properties in suitable proportions and compacted in the shape and size desired.

Suitable solid excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents are added, such as the cross-linked polyvinyl pyrrolidone, agar, alginic acid, or a salt thereof, such as sodium alginate.

Liquid form preparations include solutions, suspensions, and emulsions, for example, water or water/propylene glycol solutions. For parenteral injection, liquid preparations can be formulated in solution in aqueous polyethylene glycol solution.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

When the compositions of this invention comprise a combination of a peptidomimetic macrocycle and one or more additional therapeutic or prophylactic agents, both the compound and the additional agent should be present at dosage levels of between about 1 to 100%, and more preferably between about 5 to 95% of the dosage normally administered in a monotherapy regimen. In some embodiments, the additional agents are administered separately, as part of a multiple dose regimen, from the compounds of this invention. Alternatively, those agents are part of a single dosage form, mixed together with the compounds of this invention in a single composition.

In some embodiments, the compositions are present as unit dosage forms that can deliver, for example, from about 0.0001 mg to about 1,000 mg of the peptidomimetic macrocycles, salts thereof, prodrugs thereof, derivatives thereof, or any combination of these. Thus, the unit dosage forms can deliver, for example, in some embodiments, from about 1 mg to about 900 mg, from about 1 mg to about 800 mg, from about 1 mg to about 700 mg, from about 1 mg to about 600 mg, from about 1 mg to about 500 mg, from about 1 mg to about 400 mg, from about 1 mg to about 300 mg, from about 1 mg to about 200 mg, from about 1 mg to about 100 mg, from about 1 mg to about 10 mg, from about 1 mg to about 5 mg, from about 0.1 mg to about 10 mg, from about 0.1 mg to about 5 mg, from about 10 mg to about 1,000 mg, from about 50 mg to about 1,000 mg, from about 100 mg to about 1,000 mg, from about 200 mg to about 1,000 mg, from about 300 mg to about 1000 mg, from about 400 mg to about 1,000 mg, from about 500 mg to about 1,000 mg, from about 600 mg to about 1,000 mg, from about 700 mg to about 1,000 mg, from about 800 mg to about 1,000 mg, from about 900 mg to about 1,000 mg, from about 10 mg to about 900 mg, from about 100 mg to about 800 mg, from about 200 mg to about 700 mg, or from about 300 mg to about 600 mg of the peptidomimetic macrocycles, salts thereof, prodrugs thereof, derivatives thereof, or any combination of these.

In some embodiments, the compositions are present as unit dosage forms that can deliver, for example, about 1 mg, about 2 mg, about 3 mg, about 4 mg, about 5 mg, about 6 mg, about 7 mg, about 8 mg, about 9 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 350 mg, about 400 mg, about 500 mg, about 600 mg, about 700 mg, about 800 mg, or about 800 mg of peptidomimetic macrocycles, salts thereof, prodrugs thereof, derivatives thereof, or any combination of these.

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a composition as described herein is administered in a local rather than systemic manner, for example, via injection of the compound directly into an organ. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

In another embodiment, compositions described herein are formulated for oral administration. Compositions described herein are formulated by combining a peptidomimetic macrocycle with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the peptidomimetic macrocycles described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methyl cellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the peptidomimetic macrocycles described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the peptidomimetic macrocycles described herein are formulated for buccal or sublingual administration. Formulations suitable for buccal or sublingual administration include, by way of example only, tablets, lozenges, or gels. In still other embodiments, the peptidomimetic macrocycles described herein are formulated for parenteral injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, pharmaceutical compositions are formulated in a form suitable for parenteral injection as a sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

Pharmaceutical compositions herein can be administered, for example, once or twice or three or four or five or six times per day, or once or twice or three or four or five or six times per week, and can be administered, for example, for a day, a week, a month, 3 months, six months, a year, five years, or for example ten years.

METHODS OF USE

In one aspect, the present invention provides novel peptidomimetic macrocycles that are useful in competitive binding assays to identify agents which bind to the natural ligand(s) of the proteins or peptides upon which the peptidomimetic macrocycles are modeled. For example, in the HIF1α/CBPp300 system, labeled peptidomimetic macrocycles based on HIF1α can be used in a CBP/p300 binding assay along with small molecules that competitively bind to CBP/p300. Competitive binding studies allow for rapid in vitro evaluation and determination of drug candidates specific for the HIF1α/CBP/p300 system. Such binding studies may be performed with any of the peptidomimetic macrocycles disclosed herein and their binding partners.

The invention further provides for the generation of antibodies against the peptidomimetic macrocycles. In some embodiments, these antibodies specifically bind both the peptidomimetic macrocycle and the precursor peptides, such as HIF1α, to which the peptidomimetic macrocycles are related. Such antibodies, for example, disrupt the native protein-protein interaction, for example, binding between HIF1α and CBP/p300.

In other aspects, the present invention provides for both prophylactic and therapeutic methods of treating a subject at risk of (or susceptible to) a disorder or having a disorder associated with aberrant (e.g., insufficient or excessive) expression or activity of the molecules including HIF-family proteins, such as HIF1α.

In another embodiment, a disorder is caused, at least in part, by an abnormal level of HIF1α, (e.g. over or under expression), or by the presence of HIF1α exhibiting abnormal activity. As such, the reduction in the level and/or activity of HIF1α, or the enhancement of the level and/or activity of HIF1α, by peptidomimetic macrocycles derived from HIF1α, is used, for example, to ameliorate or reduce the adverse symptoms of the disorder.

In another aspect, the present invention provides methods for treating or preventing a disease including hyperproliferative disease and inflammatory disorder by interfering with the interaction or binding between binding partners, for example, between HIF1α and CBP/p300. These methods comprise administering an effective amount of a compound of the invention to a warm blooded animal, including a human. In some embodiments, the administration of the compounds of the present invention induces cell growth arrest or apoptosis.

As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease.

In some embodiments, the peptidomimetic macrocycles of the invention is used to treat, prevent, and/or diagnose cancers and neoplastic conditions. As used herein, the terms "cancer", "hyperproliferative" and "neoplastic" refer to cells having the capacity for autonomous growth i.e. an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. A metastatic tumor can arise from a multitude of primary tumor types, including but not limited to those of breast, lung, liver, colon and ovarian origin. "Pathologic hyperproliferative" cells occur in disease states characterized by malignant tumor growth. Examples of non-pathologic hyperproliferative cells include proliferation of cells associated with wound repair. Examples of cellular proliferative and/or differentiative disorders include cancer, e.g., carcinoma, sarcoma, or metastatic disorders. In some embodiments, the peptidomimetic macrocycles are novel therapeutic agents for controlling breast cancer, ovarian cancer, colon cancer, lung cancer, metastasis of such cancers and the like.

Examples of cancers or neoplastic conditions include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

Examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Steinberg disease.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Examples of cellular proliferative and/or differentiative disorders of the colon include, but are not limited to, non-neoplastic polyps, adenomas, familial syndromes, colorectal carcinogenesis, colorectal carcinoma, and carcinoid tumors.

Examples of cellular proliferative and/or differentiative disorders of the liver include, but are not limited to, nodular hyperplasias, adenomas, and malignant tumors, including primary carcinoma of the liver and metastatic tumors.

Examples of cellular proliferative and/or differentiative disorders of the ovary include, but are not limited to, ovarian tumors such as, tumors of coelomic epithelium, serous tumors, mucinous tumors, endometrioid tumors, clear cell adenocarcinoma, cystadenofibroma, Brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecomafibromas, androblastomas, hill cell tumors, and gonadoblastoma; and metastatic tumors such as Krukenberg tumors.

In other or further embodiments, the peptidomimetic macrocycles described herein are used to treat, prevent or diagnose conditions characterized by overactive cell death or cellular death due to physiologic insult, etc. Some examples of conditions characterized by premature or unwanted cell death are or alternatively unwanted or excessive cellular proliferation include, but are not limited to hypocellular/hypoplastic, acellular/aplastic, or hypercellular/hyperplastic conditions. Some examples include hematologic disorders including but not limited to fanconi anemia, aplastic anemia, thalaessemia, congenital neutropenia, and myelodysplasia.

In other or further embodiments, the peptidomimetic macrocycles of the invention that act to decrease apoptosis are used to treat disorders associated with an undesirable level of cell death. Thus, in some embodiments, the anti-apoptotic peptidomimetic macrocycles of the invention are used to treat disorders such as those that lead to cell death associated with viral infection, e.g., infection associated with infection with human immunodeficiency virus (HIV). A wide variety of neurological diseases are characterized by the gradual loss of specific sets of neurons. One example is Alzheimer's disease (AD). Alzheimer's disease is characterized by loss of neurons and synapses in the cerebral cortex and certain subcortical regions. This loss results in gross atrophy of the affected regions. Both amyloid plaques and neurofibrillary tangles are visible in brains of those afflicted by AD. Alzheimer's disease has been identified as a protein misfolding disease, due to the accumulation of abnormally folded A-beta and tau proteins in the brain. Plaques are made up of β-amyloid. β-amyloid is a fragment from a larger protein called amyloid precursor protein (APP). APP is critical to neuron growth, survival and post-injury repair. In AD, an unknown process causes APP to be cleaved into smaller fragments by enzymes through proteolysis. One of these fragments is fibrils of β-amyloid, which form clumps that deposit outside neurons in dense formations known as senile plaques. Plaques continue to grow into insoluble twisted fibers within the nerve cell, often called tangles. Disruption of the interaction between β-amyloid and its native receptor is therefore important in the treatment of AD. The anti-apoptotic peptidomimetic macrocycles of the invention are used, in some embodiments, in the treatment of AD and other neurological disorders associated with cell apoptosis. Such neurological disorders include Alzheimer's disease, Parkinson's disease, amyotrophic lateral sclerosis (ALS) retinitis pigmentosa, spinal muscular atrophy, and various forms of cerebellar degeneration. The cell loss in these diseases does not induce an inflammatory response, and apoptosis appears to be the mechanism of cell death.

In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses. Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis. In other or further embodiments, the anti-apoptotic peptidomimetic macrocycles of the invention are used to treat all such disorders associated with undesirable cell death.

Some examples of neurologic disorders that are treated with the peptidomimetic macrocycles described herein include but are not limited to Alzheimer's Disease, Down's Syndrome, Dutch Type Hereditary Cerebral Hemorrhage Amyloidosis, Reactive Amyloidosis, Familial Amyloid Nephropathy with Urticaria and Deafness, Muckle-Wells Syndrome, Idiopathic Myeloma; Macroglobulinemia-Associated Myeloma, Familial Amyloid Polyneuropathy, Familial Amyloid Cardiomyopathy, Isolated Cardiac Amyloid, Systemic Senile Amyloidosis, Adult Onset Diabetes, Insulinoma, Isolated Atrial Amyloid, Medullary Carcinoma of the Thyroid, Familial Amyloidosis, Hereditary Cerebral Hemorrhage With Amyloidosis, Familial Amyloidotic Polyneuropathy, Scrapie, Creutzfeldt-Jacob Disease, Gerstmann Straussler-Scheinker Syndrome, Bovine Spongiform Encephalitis, a prion-mediated disease, and Huntington's Disease.

In another embodiment, the peptidomimetic macrocycles described herein are used to treat, prevent or diagnose inflammatory disorders. Numerous types of inflammatory disorders exist. Certain inflammatory diseases are associated with the immune system, for example, autoimmune diseases. Autoimmune diseases arise from an overactive immune response of the body against substances and tissues normally present in the body, i.e. self antigens. In other words, the immune system attacks its own cells. Autoimmune diseases are a major cause of immune-mediated diseases. Rheumatoid arthritis is an example of an autoimmune disease, in which the immune system attacks the joints where it causes inflammation (i.e. arthritis) and destruction. It can also damage some organs, such as the lungs and skin. Rheumatoid arthritis can lead to substantial loss of functioning and mobility. Rheumatoid arthritis is diagnosed with blood tests especially the rheumatoid factor test. Some examples of autoimmune diseases that are treated with the peptidomimetic macrocycles described herein include, but are not limited to, acute disseminated encephalomyelitis (ADEM), Addison's disease, ankylosing spondylitis, antiphospholipid antibody syndrome (APS), autoimmune hemolytic anemia, autoimmune hepatitis, autoimmune inner ear disease, Bechet's disease, bullous pemphigoid, coeliac disease, Chagas disease, Churg-Strauss syndrome, chronic obstructive pulmonary disease (COPD), Crohns disease, dermatomyositis, diabetes mellitus type 1, endometriosis Goodpasture's syndrome, Graves' disease, Guillain-Barré syndrome (GBS), Hashimoto's disease, Hidradenitis suppurativa, idiopathic thrombocytopenic purpura, inflammatory bowel disease (IBD), interstitial cystitis, lupus erythematosus, morphea, multiple sclerosis, myasthenia gravis, narcolepsy, neuromyotonia, pemphigus vulgaris, pernicious anaemia, Polymyositis, polymyalgia rheumatica, primary biliary cirrhosis, psoriasis, rheumatoid arthritis, schizophrenia, scleroderma, Sjögren's syndrome, temporal arteritis (also known as "giant cell arteritis"), Takayasu's arteritis, Vasculitis, Vitiligo, and Wegener's granulomatosis.

Some examples of other types of inflammatory disorders that are treated with the peptidomimetic macrocycles described herein include, but are not limited to, allergy including allergic rhinitis/sinusitis, skin allergies (urticaria/hives, angioedema, atopic dermatitis), food allergies, drug allergies, insect allergies, and rare allergic disorders such as mastocytosis, asthma, arthritis including osteoarthritis, rheumatoid arthritis, and spondyloarthropathies, primary angitis of the CNS, sarcoidosis, organ transplant rejection, fibromyalgia, fibrosis, pancreatitis, and pelvic inflammatory disease.

Examples of cardiovascular disorders (e.g., inflammatory disorders) that are treated or prevented with the peptidomimetic macrocycles of the invention include, but are not limited to, aortic valve stenosis, atherosclerosis, myocardial infarction, stroke, thrombosis, aneurism, heart failure, ischemic heart disease, angina pectoris, sudden cardiac death, hypertensive heart disease; non-coronary vessel disease, such as arteriolosclerosis, small vessel disease, nephropathy, hypertriglycedemia, hypercholesterolemia, hyperlipidemia, xanthomatosis, asthma, hypertension, emphysema and chronic pulmonary disease; or a cardiovascular condition associated with interventional procedures ("procedural vascular trauma"), such as restenosis following angioplasty, placement of a shunt, stent, synthetic or natural excision grafts, indwelling catheter, valve or other implantable devices. Preferred cardiovascular disorders include atherosclerosis, myocardial infarction, aneurism, and stroke.

Other disorders that can be treated or prevented include, for example, retinal ischemia, pulmonary hypertension, intrauterine growth retardation, diabetic retinopathy, age-related macular degeneration, and diabetic macular edema. Yet another embodiment of this aspect of the present invention relates to a method of reducing or preventing angiogenesis in a tissue.

In another aspect, the compositions of the invention may be used to reduce transcription of a gene in a cell, where transcription of the gene is mediated by an interaction of HIF, such as interaction of HIF1α with CBP and/or p300. Genes whose transcription is mediated by interaction of HIF1α with CBP and/or p300 include adenylate kinase 3, aldolase A, aldolase C, enolase 1, glucose transporter 1, glucose transporter 3, glyceraldehyde-3-phosphate dehydrogenase, hexokinase 1, hexokinase 2, insulin-like growth factor 2, IGF binding protein 1, IGF binding protein 3, lactate dehydrogenase A, phosphoglycerate kinase 1, pyruvate kinase M, p21, transforming growth factor β3, ceruloplasmin, erythropoietin, transferrin, tranferrin receptor, alB-adrenergic receptor, adrenomedullin, endothelin-1, heme oxygenase 1, nitric oxide synthase 2, plasminogen activator inhibitor, vascular endothelial growth factor, vascular endothelial growth factor receptor FLT-1, vascular endothelial growth factor receptor KDR/Flk-1, and p35srg.

A second aspect of the present invention relates to inhibiting the HIF1α-p300/CBP interaction using the peptides of the present invention. One embodiment of this aspect of the present invention relates to a method of reducing transcription of a gene in a cell, where transcription of the gene is mediated by interaction of HIF1α with CREB-binding protein and/or p300. This method involves contacting the cell with a peptide of the present invention under conditions effective to cause nuclear uptake of the peptide, where the peptide disrupts interaction of HIF1α and p300/CBP and thereby reduces transcription of the gene. Genes whose transcription is mediated by interaction of HIF1α with CBP and/or p300 include adenylate kinase 3, aldolase A, aldolase C, enolase 1, glucose transporter 1, glucose transporter 3, glyceraldehyde-3-phosphate dehydrogenase, hexokinase 1, hexokinase 2, insulin-like growth factor 2, IGF binding protein 1, IGF binding protein 3, lactate dehydrogenase A, phosphoglycerate kinase 1, pyruvate kinase M, p21, transforming growth factor β3, ceruloplasmin, erythropoietin, transferrin, tranferrin receptor, alB-adrenergic receptor, adrenomedullin, endothelin-1, heme oxygenase 1, nitric oxide synthase 2, plasminogen activator inhibitor 1, vascular endothelial growth factor, vascular endothelial growth factor receptor FLT-1, vascular endothelial growth factor receptor KDR/Flk-1, and p35$^{srg}$. Some uses for inhibiting transcription of these genes are shown in Table 4.

TABLE 4

Example disorders.

| Gene | Disease to treat/prevent |
|---|---|
| Enolase 1 | Hashimoto's encelopathy, severe asthma |
| Glucose transporter 1 | Aerobic glycolysis (Warburg effect) |
| Glucose transporter 3 | Aerobic glycolysis (Warburg effect) |
| Hexokinase 1 | Aerobic glycolysis (Warburg effect) |
| Hexokinase 2 | Aerobic glycolysis (Warburg effect) |
| Insulin-like growth factor 2 | Abnormal development and function of organs (brain, liver) |
| IGF binding protein 1 | Abnormal development and function of organs (brain, liver) |
| IGF binding protein 3 | Abnormal development and function of organs (brain, liver) |
| Lactate dehydrogenase A | Myocardial infarction |
| Ceruloplasmin | Lymphoma, acute and chronic inflammation, rheumatoid arthritis |
| Erythropoietin | Abnormal oxygen transport |
| Transferrin | Abnormal iron uptake/metabolism |
| Transferrin receptor | Abnormal iron uptake/metabolism |
| Adrenomedullin | Pheochromocytoma |
| Endothelin-1 | Abnormal vasoconstriction |
| Heme oxygenase 1 | Abnormal oxygen transport |
| Nitric oxide synthase 2 | Abnormal vasomotor tone |
| Vascular endothelial growth factor | Angiogenesis (tumors, including cancer) |
| Vascular endothelial growth factor receptor FLT-1 | Angiogenesis (tumors, including cancer) |
| Vascular endothelial growth factor receptor KDR/Flk-1 | Angiogenesis (tumors, including cancer) |

Another embodiment of this aspect of the present invention relates to a method of treating or preventing in a subject in need thereof a disorder mediated by interaction of HIF1α c with CBP and/or p300. This method involves administering a peptide of the present invention to the subject under conditions effective to treat or prevent the disorder.

Disorders that can be treated or prevented include, for example, retinal ischemia (Zhu et al., "Long-term Tolerance to Retinal Ischemia by Repetitive Hypoxic Preconditioning: Role of HIF-1α and Heme Oxygenase-1," Invest. Ophthalmol. Vis. Sci. 48: 1735-43 (2007); Ding et al., "Retinal Disease in Mice. Lacking Hypoxia-inducible Transcription Factor-2a," Invest. Ophthalmol. Vis. Sci. 46:1010-6 (2005), each of which is hereby incorporated by reference in its entirety), pulmonary hypertension (Simon et al., "Hypoxia-induced Signaling in the Cardiovascular System," Annu. Rev. Physiol. 70:51-71 (2008); Eul et al., "Impact of HIF-1α and HIF-2α on Proliferation and Migration of Human Pulmonary Artery Fibroblasts in Hypoxia," FASEB J. 20:163-5 (2006), each of which is hereby incorporated by reference in its entirety), intrauterine growth retardation (Caramelo et al., "Respuesta a la Hipoxia. Un Mecanismo Sistemico Basado en el Control de la Expresion Genica [Response to Hypoxia. A Systemic Mechanism Based on the Control of Gene Expression]," Medicina B. Aires 66: 155-{54 (2006); Tazuke et al., "Hypoxia Stimulates Insulin-like Growth Factor Binding Protein I (IGFBP-1) Gene Expression in HepG2 Cells: A Possible Model for IGFBP-1 Expression in Fetal Hypoxia," Proc. Nat'l Acad Sci. USA 95:10188-93 (1998), each of which is hereby incorporated by reference in its entirety), diabetic retinopathy (Ritter et al., "Myeloid Progenitors Differentiate into Microglia and Promote Vascular Repair in a Model of Ischemic Retinopathy," J. Clin Invest. 116:3266-76 (2006); Wilkinson-Berka et al., "The Role of Growth Hormone, Insulin-like Growth Factor and Somatostatin in Diabetic Retinopathy," Curr. Med Chem. 13:3307-17 (2006); Vinores et al., "Implication of the Hypoxia Response Element of the Vegf Promoter in Mouse Models of Retinal and Choroidal Neovascularization, but Not Retinal Vascular Development," J. Cell. Physiol. 206: 749-58 (2006); Caldwell et al., "Vascular Endothelial Growth Factor and Diabetic Retinopathy: Role of Oxidative Stress," Curr. Drug Targets 6:511-24 (2005), each of which is hereby incorporated by reference in its entirety), age-related macular degeneration (Inoue et al., "Expression of Hypoxia-inducible Factor 1a and 2a in Choroidal Neovascular Membranes Associated with Age-related Macular Degeneration," Br. J Ophthalmol. 91:1720-1 (2007); Zuluaga et al., "Synergies of VEGF Inhibition and Photodynamic Therapy in the Treatment of Age-related Macular Degeneration," Invest. Ophthalmol. Vis. Sci 48:1767-72 (2007); Provis, "Development of the Primate Retinal Vasculature," Prog. Retin Eye Res. 20:799-821 (2001), each of which is hereby incorporated by reference in its entirety), diabetic macular edema (Vinores et al., "Implication of the Hypoxia Response Element of the Vegf Promoter in Mouse Models of Retinal and Choroidal Neovascularization, but Not Retinal Vascular Development," J Cell. Physiol. 206: 749-58 (2006); Forooghian & Das, "Anti-angiogenic Effects of Ribonucleic Acid Interference Targeting Vascular Endothelial Growth Factor and Hypoxia-inducible Factor-1α," Am. J Ophthalmol. 144:761-8 (2007), each of which is hereby incorporated by reference in its entirety), and cancer (Marignol et al., "Hypoxia in Prostate Cancer: A Powerful Shield Against Tumour Destruction?" Cancer Treat. Rev. 34:313-27 (2008); Galanis et al, "Reactive Oxygen Species and HIF-Signalling in Cancer," Cancer Lett. 266: 12-20 (2008); Ushio-Fukai & Nakamura, "Reactive Oxygen Species and Angiogenesis: NADPH Oxidase as Target for Cancer Therapy," Cancer Lett. 266:37-52 (2008); Adamski et al, "The Cellular Adaptations to Hypoxia as Novel Therapeutic Targets in Childhood Cancer," Cancer Treat. Rev. 34:231-46 (2008); Toffoli & Michiels, "Intermittent Hypoxia Is a Key Regulator of Cancer Cell and Endothelial Cell Interplay in Tumours," FEBS J. 275:2991-3002 (2008), each of which is hereby incorporated by reference in its entirety).

Yet another embodiment of this aspect of the present invention relates to a method of reducing or preventing angiogenesis in a tissue. This method involves contacting the tissue with a peptide of the present invention under conditions effective to reduce or prevent angiogenesis in the tissue. Another embodiment of this aspect of the present invention relates to a method of inducing apoptosis of a cell. This method involves contacting the cell with a peptide of the present invention under conditions effective to induce apoptosis of the cell. Another embodiment of this aspect of the present invention relates to a method of decreasing survival and/or proliferation of a cell. This method involves contacting the cell with a peptide of the present invention under conditions effective to decrease survival and/or proliferation of the cell. Contacting (including administering) according to this aspect of the present invention can be carried out using methods that will be apparent to the skilled artisan and as described above, and can be done in vitro or in vivo.

Some example target cells, tissues and/or organs for the embodiments described above are shown in Table 5.

TABLE 5

Example Targets.

| Desired effect | Example Target(s) |
|---|---|
| Inhibit transcription of: | |
| Enolase 1 | Liver, brain, kidney, spleen, adipose, lung |
| Glucose transporter 1 | Tumor, incl. cancer |
| Glucose transporter 3 | Tumor, incl. cancer |
| Hexokinase 1 | Tumor, incl. cancer |
| Hexokinase 2 | Tumor, incl. cancer |
| Insulin-like growth factor 2 | Brain, liver |
| IGF binding protein 1 | Brain, liver |
| IGF binding protein 3 | Brain, liver |
| Lactate dehydrogenase A | Heart |
| Ceruloplasmin | Lymphocytes/lymphatic tissue, inflamed tissue, rheumatoid arthritic tissue |
| Erythropoietin | Liver, kidney |
| Transferrin | Liver |
| Adrenomedullin | Pheochromocytoma |
| Endothelin-1 | Endothelium |
| Nitric oxide synthase 2 | Vessels, cariovascular cells/tissue |
| Vascular endothelial growth factor | Tumor cells/tissue, incl. cancer |
| Vascular endothelial growth factor receptor FLT-1 | Tumor cells/tissue, incl. cancer |
| Vascular endothelial growth factor receptor KDR/Flk-1 | Tumor cells/tissue, incl. cancer |
| Treat or prevent: | |
| Retinal ischemia | Retina (eye) |
| Pulmonary hypertension | Lungs |
| Intrauterine growth retardation | Uterus |
| Diabetic retinopathy | Retina (eye) |
| Age-related macular degeneration | Retina (eye) |
| Diabetic macular edema | Retina (eye) |
| Angiogenesis | Tumor cells/tissue, incl. cancer |
| Decrease cell survival and/or proliferation | Cancerous cells, cells contained in the endothelial vasculature of a tissue that contains cancerous cells |

Another aspect of the present invention relates to a method of identifying an agent that potentially inhibits interaction of HIF1α with CBP and/or p300. This method involves providing a peptide of the present invention, contacting the peptide with a test agent, and determining whether the test agent selectively binds to the peptide, wherein a test agent that selectively binds to the peptide is identified as a potential inhibitor of interaction between HIF1α with CBP and/or p300.

This aspect of the present invention can be carried out in a variety of ways, which will be apparent to the skilled artisan. For example, the affinity of the test agent for the peptide of the present invention may be measured using isothermal titration calorimetry analysis, as described in Example 4 (Wiseman et al., "Rapid Measurement of Binding Constants and Heats of Binding Using a New Titration Calorimeter," Anal. Biochem. 179: 131-7 (1989); Freire et al., "Isothermal Titration Calorimetry," Anal. Chem. 62:A950-A959 (1990); Chervenak & Toone, "Calorimetric Analysis of the Binding of Lectins with Overlapping Carbohydrate-binding Ligand Specificities," Biochemistry 34:5685-95 (1995); Aki et al., "Competitive Binding of Drugs to the Multiple Binding Sites on Human Serum Albumin. A Calorimetric Study," J Thermal Anal. Calorim. 57:361-70 (1999); Graziano et al., "Linkage of Proton Binding to the Thermal Unfolding of Sso7d from the Hyperthermophilic Archaebacterium *Sulfolobus solfataricus*," Int'l J Biol. Macromolecules 26:45-53 (1999): Pluschke & Mutz, "Use of Isothennal Titration Calorimetry in the Development of Molecularly Defined Vaccines," J. Thermal Anal. Calorim. 57:377-88 (1999); Corbell et al., "A Comparison of Biological and Calorimetric Analyses of Multivalent Glycodendrimer Ligands for Concanavalin A," Tetrahedron-Asymmetry 11:95-111 (2000), which are hereby incorporated by reference in their entirety). In one embodiment, a test agent is identified as a potential inhibitor of interaction between HIF1α with CBP and/or p300 if the dissociation constant (Kd) for the test agent and the peptide of the invention is 50 or less. In another embodiment, the Kd is 200 nM or less. In yet another embodiment, the Kd is 100 nM or less.

Test agents identified as potential inhibitors of HIF1α-p300/CREB interaction may be subjected to further testing to confirm their ability to inhibit interaction between HIF1α with CBP and/or p300.

As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease.

rocycles were designed by replacing two or more naturally occurring amino acids with the corresponding synthetic amino acids. Substitutions were made at i and i+4, and i and i+7 positions. Peptide synthesis was performed either manually or on an automated peptide synthesizer (Applied Biosystems, model 433A), using solid phase conditions, rink amide AM resin (Novabiochem), and Fmoc main-chain protecting group chemistry. For the coupling of natural Fmoc-protected amino acids (Novabiochem), 10 equivalents of amino acid and a 1:1:2 molar ratio of coupling reagents HBTU/HOBt (Novabiochem)/DIEA were employed. Non-natural amino acids (4 equiv) were coupled with a 1:1:2 molar ratio of HATU (Applied Biosystems)/HOBt/DIEA. The N-termini of the synthetic peptides were acetylated, while the C-termini were amidated.

Purification of cross-linked compounds was achieved by high performance liquid chromatography (HPLC) (Varian ProStar) on a reverse phase C18 column (Varian) to yield the pure compounds. Chemical composition of the pure products was confirmed by LC/MS mass spectrometry (Micromass LCT interfaced with Agilent 1100 HPLC system) and amino acid analysis (Applied Biosystems, model 420A).

Exemplary structures of several peptidomimetic macrocycles are shown. SP-5 (X=S) (SEQ ID NO: 21) and SP-6 (X=CH$_2$) (SEQ ID NO: 22)

Ac-Phe-Ile-Asp-Glu-Glu-Val-Leu-[...]-Leu-Val-Ile-[...]-Ala-Leu-Asp-Arg-Ile-NH$_2$

X = S or CH$_2$

SP-215 (SEQ ID NO: 231)

Ac-Phe-Ile-Asp-Ile-[...]-Val-Leu-Nle-[...]-Leu-Val-Ile-[...]-Nle-Ala-Leu-NH$_2$

EXAMPLES

Example 1: Peptidomimetic Macrocycles of the Invention

Peptidomimetic macrocycles were synthesized, purified and analyzed as previously described and as described below (Schafmeister et al., J. Am. Chem. Soc. 122:5891-5892 (2000); Schafeister & Verdine, J. Am. Chem. Soc. 122:5891 (2005), Walensky et al., Science 305:1466-1470 (2004); and U.S. Pat. No. 7,192,713). Peptidomimetic mac- Example 2: HIF1α p300 Displacement Assays The ability of peptides to displace HIF1α c-terminal trans-activation domain from p300-CH was measured by a TR FRET assay. A complex of flag-tagged HIF1α (AA 786-826) and His6-tagged p300 ("His6" disclosed as SEQ ID NO: 390) (AA 323-423) was co-expressed using pET-Duet vector (EMDMillipore, Bellrica MA) and purified from *E. coli* in the presence of 0.1 mM ZnSO$_4$. The complex was diluted to 300 nM final in complete assay media and competitor peptides were added. The complete assay media contained 150 mM NaCl (Sigma+S5150 or equivalent), 20 mM HEPES pH 7.4 (Boston Bioproducts, Ashland, Mass.; #BB-2076), 7.5 mM CHAPS (Thermo #28300 or equivalent), and 1 mM DTT. Protein and peptide were incubated at room temperature for 1 hour before the addition of anti-Flag-K and anti-6×HIS-D2 ("6×HIS" disclosed as SEQ ID NO: 390) (CisBio, Bedford Mass.) HTRF reconstitution buffer (50 mM Phosphate pH 7, 0.8 Potassium Flouride, BSA 0.2%)[1] to a final concentration of 0.5 µM and 4 nM respectively. The reaction continued for an additional two hours at room temperature. The reaction was read on a TECAN F500 plate reader with settings recommended by CisBio. The ratio of donor to acceptor fluorescence was calculated. The resulting data was analyzed with Graphpad Prism 5.0. IC50 values were calculated for both proteins using the One Site Fit—Log IC50 equation and presented in the column "$IC_{50}$ (nM) (HIF1α_p300 Displacement+ CHAPS)" of Table 6.

[1] Cisbio USA, Bedford, Mass. 61HISDLB (lot 007A), 61FG2KLB (024A). HTRF Buffer (62RB3RDF)

Example 3: Reporter Gene Assay

The following reagents were used:

| Media | Growth Medium | Assay Medium |
| --- | --- | --- |
| DMEM + GlutaMAX | 1000 ml | — |
| Opti-MEM | — | 500 ml |
| Dialyzed FBS | 110 ml | 5 ml |
| NEAA (100X) | 11 ml | 5 ml |
| Sodium Pyruvate (100X) | 11 ml | 5 ml |
| HEPES (1M) | 11 ml | 5 ml |
| Pen/Strep | 11 ml | 5 ml |
| Blasticidin | 550 ml | — |

DMEM+GlutaMAX: (#10569044, Invitrogen)
Black clear bottom plates: (#3603, Costar)
HRE-bla-ME-180 cell line: (#K1644, Invitrogen)
Gene-Blazer reagent & protocol: (#K1096, Invitrogen)
Plate reader: Biotek Synergy 2
Chetomin: (C9623, Sigma)

At Day 0:
4 hours prior to experiment: HRE-bla ME-180 cells were seeded at a density of 20,000 cells/well in a volume of 180 µl in black clear bottom 96-well plates. 180 µl of assay medium was added to the cell-free control wells. Incubation was conducted at 37° C., 5% $CO_2$ for 4 hours.

Diluted chetomin was used as a positive control. Chetomin was diluted in 100% DMSO to a 10 mM stock concentration. A 1 mM stock of chetomin was prepared in 100%, DMSO. Then the 1 mM chetomin stock was serially diluted in 1:4 in 100% DMSO. Finally, 50, 12.5, 3.125, 0.78, 0.2, 0.05 µM stock of chetomin in 5% DMSO/water were prepared by adding 114 µL water+6 µL chetomin in DMSO.

Test peptides were diluted before use. The test peptides were diluted in 100% DMSO to a 10 mM stock concentration. Then each 10 mM peptide stock was diluted in 1:3 in 100% DMSO. Finally, 300, 100, 33.3, 11.1, 3.7, 1.2 M stock of each peptide in 5% DMSO/water were prepared by adding 129.2 µL water+4 µL peptide in DMSO.

20 µl of peptide, chetomin dilution, or DMSO/water control were added to the appropriate wells of a plate to achieve 200 µL final volumes in 0.3% DMSO/media. The plate was first incubated for 18-20 hours in normoxia incubator (37° C. in humidified 5% $CO_2$, 20% $O_2$ atmosphere). Then the plate was transferred to hypoxia incubator for 24 hours (37° C. in humidified 5% $CO_2$, 1% $O_2$ atmosphere)

Day +1: (all Work in the Absence of Strong Light)
6× LiveBLAzer™-FRET B/G (CCF4-AM) Substrate Mixture was prepared according to CellSensor™ HRE-bla ME-180 Cell-based Assay Protocol (Invitrogen) and added into each well. Solution A (CCF4-AM) was reconstituted in DMSO to a working concentration of 1 mM, divided in aliquots, and stored at −20° C. The 6× LiveBLAzer-FRET B/G (CCF4-AM) Substrate mixture was prepared by mixing 6 µl of Solution A, 60 µl of Solution B, and 934 µl Solution C.

The plates were removed from incubator and equilibrated to RT for a few minutes. Then 20 µl of 6× Substrate mixture was added to each well. The plates were then incubated at room temperature for 3 hr in the dark and read at 409 Ex/460Em and 409Ex/530Em using the "GeneBlazer-Tungsten with export" program on the Synergy 2.

Results:
The average percentage of maximum inhibition was obtained by comparing the peptide treated cells (30 µM) to DMSO vehicle control treated cells. The results are shown in the columns "ME-80 HIF Reporter $EC_{50}$ (µM)—24 hr normoxia" and "18 h Avg % max inhibition at top conc (HIF Rptr-24 hrsnormoxia) (µM)" of Table 6.

SP-6 effectively inhibited several known HIF1α targets, including ANGPTL4, CA9 and ALDOC which regulate angiogenesis and tumor metabolism in ME-180 cervical cancer cells, as shown in FIG. 1.

Cell Proliferation Assay
The human cervical cell line HRE-Bla ME-180 was obtained from Invitrogen. $2 \times 10^4$ ME-180 cells were plated in 96-well plates (costar) in Opti-MEM plus 1% FBS (Invitrogen). After 4 hr, cells were pretreated with chetomin, peptide or 0.5% DMSO (final concentration in media) vehicle control for 6 hr under normoxia (21% $O_2$); then incubation continued under normoxia or hypoxia (1% $O_2$) using a hypoxia incubator (Thermo Forma model). Viable cell numbers were quantified using CellTiter 96 Non-Radioactive Cell Proliferation kit (Promega, G4100). The results are presented in the column "Viability 1% FBS AVG (MTT V3-24 hr Normoxia) (AM)" of Table 6.

Example 4: qRT-PCR

The human cervical cell line HRE-Bla ME-180 was obtained from Invitrogen. $1.2 \times 10^5$ ME-180 cells were plated in 24-well plates (costar) in Opti-MEM plus 1% FBS (Invitrogen). 4 hrs later, cells were pretreated with chetomin, peptide or 0.5% DMSO (final concentration in media) vehicle control for 16 hrs under normoxia (21% $O_2$); then incubation continued under normoxia or hypoxia (1% $O_2$) for 12 hrs using a hypoxia incubator (Thermo Forma model). Total RNA was isolated with an Rneasy Plus mini Kit (Qiagen) and cDNA was synthesized with cDNA synthesis Kit and then amplified with angiopoietin-like 4 (Angptl4, Hs01101127_m1, Invitrogen); CA9 (Hs00154208_m1, Invitrogen); aldolase C (ALDOC, Hs00193059_m1, Invitrogen); SLC2A1 (Glut, Hs00892681_m1, Invitrogen); EP300 (p300, Hs00914223_m1, Invitrogen); ARNT (HIF1b Hs00231048_m1, Invitrogen).

Example 5: Western Blot Analysis

Figure 2:
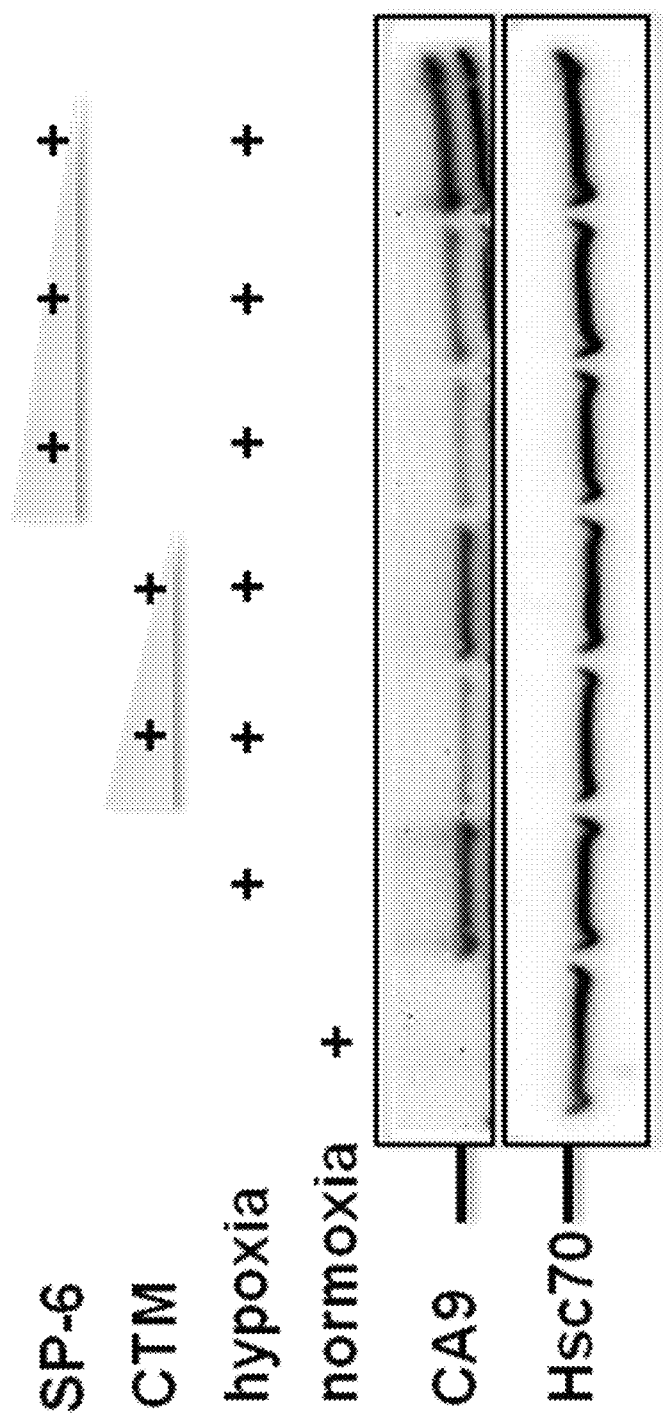
FIG. 2 is a western blot image that show protein levels of Carbonic anhydrase 9 (CA9) in ME-180 cells treated with the peptidomimetic macrocycle SP-6.

The human cervical cell line HRE-Bla ME-180 was obtained from Invitrogen. $6.2 \times 10^5$ cells were plated in 6-well plates (costar) in Opti-MEM plus 1% FBS (Invitrogen). 4 hrs later, cells were pretreated with chetomin, peptide or 0.5% DMSO (final concentration in media) vehicle control for 16 hrs under normoxia (21% $O_2$); then incubation continued under normoxia or hypoxia (1% $O_2$) for 24 hrs using a hypoxia incubator (Thermo Forma model). Total cell lysate form control, chetomin treated or SP-6 treated ME-180 cells were separated by SDS-PAGE and probed with anti-CA9 (1:2000, NB100-47, Novus biologicals) and anti HSC70 (1:5000, ab19136, Abcam). The results demonstrate that the protein level of Carbonic anhydrase 9 (CA9) was down-regulated by treating with SP-6 in ME-180 cells, as shown in FIG. 2.

Example 6: Kinetic Studies of Binding to p300 CH1 Domain

Biolayer inferometry (ForteBio, Menlo Park Calif.) was used to measure competition of SP-6 for HIF1α (AAs 788-826). Biotinylated HIF1α peptide was captured on Ni-NTA biosensor tip. The association of 300 nM GST-tagged p300 CH1 domain (AAs 302-423) in the presence or absence of varying concentrations of SP-6 was measured for 240 s. Dissociation was monitored for a minimum of 200 s in the absence of free p300 or stapled peptide. Binding of p300 to biosensor immobilized HIF1α target was analyzed with instrument software and total response (R) was proportional to binding.

Figure 3:
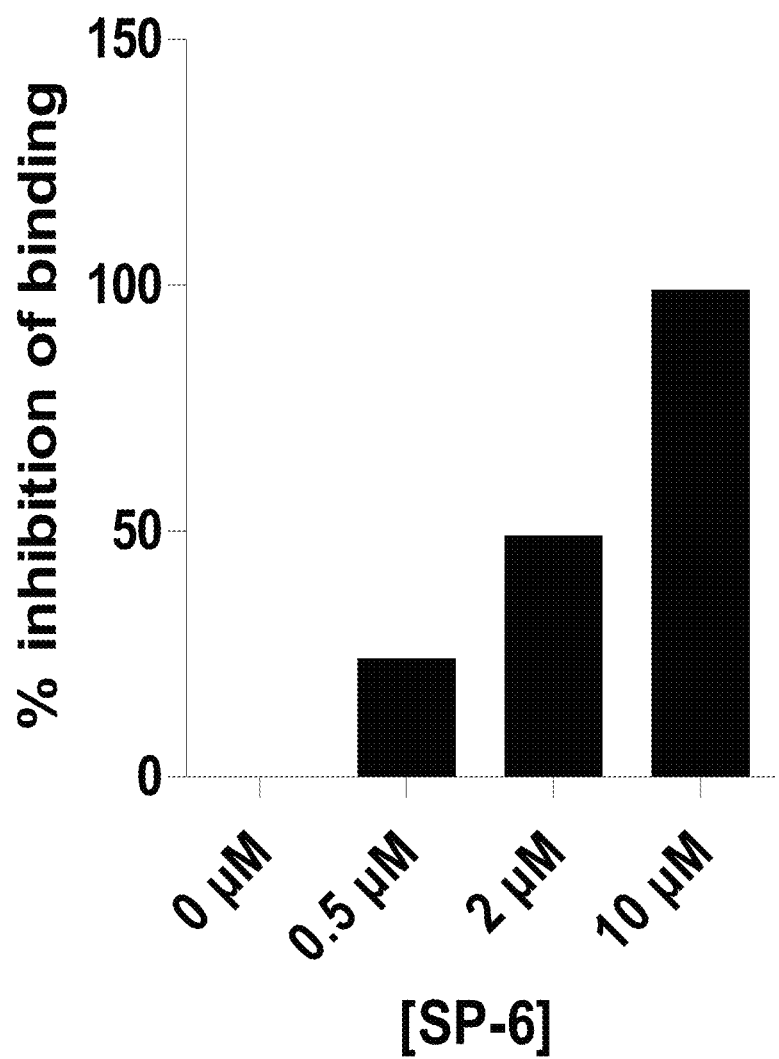
FIG. 3 is a bar graph that shows efficacy of the peptidomimetic macrocycle SP-6 in inhibiting p300/HIF1α binding.

The results are shown in FIG. 3. Inhibition of p300 binding was calculated as % inhibition=1−(R (no inhibitor)−R (with inhibitor))×100%. A concentration of 10 μM SP-6 blocked 99% of the total binding. The inhibition was dose-dependent, with 2 μM inhibiting 50% of p300/HIF1α binding.

Example 7: PC-3 Prostate Xenograft Model

A xenograft study was performed to test the efficacy of SP-6 in inhibiting tumor growth in athymic mice in the PC-3 human prostate carcinoma xenograft model. PC-3 tumor fragments were implanted subcutaneously (sc) in the flank of athymic nude mice. Once the implanted tumor fragments had grown sufficiently (Day 1), sc tumors were measured using calipers to determine their length and width and the mice were weighed. The tumor sizes were calculated using the formula (length×width$^2$)/2 and expressed as cubic millimeters (mm$^3$). Mice with tumors smaller than 108 mm$^3$ or larger than 162 mm$^3$ were excluded from subsequent group formation. Groups of mice, 10 mice per group, were formed by randomization such that the group mean tumor sizes were essentially equivalent (mean of groups±standard error of the means of groups=128.4±0.6 mm).

Each group received treatment intravenously (IV) on an every other day basis starting on Day 1 for a total of 12 injections (Days 1-24); volume of dosing solution to be administered was based on the weight of the mouse taken on each dosing day. The negative control vehicle group received vehicle administered at 10 mL/kg body weight. Two groups were administered SP-6 at either 50 or 25 mg/kg per dosing day in a single IV injection on that day of 10 mL/kg of a dosing solution of SP-6 of 5 or 2.5 mg/mL, respectively.

During the treatment and tumor measurement period (Days 1-24) the mice were weighed and tumors measured two to three times per week. Treatment with SP-6 was well-tolerated as evidenced by no significant decrease in body weight in the SP-6 treated groups compared with the negative control vehicle group. Results in terms of tumor volume are shown in FIG. 3. The vehicle negative control group showed the expected tumor growth rate for this tumor model. Tumor growth inhibition (TGI) was calculated as % TGI=100−[(TuVol$^{Treated-Day\ X}$−TuVol$^{Treated-Day\ 1}$)/(TuVol$^{Vehicle\ negative\ control-Day\ X}$−TuVol$^{Vehicle\ negative\ control-Day\ 1}$)*100], where X=day that effect of treatment is being assessed. On the final day of measurement (Day 24), treatment with SP-6 at 50 or 25 mg/g produced TGI of 64 and 39%, respectively.

Figure 4:
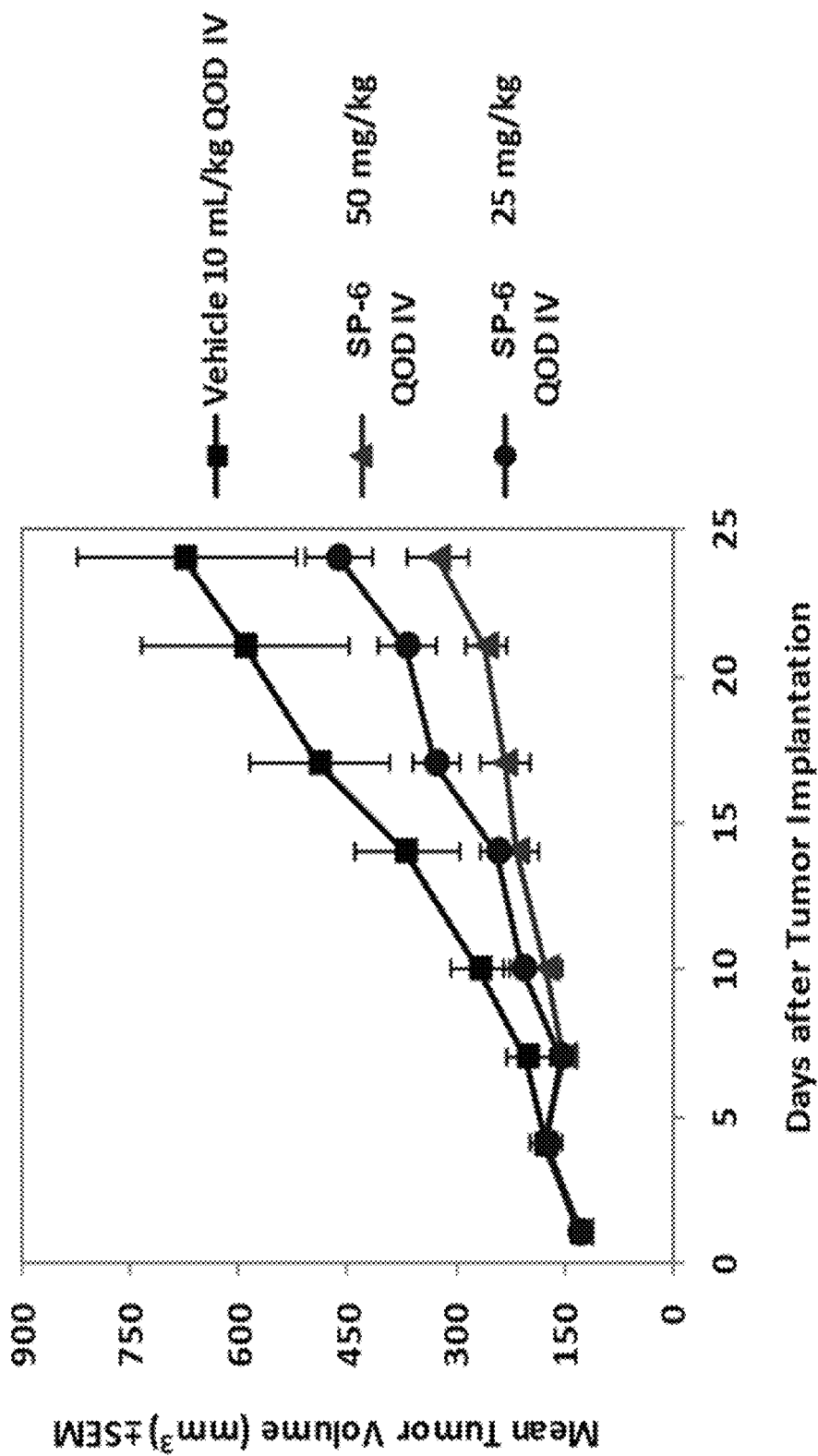
FIG. 4 is a line graph that shows efficacy of the peptidomimetic macrocycle SP-6 in the PC-3 Prostate Xenograft Model.

Results:

SP-6 effectively inhibited tumor growth, as shown in FIG. 4.

TABLE 6

| | Scale | | | |
|---|---|---|---|---|
| SP # | >700: +<br><400 but ≤700: ++<br><200 but ≤400: +++<br>≤200: ++++<br>IC50 (nM)<br>(HIF1α_p300<br>Displacement +<br>CHAPS) | >30: +<br><15 but ≤30: ++<br><5 but ≤15: +++<br>≤5: ++++<br>ME-180 HIF<br>Reporter<br>EC50 (μM) -<br>24 hour normoxia | ≥50: ++++<br>≤25 but <50: +++<br>≤10 but <25: ++<br><10: +<br>18 h Avg % max<br>inhibition at top<br>conc (HIF Rptr-24<br>hrs normoxia) (μM) | ≥30: ++++<br>≤15 but <30: +++<br>≤5 but <15: ++<br><5: +<br>Viability<br>1% FBS AVG<br>(MTT V3-24 hr<br>Normoxia) (μM) |
| SP-1 | +++ | | | |
| SP-2 | ++ | | | |
| SP-3 | +++ | + | +++ | |
| SP-4 | +++ | | | |
| SP-5 | ++ | +++ | ++++ | ++++ |
| SP-6 | ++++ | +++ | ++++ | ++++ |
| SP-7 | ++ | | | ++++ |
| SP-8 | +++ | | | ++++ |
| SP-9 | + | ++ | +++ | |
| SP-10 | + | | | |
| SP-11 | + | +++ | ++++ | |
| SP-12 | + | +++ | ++++ | |
| SP-13 | +++ | +++ | ++++ | |
| SP-14 | + | +++ | ++++ | |
| SP-15 | + | ++++ | ++++ | |
| SP-16 | + | ++++ | ++++ | |
| SP-17 | +++ | +++ | ++++ | |
| SP-18 | ++ | +++ | ++++ | |
| SP-19 | +++ | +++ | +++ | |
| SP-20 | + | +++ | ++++ | |

TABLE 6-continued

| | Scale | | | |
|---|---|---|---|---|
| | >700: +<br><400 but ≤700: ++<br><200 but ≤400: +++<br>≤200: ++++<br>IC50 (nM)<br>(HIF1α_p300<br>Displacement +<br>CHAPS) | >30: +<br><15 but ≤30: ++<br><5 but ≤15: +++<br>≤5: ++++<br>ME-180 HIF<br>Reporter<br>EC50 (μM) -<br>24 hour normoxia | ≥50: ++++<br>≤25 but <50: +++<br>≤10 but <25: ++<br><10: +<br>18 h Avg % max<br>inhibition at top<br>conc (HIF Rptr-24<br>hrs normoxia) (μM) | ≥30: ++++<br>≤15 but <30: +++<br>≤5 but <15: ++<br><5: +<br>Viability<br>1% FBS AVG<br>(MTT V3-24 hr<br>Normoxia) (μM) |
| SP # | | | | |
| SP-21 | ++ | +++ | ++++ | |
| SP-22 | ++ | +++ | ++++ | |
| SP-23 | + | +++ | ++++ | |
| SP-24 | ++ | +++ | ++++ | |
| SP-25 | ++ | +++ | +++ | |
| SP-26 | + | +++ | ++++ | |
| SP-27 | ++ | +++ | ++++ | |
| SP-28 | + | ++ | ++++ | |
| SP-29 | + | + | ++ | |
| SP-30 | + | + | ++ | |
| SP-31 | + | + | + | |
| SP-32 | + | ++ | +++ | |
| SP-33 | + | + | +++ | |
| SP-34 | + | +++ | ++++ | |
| SP-35 | + | + | + | |
| SP-36 | + | + | + | |
| SP-37 | + | + | + | |
| SP-38 | + | ++ | ++++ | |
| SP-39 | + | ++ | +++ | |
| SP-40 | +++ | + | + | |
| SP-41 | +++ | ++ | ++++ | |
| SP-42 | + | + | ++ | |
| SP-43 | ++ | + | +++ | |
| SP-44 | + | ++ | +++ | |
| SP-45 | + | + | ++ | |
| SP-46 | ++ | ++ | +++ | |
| SP-47 | +++ | +++ | ++++ | |
| SP-48 | + | ++ | +++ | |
| SP-49 | + | +++ | ++++ | |
| SP-50 | + | ++++ | ++++ | |
| SP-51 | ++ | +++ | +++ | |
| SP-52 | + | ++ | ++++ | |
| SP-53 | ++ | +++ | +++ | |
| SP-54 | ++ | ++++ | ++++ | |
| SP-55 | +++ | +++ | ++++ | |
| SP-56 | ++ | | | |
| SP-57 | ++ | +++ | ++++ | |
| SP-58 | + | + | +++ | |
| SP-59 | ++ | ++ | +++ | |
| SP-60 | + | + | + | |
| SP-61 | ++ | + | + | |
| SP-62 | + | + | ++ | |
| SP-63 | + | +++ | +++ | |
| SP-64 | + | + | + | |
| SP-65 | + | + | + | |
| SP-66 | ++ | + | ++ | |
| SP-67 | ++ | | | |
| SP-68 | + | | | |
| SP-69 | + | +++ | ++++ | |
| SP-70 | + | +++ | +++ | |
| SP-71 | + | | | |
| SP-72 | ++ | | | |
| SP-73 | ++ | | | |
| SP-74 | ++ | | | |
| SP-75 | | | | |
| SP-76 | + | + | + | |
| SP-77 | + | | | |
| SP-78 | + | | | |
| SP-79 | + | | | |
| SP-80 | | | | |
| SP-81 | + | | | |
| SP-82 | +++ | + | + | |
| SP-83 | | | | |
| SP-84 | ++++ | + | + | |
| SP-85 | | | | |

TABLE 6-continued

| | Scale | | | |
|---|---|---|---|---|
| | >700: +<br><400 but ≤700: ++<br><200 but ≤400: +++<br>≤200: ++++<br>IC50 (nM)<br>(HIF1α_p300<br>Displacement +<br>CHAPS) | >30: +<br><15 but ≤30: ++<br><5 but ≤15: +++<br>≤5: ++++<br>ME-180 HIF<br>Reporter<br>EC50 (μM) -<br>24 hour normoxia | ≥50: ++++<br>≤25 but <50: +++<br>≤10 but <25: ++<br><10: +<br>18 h Avg % max<br>inhibition at top<br>conc (HIF Rptr-24<br>hrs normoxia) (μM) | ≥30: ++++<br>≤15 but <30: +++<br>≤5 but <15: ++<br><5: +<br>Viability<br>1% FBS AVG<br>(MTT V3-24 hr<br>Normoxia) (μM) |
| SP # | | | | |
| SP-86 | ++++ | +++ | ++++ | |
| SP-87 | | ++ | ++++ | |
| SP-88 | | | | |
| SP-89 | ++++ | +++ | +++ | |
| SP-90 | + | | | |
| SP-91 | | | | |
| SP-92 | | | | |
| SP-93 | + | | | |
| SP-94 | | | | |
| SP-95 | | | | |
| SP-96 | | | | |
| SP-97 | + | | | |
| SP-98 | + | | | |
| SP-99 | + | | | |
| SP-100 | + | | | |
| SP-101 | + | | | |
| SP-102 | + | | | |
| SP-103 | + | | | |
| SP-104 | +++ | +++ | ++++ | ++++ |
| SP-105 | ++++ | + | | |
| SP-106 | +++ | + | | |
| SP-107 | ++++ | + | | |
| SP-108 | ++++ | + | ++ | ++++ |
| SP-109 | +++ | + | + | ++ |
| SP-110 | ++ | + | +++ | ++++ |
| SP-111 | +++ | + | ++++ | ++++ |
| SP-112 | ++++ | +++ | +++ | ++++ |
| SP-113 | ++ | +++ | ++++ | ++++ |
| SP-114 | | ++++ | +++ | ++++ |
| SP-115 | + | | | |
| SP-116 | + | + | +++ | ++++ |
| SP-117 | + | + | +++ | ++++ |
| SP-118 | ++++ | ++ | +++ | ++++ |
| SP-119 | ++++ | + | +++ | ++++ |
| SP-120 | ++++ | + | + | |
| SP-121 | ++ | + | | |
| SP-122 | +++ | + | ++ | |
| SP-123 | | + | + | ++++ |
| SP-124 | | + | | |
| SP-125 | +++ | + | + | |
| SP-126 | +++ | ++ | ++++ | |
| SP-127 | | + | + | ++++ |
| SP-128 | | + | +++ | ++++ |
| SP-129 | + | + | ++ | ++++ |
| SP-130 | ++ | + | +++ | ++++ |
| SP-131 | +++ | ++ | ++++ | ++++ |
| SP-132 | + | | | |
| SP-133 | + | | | |
| SP-134 | +++ | + | +++ | ++++ |
| SP-135 | + | | | |
| SP-136 | + | | | |
| SP-137 | + | | | |
| SP-138 | +++ | + | +++ | ++++ |
| SP-139 | ++ | + | +++ | ++ |
| SP-140 | ++ | + | +++ | +++ |
| SP-141 | ++ | ++ | ++++ | ++ |
| SP-142 | ++ | + | +++ | ++++ |
| SP-143 | ++ | +++ | ++++ | ++ |
| SP-144 | ++ | + | ++++ | +++ |
| SP-145 | +++ | | | ++++ |
| SP-146 | + | + | +++ | ++++ |
| SP-147 | + | ++ | +++ | ++++ |
| SP-148 | + | + | +++ | ++++ |
| SP-149 | ++ | +++ | ++++ | + |
| SP-150 | +++ | | | |

TABLE 6-continued

| | Scale | | | |
|---|---|---|---|---|
| | >700: +<br><400 but ≤700: ++<br><200 but ≤400: +++<br>≤200: ++++<br>IC50 (nM)<br>(HIF1α_p300<br>Displacement +<br>CHAPS) | >30: +<br><15 but ≤30: ++<br><5 but ≤15: +++<br>≤5: ++++<br>ME-180 HIF<br>Reporter<br>EC50 (µM) -<br>24 hour normoxia | ≥50: ++++<br>≤25 but <50: +++<br>≤10 but <25: ++<br><10: +<br>18 h Avg % max<br>inhibition at top<br>conc (HIF Rptr-24<br>hrs normoxia) (µM) | ≥30: ++++<br>≤15 but <30: +++<br>≤5 but <15: ++<br><5: +<br>Viability<br>1% FBS AVG<br>(MTT V3-24 hr<br>Normoxia) (µM) |
| SP # | | | | |
| SP-151 | ++ | ++++ | ++++ | |
| SP-152 | ++ | + | +++ | ++++ |
| SP-153 | ++ | + | + | ++++ |
| SP-154 | +++ | + | + | ++++ |
| SP-155 | + | + | ++ | ++++ |
| SP-156 | +++ | + | ++ | ++++ |
| SP-157 | + | + | + | |
| SP-158 | | | | |
| SP-159 | | | | |
| SP-160 | | | | |
| SP-161 | | | | |
| SP-162 | | ++ | ++++ | |
| SP-163 | | | | |
| SP-164 | | | | |
| SP-165 | | | | |
| SP-166 | | | | |
| SP-167 | | | | |
| SP-168 | | | | |
| SP-169 | | | | |
| SP-170 | | | | |
| SP-171 | | | | |
| SP-172 | | | | |
| SP-173 | | | | |
| SP-174 | | + | +++ | ++++ |
| SP-175 | ++ | + | ++ | ++++ |
| SP-176 | + | + | ++++ | ++++ |
| SP-177 | ++ | +++ | ++++ | +++ |
| SP-178 | + | | | |
| SP-179 | + | | | |
| SP-180 | + | | | |
| SP-181 | + | | | |
| SP-182 | + | | | |
| SP-183 | | | | |
| SP-184 | + | | | |
| SP-185 | + | | | |
| SP-186 | + | | | |
| SP-187 | + | | | |
| SP-188 | + | | | |
| SP-189 | + | | | |
| SP-190 | | + | ++ | ++++ |
| SP-191 | +++ | + | ++ | ++++ |
| SP-192 | +++ | + | ++ | ++++ |
| SP-193 | ++ | + | + | |
| SP-194 | | | | |
| SP-195 | ++ | ++++ | ++++ | ++ |
| SP-196 | +++ | ++++ | ++++ | ++++ |
| SP-197 | + | +++ | ++++ | ++++ |
| SP-198 | + | | | |
| SP-199 | +++ | + | + | ++++ |
| SP-200 | ++++ | + | ++++ | ++++ |
| SP-201 | | + | +++ | ++++ |
| SP-202 | | + | + | ++++ |
| SP-203 | | ++++ | ++++ | ++++ |
| SP-204 | + | | | |
| SP-205 | +++ | + | + | ++++ |
| SP-206 | + | + | + | |
| SP-207 | ++++ | + | + | ++++ |
| SP-208 | + | +++ | +++ | ++ |
| SP-209 | + | + | ++ | |
| SP-210 | +++ | +++ | ++++ | + |
| SP-211 | +++ | + | + | ++++ |
| SP-212 | +++ | +++ | ++++ | ++ |
| SP-213 | + | + | + | ++++ |
| SP-214 | + | + | +++ | |
| SP-215 | | | | |

TABLE 6-continued

| | Scale | | | |
|---|---|---|---|---|
| | >700: +<br><400 but ≤700: ++<br><200 but ≤400: +++<br>≤200: ++++<br>IC50 (nM)<br>(HIF1α_p300<br>Displacement +<br>CHAPS) | >30: +<br><15 but ≤30: ++<br><5 but ≤15: +++<br>≤5: ++++<br>ME-180 HIF<br>Reporter<br>EC50 (µM) -<br>24 hour normoxia | ≥50: ++++<br>≤25 but <50: +++<br>≤10 but <25: ++<br><10: +<br>18 h Avg % max<br>inhibition at top<br>conc (HIF Rptr-24<br>hrs normoxia) (µM) | ≥30: ++++<br>≤15 but <30: +++<br>≤5 but <15: ++<br><5: +<br>Viability<br>1% FBS AVG<br>(MTT V3-24 hr<br>Normoxia) (µM) |
| SP # | | | | |
| SP-216 | | | | |
| SP-217 | + | + | +++ | ++++ |
| SP-218 | | + | + | ++++ |
| SP-219 | ++ | + | ++ | |
| SP-220 | + | + | + | ++++ |
| SP-221 | +++ | ++ | ++++ | ++++ |
| SP-222 | +++ | | | |
| SP-223 | + | | | |
| SP-224 | ++ | + | ++ | ++++ |
| SP-225 | + | + | +++ | ++++ |
| SP-226 | ++ | + | ++ | ++++ |
| SP-227 | + | + | ++ | ++++ |
| SP-228 | +++ | + | +++ | ++++ |
| SP-229 | ++ | + | + | ++++ |
| SP-230 | ++ | + | + | ++++ |
| SP-231 | + | + | + | |
| SP-232 | ++ | + | ++ | |
| SP-233 | ++ | ++ | +++ | |
| SP-234 | ++ | + | +++ | ++++ |
| SP-235 | + | ++ | +++ | ++++ |
| SP-236 | + | + | +++ | ++++ |
| SP-237 | + | + | +++ | |
| SP-238 | ++ | + | ++ | |
| SP-239 | ++ | + | ++ | ++++ |
| SP-240 | ++ | + | +++ | ++++ |
| SP-241 | ++ | | | |
| SP-242 | ++++ | | | |
| SP-243 | ++ | ++ | ++++ | ++++ |
| SP-244 | + | ++++ | ++++ | ++++ |
| SP-245 | | | | ++++ |
| SP-246 | + | + | + | ++++ |
| SP-247 | ++ | ++ | +++ | ++++ |
| SP-248 | + | + | +++ | ++++ |
| SP-249 | + | + | + | ++++ |
| SP-250 | + | + | + | ++++ |
| SP-251 | + | ++++ | ++++ | + |
| SP-252 | + | ++++ | ++++ | ++ |
| SP-253 | | | | |
| SP-254 | + | ++++ | +++ | + |
| SP-255 | + | ++++ | ++++ | + |
| SP-256 | + | ++++ | ++++ | ++ |
| SP-257 | + | +++ | ++++ | ++ |
| SP-258 | + | +++ | +++ | ++ |
| SP-259 | + | ++++ | ++++ | + |
| SP-260 | + | ++++ | ++++ | + |
| SP-261 | | | | ++++ |
| SP-262 | | + | ++ | ++++ |
| SP-263 | ++ | +++ | ++++ | ++++ |
| SP-264 | ++ | ++ | ++ | ++++ |
| SP-265 | +++ | +++ | ++++ | ++++ |
| SP-266 | +++ | | | ++++ |
| SP-267 | ++ | + | +++ | ++++ |
| SP-268 | + | + | +++ | ++++ |
| SP-269 | ++ | ++ | +++ | ++++ |
| SP-270 | + | + | ++ | ++++ |
| SP-271 | + | + | +++ | ++++ |
| SP-272 | + | ++++ | ++++ | ++ |
| SP-273 | + | + | +++ | ++++ |
| SP-274 | | +++ | ++++ | ++++ |
| SP-275 | | +++ | ++++ | ++++ |
| SP-276 | | + | ++ | ++++ |
| SP-277 | | ++++ | ++++ | ++++ |
| SP-278 | | + | ++ | ++++ |
| SP-279 | | ++++ | ++++ | ++++ |
| SP-280 | | +++ | ++++ | ++++ |

TABLE 6-continued

| | Scale | | | |
|---|---|---|---|---|
| SP # | >700: +<br><400 but ≤700: ++<br><200 but ≤400: +++<br>≤200: ++++<br>IC50 (nM)<br>(HIF1α_p300<br>Displacement +<br>CHAPS) | >30: +<br><15 but ≤30: ++<br><5 but ≤15: +++<br>≤5: ++++<br>ME-180 HIF<br>Reporter<br>EC50 (μM) -<br>24 hour normoxia | ≥50: ++++<br>≤25 but <50: +++<br>≤10 but <25: ++<br><10: +<br>18 h Avg % max<br>inhibition at top<br>conc (HIF Rptr-24<br>hrs normoxia) (μM) | ≥30: ++++<br>≤15 but <30: +++<br>≤5 but <15: ++<br><5: +<br>Viability<br>1% FBS AVG<br>(MTT V3-24 hr<br>Normoxia) (μM) |
| SP-281 | ++ | +++ | ++++ | ++++ |
| SP-282 | ++++ | ++++ | ++++ | ++++ |
| SP-283 | + | + | +++ | ++++ |
| SP-284 | ++ | +++ | +++ | ++++ |
| SP-285 | + | + | +++ | ++++ |
| SP-286 | + | + | ++ | ++++ |
| SP-287 | + | +++ | ++++ | ++++ |
| SP-288 | + | + | + | ++++ |
| SP-289 | | | | |
| SP-290 | | + | + | |
| SP-291 | | + | +++ | |
| SP-292 | | + | + | |
| SP-293 | | + | + | |
| SP-294 | | | | |
| SP-295 | | | | |
| SP-296 | | ++++ | ++++ | |
| SP-297 | | | | |
| SP-298 | | +++ | ++++ | |
| SP-299 | | ++++ | ++++ | |
| SP-300 | | +++ | ++++ | |
| SP-301 | | ++ | +++ | |
| SP-302 | + | | | |
| SP-303 | + | | | |
| SP-304 | + | | | |
| SP-305 | ++++ | + | ++++ | ++++ |
| SP-306 | ++++ | + | +++ | ++++ |
| SP-307 | + | + | +++ | ++++ |
| SP-308 | +++ | ++ | ++++ | ++++ |
| SP-309 | +++ | + | + | ++++ |
| SP-310 | ++ | + | + | ++++ |
| SP-311 | + | + | ++ | ++++ |
| SP-312 | + | ++++ | ++++ | ++++ |
| SP-313 | +++ | + | + | ++++ |
| SP-314 | + | | | |
| SP-315 | + | | | |
| SP-316 | + | | | |
| SP-317 | + | | | |
| SP-318 | ++ | + | + | ++++ |
| SP-319 | +++ | + | + | ++++ |
| SP-320 | +++ | + | + | ++++ |
| SP-321 | +++ | ++ | +++ | ++++ |
| SP-322 | +++ | + | + | ++++ |
| SP-323 | +++ | + | + | ++++ |
| SP-324 | ++ | | | |
| SP-325 | + | + | + | ++++ |
| SP-326 | + | | | ++++ |
| SP-327 | + | + | + | ++++ |
| SP-328 | ++++ | + | + | ++++ |
| SP-329 | + | | | |
| SP-330 | + | + | + | ++++ |
| SP-331 | + | | | |
| SP-332 | ++++ | + | + | ++++ |
| SP-333 | ++ | | | |
| SP-334 | +++ | + | + | ++++ |
| SP-335 | ++ | + | + | ++++ |
| SP-336 | + | + | + | ++++ |
| SP-337 | ++ | + | + | ++++ |
| SP-338 | + | + | +++ | ++++ |
| SP-339 | +++ | + | + | ++++ |
| SP-340 | + | + | ++ | ++++ |
| SP-341 | +++ | + | + | ++++ |
| SP-342 | + | + | +++ | ++++ |
| SP-343 | +++ | + | + | ++++ |
| SP-344 | ++ | + | + | ++++ |
| SP-345 | | | | |

TABLE 6-continued

| | Scale | | | |
|---|---|---|---|---|
| SP # | >700: +<br><400 but ≤700: ++<br><200 but ≤400: +++<br>≤200: ++++<br>IC50 (nM)<br>(HIF1α_p300<br>Displacement +<br>CHAPS) | >30: +<br><15 but ≤30: ++<br><5 but ≤15: +++<br>≤5: ++++<br>ME-180 HIF<br>Reporter<br>EC50 (µM) -<br>24 hour normoxia | ≥50: ++++<br>≤25 but <50: +++<br>≤10 but <25: ++<br><10: +<br>18 h Avg % max<br>inhibition at top<br>conc (HIF Rptr-24<br>hrs normoxia) (µM) | ≥30: ++++<br>≤15 but <30: +++<br>≤5 but <15: ++<br><5: +<br>Viability<br>1% FBS AVG<br>(MTT V3-24 hr<br>Normoxia) (µM) |
| SP-346 | ++++ | + | ++ | ++++ |
| SP-347 | ++ | + | +++ | |
| SP-348 | + | | | |
| SP-349 | ++++ | + | +++ | ++++ |
| SP-350 | ++++ | +++ | +++ | ++++ |
| SP-351 | +++ | + | ++ | ++++ |
| SP-352 | ++++ | + | ++ | ++++ |
| SP-353 | ++++ | + | +++ | ++++ |
| SP-354 | +++ | + | +++ | ++++ |
| SP-355 | ++++ | + | ++ | ++++ |
| SP-356 | + | | | |
| SP-357 | ++++ | + | ++ | ++++ |
| SP-358 | +++ | + | + | ++++ |
| SP-359 | +++ | + | +++ | ++++ |
| SP-360 | +++ | + | ++ | ++++ |
| SP-361 | + | + | ++ | ++++ |
| SP-362 | ++ | +++ | ++++ | ++++ |
| SP-363 | + | + | ++ | ++++ |
| SP-364 | + | + | ++ | ++++ |
| SP-365 | + | + | +++ | ++++ |
| SP-366 | + | ++++ | ++++ | ++++ |
| SP-367 | ++ | ++++ | ++++ | ++++ |
| SP-368 | | | | |
| SP-369 | | + | ++ | ++++ |
| SP-370 | + | | | |
| SP-371 | | + | ++ | ++++ |
| SP-372 | ++ | + | ++++ | ++++ |
| SP-373 | +++ | + | +++ | ++++ |

While preferred embodiments of the present invention have been shown and described herein, it will be obvious to those skilled in the art that such embodiments are provided by way of example only. Numerous variations, changes, and substitutions will now occur to those killed in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A peptidomimetic macrocycle having the formula

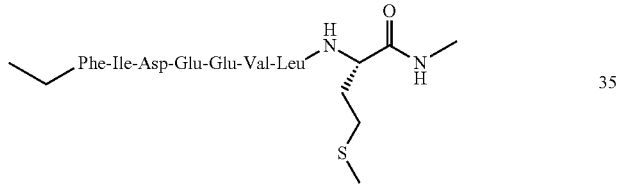

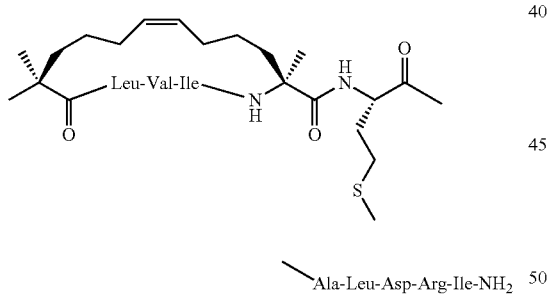

or a pharmaceutically acceptable salt thereof.

2. A peptidomimetic macrocycle having the formula

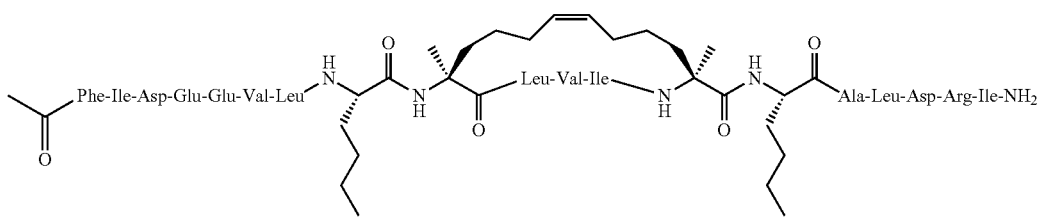

or a pharmaceutically acceptable salt thereof.

3. A peptidomimetic macrocycle having the formula
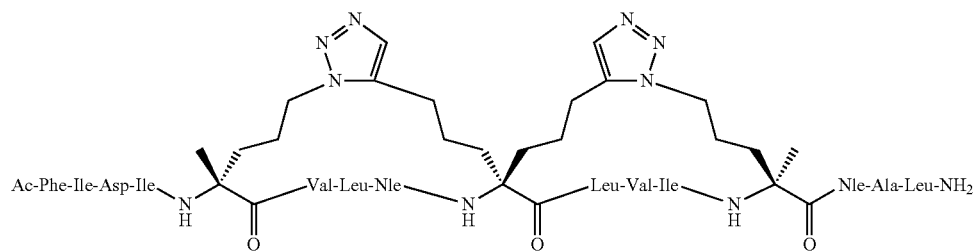
or a pharmaceutically acceptable salt thereof.
* * * * *

SEQUENCE LISTING

```
<160> NUMBER OF SEQ ID NOS: 391

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Any amino acid available for cross-linking
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
```

```
<220> FEATURE:
<221> NAME/KEY: MOD_RES
<222> LOCATION: (9)..(9)
<223> OTHER INFORMATION: Any amino acid available for cross-linking
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Any amino acid available for cross-linking
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 1

Phe Ile Asp Ile Xaa Val Leu Leu Xaa Leu Val Ile Xaa Leu Ala Leu
1               5                   10                  15

<210> SEQ ID NO 2
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(2)
<223> OTHER INFORMATION: Any hydrophobic amino acid or absent
<220> FEATURE:
<221> NAME/KEY: MOD_RES
<222> LOCATION: (3)..(3)
<223> OTHER INFORMATION: Any negatively charged amino acid, positively
      charged amino acid or absent
<220> FEATURE:
<221> NAME/KEY: MOD_RES
<222> LOCATION: (4)..(4)
<223> OTHER INFORMATION: Any uncharged polar amino acid or absent
<220> FEATURE:
<221> NAME/KEY: MOD_RES
<222> LOCATION: (5)..(5)
<223> OTHER INFORMATION: Any negatively charged amino acid or absent
<220> FEATURE:
<221> NAME/KEY: MOD_RES
<222> LOCATION: (6)..(6)
<223> OTHER INFORMATION: Any hydrophobic amino acid, negatively charged
      amino acid, positively charged amino acid, uncharged polar
      amino acid or absent
<220> FEATURE:
<221> NAME/KEY: MOD_RES
<222> LOCATION: (7)..(7)
<223> OTHER INFORMATION: Any hydrophobic amino acid, negatively charged
      amino acid or absent
<220> FEATURE:
<221> NAME/KEY: MOD_RES
<222> LOCATION: (8)..(8)
<223> OTHER INFORMATION: Any negatively charged amino acid, positively
      charged amino acid or absent
<220> FEATURE:
<221> NAME/KEY: MOD_RES
<222> LOCATION: (9)..(9)
<223> OTHER INFORMATION: Any negatively charged amino acid, absent or
      any amino acid available for cross-linking
<220> FEATURE:
<221> NAME/KEY: MOD_RES
<222> LOCATION: (10)..(10)
<223> OTHER INFORMATION: Any negatively charged amino acid, positively
      charged amino acid, uncharged polar amino acid or any amino acid
      available for cross-linking
<220> FEATURE:
<221> NAME/KEY: MOD_RES
<222> LOCATION: (11)..(11)
```

```
<223> OTHER INFORMATION: Any hydrophobic amino acid, negatively charged
      amino acid, positively charged amino acid or any amino acid
      available for cross-linking
<220> FEATURE:
<221> NAME/KEY: MOD_RES
<222> LOCATION: (12)..(12)
<223> OTHER INFORMATION: Any hydrophobic amino acid, negatively charged
      amino acid or any amino acid available for cross-linking
<220> FEATURE:
<221> NAME/KEY: MOD_RES
<222> LOCATION: (13)..(13)
<223> OTHER INFORMATION: Any hydrophobic amino acid, hydrophobic amino
      acid, negatively charged amino acid or any amino acid
      available for cross-linking
<220> FEATURE:
<221> NAME/KEY: MOD_RES
<222> LOCATION: (14)..(14)
<223> OTHER INFORMATION: Any amino acid available for cross-linking
<220> FEATURE:
<221> NAME/KEY: MOD_RES
<222> LOCATION: (15)..(16)
<223> OTHER INFORMATION: Any hydrophobic amino acid, negatively charged
      amino acid or any amino acid available for cross-linking
<220> FEATURE:
<221> NAME/KEY: MOD_RES
<222> LOCATION: (17)..(17)
<223> OTHER INFORMATION: Any hydrophobic amino acid, negatively charged
      amino acid, positively charged amino acid or any amino acid
      available for cross-linking
<220> FEATURE:
<221> NAME/KEY: MOD_RES
<222> LOCATION: (18)..(18)
<223> OTHER INFORMATION: Any amino acid available for cross-linking
<220> FEATURE:
<221> NAME/KEY: MOD_RES
<222> LOCATION: (19)..(19)
<223> OTHER INFORMATION: Any hydrophobic amino acid, negatively charged
      amino acid, positively charged amino acid or any amino acid
      available for cross-linking
<220> FEATURE:
<221> NAME/KEY: MOD_RES
<222> LOCATION: (20)..(20)
<223> OTHER INFORMATION: Any negatively charged amino acid, hydrophobic
      amino acid or any amino acid available for cross-linking
<220> FEATURE:
<221> NAME/KEY: MOD_RES
<222> LOCATION: (21)..(21)
<223> OTHER INFORMATION: Any hydrophobic amino acid or negatively
      charged amino acid
<220> FEATURE:
<221> NAME/KEY: MOD_RES
<222> LOCATION: (22)..(22)
<223> OTHER INFORMATION: Any negatively charged amino acid or absent
<220> FEATURE:
<221> NAME/KEY: MOD_RES
<222> LOCATION: (23)..(23)
<223> OTHER INFORMATION: Any positively charged amino acid, negatively
      charged amino acid or absent
<220> FEATURE:
<221> NAME/KEY: MOD_RES
<222> LOCATION: (24)..(25)
<223> OTHER INFORMATION: Any hydrophobic amino acid, negatively charged
      amino acid or absent
<220> FEATURE:
<221> NAME/KEY: MOD_RES
<222> LOCATION: (26)..(26)
<223> OTHER INFORMATION: Any negatively charged amino acid or absent
<220> FEATURE:
<221> NAME/KEY: MOD_RES
<222> LOCATION: (27)..(28)
<223> OTHER INFORMATION: Any hydrophobic amino acid or absent
<220> FEATURE:
<221> NAME/KEY: MOD_RES
<222> LOCATION: (29)..(29)
<223> OTHER INFORMATION: Any negatively charged amino acid, uncharged
      polar amino acid or absent
<220> FEATURE:
<221> NAME/KEY: MOD_RES
<222> LOCATION: (30)..(32)
```

```
<223> OTHER INFORMATION: Any hydrophobic amino acid or absent
<220> FEATURE:
<221> NAME/KEY: misc_feature
<222> LOCATION: (1)..(32)
<223> OTHER INFORMATION: This sequence contains at least one macrocycle-
      forming linker which connects at least one pair of amino acids
      at positions 1 to 28
<220> FEATURE:
<223> OTHER INFORMATION: see specification as filed for detailed
      description of substitutions and preferred embodiments

<400> SEQUENCE: 2

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

<210> SEQ ID NO 3
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (2)..(2)
<223> OTHER INFORMATION: Ile, Phe or absent
<220> FEATURE:
<221> NAME/KEY: MOD_RES
<222> LOCATION: (3)..(3)
<223> OTHER INFORMATION: Asp, Arg or absent
<220> FEATURE:
<221> NAME/KEY: MOD_RES
<222> LOCATION: (4)..(5)
<223> OTHER INFORMATION: May or may not be present
<220> FEATURE:
<221> NAME/KEY: MOD_RES
<222> LOCATION: (6)..(6)
<223> OTHER INFORMATION: Phe, Ala, Glu, Ser, Dpr, Asn or absent
<220> FEATURE:
<221> NAME/KEY: MOD_RES
<222> LOCATION: (7)..(7)
<223> OTHER INFORMATION: Ile, Ala, Glu, Ser or absent
<220> FEATURE:
<221> NAME/KEY: MOD_RES
<222> LOCATION: (8)..(8)
<223> OTHER INFORMATION: Asp, Ala, Ser, Dpr or absent
<220> FEATURE:
<221> NAME/KEY: MOD_RES
<222> LOCATION: (9)..(9)
<223> OTHER INFORMATION: Glu, Ala, absent or any amino acid available
      for cross-linking
<220> FEATURE:
<221> NAME/KEY: MOD_RES
<222> LOCATION: (10)..(10)
<223> OTHER INFORMATION: Glu, Ala, Ser, Dpr, Gln or any amino acid
      available for cross-linking
<220> FEATURE:
<221> NAME/KEY: MOD_RES
<222> LOCATION: (11)..(11)
<223> OTHER INFORMATION: Val, Ala, Asp, Ser, Dpr or any amino acid
      available for cross-linking
<220> FEATURE:
<221> NAME/KEY: MOD_RES
<222> LOCATION: (12)..(12)
<223> OTHER INFORMATION: Leu, Ala, Glu, Ser, pL or any amino acid
      available for cross-linking
<220> FEATURE:
<221> NAME/KEY: MOD_RES
<222> LOCATION: (13)..(13)
<223> OTHER INFORMATION: Met, Nle, Ala, Asp or any amino acid available
```

```
              for cross-linking
<220> FEATURE:
<221> NAME/KEY: MOD_RES
<222> LOCATION: (14)..(14)
<223> OTHER INFORMATION: Ser or any amino acid available for cross-
      linking
<220> FEATURE:
<221> NAME/KEY: MOD_RES
<222> LOCATION: (15)..(15)
<223> OTHER INFORMATION: Leu, Ala, Asp, Ser or any amino acid available
      for cross-linking
<220> FEATURE:
<221> NAME/KEY: MOD_RES
<222> LOCATION: (16)..(16)
<223> OTHER INFORMATION: Val, Ala, Glu, Ser, pL or any amino acid
      available for cross-linking
<220> FEATURE:
<221> NAME/KEY: MOD_RES
<222> LOCATION: (17)..(17)
<223> OTHER INFORMATION: Ile, Ala, Glu, Ser, Dpr, Bpa or any amino acid
      available for cross-linking
<220> FEATURE:
<221> NAME/KEY: MOD_RES
<222> LOCATION: (18)..(18)
<223> OTHER INFORMATION: Glu or any amino acid available for cross-
      linking
<220> FEATURE:
<221> NAME/KEY: MOD_RES
<222> LOCATION: (19)..(19)
<223> OTHER INFORMATION: Met, Nle, Ala, Glu, Ser, Dpr, Bpa or any amino
      acid available for cross-linking
<220> FEATURE:
<221> NAME/KEY: MOD_RES
<222> LOCATION: (20)..(20)
<223> OTHER INFORMATION: Gly, Ala, Glu, Ser or any amino acid available
      for cross-linking
<220> FEATURE:
<221> NAME/KEY: MOD_RES
<222> LOCATION: (21)..(21)
<223> OTHER INFORMATION: Leu, Ala, Glu or Ser
<220> FEATURE:
<221> NAME/KEY: MOD_RES
<222> LOCATION: (22)..(22)
<223> OTHER INFORMATION: Asp, Ala, Ser or absent
<220> FEATURE:
<221> NAME/KEY: MOD_RES
<222> LOCATION: (23)..(23)
<223> OTHER INFORMATION: Arg, Ala, Glu, Ser, Dpr or absent
<220> FEATURE:
<221> NAME/KEY: MOD_RES
<222> LOCATION: (24)..(24)
<223> OTHER INFORMATION: Ile, Ala, Glu, Ser or absent
<220> FEATURE:
<221> NAME/KEY: MOD_RES
<222> LOCATION: (25)..(25)
<223> OTHER INFORMATION: Lys, Glu or absent
<220> FEATURE:
<221> NAME/KEY: MOD_RES
<222> LOCATION: (26)..(28)
<223> OTHER INFORMATION: May or may not be present
<220> FEATURE:
<221> NAME/KEY: MOD_RES
<222> LOCATION: (29)..(29)
<223> OTHER INFORMATION: Glu, Gln or absent
<220> FEATURE:
<221> NAME/KEY: MOD_RES
<222> LOCATION: (30)..(32)
<223> OTHER INFORMATION: May or may not be present
<220> FEATURE:
<221> NAME/KEY: misc_feature
<222> LOCATION: (1)..(32)
<220> FEATURE:
<221> NAME/KEY: misc_feature
<222> LOCATION: (1)..(32)
<223> OTHER INFORMATION: This sequence contains at least one macrocycle-
      forming linker which connects at least one pair of amino acids
      at positions 1 to 28
<220> FEATURE:
<223> OTHER INFORMATION: see specification as filed for detailed
``` description of substitutions and preferred embodiments

<400> SEQUENCE: 3

Val Xaa Xaa Thr Asp Xaa Xaa Xaa Xaa Xaa Xaa Xaa Xaa Xaa Xaa
1               5                   10                  15

Xaa Xaa Xaa Xaa Xaa Xaa Xaa Xaa Xaa Glu Leu Pro Xaa Leu Trp Leu
            20                  25                  30

<210> SEQ ID NO 4
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (2)..(2)
<223> OTHER INFORMATION: Ile, Phe or absent
<220> FEATURE:
<221> NAME/KEY: MOD_RES
<222> LOCATION: (3)..(3)
<223> OTHER INFORMATION: Asp, Arg or absent
<220> FEATURE:
<221> NAME/KEY: MOD_RES
<222> LOCATION: (4)..(5)
<223> OTHER INFORMATION: May or may not be present
<220> FEATURE:
<221> NAME/KEY: MOD_RES
<222> LOCATION: (6)..(6)
<223> OTHER INFORMATION: Phe, Ala, Glu, Ser, Dpr, Asn or absent
<220> FEATURE:
<221> NAME/KEY: MOD_RES
<222> LOCATION: (7)..(7)
<223> OTHER INFORMATION: Ile, Ala, Glu, Ser or absent
<220> FEATURE:
<221> NAME/KEY: MOD_RES
<222> LOCATION: (8)..(8)
<223> OTHER INFORMATION: Asp, Ala, Ser, Dpr or absent
<220> FEATURE:
<221> NAME/KEY: MOD_RES
<222> LOCATION: (9)..(9)
<223> OTHER INFORMATION: Glu, Ala, absent or any amino acid available
      for cross-linking
<220> FEATURE:
<221> NAME/KEY: MOD_RES
<222> LOCATION: (10)..(10)
<223> OTHER INFORMATION: Glu, Ala, Ser, Dpr, Gln or any amino acid
      available for cross-linking
<220> FEATURE:
<221> NAME/KEY: MOD_RES
<222> LOCATION: (11)..(11)
<223> OTHER INFORMATION: Val, Ala, Asp, Ser, Dpr or any amino acid
      available for cross-linking
<220> FEATURE:
<221> NAME/KEY: MOD_RES
<222> LOCATION: (12)..(12)
<223> OTHER INFORMATION: Leu, Ala, Glu, Ser, pL or any amino acid
      available for cross-linking
<220> FEATURE:
<221> NAME/KEY: MOD_RES
<222> LOCATION: (13)..(13)
<223> OTHER INFORMATION: Met, Nle, Ala, Asp or any amino acid available
      for cross-linking
<220> FEATURE:
<221> NAME/KEY: MOD_RES
<222> LOCATION: (14)..(14)
<223> OTHER INFORMATION: Ser or any amino acid available for cross-
      linking
<220> FEATURE:
<221> NAME/KEY: MOD_RES
<222> LOCATION: (15)..(15)

```
<223> OTHER INFORMATION: Leu, Ala, Asp, Ser or any amino acid available
      for cross-linking
<220> FEATURE:
<221> NAME/KEY: MOD_RES
<222> LOCATION: (16)..(16)
<223> OTHER INFORMATION: Val, Ala, Glu, Ser, pL or any amino acid
      available for cross-linking
<220> FEATURE:
<221> NAME/KEY: MOD_RES
<222> LOCATION: (17)..(17)
<223> OTHER INFORMATION: Ile, Ala, Glu, Ser, Dpr, Bpa or any amino acid
      available for cross-linking
<220> FEATURE:
<221> NAME/KEY: MOD_RES
<222> LOCATION: (18)..(18)
<223> OTHER INFORMATION: Glu or any amino acid available for cross-
      linking
<220> FEATURE:
<221> NAME/KEY: MOD_RES
<222> LOCATION: (19)..(19)
<223> OTHER INFORMATION: Met, Nle, Ala, Glu, Ser, Dpr, Bpa or any amino
      acid available for cross-linking
<220> FEATURE:
<221> NAME/KEY: MOD_RES
<222> LOCATION: (20)..(20)
<223> OTHER INFORMATION: Gly, Ala, Glu, Ser or any amino acid available
      for cross-linking
<220> FEATURE:
<221> NAME/KEY: MOD_RES
<222> LOCATION: (21)..(21)
<223> OTHER INFORMATION: Leu, Ala, Glu or Ser
<220> FEATURE:
<221> NAME/KEY: MOD_RES
<222> LOCATION: (22)..(22)
<223> OTHER INFORMATION: Asp, Ala, Ser or absent
<220> FEATURE:
<221> NAME/KEY: MOD_RES
<222> LOCATION: (23)..(23)
<223> OTHER INFORMATION: Arg, Ala, Glu, Ser, Dpr or absent
<220> FEATURE:
<221> NAME/KEY: MOD_RES
<222> LOCATION: (24)..(24)
<223> OTHER INFORMATION: Ile, Ala, Glu, Ser or absent
<220> FEATURE:
<221> NAME/KEY: MOD_RES
<222> LOCATION: (25)..(25)
<223> OTHER INFORMATION: Lys, Glu or absent
<220> FEATURE:
<221> NAME/KEY: MOD_RES
<222> LOCATION: (26)..(28)
<223> OTHER INFORMATION: May or may not be present
<220> FEATURE:
<221> NAME/KEY: MOD_RES
<222> LOCATION: (29)..(29)
<223> OTHER INFORMATION: Glu, Gln or absent
<220> FEATURE:
<221> NAME/KEY: MOD_RES
<222> LOCATION: (30)..(32)
<223> OTHER INFORMATION: May or may not be present
<220> FEATURE:
<221> NAME/KEY: misc_feature
<222> LOCATION: (1)..(32)
<223> OTHER INFORMATION: This sequence contains at least one macrocycle-
      forming linker which connects at least one pair of amino acids
      at positions 1 to 28
<220> FEATURE:
<223> OTHER INFORMATION: see specification as filed for detailed
      description of substitutions and preferred embodiments

<400> SEQUENCE: 4

Val Xaa Xaa Thr Asp Xaa Xaa Xaa Xaa Xaa Xaa Xaa Xaa Xaa Xaa
1               5                   10                  15

Xaa Xaa Xaa Xaa Xaa Xaa Xaa Xaa Xaa Glu Leu Pro Xaa Leu Trp Leu
            20                  25                  30

<210> SEQ ID NO 5
```

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Phe Ile Asp Glu Glu Val Leu Met Ser Leu Val Ile Glu Met Ala Leu
1               5                   10                  15

Asp Arg Ile

<210> SEQ ID NO 6
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term may be Ac
<220> FEATURE:
<221> NAME/KEY: MOD_RES
<222> LOCATION: (9)..(9)
<223> OTHER INFORMATION: Any amino acid available for cross-linking
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Any amino acid available for cross-linking
<220> FEATURE:
<223> OTHER INFORMATION: C-term may be NH2

<400> SEQUENCE: 6

Phe Ile Asp Glu Glu Val Leu Met Xaa Leu Val Ile Xaa Met Ala Leu
1               5                   10                  15

Asp Arg Ile

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (14)..(14)
<223> OTHER INFORMATION: Nle

<400> SEQUENCE: 7

Phe Ile Asp Glu Glu Val Leu Leu Ser Leu Val Ile Glu Leu Ala Leu
1               5                   10                  15

Asp Arg Ile

<210> SEQ ID NO 8
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: N-term may be Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Any amino acid available for cross-linking
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Any amino acid available for cross-linking
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term may be NH2

<400> SEQUENCE: 8

Phe Ile Asp Glu Glu Val Leu Leu Xaa Leu Val Ile Xaa Leu Ala Leu
1               5                   10                  15

Asp Arg Ile

<210> SEQ ID NO 9
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Phe Ile Asp Glu Glu Val Leu Met Ser Leu Val Ile Glu Met Gly Leu
1               5                   10                  15

Asp Arg Ile Lys Glu Leu Pro Glu Leu Trp Leu
            20                  25

<210> SEQ ID NO 10
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid available for cross-linking
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Any amino acid available for cross-linking

<400> SEQUENCE: 10

Phe Ile Asp Glu Glu Val Leu Met Xaa Leu Val Ile Xaa Met Gly Leu
1               5                   10                  15

Asp Arg Ile Lys Glu Leu Pro Glu Leu Trp Leu
            20                  25

<210> SEQ ID NO 11
```

```
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(23)
<223> OTHER INFORMATION: Any amino acid
<220> FEATURE:
<223> OTHER INFORMATION: see specification as filed for detailed
      description of substitutions and preferred embodiments

<400> SEQUENCE: 11

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Leu Gln Gly Glu Glu Leu Leu Arg Ala Leu Asp Gln Val
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: misc_feature
<222> LOCATION: (8)..(12)
<223> OTHER INFORMATION: Cross-link between residues
<220> FEATURE:
<221> NAME/KEY: MOD_RES
<222> LOCATION: (12)..(12)
<223> OTHER INFORMATION: Any amino acid available for cross-linking

<400> SEQUENCE: 13

Leu Leu Gln Gly Glu Glu Leu Xaa Arg Ala Leu Xaa Gln Val
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid available for cross-linking
<220> FEATURE:
<221> NAME/KEY: misc_feature
<222> LOCATION: (6)..(13)
<223> OTHER INFORMATION: Cross-link between residues
<220> FEATURE:
```

```
<221> NAME/KEY: MOD_RES
<222> LOCATION: (13)..(13)
<223> OTHER INFORMATION: Any amino acid available for cross-linking

<400> SEQUENCE: 14

Leu Leu Gln Gly Glu Xaa Leu Leu Arg Ala Leu Asp Xaa Val
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Leu Thr Ser Tyr Asp Cys Glu Val Asn Ala
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid available for cross-linking
<220> FEATURE:
<221> NAME/KEY: misc_feature
<222> LOCATION: (4)..(8)
<223> OTHER INFORMATION: Cross-link between residues
<220> FEATURE:
<221> NAME/KEY: MOD_RES
<222> LOCATION: (7)..(7)
<223> OTHER INFORMATION: Abu
<220> FEATURE:
<221> NAME/KEY: MOD_RES
<222> LOCATION: (8)..(8)
<223> OTHER INFORMATION: Any amino acid available for cross-linking

<400> SEQUENCE: 16

Gln Leu Thr Xaa Tyr Asp Xaa Xaa Val Asn Ala
1               5                   10

<210> SEQ ID NO 17
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
```

```
<220> FEATURE:
<223> OTHER INFORMATION: C-term NH2

<400> SEQUENCE: 17

Phe Ile Asp Glu Glu Val Leu Met Ala Leu Val Ile Ala Met Gly Leu
1               5                   10                  15

Asp Arg Ile Lys Glu Leu Pro Glu Leu Trp Leu
            20                  25

<210> SEQ ID NO 18
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 18

Phe Ile Asp Glu Glu Val Leu Leu Ala Leu Val Ile Ala Leu Gly Leu
1               5                   10                  15

Asp Arg Ile Lys Glu Leu Pro Glu Leu Trp Leu
            20                  25

<210> SEQ ID NO 19
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
```

```
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 19

Phe Ile Asp Glu Glu Val Leu Met Ala Leu Val Ile Ala Met Ala Leu
1               5                   10                  15

Asp Arg Ile Lys Glu Leu Pro Glu Leu Trp Leu
            20                  25

<210> SEQ ID NO 20
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 20

Phe Ile Asp Glu Glu Val Leu Leu Ala Leu Val Ile Ala Leu Ala Leu
1               5                   10                  15

Asp Arg Ile Lys Glu Leu Pro Glu Leu Trp Leu
            20                  25

<210> SEQ ID NO 21
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
```

```
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 21

Phe Ile Asp Glu Glu Val Leu Met Ala Leu Val Ile Ala Met Ala Leu
1               5                   10                  15

Asp Arg Ile

<210> SEQ ID NO 22
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 22

Phe Ile Asp Glu Glu Val Leu Leu Ala Leu Val Ile Ala Leu Ala Leu
1               5                   10                  15

Asp Arg Ile

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
```

```
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 23

Phe Ile Asp Glu Glu Val Leu Met Ala Leu Val Ile Ala Met Ala Leu
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 24

Phe Ile Asp Glu Glu Val Leu Leu Ala Leu Val Ile Ala Leu Ala Leu
1               5                   10                  15

<210> SEQ ID NO 25
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
```

```
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 25

Ala Ile Asp Glu Glu Val Leu Leu Ala Leu Val Ile Ala Leu Ala Leu
1               5                   10                  15

Asp Arg Ile

<210> SEQ ID NO 26
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 26

Phe Ala Asp Glu Glu Val Leu Leu Ala Leu Val Ile Ala Leu Ala Leu
1               5                   10                  15

Asp Arg Ile

<210> SEQ ID NO 27
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
```

```
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 27

Phe Ile Ala Glu Glu Val Leu Leu Ala Leu Val Ile Ala Leu Ala Leu
1               5                   10                  15

Asp Arg Ile

<210> SEQ ID NO 28
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 28

Phe Ile Asp Ala Glu Val Leu Leu Ala Leu Val Ile Ala Leu Ala Leu
1               5                   10                  15

Asp Arg Ile

<210> SEQ ID NO 29
<211> LENGTH: 19
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 29

Phe Ile Asp Glu Ala Val Leu Leu Ala Leu Val Ile Ala Leu Ala Leu
1               5                   10                  15

Asp Arg Ile

<210> SEQ ID NO 30
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 30
```

Phe Ile Asp Glu Glu Ala Leu Leu Ala Leu Val Ile Ala Leu Ala Leu
1               5                   10                  15

Asp Arg Ile

<210> SEQ ID NO 31
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 31

Phe Ile Asp Glu Glu Val Ala Leu Ala Leu Val Ile Ala Leu Ala Leu
1               5                   10                  15

Asp Arg Ile

<210> SEQ ID NO 32
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle

```
<220> FEATURE:
<223> OTHER INFORMATION: C-term NH2

<400> SEQUENCE: 32

Phe Ile Asp Glu Glu Val Leu Ala Ala Leu Val Ile Ala Leu Ala Leu
1               5                   10                  15

Asp Arg Ile

<210> SEQ ID NO 33
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 33

Phe Ile Asp Glu Glu Val Leu Leu Ala Ala Val Ile Ala Leu Ala Leu
1               5                   10                  15

Asp Arg Ile

<210> SEQ ID NO 34
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
```

```
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 34

Phe Ile Asp Glu Glu Val Leu Leu Ala Leu Ala Ile Ala Leu Ala Leu
1               5                   10                  15

Asp Arg Ile

<210> SEQ ID NO 35
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 35

Phe Ile Asp Glu Glu Val Leu Leu Ala Leu Val Ala Ala Leu Ala Leu
1               5                   10                  15

Asp Arg Ile

<210> SEQ ID NO 36
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
```

```
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 36

Phe Ile Asp Glu Glu Val Leu Leu Ala Leu Val Ile Ala Ala Ala Leu
1               5                   10                  15

Asp Arg Ile

<210> SEQ ID NO 37
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 37

Phe Ile Asp Glu Glu Val Leu Leu Ala Leu Val Ile Ala Leu Gly Leu
1               5                   10                  15

Asp Arg Ile

<210> SEQ ID NO 38
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
```

```
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 38

Phe Ile Asp Glu Glu Val Leu Leu Ala Leu Val Ile Ala Leu Ala Ala
1               5                   10                  15

Asp Arg Ile

<210> SEQ ID NO 39
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 39

Phe Ile Asp Glu Glu Val Leu Leu Ala Leu Val Ile Ala Leu Ala Leu
1               5                   10                  15

Ala Arg Ile

<210> SEQ ID NO 40
```

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 40

Phe Ile Asp Glu Glu Val Leu Leu Ala Leu Val Ile Ala Leu Ala Leu
1               5                   10                  15

Asp Ala Ile

<210> SEQ ID NO 41
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2
```

```
<400> SEQUENCE: 41

Phe Ile Asp Glu Glu Val Leu Leu Ala Leu Val Ile Ala Leu Ala Leu
1               5                   10                  15

Asp Arg Ala

<210> SEQ ID NO 42
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 42

Phe Ile Asp Glu Glu Val Leu Ala Ala Leu Val Ile Ala Ala Ala Leu
1               5                   10                  15

Asp Arg Ile

<210> SEQ ID NO 43
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2
```

<400> SEQUENCE: 43

Phe Ile Asp Glu Glu Val Leu Leu Ala Leu Val Ile Ala Leu Ala Leu
1               5                   10                  15

Asp Arg

<210> SEQ ID NO 44
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 44

Phe Ile Asp Glu Glu Val Leu Ala Ala Leu Val Ile Ala Ala Ala Leu
1               5                   10                  15

Asp Arg

<210> SEQ ID NO 45
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Nle
<220> FEATURE:
<221> NAME/KEY: MOD_RES
<222> LOCATION: (10)..(10)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (10)..(14)
<223> OTHER INFORMATION: Cross-link between residues
<220> FEATURE:
<221> NAME/KEY: MOD_RES
<222> LOCATION: (14)..(14)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (15)..(15)
<223> OTHER INFORMATION: Nle
<220> FEATURE:

<223> OTHER INFORMATION: C-term NH2

<400> SEQUENCE: 45

Asp Phe Ile Asp Glu Glu Val Leu Leu Ala Leu Val Ile Ala Leu Ala
1               5                   10                  15

Leu Asp Arg Ile
            20

<210> SEQ ID NO 46
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 46

Glu Ile Asp Glu Glu Val Leu Leu Ala Leu Val Ile Ala Leu Ala Leu
1               5                   10                  15

Asp Arg Ile

<210> SEQ ID NO 47
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:

```
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 47

Phe Glu Asp Glu Glu Val Leu Leu Ala Leu Val Ile Ala Leu Ala Leu
1               5                   10                  15

Asp Arg Ile

<210> SEQ ID NO 48
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 48

Phe Ile Asp Glu Glu Asp Leu Leu Ala Leu Val Ile Ala Leu Ala Leu
1               5                   10                  15

Asp Arg Ile

<210> SEQ ID NO 49
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
```

```
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 49

Phe Ile Asp Glu Glu Val Glu Leu Ala Leu Val Ile Ala Leu Ala Leu
1               5                   10                  15

Asp Arg Ile

<210> SEQ ID NO 50
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 50

Phe Ile Asp Glu Glu Val Leu Asp Ala Leu Val Ile Ala Leu Ala Leu
1               5                   10                  15

Asp Arg Ile

<210> SEQ ID NO 51
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
```

<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 51

Phe Ile Asp Glu Glu Val Leu Leu Ala Asp Val Ile Ala Leu Ala Leu
1               5                   10                  15

Asp Arg Ile

<210> SEQ ID NO 52
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 52

Phe Ile Asp Glu Glu Val Leu Leu Ala Leu Glu Ile Ala Leu Ala Leu
1               5                   10                  15

Asp Arg Ile

<210> SEQ ID NO 53

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 53

Phe Ile Asp Glu Glu Val Leu Leu Ala Leu Val Glu Ala Leu Ala Leu
1               5                   10                  15

Asp Arg Ile

<210> SEQ ID NO 54
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 54

Phe Ile Asp Glu Glu Val Leu Leu Ala Leu Val Ile Ala Glu Ala Leu
1               5                   10                  15
```

Asp Arg Ile

<210> SEQ ID NO 55
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 55

Phe Ile Asp Glu Glu Val Leu Leu Ala Leu Val Ile Ala Leu Glu Leu
1               5                   10                  15

Asp Arg Ile

<210> SEQ ID NO 56
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES

```
<222> LOCATION: (14)..(14)
<223> OTHER INFORMATION: Nle
<220> FEATURE:
<223> OTHER INFORMATION: C-term NH2

<400> SEQUENCE: 56

Phe Ile Asp Glu Glu Val Leu Leu Ala Leu Val Ile Ala Leu Ala Glu
1               5                   10                  15

Asp Arg Ile

<210> SEQ ID NO 57
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 57

Phe Ile Asp Glu Glu Val Leu Leu Ala Leu Val Ile Ala Leu Ala Leu
1               5                   10                  15

Asp Glu Ile

<210> SEQ ID NO 58
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
```

```
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 58

Phe Ile Asp Glu Glu Val Leu Leu Ala Leu Val Ile Ala Leu Ala Leu
1               5                   10                  15

Asp Arg Glu

<210> SEQ ID NO 59
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 59

Phe Ile Asp Glu Glu Val Leu Leu Ala Leu Val Ile Ala Leu Ala Leu
1               5                   10                  15

Asp Arg Ile Glu
            20

<210> SEQ ID NO 60
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
```

```
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 60

Ser Ile Asp Glu Glu Val Leu Leu Ala Leu Val Ile Ala Leu Ala Leu
1               5                   10                  15

Asp Arg Ile

<210> SEQ ID NO 61
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 61

Phe Ser Asp Glu Glu Val Leu Leu Ala Leu Val Ile Ala Leu Ala Leu
1               5                   10                  15

Asp Arg Ile

<210> SEQ ID NO 62
<211> LENGTH: 19
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 62

Phe Ile Ser Glu Glu Val Leu Leu Ala Leu Val Ile Ala Leu Ala Leu
1               5                   10                  15

Asp Arg Ile

<210> SEQ ID NO 63
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 63
```

Phe Ile Asp Glu Ser Val Leu Leu Ala Leu Val Ile Ala Leu Ala Leu
1               5                   10                  15

Asp Arg Ile

<210> SEQ ID NO 64
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 64

Phe Ile Asp Glu Glu Ser Leu Leu Ala Leu Val Ile Ala Leu Ala Leu
1               5                   10                  15

Asp Arg Ile

<210> SEQ ID NO 65
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond

```
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 65

Phe Ile Asp Glu Glu Val Ser Leu Ala Leu Val Ile Ala Leu Ala Leu
1               5                   10                  15

Asp Arg Ile

<210> SEQ ID NO 66
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 66

Phe Ile Asp Glu Glu Val Leu Ser Ala Leu Val Ile Ala Leu Ala Leu
1               5                   10                  15

Asp Arg Ile

<210> SEQ ID NO 67
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
```

<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 67

Phe Ile Asp Glu Glu Val Leu Leu Ala Ser Val Ile Ala Leu Ala Leu
1               5                   10                  15

Asp Arg Ile

<210> SEQ ID NO 68
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 68

Phe Ile Asp Glu Glu Val Leu Leu Ala Leu Ser Ile Ala Leu Ala Leu
1               5                   10                  15

Asp Arg Ile

<210> SEQ ID NO 69
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES

```
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 69

Phe Ile Asp Glu Glu Val Leu Leu Ala Leu Val Ser Ala Leu Ala Leu
1               5                   10                  15

Asp Arg Ile

<210> SEQ ID NO 70
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 70

Phe Ile Asp Glu Glu Val Leu Leu Ala Leu Val Ile Ala Ser Ala Leu
1               5                   10                  15

Asp Arg Ile

<210> SEQ ID NO 71
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
```

```
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 71

Phe Ile Asp Glu Glu Val Leu Leu Ala Leu Val Ile Ala Leu Ser Leu
1               5                   10                  15

Asp Arg Ile

<210> SEQ ID NO 72
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 72

Phe Ile Asp Glu Glu Val Leu Leu Ala Leu Val Ile Ala Leu Ala Ser
1               5                   10                  15

Asp Arg Ile

<210> SEQ ID NO 73
```

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 73

Phe Ile Asp Glu Glu Val Leu Leu Ala Leu Val Ile Ala Leu Ala Leu
1               5                   10                  15

Ser Arg Ile

<210> SEQ ID NO 74
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2
```

-continued

```
<400> SEQUENCE: 74

Phe Ile Asp Glu Glu Val Leu Leu Ala Leu Val Ile Ala Leu Ala Leu
1               5                   10                  15

Asp Ser Ile

<210> SEQ ID NO 75
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 75

Phe Ile Asp Glu Glu Val Leu Leu Ala Leu Val Ile Ala Leu Ala Leu
1               5                   10                  15

Asp Arg Ser

<210> SEQ ID NO 76
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2
```

<400> SEQUENCE: 76

Phe Ile Asp Glu Glu Val Leu Ala Ala Leu Val Ile Ala Ala Ala Leu
1               5                   10                  15

Asp

<210> SEQ ID NO 77
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Dpr
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 77

Xaa Ile Asp Glu Glu Val Leu Leu Ala Leu Val Ile Ala Leu Ala Leu
1               5                   10                  15

Asp Arg Ile

<210> SEQ ID NO 78
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: Dpr
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker

```
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 78

Phe Ile Xaa Glu Glu Val Leu Leu Ala Leu Val Ile Ala Leu Ala Leu
 1               5                  10                  15

Asp Arg Ile

<210> SEQ ID NO 79
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Dpr
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 79

Phe Ile Asp Glu Xaa Val Leu Leu Ala Leu Val Ile Ala Leu Ala Leu
 1               5                  10                  15

Asp Arg Ile

<210> SEQ ID NO 80
<211> LENGTH: 19
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Dpr
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 80

Phe Ile Asp Glu Glu Xaa Leu Leu Ala Leu Val Ile Ala Leu Ala Leu
1               5                   10                  15

Asp Arg Ile

<210> SEQ ID NO 81
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (12)..(12)
<223> OTHER INFORMATION: Dpr
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
```

<223> OTHER INFORMATION: Nle
<220> FEATURE:
<223> OTHER INFORMATION: C-term NH2

<400> SEQUENCE: 81

Phe Ile Asp Glu Glu Val Leu Leu Ala Leu Val Xaa Ala Leu Ala Leu
1               5                   10                  15

Asp Arg Ile

<210> SEQ ID NO 82
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Dpr
<220> FEATURE:
<223> OTHER INFORMATION: C-term NH2

<400> SEQUENCE: 82

Phe Ile Asp Glu Glu Val Leu Leu Ala Leu Val Ile Ala Xaa Ala Leu
1               5                   10                  15

Asp Arg Ile

<210> SEQ ID NO 83
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues

```
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<221> NAME/KEY: MOD_RES
<222> LOCATION: (18)..(18)
<223> OTHER INFORMATION: Dpr
<220> FEATURE:
<223> OTHER INFORMATION: C-term NH2

<400> SEQUENCE: 83

Phe Ile Asp Glu Glu Val Leu Leu Ala Leu Val Ile Ala Leu Ala Leu
1               5                   10                  15

Asp Xaa Ile

<210> SEQ ID NO 84
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<221> NAME/KEY: MOD_RES
<222> LOCATION: (18)..(18)
<223> OTHER INFORMATION: Dpr
<220> FEATURE:
<223> OTHER INFORMATION: C-term NH2

<400> SEQUENCE: 84

Phe Ile Asp Glu Glu Val Leu Leu Ala Leu Val Ile Ala Leu Ala Leu
1               5                   10                  15

Asp Xaa

<210> SEQ ID NO 85
<211> LENGTH: 19
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 85

Phe Ile Asp Glu Gln Val Leu Leu Ala Leu Val Ile Ala Leu Ala Leu
1               5                   10                  15

Asp Arg Ile

<210> SEQ ID NO 86
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 86

Phe Ile Asp Glu Gln Val Leu Ala Ala Leu Val Ile Ala Ala Ala Leu
1               5                   10                  15

Asp Arg Ile

<210> SEQ ID NO 87
<211> LENGTH: 19
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (7)..(7)
<223> OTHER INFORMATION: pLeu
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 87

Phe Ile Asp Glu Glu Val Leu Leu Ala Leu Val Ile Ala Leu Ala Leu
1               5                   10                  15

Asp Arg Ile

<210> SEQ ID NO 88
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (11)..(11)
<223> OTHER INFORMATION: pLeu
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
```

```
<223> OTHER INFORMATION: Nle
<220> FEATURE:
<223> OTHER INFORMATION: C-term NH2

<400> SEQUENCE: 88

Phe Ile Asp Glu Glu Val Leu Leu Ala Leu Leu Ile Ala Leu Ala Leu
1               5                   10                  15

Asp Arg Ile

<210> SEQ ID NO 89
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (12)..(12)
<223> OTHER INFORMATION: Bpa
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 89

Phe Ile Asp Glu Glu Val Leu Leu Ala Leu Val Ala Ala Leu Ala Leu
1               5                   10                  15

Asp Arg Ile

<210> SEQ ID NO 90
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
```

```
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Bpa
<220> FEATURE:
<223> OTHER INFORMATION: C-term NH2

<400> SEQUENCE: 90

Phe Ile Asp Glu Glu Val Leu Leu Ala Leu Val Ile Ala Ala Ala Leu
1               5                   10                  15

Asp Arg Ile

<210> SEQ ID NO 91
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 91

Phe Ile Asp Glu Glu Val Leu Met Ser Leu Val Ile Glu Met Gly Leu
1               5                   10                  15

Asp Arg Ile Lys Glu Leu Pro Glu Leu Trp Leu
            20                  25

<210> SEQ ID NO 92
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (4)..(8)
<223> OTHER INFORMATION: Cross-link between residues
<220> FEATURE:
<221> NAME/KEY: MOD_RES
<222> LOCATION: (8)..(8)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 92

Phe Ile Asp Ala Glu Val Leu Ala Ser Leu Val Ile Glu Met Gly Leu
1               5                   10                  15
```

Asp Arg Ile Lys Glu Leu Pro Glu Leu Trp Leu
            20                  25

<210> SEQ ID NO 93
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (6)..(10)
<223> OTHER INFORMATION: Cross-link between residues
<220> FEATURE:
<221> NAME/KEY: MOD_RES
<222> LOCATION: (10)..(10)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 93

Phe Ile Asp Glu Glu Ala Leu Met Ser Ala Val Ile Glu Met Gly Leu
1               5                   10                  15

Asp Arg Ile Lys Glu Leu Pro Glu Leu Trp Leu
            20                  25

<210> SEQ ID NO 94
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (7)..(7)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (7)..(11)
<223> OTHER INFORMATION: Cross-link between residues
<220> FEATURE:
<221> NAME/KEY: MOD_RES
<222> LOCATION: (11)..(11)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 94

Phe Ile Asp Glu Glu Val Ala Met Ser Leu Ala Ile Glu Met Gly Leu
1               5                   10                  15

Asp Arg Ile Lys Glu Leu Pro Glu Leu Trp Leu
            20                  25

<210> SEQ ID NO 95

```
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (8)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 95

Phe Ile Asp Glu Glu Val Leu Ala Ser Leu Val Ala Glu Met Gly Leu
1               5                   10                  15

Asp Arg Ile Lys Glu Leu Pro Glu Leu Trp Leu
            20                  25

<210> SEQ ID NO 96
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (10)..(10)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (10)..(14)
<223> OTHER INFORMATION: Cross-link between residues
<220> FEATURE:
<221> NAME/KEY: MOD_RES
<222> LOCATION: (14)..(14)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 96

Phe Ile Asp Glu Glu Val Leu Met Ser Ala Val Ile Glu Ala Gly Leu
1               5                   10                  15

Asp Arg Ile Lys Glu Leu Pro Glu Leu Trp Leu
            20                  25

<210> SEQ ID NO 97
<211> LENGTH: 27
<212> TYPE: PRT
<213> ORGANISM: Artificial Sequence
<220> FEATURE:
<223> OTHER INFORMATION: Description of Artificial Sequence: Synthetic
```

```
           peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (4)..(11)
<223> OTHER INFORMATION: Cross-link between residues
<220> FEATURE:
<221> NAME/KEY: MOD_RES
<222> LOCATION: (11)..(11)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 97

Phe Ile Asp Ala Glu Val Leu Met Ser Leu Ala Ile Glu Met Gly Leu
1               5                   10                  15

Asp Arg Ile Lys Glu Leu Pro Glu Leu Trp Leu
            20                  25

<210> SEQ ID NO 98
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (5)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 98

Phe Ile Asp Glu Ala Val Leu Met Ser Leu Val Ala Glu Met Gly Leu
1               5                   10                  15

Asp Arg Ile Lys Glu Leu Pro Glu Leu Trp Leu
            20                  25

<210> SEQ ID NO 99
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
```

```
<222> LOCATION: (6)..(6)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (6)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 99

Phe Ile Asp Glu Glu Ala Leu Met Ser Leu Val Ile Ala Met Gly Leu
1               5                   10                  15

Asp Arg Ile Lys Glu Leu Pro Glu Leu Trp Leu
            20                  25

<210> SEQ ID NO 100
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (7)..(7)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (7)..(14)
<223> OTHER INFORMATION: Cross-link between residues
<220> FEATURE:
<221> NAME/KEY: MOD_RES
<222> LOCATION: (14)..(14)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 100

Phe Ile Asp Glu Glu Val Ala Met Ser Leu Val Ile Glu Ala Gly Leu
1               5                   10                  15

Asp Arg Ile Lys Glu Leu Pro Glu Leu Trp Leu
            20                  25

<210> SEQ ID NO 101
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Alpha-Me R8-octenyl-alanine olefin amino acid
      connected by an all-carbon i to i+7 crosslinker
      comprising one double bond
<220> FEATURE:
```

```
<221> NAME/KEY: misc_feature
<222> LOCATION: (8)..(15)
<223> OTHER INFORMATION: Cross-link between residues
<220> FEATURE:
<221> NAME/KEY: MOD_RES
<222> LOCATION: (15)..(15)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 101

Phe Ile Asp Glu Glu Val Leu Ala Ser Leu Val Ile Glu Met Ala Leu
1               5                   10                  15

Asp Arg Ile Lys Glu Leu Pro Glu Leu Trp Leu
            20                  25

<210> SEQ ID NO 102
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (8)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 102

Ile Asp Glu Glu Val Leu Met Ala Leu Val Ile Ala Met Gly Leu Asp
1               5                   10                  15

Arg Ile Lys Glu Leu Pro Glu Leu Trp Leu
            20                  25

<210> SEQ ID NO 103
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (7)..(7)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (7)..(11)
<223> OTHER INFORMATION: Cross-link between residues
<220> FEATURE:
<221> NAME/KEY: MOD_RES
```

<222> LOCATION: (11)..(11)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 103

Asp Glu Glu Val Leu Met Ala Leu Val Ile Ala Met Gly Leu Asp Arg
1               5                   10                  15

Ile Lys Glu Leu Pro Glu Leu Trp Leu
            20                  25

<210> SEQ ID NO 104
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (6)..(10)
<223> OTHER INFORMATION: Cross-link between residues
<220> FEATURE:
<221> NAME/KEY: MOD_RES
<222> LOCATION: (10)..(10)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 104

Glu Glu Val Leu Met Ala Leu Val Ile Ala Met Gly Leu Asp Arg Ile
1               5                   10                  15

Lys Glu Leu Pro Glu Leu Trp Leu
            20

<210> SEQ ID NO 105
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:

```
<223> OTHER INFORMATION: C-term NH2

<400> SEQUENCE: 105

Glu Val Leu Met Ala Leu Val Ile Ala Met Gly Leu Asp Arg Ile Lys
1               5                   10                  15

Glu Leu Pro Glu Leu Trp Leu
            20

<210> SEQ ID NO 106
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 106

Phe Ile Asp Glu Glu Val Leu Met Ala Leu Val Ile Ala Met Gly Leu
1               5                   10                  15

Asp Arg Ile Lys Glu Leu Pro Glu Leu Trp
            20                  25

<210> SEQ ID NO 107
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 107

Phe Ile Asp Glu Glu Val Leu Met Ala Leu Val Ile Ala Met Gly Leu
```

```
1               5                   10                  15

Asp Arg Ile Lys Glu Leu Pro Glu Leu
            20                  25
```

<210> SEQ ID NO 108
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 108

```
Phe Ile Asp Glu Glu Val Leu Met Ala Leu Val Ile Ala Met Gly Leu
1               5                   10                  15

Asp Arg Ile Lys Glu Leu Pro Glu
            20
```

<210> SEQ ID NO 109
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 109

```
Phe Ile Asp Glu Glu Val Leu Met Ala Leu Val Ile Ala Met Gly Leu
1               5                   10                  15

Asp Arg Ile Lys Glu Leu Pro
            20
```

<210> SEQ ID NO 110
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 110

Phe Ile Asp Glu Glu Val Leu Met Ala Leu Val Ile Ala Met Gly Leu
1               5                   10                  15

Asp Arg Ile Lys Glu Leu
            20

<210> SEQ ID NO 111
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 111

Phe Ile Asp Glu Glu Val Leu Met Ala Leu Val Ile Ala Met Gly Leu
1               5                   10                  15

Asp Arg Ile Lys Glu
            20

<210> SEQ ID NO 112
<211> LENGTH: 20
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 112

Phe Ile Asp Glu Glu Val Leu Met Ala Leu Val Ile Ala Met Gly Leu
1               5                   10                  15

Asp Arg Ile Lys
            20

<210> SEQ ID NO 113
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 113

Phe Ile Asp Glu Glu Val Leu Met Ala Leu Val Ile Ala Met Gly Leu
1               5                   10                  15

Asp Arg Ile

<210> SEQ ID NO 114
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
```

<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 114

Phe Ile Asp Glu Glu Val Leu Met Ala Leu Val Ile Ala Met Gly Leu
1               5                   10                  15

Asp

<210> SEQ ID NO 115
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 115

Phe Ile Asp Glu Glu Val Leu Met Ala Leu Val Ile Ala Met Gly
1               5                   10                  15

<210> SEQ ID NO 116
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues

```
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 116

Phe Ile Asp Glu Glu Val Leu Met Ala Leu Val Ile Ala Met Ala Leu
1               5                   10                  15

Asp Arg Ile Lys Glu
            20

<210> SEQ ID NO 117
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 117

Phe Ile Asp Glu Glu Val Leu Met Ala Leu Val Ile Ala Met Ala Leu
1               5                   10                  15

Asp

<210> SEQ ID NO 118
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
```

```
<220> FEATURE:
<223> OTHER INFORMATION: C-term NH2

<400> SEQUENCE: 118

Phe Ile Asp Glu Glu Val Leu Met Ala Leu Val Ile Ala Met Ala
1               5                   10                  15

<210> SEQ ID NO 119
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 119

Phe Ile Asp Glu Glu Val Leu Met Ala Leu Val Ile Ala Met Ala Ala
1               5                   10                  15

<210> SEQ ID NO 120
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 120

Phe Ile Asp Glu Ala Val Leu Met Ala Leu Val Ile Glu Met Gly Leu
1               5                   10                  15

Asp Arg Ile Lys Glu Leu Pro Glu Leu Trp Leu
            20                  25
```

```
<210> SEQ ID NO 121
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 121

Phe Ile Asp Glu Ala Val Leu Leu Ala Leu Val Ile Glu Leu Gly Leu
1               5                   10                  15

Asp Arg Ile Lys Glu Leu Pro Glu Leu Trp Leu
            20                  25

<210> SEQ ID NO 122
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
```

```
<220> FEATURE:
<223> OTHER INFORMATION: C-term NH2

<400> SEQUENCE: 122

Phe Ile Asp Glu Ala Val Leu Leu Ala Leu Val Ile Glu Leu Ala Leu
1               5                   10                  15

Asp Arg Ile Lys Glu Leu Pro Glu Leu Trp Leu
            20                  25

<210> SEQ ID NO 123
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 123

Phe Ile Asp Glu Ala Val Leu Met Ala Leu Val Ile Glu Met Ala Leu
1               5                   10                  15

Asp Arg Ile Lys Glu Leu Pro Glu Leu Trp Leu
            20                  25

<210> SEQ ID NO 124
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 124
```

Phe Ile Asp Glu Ala Val Leu Met Ala Leu Val Ile Glu Met Ala Leu
1               5                   10                  15

Asp Arg Ile

<210> SEQ ID NO 125
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 125

Phe Ile Asp Glu Ala Val Leu Leu Ala Leu Val Ile Glu Leu Ala Leu
1               5                   10                  15

Asp Arg Ile

<210> SEQ ID NO 126
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 126

```
Phe Ile Asp Glu Ala Val Leu Met Ala Leu Val Ile Glu Met Ala Leu
1               5                   10                  15
```

<210> SEQ ID NO 127
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 127

```
Phe Ile Asp Glu Ala Val Leu Leu Ala Leu Val Ile Glu Leu Ala Leu
1               5                   10                  15
```

<210> SEQ ID NO 128
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 128

```
Phe Ile Asp Glu Ala Val Leu Ala Ala Leu Val Ile Glu Met Ala Leu
1               5                   10                  15
```

Asp Arg Ile Lys Glu Leu Pro Glu Leu Trp Leu
            20                  25

<210> SEQ ID NO 129
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 129

Phe Ile Asp Glu Ala Val Leu Met Ala Leu Val Ile Glu Met Ala Leu
1               5                   10                  15

Asp Arg Ile Lys Glu
            20

<210> SEQ ID NO 130
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 130

Phe Ile Asp Glu Ala Val Leu Met Ala Leu Val Ile Glu Met Ala Leu
1               5                   10                  15

Asp

<210> SEQ ID NO 131

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 131

Phe Ile Asp Glu Ala Val Leu Met Ala Leu Val Ile Glu Met Ala
1               5                   10                  15

<210> SEQ ID NO 132
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 132

Phe Ile Asp Glu Ala Val Leu Met Ala Leu Val Ile Glu Met Ala Ala
1               5                   10                  15

<210> SEQ ID NO 133
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
```

```
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 133

Phe Ile Asp Glu Ala Val Leu Met Ala Leu Val Ile Glu Met Ala Ala
1               5                   10                  15

Ala

<210> SEQ ID NO 134
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 134

Phe Ile Asp Glu Ala Val Leu Leu Ala Leu Val Ile Glu Met Ala Leu
1               5                   10                  15

Asp Arg Ile

<210> SEQ ID NO 135
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
```

```
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 135

Phe Ile Asp Glu Ala Val Leu Met Ala Leu Val Ile Glu Leu Ala Leu
1               5                   10                  15

Asp Arg Ile

<210> SEQ ID NO 136
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 136

Phe Ile Ala Glu Ala Val Leu Leu Ala Leu Val Ile Glu Leu Ala Leu
1               5                   10                  15

Asp Ala Ile

<210> SEQ ID NO 137
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
```

<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 137

Phe Ile Ala Glu Ala Val Leu Leu Ala Leu Val Ile Ala Leu Ala Leu
1               5                   10                  15

Asp Ala Ile

<210> SEQ ID NO 138
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 138

Phe Ile Asp Glu Ala Val Leu Leu Ala Leu Val Ile Ala Leu Ala Leu
1               5                   10                  15

<210> SEQ ID NO 139
<211> LENGTH: 16
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 139

Phe Ile Ala Glu Ala Val Leu Leu Ala Leu Val Ile Ala Leu Ala Leu
1               5                   10                  15

<210> SEQ ID NO 140
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<221> NAME/KEY: MOD_RES
<222> LOCATION: (19)..(19)
<223> OTHER INFORMATION: Nle
<220> FEATURE:
<223> OTHER INFORMATION: C-term NH2
```

<400> SEQUENCE: 140

Phe Ile Asp Glu Ala Val Leu Leu Ala Leu Val Ile Leu Leu Ala Leu
1               5                   10                  15

Ala Ala Leu

<210> SEQ ID NO 141
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<221> NAME/KEY: MOD_RES
<222> LOCATION: (19)..(19)
<223> OTHER INFORMATION: Nle
<220> FEATURE:
<223> OTHER INFORMATION: C-term NH2

<400> SEQUENCE: 141

Phe Ile Asp Glu Ala Val Leu Leu Ala Leu Val Ile Ala Leu Ala Leu
1               5                   10                  15

Asp Arg Leu

<210> SEQ ID NO 142
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle

```
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<221> NAME/KEY: MOD_RES
<222> LOCATION: (16)..(16)
<223> OTHER INFORMATION: Nle
<220> FEATURE:
<221> NAME/KEY: MOD_RES
<222> LOCATION: (19)..(19)
<223> OTHER INFORMATION: Nle
<220> FEATURE:
<223> OTHER INFORMATION: C-term NH2

<400> SEQUENCE: 142

Phe Ile Asp Glu Ala Val Leu Leu Ala Leu Val Ile Leu Leu Ala Leu
1               5                   10                  15

Ala Ala Leu

<210> SEQ ID NO 143
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 143

Phe Ile Asp Glu Ala Val Leu Leu Ala Leu Val Ile Ala Leu Ala Leu
1               5                   10                  15

Ala Ala Ile

<210> SEQ ID NO 144
<211> LENGTH: 19
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 144

Phe Ile Asp Glu Ala Val Leu Leu Ala Leu Val Ile Leu Leu Ala Leu
1               5                   10                  15

Ser Ser Ile

<210> SEQ ID NO 145
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 145

Phe Ile Asp Glu Ala Val Leu Leu Ala Leu Val Ile Ala Leu Ala Leu
1               5                   10                  15
```

Ser Ser Ile

```
<210> SEQ ID NO 146
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 5-FAM
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (6)..(6)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (6)..(10)
<223> OTHER INFORMATION: Cross-link between residues
<220> FEATURE:
<221> NAME/KEY: MOD_RES
<222> LOCATION: (9)..(9)
<223> OTHER INFORMATION: Nle
<220> FEATURE:
<221> NAME/KEY: MOD_RES
<222> LOCATION: (10)..(10)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (15)..(15)
<223> OTHER INFORMATION: Nle
<220> FEATURE:
<223> OTHER INFORMATION: C-term NH2

<400> SEQUENCE: 146

Ala Phe Ile Asp Glu Ala Val Leu Leu Ala Leu Val Ile Glu Leu Ala
1               5                   10                  15

Leu

<210> SEQ ID NO 147
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 5-FAM
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (6)..(6)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (6)..(10)
<223> OTHER INFORMATION: Cross-link between residues
<220> FEATURE:
<221> NAME/KEY: MOD_RES
<222> LOCATION: (9)..(9)
<223> OTHER INFORMATION: Nle
<220> FEATURE:
```

```
<221> NAME/KEY: MOD_RES
<222> LOCATION: (10)..(10)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (15)..(15)
<223> OTHER INFORMATION: Nle
<220> FEATURE:
<223> OTHER INFORMATION: C-term NH2

<400> SEQUENCE: 147

Ala Phe Ile Asp Glu Ala Val Leu Leu Ala Leu Val Ile Glu Leu Ala
1               5                   10                  15

Leu Asp Arg Ile
            20

<210> SEQ ID NO 148
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 148

Phe Ile Asp Glu Ala Val Leu Leu Ala Leu Val Ile Glu Leu Ala Leu
1               5                   10                  15

Lys

<210> SEQ ID NO 149
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
``` comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
        connected by an all-carbon i to i+4 crosslinker
        comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 149

Phe Ile Asp Glu Ala Val Leu Leu Ala Leu Val Ile Glu Leu Ala Leu
1               5                   10                  15

Lys Lys

<210> SEQ ID NO 150
<211> LENGTH: 17
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me S5-pentenyl-alanine olefin amino acid
        connected by an all-carbon i to i+4 crosslinker
        comprising one double bond
<220> FEATURE:
<221> NAME/KEY: misc_feature
<222> LOCATION: (6)..(10)
<223> OTHER INFORMATION: Cross-link between residues
<220> FEATURE:
<221> NAME/KEY: MOD_RES
<222> LOCATION: (9)..(9)
<223> OTHER INFORMATION: Nle
<220> FEATURE:
<221> NAME/KEY: MOD_RES
<222> LOCATION: (10)..(10)
<223> OTHER INFORMATION: Alpha-Me S5-pentenyl-alanine olefin amino acid
        connected by an all-carbon i to i+4 crosslinker
        comprising one double bond
<220> FEATURE:
<221> NAME/KEY: MOD_RES
<222> LOCATION: (15)..(15)
<223> OTHER INFORMATION: Nle
<220> FEATURE:
<223> OTHER INFORMATION: C-term NH2

<400> SEQUENCE: 150

Lys Phe Ile Asp Glu Ala Val Leu Leu Ala Leu Val Ile Glu Leu Ala
1               5                   10                  15

Leu

<210> SEQ ID NO 151
<211> LENGTH: 18
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (7)..(7)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (7)..(11)
<223> OTHER INFORMATION: Cross-link between residues
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (16)..(16)
<223> OTHER INFORMATION: Nle
<220> FEATURE:
<223> OTHER INFORMATION: C-term NH2

<400> SEQUENCE: 151

Lys Lys Phe Ile Asp Glu Ala Val Leu Leu Ala Leu Val Ile Glu Leu
1               5                   10                  15

Ala Leu

<210> SEQ ID NO 152
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (6)..(10)
<223> OTHER INFORMATION: Cross-link between residues
<220> FEATURE:
<221> NAME/KEY: MOD_RES
<222> LOCATION: (9)..(9)
<223> OTHER INFORMATION: Nle
<220> FEATURE:
<221> NAME/KEY: MOD_RES
<222> LOCATION: (10)..(10)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (15)..(15)
<223> OTHER INFORMATION: Nle
<220> FEATURE:
<223> OTHER INFORMATION: C-term NH2

<400> SEQUENCE: 152

Lys Phe Ile Asp Glu Ala Val Leu Leu Ala Leu Val Ile Glu Leu Ala
1               5                   10                  15
```

Leu Lys

```
<210> SEQ ID NO 153
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (7)..(7)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (7)..(11)
<223> OTHER INFORMATION: Cross-link between residues
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (16)..(16)
<223> OTHER INFORMATION: Nle
<220> FEATURE:
<223> OTHER INFORMATION: C-term NH2

<400> SEQUENCE: 153

Lys Lys Phe Ile Asp Glu Ala Val Leu Leu Ala Leu Val Ile Glu Leu
1               5                   10                  15

Ala Leu Lys Lys
            20

<210> SEQ ID NO 154
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
```

```
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 154

Phe Ile Asp Glu Ala Ala Leu Leu Ala Leu Val Ile Glu Leu Ala Leu
 1               5                  10                  15

<210> SEQ ID NO 155
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 155

Phe Ile Asp Glu Ala Thr Leu Leu Ala Leu Val Ile Glu Leu Ala Leu
 1               5                  10                  15

<210> SEQ ID NO 156
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
```

```
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 156

Phe Ile Asp Glu Ala Ser Leu Leu Ala Leu Val Ile Glu Leu Ala Leu
1               5                   10                  15

<210> SEQ ID NO 157
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 157

Phe Ile Asp Glu Ala Asn Leu Leu Ala Leu Val Ile Glu Leu Ala Leu
1               5                   10                  15

<210> SEQ ID NO 158
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
```

-continued

```
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 158

Phe Ile Asp Glu Ala Val Leu Leu Ala Ala Val Ile Glu Leu Ala Leu
1               5                   10                  15

<210> SEQ ID NO 159
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 159

Phe Ile Asp Glu Ala Val Leu Leu Ala Asn Val Ile Glu Leu Ala Leu
1               5                   10                  15

<210> SEQ ID NO 160
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
```

```
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 160

Phe Ile Asp Glu Ala Val Leu Leu Ala Ser Val Ile Glu Leu Ala Leu
1               5                   10                  15

<210> SEQ ID NO 161
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 161

Phe Ile Asp Glu Ala Val Leu Leu Ala Leu Val Ile Glu Ala Ala Leu
1               5                   10                  15

<210> SEQ ID NO 162
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
```

```
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 162

Phe Ile Asp Glu Ala Val Leu Leu Ala Leu Val Ile Glu Gln Ala Leu
1               5                   10                  15

<210> SEQ ID NO 163
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 163

Phe Ile Asp Glu Ala Val Leu Leu Ala Leu Val Ile Glu Ser Ala Leu
1               5                   10                  15

<210> SEQ ID NO 164
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
```

<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 164

Phe Ile Asp Ala Ala Val Leu Leu Ala Leu Val Ile Glu Leu Ala Leu
1               5                   10                  15

<210> SEQ ID NO 165
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 165

Phe Ile Asp Ala Ala Thr Leu Leu Ala Leu Val Ile Glu Leu Ala Leu
1               5                   10                  15

<210> SEQ ID NO 166
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)

```
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 166

Phe Ile Asp Ala Ala Val Leu Leu Ala Asn Val Ile Glu Leu Ala Leu
1               5                   10                  15

<210> SEQ ID NO 167
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 167

Phe Ile Asp Ala Ala Thr Leu Leu Ala Asn Val Ile Glu Leu Ala Leu
1               5                   10                  15

<210> SEQ ID NO 168
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 168

Phe Ile Asp Glu Ala Val Leu Ala Ala Leu Val Ile Glu Leu Ala Leu
1               5                   10                  15

<210> SEQ ID NO 169
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 169

Phe Thr Asp Glu Ala Val Leu Leu Ala Leu Val Ile Glu Leu Ala Leu
1               5                   10                  15

<210> SEQ ID NO 170
<211> LENGTH: 16
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 170

Phe Ser Asp Glu Ala Val Leu Leu Ala Leu Val Ile Glu Leu Ala Leu
1               5                   10                  15

<210> SEQ ID NO 171
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 171

Phe Ile Arg Glu Ala Val Leu Leu Ala Leu Val Ile Glu Leu Ala Leu
1               5                   10                  15

<210> SEQ ID NO 172
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 172

Phe Ile Asp Arg Ala Val Leu Leu Ala Leu Val Ile Glu Leu Ala Leu
1               5                   10                  15

<210> SEQ ID NO 173
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 173
```

Phe Ile Asp Glu Ala Val Leu Leu Ala Leu Val Ile Arg Leu Ala Leu
1               5                   10                  15

<210> SEQ ID NO 174
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (4)..(8)
<223> OTHER INFORMATION: Cross-link between residues
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (8)..(8)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (13)..(13)
<223> OTHER INFORMATION: Nle
<220> FEATURE:
<223> OTHER INFORMATION: C-term NH2

<400> SEQUENCE: 174

Ile Asp Glu Ala Val Phe Leu Ala Leu Val Ile Glu Leu Ala Leu
1               5                   10                  15

<210> SEQ ID NO 175
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (3)..(7)
<223> OTHER INFORMATION: Cross-link between residues
<220> FEATURE:
<221> NAME/KEY: MOD_RES
<222> LOCATION: (6)..(6)
<223> OTHER INFORMATION: Nle
<220> FEATURE:
<221> NAME/KEY: MOD_RES
<222> LOCATION: (7)..(7)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (12)..(12)
<223> OTHER INFORMATION: Nle

```
<220> FEATURE:
<223> OTHER INFORMATION: C-term NH2

<400> SEQUENCE: 175

Asp Glu Ala Val Phe Leu Ala Leu Val Ile Glu Leu Ala Leu
1               5                   10

<210> SEQ ID NO 176
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 176

Phe Ile Asp Glu Ala Val Phe Leu Ala Leu Val Ile Glu Leu Ala Leu
1               5                   10                  15

<210> SEQ ID NO 177
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
```

```
<223> OTHER INFORMATION: Nle
<220> FEATURE:
<223> OTHER INFORMATION: C-term NH2

<400> SEQUENCE: 177

Phe Ile Asp Glu Ala Val Phe Ala Ala Leu Val Ile Glu Leu Ala Leu
1               5                   10                  15

<210> SEQ ID NO 178
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 178

Phe Ile Asp Glu Ala Val Phe Ala Ala Leu Val Ile Glu Ser Ala Leu
1               5                   10                  15

<210> SEQ ID NO 179
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 179

Phe Ile Asp Glu Ala Val Phe Leu Ala Leu Val Ile Glu Ala Ala Leu
```

<210> SEQ ID NO 180
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 180

Phe Ile Asn Gln Ala Val Phe Leu Ala Leu Val Ile Gln Leu Ala Leu
1               5                   10                  15

<210> SEQ ID NO 181
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 181

Phe Ile Asn Gln Ala Val Phe Ala Ala Leu Val Ile Gln Leu Ala Leu
1               5                   10                  15

<210> SEQ ID NO 182
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 182

Phe Ile Asn Gln Ala Val Phe Ala Ala Leu Val Ile Gln Ala Ala Leu
1               5                   10                  15

<210> SEQ ID NO 183
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 183

Phe Ile Asn Gln Ala Val Phe Leu Ala Leu Val Ile Gln Ala Ala Leu
1               5                   10                  15

<210> SEQ ID NO 184
<211> LENGTH: 16
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 184

Phe Ile Arg Glu Ala Val Phe Leu Ala Leu Val Ile Glu Leu Ala Leu
1               5                   10                  15

<210> SEQ ID NO 185
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 185

Phe Ile Arg Glu Ala Val Phe Ala Ala Leu Val Ile Glu Leu Ala Leu
1               5                   10                  15

<210> SEQ ID NO 186
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 186

Phe Ile Asp Glu Ala Val Phe Ala Ala Leu Val Ile Arg Leu Ala Leu
1               5                   10                  15

<210> SEQ ID NO 187
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 187

Phe Ile Arg Glu Ala Val Phe Leu Ala Leu Val Ile Glu Ala Ala Leu
1               5                   10                  15

<210> SEQ ID NO 188
<211> LENGTH: 16
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 188

Phe Ile Asp Glu Ala Val Phe Leu Ala Leu Val Ile Arg Ala Ala Leu
1               5                   10                  15

<210> SEQ ID NO 189
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Dma ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 189

Phe Ile Asp Glu Ala Val Phe Leu Ala Leu Val Ile Glu Leu Ala Leu
1               5                   10                  15

<210> SEQ ID NO 190
<211> LENGTH: 21
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (5)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 190

Phe Ile Asp Glu Ala Val Leu Met Ser Leu Val Ala Glu Met Ala Leu
1               5                   10                  15

Asp Arg Ile Lys Glu
            20

<210> SEQ ID NO 191
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (5)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 191

Phe Ile Asp Glu Ala Val Leu Met Ser Leu Val Ala Glu Met Ala Leu
1               5                   10                  15

Asp Arg Ile

<210> SEQ ID NO 192
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
```

```
<221> NAME/KEY: MOD_RES
<222> LOCATION: (5)..(5)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (5)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 192

Phe Ile Asp Glu Ala Val Leu Met Ser Leu Val Ala Glu Met Ala Leu
1               5                   10                  15

Asp

<210> SEQ ID NO 193
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (5)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 193

Phe Ile Asp Glu Ala Val Leu Met Ser Leu Val Ala Glu Met Ala Leu
1               5                   10                  15

<210> SEQ ID NO 194
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (5)..(12)
<223> OTHER INFORMATION: Cross-link between residues
```

```
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 194

Phe Ile Asp Glu Ala Val Leu Met Ser Leu Val Ala Glu Met Ala Ala
1               5                   10                  15

<210> SEQ ID NO 195
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (5)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 195

Phe Ile Asp Glu Ala Val Leu Met Ser Leu Val Ala Glu Met Ala Ala
1               5                   10                  15

Ala

<210> SEQ ID NO 196
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (4)..(11)
<223> OTHER INFORMATION: Cross-link between residues
<220> FEATURE:
<221> NAME/KEY: MOD_RES
<222> LOCATION: (11)..(11)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2
```

-continued

<400> SEQUENCE: 196

Leu Thr Glu Ala Val Leu Met Ser Leu Val Ala Ser Met Ala
1               5                   10

<210> SEQ ID NO 197
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (4)..(11)
<223> OTHER INFORMATION: Cross-link between residues
<220> FEATURE:
<221> NAME/KEY: MOD_RES
<222> LOCATION: (11)..(11)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 197

Leu Thr Glu Ala Val Leu Met Ser Leu Val Ala Ser Ala Ala
1               5                   10

<210> SEQ ID NO 198
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (4)..(11)
<223> OTHER INFORMATION: Cross-link between residues
<220> FEATURE:
<221> NAME/KEY: MOD_RES
<222> LOCATION: (11)..(11)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 198

Leu Thr Phe Ala Val Leu Met Ser Leu Val Ala Ser Ala Ala
1               5                   10

<210> SEQ ID NO 199
<211> LENGTH: 27
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (5)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 199

Phe Ile Asp Glu Ala Val Leu Ala Ser Leu Val Ala Glu Met Gly Leu
1               5                   10                  15

Asp Arg Ile Lys Glu Leu Pro Glu Leu Trp Leu
            20                  25

<210> SEQ ID NO 200
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (5)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 200

Phe Ile Asp Glu Ala Val Leu Ala Ser Leu Val Ala Glu Met Gly
1               5                   10                  15

<210> SEQ ID NO 201
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me R8-octenyl-alanine olefin amino acid
```

```
        connected by an all-carbon i to i+7 crosslinker
        comprising one double bond
<220> FEATURE:
<221> NAME/KEY: misc_feature
<222> LOCATION: (5)..(12)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (12)..(12)
<223> OTHER INFORMATION: Alpha-Me S5-pentenyl-alanine olefin amino acid
        connected by an all-carbon i to i+4 crosslinker
        comprising one double bond
<220> FEATURE:
<223> OTHER INFORMATION: C-term NH2

<400> SEQUENCE: 201

Phe Ile Asp Glu Ala Val Leu Leu Ser Leu Val Ala Glu Met Gly
1               5                   10                  15

<210> SEQ ID NO 202
<211> LENGTH: 15
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me R8-octenyl-alanine olefin amino acid
        connected by an all-carbon i to i+7 crosslinker
        comprising one double bond
<220> FEATURE:
<221> NAME/KEY: misc_feature
<222> LOCATION: (5)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
        connected by an all-carbon i to i+4 crosslinker
        comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 202

Phe Ile Asp Glu Ala Val Leu Met Ser Leu Val Ala Glu Leu Gly
1               5                   10                  15

<210> SEQ ID NO 203
<211> LENGTH: 16
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me R8-octenyl-alanine olefin amino acid
        connected by an all-carbon i to i+7 crosslinker
        comprising one double bond
<220> FEATURE:
```

```
<221> NAME/KEY: misc_feature
<222> LOCATION: (5)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 203

Phe Ile Asp Glu Ala Val Leu Met Ser Leu Val Ala Glu Met Gly Leu
1               5                   10                  15

<210> SEQ ID NO 204
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (5)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 204

Phe Ile Asp Glu Ala Val Leu Met Ser Leu Val Ala Glu Met Gly Leu
1               5                   10                  15

Asp

<210> SEQ ID NO 205
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (5)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
```

<220> FEATURE:
<223> OTHER INFORMATION: C-term NH2

<400> SEQUENCE: 205

Phe Ile Asp Glu Ala Val Leu Met Ser Leu Val Ala Glu Met Gly Leu
1               5                   10                  15

Asp Arg

<210> SEQ ID NO 206
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (5)..(12)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 206

Phe Ile Asp Glu Ala Val Leu Leu Ser Leu Val Ala Glu Leu Ala Leu
1               5                   10                  15

Asp Arg Ile

<210> SEQ ID NO 207
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (5)..(12)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:

```
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 207

Phe Ile Asp Glu Ala Val Leu Leu Ser Leu Val Ala Ala Leu Ala Leu
1               5                   10                  15

Asp Ala Ile

<210> SEQ ID NO 208
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (5)..(12)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 208

Phe Ile Ala Glu Ala Val Leu Leu Ser Leu Val Ala Glu Leu Ala Leu
1               5                   10                  15

Asp Ala Ile

<210> SEQ ID NO 209
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me R8-octenyl-alanine olefin amino acid
      connected by an all-carbon i to i+7 crosslinker
      comprising one double bond
```

```
<220> FEATURE:
<221> NAME/KEY: misc_feature
<222> LOCATION: (5)..(12)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 209

Phe Ile Ala Glu Ala Val Leu Leu Ser Leu Val Ala Ala Leu Ala Leu
1               5                   10                  15

Asp Ala Ile

<210> SEQ ID NO 210
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (5)..(12)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 210

Phe Ile Ala Glu Ala Val Leu Leu Ser Leu Val Ala Ala Leu Ala Leu
1               5                   10                  15

Ala Ala Ile

<210> SEQ ID NO 211
<211> LENGTH: 16
<212> TYPE: PRT
<213> ORGANISM: Artificial Sequence
<220> FEATURE:
<223> OTHER INFORMATION: Description of Artificial Sequence: Synthetic
```

```
              peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (5)..(12)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 211

Phe Ile Asp Glu Ala Val Leu Leu Ser Leu Val Ala Glu Leu Ala Leu
1               5                   10                  15

<210> SEQ ID NO 212
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (5)..(12)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 212

Phe Ile Asp Glu Ala Val Leu Leu Ser Leu Val Ala Ala Leu Ala Leu
1               5                   10                  15

<210> SEQ ID NO 213
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (5)..(12)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 213

Phe Ile Ala Glu Ala Val Leu Leu Ser Leu Val Ala Glu Leu Ala Leu
1               5                   10                  15

<210> SEQ ID NO 214
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (5)..(12)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 214
```

Phe Ile Ala Glu Ala Val Leu Leu Ser Leu Val Ala Ala Leu Ala Leu
1               5                   10                  15

<210> SEQ ID NO 215
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (6)..(13)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 215

Phe Ile Asp Glu Glu Ala Leu Leu Ser Leu Val Ile Ala Leu Ala Leu
1               5                   10                  15

<210> SEQ ID NO 216
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (6)..(13)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle

```
<220> FEATURE:
<223> OTHER INFORMATION: C-term NH2

<400> SEQUENCE: 216

Phe Ile Asp Glu Glu Ala Leu Leu Ser Leu Val Ile Ala Leu Ala Leu
1               5                   10                  15

Asp Arg Ile

<210> SEQ ID NO 217
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me R5-pentenyl-alanine olefin amino acid
      connected by an all-carbon comprising one double
      bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: Amino acid comprising two pentenyl-alanine
      olefin side chains, each of which is crosslinked to another
      amino acid as indicated
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 217

Phe Ile Asp Glu Ala Val Leu Met Ala Leu Val Ile Ala Met Gly Leu
1               5                   10                  15

Asp Arg Ile Lys Glu Leu Pro Glu Leu Trp Leu
            20                  25

<210> SEQ ID NO 218
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me R5-pentenyl-alanine olefin amino acid
      connected by an all-carbon comprising one double
      bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
```

```
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Amino acid comprising two pentenyl-alanine
      olefin side chains, each of which is crosslinked to another
      amino acid as indicated
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 218

Phe Ile Asp Glu Ala Val Leu Leu Ala Leu Val Ile Ala Leu Ala Leu
1               5                   10                  15

<210> SEQ ID NO 219
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: Amino acid comprising two pentenyl-alanine
      olefin side chains, each of which is crosslinked to another
      amino acid as indicated
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me R5-pentenyl-alanine olefin amino acid
      connected by an all-carbon comprising one double
      bond
<220> FEATURE:
<223> OTHER INFORMATION: C-term NH2

<400> SEQUENCE: 219

Phe Ile Asp Glu Ala Val Leu Met Ala Leu Val Ile Ala Met Ala
1               5                   10                  15

<210> SEQ ID NO 220
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Amino acid comprising two pentenyl-alanine
      olefin side chains, each of which is crosslinked to another
      amino acid as indicated
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me R5-pentenyl-alanine olefin amino acid
      connected by an all-carbon comprising one double
      bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 220

Phe Ile Asp Glu Ala Val Leu Leu Ala Leu Val Ile Ala Leu Ala Leu
1               5                   10                  15

<210> SEQ ID NO 221
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: Amino acid comprising two pentenyl-alanine
      olefin side chains, each of which is crosslinked to another
      amino acid as indicated
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
```

```
<222> LOCATION: (13)..(13)
<223> OTHER INFORMATION: Alpha-Me R5-pentenyl-alanine olefin amino acid
      connected by an all-carbon comprising one double
      bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 221

Phe Ile Asp Glu Ala Val Leu Glu Ala Leu Val Ile Ala Leu Ala Leu
1               5                   10                  15

<210> SEQ ID NO 222
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Amino acid comprising two pentenyl-alanine
      olefin side chains, each of which is crosslinked to another
      amino acid as indicated
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me R5-pentenyl-alanine olefin amino acid
      connected by an all-carbon comprising one double
      bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 222

Phe Ile Asp Glu Ala Arg Leu Leu Ala Leu Val Ile Ala Leu Ala Leu
1               5                   10                  15

<210> SEQ ID NO 223
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
```

-continued

```
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Amino acid comprising two pentenyl-alanine
      olefin side chains, each of which is crosslinked to another
      amino acid as indicated
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me R5-pentenyl-alanine olefin amino acid
      connected by an all-carbon comprising one double
      bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 223

Phe Ile Asp Glu Ala Thr Leu Leu Ala Leu Val Ile Ala Leu Ala Leu
1               5                   10                  15

<210> SEQ ID NO 224
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Amino acid comprising two pentenyl-alanine
      olefin side chains, each of which is crosslinked to another
      amino acid as indicated
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me R5-pentenyl-alanine olefin amino acid
```

```
            connected by an all-carbon comprising one double
            bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 224

Phe Ile Asp Glu Ala Asn Leu Leu Ala Leu Val Ile Ala Leu Ala Leu
1               5                   10                  15

<210> SEQ ID NO 225
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Amino acid comprising two pentenyl-alanine
      olefin side chains, each of which is crosslinked to another
      amino acid as indicated
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me R5-pentenyl-alanine olefin amino acid
      connected by an all-carbon comprising one double
      bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 225

Phe Ile Asp Glu Ala Val Leu Leu Ala Arg Val Ile Ala Leu Ala Leu
1               5                   10                  15

<210> SEQ ID NO 226
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
```

```
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Amino acid comprising two pentenyl-alanine
      olefin side chains, each of which is crosslinked to another
      amino acid as indicated
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me R5-pentenyl-alanine olefin amino acid
      connected by an all-carbon comprising one double
      bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 226

Phe Ile Asp Glu Ala Val Leu Leu Ala Asn Val Ile Ala Leu Ala Leu
1               5                   10                  15

<210> SEQ ID NO 227
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Amino acid comprising two pentenyl-alanine
      olefin side chains, each of which is crosslinked to another
      amino acid as indicated
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me R5-pentenyl-alanine olefin amino acid
      connected by an all-carbon comprising one double
      bond
```

```
<220> FEATURE:
<223> OTHER INFORMATION: C-term NH2

<400> SEQUENCE: 227

Phe Ile Asp Glu Ala Val Leu Leu Ala Leu Val Ile Ala Ala Ala Leu
1               5                   10                  15

<210> SEQ ID NO 228
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Amino acid comprising two pentenyl-alanine
      olefin side chains, each of which is crosslinked to another
      amino acid as indicated
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me R5-pentenyl-alanine olefin amino acid
      connected by an all-carbon comprising one double
      bond
<220> FEATURE:
<223> OTHER INFORMATION: C-term NH2

<400> SEQUENCE: 228

Phe Ile Asp Glu Ala Val Leu Leu Ala Leu Val Ile Ala Gln Ala Leu
1               5                   10                  15

<210> SEQ ID NO 229
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
```

```
<223> OTHER INFORMATION: Nle
<220> FEATURE:
<221> NAME/KEY: MOD_RES
<222> LOCATION: (9)..(9)
<223> OTHER INFORMATION: Amino acid comprising two pentenyl-alanine
      olefin side chains, each of which is crosslinked to another
      amino acid as indicated
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me R5-pentenyl-alanine olefin amino acid
      connected by an all-carbon comprising one double
      bond
<220> FEATURE:
<223> OTHER INFORMATION: C-term NH2

<400> SEQUENCE: 229

Phe Ile Asp Glu Ala Val Leu Leu Ala Leu Val Ile Ala Arg Ala Leu
1               5                   10                  15

<210> SEQ ID NO 230
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Amino acid comprising two pentenyl-alanine
      olefin side chains, each of which is crosslinked to another
      amino acid as indicated
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me R5-pentenyl-alanine olefin amino acid
      connected by an all-carbon comprising one double
      bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 230

Phe Ile Asp Ala Ala Thr Leu Leu Ala Ser Val Ile Ala Leu Ala Leu
1               5                   10                  15

<210> SEQ ID NO 231
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me R-azide 1,5 triazole (3 carbon)
      alanine olefin amino acid connected by an all-carbon
      crosslinker comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Amino acid comprising two R5-pentenyl-alanine
      olefin side chains, each of which is crosslinked to another
      amino acid as indicated
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me azide 1,5 triazole (3 carbon) alanine
      olefin amino acid connected by an all-carbon
      crosslinker comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 231

Phe Ile Asp Glu Ala Val Leu Leu Ala Leu Val Ile Ala Leu Ala Leu
1               5                   10                  15

<210> SEQ ID NO 232
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Aib
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
```

```
         comprising one double bond
<220> FEATURE:
<223> OTHER INFORMATION: C-term NH2

<400> SEQUENCE: 232

Phe Ile Asp Glu Xaa Val Leu Met Ala Leu Val Ile Ala Met Ala
1               5                   10                  15

<210> SEQ ID NO 233
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 233

Ala Ile Asp Glu Glu Val Leu Met Ala Leu Val Ile Ala Met Ala Leu
1               5                   10                  15

<210> SEQ ID NO 234
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 234

Phe Ile Asp Ala Glu Val Leu Met Ala Leu Val Ile Ala Met Ala Leu
1               5                   10                  15

<210> SEQ ID NO 235
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 235

Phe Ile Asp Glu Glu Val Leu Leu Ala Phe Val Ile Ala Leu Ala Leu
1               5                   10                  15

<210> SEQ ID NO 236
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 236
```

Phe Ile Asp Glu Glu Val Leu Leu Ala Leu Val Ile Ala Leu Ala Phe
1               5                   10                  15

<210> SEQ ID NO 237
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 237

Phe Ile Ala Glu Glu Val Leu Leu Ala Leu Val Ile Ala Leu Ala Leu
1               5                   10                  15

Asp Ala Ile

<210> SEQ ID NO 238
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES

```
<222> LOCATION: (14)..(14)
<223> OTHER INFORMATION: Nle
<220> FEATURE:
<223> OTHER INFORMATION: C-term NH2

<400> SEQUENCE: 238

Phe Ile Ala Glu Ala Val Leu Leu Ala Leu Val Ile Ala Leu Ala Leu
1               5                   10                  15

Asp Ala Ile

<210> SEQ ID NO 239
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 239

Phe Ile Ala Glu Ala Val Leu Leu Ala Leu Val Ile Ala Leu Ala Leu
1               5                   10                  15

Ala Ala Ile

<210> SEQ ID NO 240
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
```

<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 240

Phe Ile Asp Glu Glu Val Leu Leu Ala Leu Val Ile Ala Met Ala Leu
1               5                   10                  15

<210> SEQ ID NO 241
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 241

Phe Ile Asp Glu Glu Val Leu Met Ala Leu Val Ile Ala Leu Ala Leu
1               5                   10                  15

<210> SEQ ID NO 242
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond

```
<220> FEATURE:
<223> OTHER INFORMATION: C-term NH2

<400> SEQUENCE: 242

Phe Ile Asp Glu Glu Val Leu Met Ala Leu Val Ile Ala Met Ala Phe
1               5                   10                  15

<210> SEQ ID NO 243
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (16)..(16)
<223> OTHER INFORMATION: Nle
<220> FEATURE:
<223> OTHER INFORMATION: C-term NH2

<400> SEQUENCE: 243

Phe Ile Asp Glu Glu Val Leu Met Ala Leu Val Ile Ala Met Ala Leu
1               5                   10                  15

<210> SEQ ID NO 244
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Phe-4cooh
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2
```

```
<400> SEQUENCE: 244

Phe Ile Asp Phe Glu Val Leu Met Ala Leu Val Ile Ala Met Ala Phe
1               5                   10                  15

<210> SEQ ID NO 245
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 245

Phe Ile Asp Glu Glu Val Leu Met Ala Leu Val Ile Ala Met Ala Leu
1               5                   10                  15

Leu

<210> SEQ ID NO 246
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 246

Phe Ile Ser Glu Glu Val Leu Met Ala Leu Val Ile Ala Met Ala Leu
1               5                   10                  15

<210> SEQ ID NO 247
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 247

Phe Ile Thr Glu Glu Val Leu Met Ala Leu Val Ile Ala Met Ala Leu
1               5                   10                  15

<210> SEQ ID NO 248
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 248

Phe Ile Asn Glu Glu Val Leu Met Ala Leu Val Ile Ala Met Ala Leu
1               5                   10                  15

<210> SEQ ID NO 249
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
``` comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
    connected by an all-carbon i to i+4 crosslinker
    comprising one double bond
<220> FEATURE:
<223> OTHER INFORMATION: C-term NH2

<400> SEQUENCE: 249

Phe Ile Asp Gln Glu Val Leu Met Ala Leu Val Ile Ala Met Ala Leu
1               5                   10                  15

<210> SEQ ID NO 250
<211> LENGTH: 16
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
    connected by an all-carbon i to i+4 crosslinker
    comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
    connected by an all-carbon i to i+4 crosslinker
    comprising one double bond
<220> FEATURE:
<223> OTHER INFORMATION: C-term NH2

<400> SEQUENCE: 250

Phe Ile Asp Glu Gln Val Leu Met Ala Leu Val Ile Ala Met Ala Leu
1               5                   10                  15

<210> SEQ ID NO 251
<211> LENGTH: 16
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
    connected by an all-carbon i to i+4 crosslinker
    comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
    connected by an all-carbon i to i+4 crosslinker
    comprising one double bond

```
<220> FEATURE:
<223> OTHER INFORMATION: C-term NH2

<400> SEQUENCE: 251

Phe Ile Asp Glu Asn Val Leu Met Ala Leu Val Ile Ala Met Ala Leu
1               5                   10                  15

<210> SEQ ID NO 252
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 252

Phe Ile Asp Glu Glu Val Leu Met Ala Phe Val Ile Ala Met Ala Leu
1               5                   10                  15

<210> SEQ ID NO 253
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (16)..(16)
<223> OTHER INFORMATION: Cba
<220> FEATURE:
<223> OTHER INFORMATION: C-term NH2

<400> SEQUENCE: 253

Phe Ile Asp Glu Glu Val Leu Met Ala Leu Val Ile Ala Met Ala Ala
1               5                   10                  15
```

<210> SEQ ID NO 254
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 254

Phe Ile Asp Glu Ser Val Leu Met Ala Leu Val Ile Ala Met Ala Leu
1               5                   10                  15

<210> SEQ ID NO 255
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 255

Phe Ile Asp Glu Thr Val Leu Met Ala Leu Val Ile Ala Met Ala Leu
1               5                   10                  15

<210> SEQ ID NO 256
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 5-FAM

```
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (9)..(9)
<223> OTHER INFORMATION: Nle
<220> FEATURE:
<221> NAME/KEY: MOD_RES
<222> LOCATION: (10)..(10)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (10)..(14)
<223> OTHER INFORMATION: Cross-link between residues
<220> FEATURE:
<221> NAME/KEY: MOD_RES
<222> LOCATION: (14)..(14)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (15)..(15)
<223> OTHER INFORMATION: Nle
<220> FEATURE:
<223> OTHER INFORMATION: C-term NH2

<400> SEQUENCE: 256

Ala Phe Ile Asp Glu Glu Val Leu Leu Ala Leu Val Ile Ala Leu Ala
1               5                   10                  15

Leu

<210> SEQ ID NO 257
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me R5-pentenyl-alanine olefin amino acid
      connected by an all-carbon comprising one double
      bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me R5-pentenyl-alanine olefin amino acid
      connected by an all-carbon comprising one double
      bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 257

Phe Ile Asp Glu Glu Val Leu Leu Ala Leu Val Ile Ala Leu Ala Leu
1               5                   10                  15
```

```
<210> SEQ ID NO 258
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 258

Phe Ile Asp Glu Glu Val Phe Leu Ala Leu Val Ile Ala Leu Ala Leu
1               5                   10                  15

Leu

<210> SEQ ID NO 259
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (8)..(8)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (8)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (13)..(13)
<223> OTHER INFORMATION: Nle
```

-continued

```
<220> FEATURE:
<223> OTHER INFORMATION: C-term NH2

<400> SEQUENCE: 259

Ile Asp Glu Glu Val Phe Leu Ala Leu Val Ile Ala Leu Ala Leu Leu
1               5                   10                  15

<210> SEQ ID NO 260
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Nle
<220> FEATURE:
<221> NAME/KEY: MOD_RES
<222> LOCATION: (7)..(7)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (7)..(11)
<223> OTHER INFORMATION: Cross-link between residues
<220> FEATURE:
<221> NAME/KEY: MOD_RES
<222> LOCATION: (11)..(11)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (12)..(12)
<223> OTHER INFORMATION: Nle
<220> FEATURE:
<223> OTHER INFORMATION: C-term NH2

<400> SEQUENCE: 260

Asp Glu Glu Val Phe Leu Ala Leu Val Ile Ala Leu Ala Leu Leu
1               5                   10                  15

<210> SEQ ID NO 261
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
```

```
    comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 261

Phe Ile Asp Glu Glu Val Phe Leu Ala Leu Val Ile Ala Leu Ala Leu
1               5                   10                  15

Leu

<210> SEQ ID NO 262
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 262

Phe Ile Asp Glu Glu Val Phe Ala Ala Leu Val Ile Ala Leu Ala Leu
1               5                   10                  15

Leu

<210> SEQ ID NO 263
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
```

```
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 263

Phe Ile Asp Glu Glu Val Phe Leu Ala Leu Val Ile Ala Ala Ala Leu
1               5                   10                  15

Leu

<210> SEQ ID NO 264
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 264

Phe Ile Asn Gln Gln Val Phe Leu Ala Leu Val Ile Ala Leu Ala Leu
1               5                   10                  15

Leu

<210> SEQ ID NO 265
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
```

```
            comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 265

Phe Ile Asp Glu Ala Val Phe Leu Ala Leu Val Ile Ala Leu Ala Leu
1               5                   10                  15

Leu

<210> SEQ ID NO 266
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 266

Phe Ile Asp Gln Ala Val Phe Leu Ala Leu Val Ile Ala Leu Ala Leu
1               5                   10                  15

Leu

<210> SEQ ID NO 267
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
```

```
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 267

Phe Ile Asp Gln Ala Val Phe Leu Ala Asn Val Ile Ala Leu Ala Leu
1               5                   10                  15

Leu

<210> SEQ ID NO 268
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 268

Phe Ile Asp Gln Ala Val Phe Leu Ala Ser Val Ile Ala Leu Ala Leu
1               5                   10                  15

Leu
```

```
<210> SEQ ID NO 269
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 269

Phe Ile Asp Gln Ala Val Phe Leu Ala Arg Val Ile Ala Leu Ala Leu
1               5                   10                  15

Leu

<210> SEQ ID NO 270
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2
```

<400> SEQUENCE: 270

Phe Ile Asp Gln Ala Val Phe Leu Ala His Val Ile Ala Leu Ala Leu
1               5                   10                  15

Leu

<210> SEQ ID NO 271
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 271

Phe Ile Asp Gln Ala Val Phe Leu Ala Leu Val Ile Ala Gln Ala Leu
1               5                   10                  15

Leu

<210> SEQ ID NO 272
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:

<223> OTHER INFORMATION: C-term NH2

<400> SEQUENCE: 272

Phe Ile Asp Gln Ala Val Phe Leu Ala Leu Val Ile Ala Arg Ala Leu
1               5                   10                  15

Leu

<210> SEQ ID NO 273
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 273

Phe Ile Asp Gln Ala Val Phe Leu Ala Leu Val Ile Ala Ser Ala Leu
1               5                   10                  15

Leu

<210> SEQ ID NO 274
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond <220> FEATURE:
<223> OTHER INFORMATION: C-term NH2

<400> SEQUENCE: 274

Phe Ile Asp Gln Ala Val Phe Leu Ala Leu Val Ile Ala His Ala Leu
1               5                   10                  15

Leu

<210> SEQ ID NO 275
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 275

Phe Ile Asp Gln Ala Val Phe Leu Ala Asn Val Ile Ala His Ala Leu
1               5                   10                  15

Leu

<210> SEQ ID NO 276
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker comprising one double bond
<220> FEATURE:
<223> OTHER INFORMATION: C-term NH2

<400> SEQUENCE: 276

Phe Ile Asp Gln Ala Val Phe Leu Ala His Val Ile Ala Gln Ala Leu
1               5                   10                  15

Leu

<210> SEQ ID NO 277
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 277

Phe Ile Asp Gln Ala Val Phe Leu Ala Ser Val Ile Ala Arg Ala Leu
1               5                   10                  15

Leu

<210> SEQ ID NO 278
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid

```
        connected by an all-carbon i to i+4 crosslinker
        comprising one double bond
<220> FEATURE:
<223> OTHER INFORMATION: C-term NH2

<400> SEQUENCE: 278

Phe Ile Asp Gln Ala Val Phe Leu Ala Arg Val Ile Ala Ser Ala Leu
1               5                   10                  15

Leu

<210> SEQ ID NO 279
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 5-FAM
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (9)..(9)
<223> OTHER INFORMATION: Nle
<220> FEATURE:
<221> NAME/KEY: MOD_RES
<222> LOCATION: (10)..(10)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (10)..(14)
<223> OTHER INFORMATION: Cross-link between residues
<220> FEATURE:
<221> NAME/KEY: MOD_RES
<222> LOCATION: (14)..(14)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (15)..(15)
<223> OTHER INFORMATION: Nle
<220> FEATURE:
<223> OTHER INFORMATION: C-term NH2

<400> SEQUENCE: 279

Ala Phe Ile Asp Glu Glu Val Leu Leu Ala Leu Val Ile Ala Leu Ala
1               5                   10                  15

Leu Asp Arg Ile
            20

<210> SEQ ID NO 280
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
```

```
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 280

Phe Ile Asp Glu Glu Val Phe Met Ala Leu Val Ile Ala Met Ala Leu
1               5                   10                  15

Asp Arg Ile

<210> SEQ ID NO 281
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 281

Phe Ile Asp Glu Glu Val Phe Leu Ala Leu Val Ile Ala Leu Ala Leu
1               5                   10                  15

Asp Arg Ile

<210> SEQ ID NO 282
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
```

```
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 282

Phe Ile Asp Glu Ala Val Leu Met Ala Leu Val Ile Ala Met Ala Leu
1               5                   10                  15

Asp Arg Ile

<210> SEQ ID NO 283
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 283

Phe Ile Asp Gln Glu Val Phe Met Ala Leu Val Ile Ala Met Ala Leu
1               5                   10                  15

Asp Arg Ile

<210> SEQ ID NO 284
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
```

```
        connected by an all-carbon i to i+4 crosslinker
        comprising one double bond
<220> FEATURE:
<223> OTHER INFORMATION: C-term NH2

<400> SEQUENCE: 284

Phe Ile Asp Gln Ala Val Phe Met Ala Leu Val Ile Ala Met Ala Leu
1               5                   10                  15

Asp Arg Ile

<210> SEQ ID NO 285
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
        connected by an all-carbon i to i+4 crosslinker
        comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
        connected by an all-carbon i to i+4 crosslinker
        comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 285

Phe Ile Asp Gln Glu Val Phe Leu Ala Leu Val Ile Ala Leu Ala Leu
1               5                   10                  15

Asp Arg Ile

<210> SEQ ID NO 286
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
        connected by an all-carbon i to i+4 crosslinker
        comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
```

<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 286

Phe Ile Asp Gln Ala Val Leu Met Ala Leu Val Ile Ala Met Ala Leu
1               5                   10                  15

Asn Arg Ile

<210> SEQ ID NO 287
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 287

Phe Ile Asn Gln Ala Val Leu Met Ala Leu Val Ile Ala Met Ala Leu
1               5                   10                  15

Asp Arg Ile

<210> SEQ ID NO 288
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 288

```
Phe Ile Asn Gln Ala Val Leu Met Ala Leu Val Ile Ala Met Ala Leu
1               5                  10                 15

Asn Arg Ile

<210> SEQ ID NO 289
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 289

Phe Ile Asp Gln Ala Val Leu Leu Ala Leu Val Ile Ala Leu Ala Leu
1               5                  10                 15

Asn Arg Ile

<210> SEQ ID NO 290
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2
```

```
<400> SEQUENCE: 290

Phe Ile Asp Glu Glu Phe Leu Met Ala Leu Val Ile Ala Met Ala Leu
1               5                   10                  15

Asp Arg Ile

<210> SEQ ID NO 291
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 291

Phe Ile Asp Glu Glu Phe Phe Met Ala Leu Val Ile Ala Met Ala Leu
1               5                   10                  15

Asp Arg Ile

<210> SEQ ID NO 292
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 292

Phe Ile Asp Glu Glu Val Phe Met Ala Leu His Ile Ala Met Ala Leu
1               5                   10                  15

Asp Arg Ile
```

```
<210> SEQ ID NO 293
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 293

Phe Ile Asp Glu Glu Val Phe Met Ala Tyr Val Ile Ala Met Ala Leu
1               5                   10                  15

Asp Arg Ile

<210> SEQ ID NO 294
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 294

Phe Ile Asp Glu Glu Val Leu Met Ala Leu His Ile Ala Met Ala Leu
1               5                   10                  15

Asp Arg Ile

<210> SEQ ID NO 295
<211> LENGTH: 19
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 295

Phe Ile Asp Glu Glu Val Leu Met Ala Tyr Val Ile Ala Met Ala Leu
1               5                   10                  15

Asp Arg Ile

<210> SEQ ID NO 296
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 296

Phe Ile Asp Glu Glu Val Ile Met Ala Leu Val Ile Ala Met Ala Val
1               5                   10                  15

Asp Arg Ile

<210> SEQ ID NO 297
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
```

```
        connected by an all-carbon i to i+4 crosslinker
        comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
        connected by an all-carbon i to i+4 crosslinker
        comprising one double bond
<220> FEATURE:
<223> OTHER INFORMATION: C-term NH2

<400> SEQUENCE: 297

Phe Ile Asp Glu Glu Val Leu Met Ala Leu Val Ile Ala Met Ala Leu
1               5                   10                  15

Asp Arg

<210> SEQ ID NO 298
<211> LENGTH: 19
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
        connected by an all-carbon i to i+4 crosslinker
        comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
        connected by an all-carbon i to i+4 crosslinker
        comprising one double bond
<220> FEATURE:
<223> OTHER INFORMATION: C-term NH2

<400> SEQUENCE: 298

Phe Ile Asp Glu Gln Val Leu Met Ala Leu Val Ile Ala Met Ala Leu
1               5                   10                  15

Asp Arg Ile

<210> SEQ ID NO 299
<211> LENGTH: 19
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
        connected by an all-carbon i to i+4 crosslinker
        comprising one double bond
<220> FEATURE:
<221> NAME/KEY: misc_feature
<222> LOCATION: (9)..(13)
<223> OTHER INFORMATION: Cross-link between residues
<220> FEATURE:
```

```
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 299

Phe Ile Asp Glu Lys Val Leu Met Ala Leu Val Ile Ala Met Ala Leu
1               5                   10                  15

Asp Arg Ile

<210> SEQ ID NO 300
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 300

Phe Ile Asp Glu His Val Leu Met Ala Leu Val Ile Ala Met Ala Leu
1               5                   10                  15

Asp Arg Ile

<210> SEQ ID NO 301
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2
```

<400> SEQUENCE: 301

Phe Ile Asn Glu Lys Val Leu Met Ala Leu Val Ile Ala Met Ala Leu
1               5                   10                  15

Asp Arg Ile

<210> SEQ ID NO 302
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 302

Phe Ile Asn Glu His Val Leu Met Ala Leu Val Ile Ala Met Ala Leu
1               5                   10                  15

Asp Arg Ile

<210> SEQ ID NO 303
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 303

Phe Ile Asp Glu Glu Val Leu Met Ala Leu Val Ile Ala Met Ala Leu
1               5                   10                  15

Ser Arg

<210> SEQ ID NO 304
<211> LENGTH: 18
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
    connected by an all-carbon i to i+4 crosslinker
    comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
    connected by an all-carbon i to i+4 crosslinker
    comprising one double bond
<220> FEATURE:
<223> OTHER INFORMATION: C-term NH2

<400> SEQUENCE: 304

Phe Ile Asn Glu Lys Val Leu Met Ala Leu Val Ile Ala Met Ala Leu
1               5                   10                  15

Ser Arg

<210> SEQ ID NO 305
<211> LENGTH: 19
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
    connected by an all-carbon i to i+4 crosslinker
    comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
    connected by an all-carbon i to i+4 crosslinker
    comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 305

Phe Ile Asn Gln Ala Val Leu Leu Ala Leu Val Ile Ala Leu Ala Leu
1               5                   10                  15

Asp Arg Ile

```
<210> SEQ ID NO 306
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (14)..(18)
<223> OTHER INFORMATION: Cross-link between residues
<220> FEATURE:
<221> NAME/KEY: MOD_RES
<222> LOCATION: (18)..(18)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 306

Val Ile Asp Thr Asp Phe Ile Asp Glu Glu Val Leu Ala Ala Leu Val
1               5                   10                  15

Ile Ala Ala Ala Leu Asp Arg Ile
            20

<210> SEQ ID NO 307
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (14)..(18)
<223> OTHER INFORMATION: Cross-link between residues
<220> FEATURE:
<221> NAME/KEY: MOD_RES
<222> LOCATION: (18)..(18)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 307

Val Phe Asp Thr Asp Phe Ile Asp Glu Gln Val Leu Ala Ala Leu Val
1               5                   10                  15

Ile Ala Ala Ala Leu Asp Arg Ile
            20

<210> SEQ ID NO 308
<211> LENGTH: 23
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (14)..(18)
<223> OTHER INFORMATION: Cross-link between residues
<220> FEATURE:
<221> NAME/KEY: MOD_RES
<222> LOCATION: (18)..(18)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 308

Val Ile Asp Thr Asp Phe Ile Asp Glu Gln Val Leu Ala Ala Leu Val
1               5                   10                  15

Ile Ala Ala Ala Leu Asp Ala
            20

<210> SEQ ID NO 309
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (14)..(18)
<223> OTHER INFORMATION: Cross-link between residues
<220> FEATURE:
<221> NAME/KEY: MOD_RES
<222> LOCATION: (18)..(18)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 309

Val Ile Arg Thr Asp Phe Ile Asp Glu Gln Val Leu Ala Ala Tyr Val
1               5                   10                  15

Ile Ala Ala Ala Leu Asp Ala
            20

<210> SEQ ID NO 310
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      that is not connected by any crosslinker
<220> FEATURE:
<221> NAME/KEY: MOD_RES
<222> LOCATION: (13)..(13)
<223> OTHER INFORMATION: Alpha-Me S5-pentenyl-alanine olefin amino acid
      that is not connected by any crosslinker
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 310

Phe Ile Asp Glu Glu Val Leu Leu Ala Leu Val Ile Ala Leu Ala Leu
1               5                   10                  15

Asp Arg Ile

<210> SEQ ID NO 311
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 311

Phe Ile Asp Glu Glu Val Leu Leu Ser Leu Val Ile Glu Leu Ala Leu
1               5                   10                  15

Asp Arg Ile

<210> SEQ ID NO 312
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me R5-pentenyl-alanine olefin amino acid
      connected by an all-carbon comprising one double
      bond
<220> FEATURE:
```

```
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me R5-pentenyl-alanine olefin amino acid
      connected by an all-carbon comprising one double
      bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 312

Phe Ile Asp Glu Glu Val Leu Leu Ala Leu Val Ile Ala Leu Ala Leu
1               5                   10                  15

Asp Arg Ile

<210> SEQ ID NO 313
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 5-TAMRA
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (9)..(9)
<223> OTHER INFORMATION: Nle
<220> FEATURE:
<221> NAME/KEY: MOD_RES
<222> LOCATION: (10)..(10)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (10)..(14)
<223> OTHER INFORMATION: Cross-link between residues
<220> FEATURE:
<221> NAME/KEY: MOD_RES
<222> LOCATION: (14)..(14)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (15)..(15)
<223> OTHER INFORMATION: Nle
<220> FEATURE:
<223> OTHER INFORMATION: C-term NH2

<400> SEQUENCE: 313

Ala Phe Ile Asp Glu Glu Val Leu Leu Ala Leu Val Ile Ala Leu Ala
1               5                   10                  15

Leu Asp Arg Ile
            20

<210> SEQ ID NO 314
<211> LENGTH: 19
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: MO
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 314

Phe Ile Asp Glu Glu Val Leu Xaa Ala Leu Val Ile Ala Leu Ala Leu
1               5                   10                  15

Asp Arg Ile

<210> SEQ ID NO 315
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: MO
<220> FEATURE:
<223> OTHER INFORMATION: C-term NH2

<400> SEQUENCE: 315

Phe Ile Asp Glu Glu Val Leu Leu Ala Leu Val Ile Ala Xaa Ala Leu
1               5                   10                  15
```

Asp Arg Ile

<210> SEQ ID NO 316
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: MO2
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 316

Phe Ile Asp Glu Glu Val Leu Xaa Ala Leu Val Ile Ala Leu Ala Leu
1               5                   10                  15

Asp Arg Ile

<210> SEQ ID NO 317
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (14)..(14)

-continued

```
<223> OTHER INFORMATION: MO2
<220> FEATURE:
<223> OTHER INFORMATION: C-term NH2

<400> SEQUENCE: 317

Phe Ile Asp Glu Glu Val Leu Leu Ala Leu Val Ile Ala Xaa Ala Leu
1               5                   10                  15

Asp Arg Ile

<210> SEQ ID NO 318
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (4)..(8)
<223> OTHER INFORMATION: Cross-link between residues
<220> FEATURE:
<221> NAME/KEY: MOD_RES
<222> LOCATION: (8)..(8)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (21)..(21)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (21)..(25)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (25)..(25)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 318

Leu Leu Gln Ala Glu Glu Leu Ala Arg Ala Leu Asp Gln Val Asn Ile
1               5                   10                  15

Asp Glu Glu Val Ala Leu Ser Leu Ala Ile Glu Leu Gly
            20                  25

<210> SEQ ID NO 319
<211> LENGTH: 29
<212> TYPE: PRT
<213> ORGANISM: Artificial Sequence
<220> FEATURE:
<223> OTHER INFORMATION: Description of Artificial Sequence: Synthetic
```

```
                                    peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (6)..(10)
<223> OTHER INFORMATION: Cross-link between residues
<220> FEATURE:
<221> NAME/KEY: MOD_RES
<222> LOCATION: (10)..(10)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (21)..(21)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (21)..(25)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (25)..(25)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 319

Leu Leu Gln Gly Glu Ala Leu Leu Arg Ala Leu Asp Gln Val Asn Ile
1               5                   10                  15

Asp Glu Glu Val Ala Leu Ser Leu Ala Ile Glu Leu Gly
            20                  25

<210> SEQ ID NO 320
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (8)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
```

```
        comprising one double bond
<220> FEATURE:
<221> NAME/KEY: MOD_RES
<222> LOCATION: (21)..(21)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (21)..(25)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (25)..(25)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 320

Leu Leu Gln Gly Glu Glu Leu Ala Arg Ala Leu Ala Gln Val Asn Ile
1               5                   10                  15

Asp Glu Glu Val Ala Leu Ser Leu Ala Ile Glu Leu Gly
            20                  25

<210> SEQ ID NO 321
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (6)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (21)..(21)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (21)..(25)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (25)..(25)
```

```
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 321

Leu Leu Gln Gly Glu Ala Leu Leu Arg Ala Leu Asp Ala Val Asn Ile
1               5                   10                  15

Asp Glu Glu Val Ala Leu Ser Leu Ala Ile Glu Leu Gly
            20                  25

<210> SEQ ID NO 322
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (4)..(8)
<223> OTHER INFORMATION: Cross-link between residues
<220> FEATURE:
<221> NAME/KEY: MOD_RES
<222> LOCATION: (8)..(8)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (23)..(23)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (23)..(27)
<223> OTHER INFORMATION: Cross-link between residues
<220> FEATURE:
<221> NAME/KEY: MOD_RES
<222> LOCATION: (27)..(27)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 322

Leu Leu Gln Ala Glu Glu Leu Ala Arg Ala Leu Asp Gln Val Asn Ile
1               5                   10                  15

Asp Glu Glu Val Leu Leu Ala Leu Val Ile Ala Leu Gly
            20                  25
```

```
<210> SEQ ID NO 323
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (6)..(10)
<223> OTHER INFORMATION: Cross-link between residues
<220> FEATURE:
<221> NAME/KEY: MOD_RES
<222> LOCATION: (10)..(10)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (23)..(23)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (23)..(27)
<223> OTHER INFORMATION: Cross-link between residues
<220> FEATURE:
<221> NAME/KEY: MOD_RES
<222> LOCATION: (27)..(27)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 323

Leu Leu Gln Gly Glu Ala Leu Leu Arg Ala Leu Asp Gln Val Asn Ile
1               5                   10                  15

Asp Glu Glu Val Leu Leu Ala Leu Val Ile Ala Leu Gly
            20                  25

<210> SEQ ID NO 324
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
```

```
<222> LOCATION: (8)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (23)..(23)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (23)..(27)
<223> OTHER INFORMATION: Cross-link between residues
<220> FEATURE:
<221> NAME/KEY: MOD_RES
<222> LOCATION: (27)..(27)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 324

Leu Leu Gln Gly Glu Glu Leu Ala Arg Ala Leu Ala Gln Val Asn Ile
1               5                   10                  15

Asp Glu Glu Val Leu Leu Ala Leu Val Ile Ala Leu Gly
            20                  25

<210> SEQ ID NO 325
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (6)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (23)..(23)
<223> OTHER INFORMATION: Alpha-Me S5-pentenyl-alanine olefin amino acid
      connected by an all-carbon i to i+4 crosslinker
      comprising one double bond
```

```
<220> FEATURE:
<221> NAME/KEY: misc_feature
<222> LOCATION: (23)..(27)
<223> OTHER INFORMATION: Cross-link between residues
<220> FEATURE:
<221> NAME/KEY: MOD_RES
<222> LOCATION: (27)..(27)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 325

Leu Leu Gln Gly Glu Ala Leu Leu Arg Ala Leu Asp Ala Val Asn Ile
1               5                   10                  15

Asp Glu Glu Val Leu Leu Ala Leu Val Ile Ala Leu Gly
            20                  25

<210> SEQ ID NO 326
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (4)..(8)
<223> OTHER INFORMATION: Cross-link between residues
<220> FEATURE:
<221> NAME/KEY: MOD_RES
<222> LOCATION: (8)..(8)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (19)..(19)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (19)..(26)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (26)..(26)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 326
```

```
Leu Leu Gln Ala Glu Glu Leu Ala Arg Ala Leu Asp Gln Val Asn Ile
1               5                   10                  15

Asp Glu Ala Val Leu Leu Ser Leu Val Ala Glu Leu Gly
                20                  25
```

<210> SEQ ID NO 327
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (6)..(10)
<223> OTHER INFORMATION: Cross-link between residues
<220> FEATURE:
<221> NAME/KEY: MOD_RES
<222> LOCATION: (10)..(10)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (19)..(19)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (19)..(26)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (26)..(26)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 327

```
Leu Leu Gln Gly Glu Ala Leu Leu Arg Ala Leu Asp Gln Val Asn Ile
1               5                   10                  15

Asp Glu Ala Val Leu Leu Ser Leu Val Ala Glu Leu Gly
                20                  25
```

<210> SEQ ID NO 328
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:

```
<221> NAME/KEY: MOD_RES
<222> LOCATION: (8)..(8)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (8)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (19)..(19)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (19)..(26)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (26)..(26)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 328

Leu Leu Gln Gly Glu Glu Leu Ala Arg Ala Leu Ala Gln Val Asn Ile
1               5                   10                  15
Asp Glu Ala Val Leu Leu Ser Leu Val Ala Glu Leu Gly
            20                  25

<210> SEQ ID NO 329
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (6)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (19)..(19)
```

```
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (19)..(26)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (26)..(26)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 329

Leu Leu Gln Gly Glu Ala Leu Leu Arg Ala Leu Asp Ala Val Asn Ile
1               5                   10                  15
Asp Glu Ala Val Leu Leu Ser Leu Val Ala Glu Leu Gly
            20                  25

<210> SEQ ID NO 330
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (4)..(8)
<223> OTHER INFORMATION: Cross-link between residues
<220> FEATURE:
<221> NAME/KEY: MOD_RES
<222> LOCATION: (8)..(8)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (21)..(21)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (21)..(28)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (28)..(28)
<223> OTHER INFORMATION: Alpha-Me S5-pentenyl-alanine olefin amino acid
      connected by an all-carbon i to i+4 crosslinker
      comprising one double bond
<220> FEATURE:
```

<223> OTHER INFORMATION: C-term NH2

<400> SEQUENCE: 330

Leu Leu Gln Ala Glu Glu Leu Ala Arg Ala Leu Asp Gln Val Asn Ile
1               5                   10                  15

Asp Glu Glu Val Ala Leu Ser Leu Val Ile Glu Ala Gly
            20                  25

<210> SEQ ID NO 331
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (6)..(10)
<223> OTHER INFORMATION: Cross-link between residues
<220> FEATURE:
<221> NAME/KEY: MOD_RES
<222> LOCATION: (10)..(10)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (21)..(21)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (21)..(28)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (28)..(28)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 331

Leu Leu Gln Gly Glu Ala Leu Leu Arg Ala Leu Asp Gln Val Asn Ile
1               5                   10                  15

Asp Glu Glu Val Ala Leu Ser Leu Val Ile Glu Ala Gly
            20                  25

<210> SEQ ID NO 332
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES

```
<222> LOCATION: (8)..(8)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (8)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (21)..(21)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (21)..(28)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (28)..(28)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 332

Leu Leu Gln Gly Glu Glu Leu Ala Arg Ala Leu Ala Gln Val Asn Ile
1               5                   10                  15

Asp Glu Glu Val Ala Leu Ser Leu Val Ile Glu Ala Gly
            20                  25

<210> SEQ ID NO 333
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (6)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (21)..(21)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
```

```
<222> LOCATION: (21)..(28)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (28)..(28)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 333

Leu Leu Gln Gly Glu Ala Leu Leu Arg Ala Leu Asp Ala Val Asn Ile
1               5                   10                  15

Asp Glu Glu Val Ala Leu Ser Leu Val Ile Glu Ala Gly
            20                  25

<210> SEQ ID NO 334
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (19)..(19)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (19)..(23)
<223> OTHER INFORMATION: Cross-link between residues
<220> FEATURE:
<221> NAME/KEY: MOD_RES
<222> LOCATION: (23)..(23)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 334

Leu Leu Gln Gly Glu Glu Leu Leu Arg Ala Leu Asp Gln Val Asn Ile
1               5                   10                  15

Asp Glu Ala Val Leu Met Ala Leu Val Ile Glu Met
            20                  25

<210> SEQ ID NO 335
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (23)..(23)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (23)..(27)
```

```
<223> OTHER INFORMATION: Cross-link between residues
<220> FEATURE:
<221> NAME/KEY: MOD_RES
<222> LOCATION: (27)..(27)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 335

Leu Leu Gln Gly Glu Glu Leu Leu Arg Ala Leu Asp Gln Val Asn Ile
1               5                   10                  15
Asp Glu Glu Val Leu Met Ala Leu Val Ile Ala Met
            20                  25

<210> SEQ ID NO 336
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (19)..(19)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (19)..(26)
<223> OTHER INFORMATION: Cross-link between residues
<220> FEATURE:
<221> NAME/KEY: MOD_RES
<222> LOCATION: (26)..(26)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 336

Leu Leu Gln Gly Glu Glu Leu Leu Arg Ala Leu Asp Gln Val Asn Ile
1               5                   10                  15
Asp Glu Ala Val Leu Met Ser Leu Val Ala Glu Met
            20                  25

<210> SEQ ID NO 337
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
``` connected by an all-carbon i to i+4 crosslinker
            comprising one double bond
<220> FEATURE:
<221> NAME/KEY: MOD_RES
<222> LOCATION: (27)..(27)
<223> OTHER INFORMATION: Alpha-Me S5-pentenyl-alanine olefin amino acid
            connected by an all-carbon i to i+4 crosslinker
            comprising one double bond
<220> FEATURE:
<221> NAME/KEY: misc_feature
<222> LOCATION: (27)..(31)
<223> OTHER INFORMATION: Cross-link between residues
<220> FEATURE:
<221> NAME/KEY: MOD_RES
<222> LOCATION: (30)..(30)
<223> OTHER INFORMATION: Abu
<220> FEATURE:
<221> NAME/KEY: MOD_RES
<222> LOCATION: (31)..(31)
<223> OTHER INFORMATION: Alpha-Me S5-pentenyl-alanine olefin amino acid
            connected by an all-carbon i to i+4 crosslinker
            comprising one double bond
<220> FEATURE:
<223> OTHER INFORMATION: C-term NH2

<400> SEQUENCE: 337

Phe Ile Asp Glu Glu Val Leu Met Ala Leu Val Ile Ala Met Gly Leu
1               5                   10                  15

Asp Arg Ile Lys Glu Leu Pro Gln Leu Thr Ala Tyr Asp Xaa Ala Val
            20                  25                  30

Asn Ala

<210> SEQ ID NO 338
<211> LENGTH: 34
<212> TYPE: PRT
<213> ORGANISM: Artificial Sequence
<220> FEATURE:
<223> OTHER INFORMATION: Description of Artificial Sequence: Synthetic
            polypeptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
            connected by an all-carbon i to i+4 crosslinker
            comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
            connected by an all-carbon i to i+4 crosslinker
            comprising one double bond
<220> FEATURE:
<221> NAME/KEY: MOD_RES
<222> LOCATION: (27)..(27)
<223> OTHER INFORMATION: Alpha-Me S5-pentenyl-alanine olefin amino acid
            connected by an all-carbon i to i+4 crosslinker
            comprising one double bond
<220> FEATURE:
<221> NAME/KEY: misc_feature
<222> LOCATION: (27)..(31)
<223> OTHER INFORMATION: Cross-link between residues
<220> FEATURE:
<221> NAME/KEY: MOD_RES
<222> LOCATION: (30)..(30)
<223> OTHER INFORMATION: Abu
<220> FEATURE:
<221> NAME/KEY: MOD_RES
<222> LOCATION: (31)..(31)
<223> OTHER INFORMATION: Alpha-Me S5-pentenyl-alanine olefin amino acid -continued

```
      connected by an all-carbon i to i+4 crosslinker
      comprising one double bond
<220> FEATURE:
<223> OTHER INFORMATION: C-term NH2

<400> SEQUENCE: 338

Phe Ile Asp Glu Ala Val Leu Met Ala Leu Val Ile Glu Met Gly Leu
1               5                   10                  15

Asp Arg Ile Lys Glu Leu Pro Gln Leu Thr Ala Tyr Asp Xaa Ala Val
            20                  25                  30

Asn Ala

<210> SEQ ID NO 339
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (5)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (27)..(27)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (27)..(31)
<223> OTHER INFORMATION: Cross-link between residues
<220> FEATURE:
<221> NAME/KEY: MOD_RES
<222> LOCATION: (30)..(30)
<223> OTHER INFORMATION: Abu
<220> FEATURE:
<221> NAME/KEY: MOD_RES
<222> LOCATION: (31)..(31)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 339

Phe Ile Asp Glu Ala Val Leu Met Ser Leu Val Ala Glu Met Gly Leu
1               5                   10                  15

Asp Arg Ile Lys Glu Leu Pro Gln Leu Thr Ala Tyr Asp Xaa Ala Val
            20                  25                  30

Asn Ala

<210> SEQ ID NO 340
<211> LENGTH: 34
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (6)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (27)..(27)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (27)..(31)
<223> OTHER INFORMATION: Cross-link between residues
<220> FEATURE:
<221> NAME/KEY: MOD_RES
<222> LOCATION: (30)..(30)
<223> OTHER INFORMATION: Abu
<220> FEATURE:
<221> NAME/KEY: MOD_RES
<222> LOCATION: (31)..(31)
<223> OTHER INFORMATION: Alpha-Me S5-pentenyl-alanine olefin amino acid
      connected by an all-carbon i to i+4 crosslinker
      comprising one double bond
<220> FEATURE:
<223> OTHER INFORMATION: C-term NH2

<400> SEQUENCE: 340

Phe Ile Asp Glu Glu Ala Leu Met Ser Leu Val Ile Ala Met Gly Leu
1               5                   10                  15
Asp Arg Ile Lys Glu Leu Pro Gln Leu Thr Ala Tyr Asp Xaa Ala Val
                20                  25                  30
Asn Ala

<210> SEQ ID NO 341
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (4)..(8)
<223> OTHER INFORMATION: Cross-link between residues
<220> FEATURE:
<221> NAME/KEY: MOD_RES
<222> LOCATION: (8)..(8)
<223> OTHER INFORMATION: Alpha-Me S5-pentenyl-alanine olefin amino acid
      connected by an all-carbon i to i+4 crosslinker
```

```
                 comprising one double bond
<220> FEATURE:
<221> NAME/KEY: MOD_RES
<222> LOCATION: (19)..(19)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (19)..(23)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (23)..(23)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 341

Leu Leu Gln Ala Glu Glu Leu Ala Arg Ala Leu Asp Gln Val Asn Ile
1               5                   10                  15

Asp Glu Ala Val Leu Leu Ala Leu Val Ile Glu Leu Gly
            20                  25

<210> SEQ ID NO 342
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (6)..(10)
<223> OTHER INFORMATION: Cross-link between residues
<220> FEATURE:
<221> NAME/KEY: MOD_RES
<222> LOCATION: (10)..(10)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (19)..(19)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (19)..(23)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (23)..(23)
```

```
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 342

Leu Leu Gln Gly Glu Ala Leu Leu Arg Ala Leu Asp Gln Val Asn Ile
1               5                   10                  15

Asp Glu Ala Val Leu Leu Ala Leu Val Ile Glu Leu Gly
            20                  25

<210> SEQ ID NO 343
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (8)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (19)..(19)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (19)..(23)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (23)..(23)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 343

Leu Leu Gln Gly Glu Glu Leu Ala Arg Ala Leu Ala Gln Val Asn Ile
1               5                   10                  15

Asp Glu Ala Val Leu Leu Ala Leu Val Ile Glu Leu Gly
            20                  25
```

```
<210> SEQ ID NO 344
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (6)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (19)..(19)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (19)..(23)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (23)..(23)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 344

Leu Leu Gln Gly Glu Ala Leu Leu Arg Ala Leu Asp Ala Val Asn Ile
1               5                   10                  15

Asp Glu Ala Val Leu Leu Ala Leu Val Ile Glu Leu Gly
            20                  25

<210> SEQ ID NO 345
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
```

```
<222> LOCATION: (4)..(8)
<223> OTHER INFORMATION: Cross-link between residues
<220> FEATURE:
<221> NAME/KEY: MOD_RES
<222> LOCATION: (8)..(8)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (20)..(20)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (20)..(27)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (27)..(27)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 345

Leu Leu Gln Ala Glu Glu Leu Ala Arg Ala Leu Asp Gln Val Asn Ile
1               5                   10                  15

Asp Glu Glu Ala Leu Leu Ser Leu Val Ile Ala Leu Gly
            20                  25

<210> SEQ ID NO 346
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (6)..(10)
<223> OTHER INFORMATION: Cross-link between residues
<220> FEATURE:
<221> NAME/KEY: MOD_RES
<222> LOCATION: (10)..(10)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (20)..(20)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (20)..(27)
<223> OTHER INFORMATION: Cross-link between residues
```

```
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (27)..(27)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 346

Leu Leu Gln Gly Glu Ala Leu Leu Arg Ala Leu Asp Gln Val Asn Ile
1               5                   10                  15

Asp Glu Glu Ala Leu Leu Ser Leu Val Ile Ala Leu Gly
            20                  25

<210> SEQ ID NO 347
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (8)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (20)..(20)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (20)..(27)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (27)..(27)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 347
```

Leu Leu Gln Gly Glu Glu Leu Ala Arg Ala Leu Ala Gln Val Asn Ile
1               5                   10                  15

Asp Glu Glu Ala Leu Leu Ser Leu Val Ile Ala Leu Gly
            20                  25

<210> SEQ ID NO 348
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (6)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (20)..(20)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (20)..(27)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (27)..(27)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 348

Leu Leu Gln Gly Glu Ala Leu Leu Arg Ala Leu Asp Ala Val Asn Ile
1               5                   10                  15

Asp Glu Glu Ala Leu Leu Ser Leu Val Ile Ala Leu Gly
            20                  25

<210> SEQ ID NO 349
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:

```
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 349

Leu Leu Gln Gly Glu Glu Leu Leu Arg Ala Leu Asp Gln Val Asn Ile
1               5                   10                  15
Asp Glu Glu Val Leu Leu Ser Leu Val Ile Glu Leu
            20                  25

<210> SEQ ID NO 350
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (19)..(19)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (19)..(23)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (23)..(23)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 350

Leu Leu Gln Gly Glu Glu Leu Leu Arg Ala Leu Asp Gln Val Asn Ile
1               5                   10                  15
Asp Glu Ala Val Leu Leu Ala Leu Val Ile Glu Leu
            20                  25

<210> SEQ ID NO 351
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
```

<222> LOCATION: (23)..(23)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (23)..(27)
<223> OTHER INFORMATION: Cross-link between residues
<220> FEATURE:
<221> NAME/KEY: MOD_RES
<222> LOCATION: (27)..(27)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 351

Leu Leu Gln Gly Glu Glu Leu Leu Arg Ala Leu Asp Gln Val Asn Ile
1               5                   10                  15
Asp Glu Glu Val Leu Leu Ala Leu Val Ile Ala Leu
            20                  25

<210> SEQ ID NO 352
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (19)..(19)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (19)..(26)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (26)..(26)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 352

Leu Leu Gln Gly Glu Glu Leu Leu Arg Ala Leu Asp Gln Val Asn Ile
1               5                   10                  15
Asp Glu Ala Val Leu Leu Ser Leu Val Ala Glu Leu
            20                  25

<210> SEQ ID NO 353
<211> LENGTH: 28
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (20)..(20)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (20)..(27)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (27)..(27)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 353

Leu Leu Gln Gly Glu Glu Leu Leu Arg Ala Leu Asp Gln Val Asn Ile
1               5                   10                  15

Asp Glu Glu Ala Leu Leu Ser Leu Val Ile Ala Leu
            20                  25

<210> SEQ ID NO 354
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (23)..(23)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (23)..(27)
```

```
<223> OTHER INFORMATION: Cross-link between residues
<220> FEATURE:
<221> NAME/KEY: MOD_RES
<222> LOCATION: (27)..(27)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 354

Leu Leu Gln Gly Ala Glu Leu Leu Ala Ala Leu Asp Gln Val Asn Ile
1               5                   10                  15

Asp Glu Glu Val Leu Leu Ala Leu Val Ile Ala Leu Gly
            20                  25

<210> SEQ ID NO 355
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (7)..(7)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (7)..(11)
<223> OTHER INFORMATION: Cross-link between residues
<220> FEATURE:
<221> NAME/KEY: MOD_RES
<222> LOCATION: (11)..(11)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (23)..(23)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (23)..(27)
<223> OTHER INFORMATION: Cross-link between residues
<220> FEATURE:
<221> NAME/KEY: MOD_RES
<222> LOCATION: (27)..(27)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 355

Leu Leu Gln Gly Glu Glu Ala Leu Arg Ala Ala Asp Gln Val Asn Ile
1               5                   10                  15
```

Asp Glu Glu Val Leu Leu Ala Leu Val Ile Ala Leu Gly
            20                  25

<210> SEQ ID NO 356
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (23)..(23)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (23)..(27)
<223> OTHER INFORMATION: Cross-link between residues
<220> FEATURE:
<221> NAME/KEY: MOD_RES
<222> LOCATION: (27)..(27)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 356

Leu Leu Gln Gly Glu Glu Leu Leu Ala Ala Leu Asp Ala Val Asn Ile
1               5                   10                  15

Asp Glu Glu Val Leu Leu Ala Leu Val Ile Ala Leu Gly
            20                  25

<210> SEQ ID NO 357
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Alpha-Me R8-octenyl-alanine olefin amino acid connected by an all-carbon i to i+7 crosslinker
comprising one double bond
<220> FEATURE:
<221> NAME/KEY: misc_feature
<222> LOCATION: (4)..(11)
<223> OTHER INFORMATION: Cross-link between residues
<220> FEATURE:
<221> NAME/KEY: MOD_RES
<222> LOCATION: (11)..(11)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (23)..(23)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (23)..(27)
<223> OTHER INFORMATION: Cross-link between residues
<220> FEATURE:
<221> NAME/KEY: MOD_RES
<222> LOCATION: (27)..(27)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 357

Leu Leu Gln Ala Glu Glu Leu Leu Arg Ala Ala Asp Gln Val Asn Ile
1               5                   10                  15

Asp Glu Glu Val Leu Leu Ala Leu Val Ile Ala Leu Gly
            20                  25

<210> SEQ ID NO 358
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (5)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (23)..(23)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (23)..(27)
<223> OTHER INFORMATION: Cross-link between residues
<220> FEATURE:
<221> NAME/KEY: MOD_RES
<222> LOCATION: (27)..(27)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 358

Leu Leu Gln Gly Ala Glu Leu Leu Arg Ala Leu Ala Gln Val Asn Ile
1               5                   10                  15

Asp Glu Glu Val Leu Leu Ala Leu Val Ile Ala Leu Gly
            20                  25

<210> SEQ ID NO 359
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (19)..(19)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (19)..(26)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (26)..(26)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 359

Leu Leu Gln Gly Ala Glu Leu Leu Ala Ala Leu Asp Gln Val Asn Ile
1               5                   10                  15

Asp Glu Ala Val Leu Leu Ser Leu Val Ala Glu Leu Gly
            20                  25

<210> SEQ ID NO 360
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (7)..(7)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (7)..(11)
<223> OTHER INFORMATION: Cross-link between residues
<220> FEATURE:
<221> NAME/KEY: MOD_RES
<222> LOCATION: (11)..(11)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (19)..(19)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (19)..(26)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (26)..(26)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 360

Leu Leu Gln Gly Glu Glu Ala Leu Arg Ala Ala Asp Gln Val Asn Ile
1               5                   10                  15

Asp Glu Ala Val Leu Leu Ser Leu Val Ala Glu Leu Gly
            20                  25

<210> SEQ ID NO 361
<211> LENGTH: 29
<212> TYPE: PRT
<213> ORGANISM: Artificial Sequence
<220> FEATURE:
<223> OTHER INFORMATION: Description of Artificial Sequence: Synthetic

```
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (4)..(11)
<223> OTHER INFORMATION: Cross-link between residues
<220> FEATURE:
<221> NAME/KEY: MOD_RES
<222> LOCATION: (11)..(11)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (19)..(19)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (19)..(26)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (26)..(26)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 361

Leu Leu Gln Ala Glu Glu Leu Leu Arg Ala Ala Asp Gln Val Asn Ile
1               5                   10                  15

Asp Glu Ala Val Leu Leu Ser Leu Val Ala Glu Leu Gly
            20                  25

<210> SEQ ID NO 362
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (6)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
```

-continued

```
      comprising one double bond
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (23)..(23)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (23)..(27)
<223> OTHER INFORMATION: Cross-link between residues
<220> FEATURE:
<221> NAME/KEY: MOD_RES
<222> LOCATION: (27)..(27)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 362

Leu Leu Gln Gly Glu Ala Leu Leu Arg Ala Leu Asp Ala Val Asn Ile
1               5                  10                  15

Asp Ala Glu Val Leu Leu Ala Leu Val Ile Ala Leu
            20                  25

<210> SEQ ID NO 363
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (6)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (23)..(23)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (23)..(27)
<223> OTHER INFORMATION: Cross-link between residues
<220> FEATURE:
<221> NAME/KEY: MOD_RES
<222> LOCATION: (27)..(27)
```

<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 363

Leu Leu Gln Gly Glu Ala Leu Leu Arg Ala Leu Asp Ala Val Asn Ile
1               5                   10                  15

Asp Glu Ala Val Leu Leu Ala Leu Val Ile Ala Leu
            20                  25

<210> SEQ ID NO 364
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (6)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (23)..(23)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (23)..(27)
<223> OTHER INFORMATION: Cross-link between residues
<220> FEATURE:
<221> NAME/KEY: MOD_RES
<222> LOCATION: (27)..(27)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 364

Leu Leu Gln Gly Ala Ala Leu Leu Arg Ala Leu Ala Ala Val Asn Ile
1               5                   10                  15

Ala Ala Ala Val Leu Leu Ala Leu Val Ile Ala Leu
            20                  25

```
<210> SEQ ID NO 365
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (6)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (23)..(23)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (23)..(27)
<223> OTHER INFORMATION: Cross-link between residues
<220> FEATURE:
<221> NAME/KEY: MOD_RES
<222> LOCATION: (27)..(27)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 365

Leu Leu Gln Gly Glu Ala Leu Leu Arg Ala Leu Asp Ala Val Asn Ile
1               5                   10                  15

Ala Glu Glu Val Leu Leu Ala Leu Val Ile Ala Leu
            20                  25

<210> SEQ ID NO 366
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
```

```
<222> LOCATION: (6)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (23)..(23)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (23)..(27)
<223> OTHER INFORMATION: Cross-link between residues
<220> FEATURE:
<221> NAME/KEY: MOD_RES
<222> LOCATION: (27)..(27)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 366

Leu Leu Gln Ala Glu Ala Leu Leu Arg Ala Leu Asp Ala Val Asn Ile
1               5                   10                  15

Asp Glu Glu Val Leu Leu Ala Leu Val Ile Ala Leu
            20                  25

<210> SEQ ID NO 367
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (2)..(9)
<223> OTHER INFORMATION: Cross-link between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (18)..(18)
<223> OTHER INFORMATION: Nle
<220> FEATURE:
<221> NAME/KEY: MOD_RES
<222> LOCATION: (19)..(19)
<223> OTHER INFORMATION: Alpha-Me S5-pentenyl-alanine olefin amino acid
      connected by an all-carbon i to i+4 crosslinker
      comprising one double bond
```

```
<220> FEATURE:
<221> NAME/KEY: misc_feature
<222> LOCATION: (19)..(23)
<223> OTHER INFORMATION: Cross-link between residues
<220> FEATURE:
<221> NAME/KEY: MOD_RES
<222> LOCATION: (23)..(23)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (24)..(24)
<223> OTHER INFORMATION: Nle
<220> FEATURE:
<223> OTHER INFORMATION: C-term NH2

<400> SEQUENCE: 367

Glu Ala Leu Leu Arg Ala Leu Asp Ala Val Asn Ile Asp Glu Glu Val
1               5                   10                  15

Leu Leu Ala Leu Val Ile Ala Leu
            20

<210> SEQ ID NO 368
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (6)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (19)..(19)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (19)..(26)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (26)..(26)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 368
```

```
Leu Leu Gln Gly Glu Ala Leu Leu Arg Ala Leu Asp Ala Ala Ala Ala
1               5                   10                  15

Ala Glu Ala Val Leu Leu Ser Leu Val Ala Glu Leu
                20                  25
```

<210> SEQ ID NO 369
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (6)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (19)..(19)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (19)..(26)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (26)..(26)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 369

```
Leu Leu Gln Gly Ala Ala Leu Leu Arg Ala Leu Asp Ala Val Asn Ile
1               5                   10                  15

Asp Glu Ala Val Leu Leu Ser Leu Val Ala Glu Leu
                20                  25
```

<210> SEQ ID NO 370
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:

```
<221> NAME/KEY: MOD_RES
<222> LOCATION: (6)..(6)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (6)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (19)..(19)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (19)..(26)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (26)..(26)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 370

Leu Leu Gln Gly Glu Ala Leu Leu Arg Ala Leu Ala Ala Val Asn Ile
1               5                   10                  15

Asp Glu Ala Val Leu Leu Ser Leu Val Ala Glu Leu
            20                  25

<210> SEQ ID NO 371
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (6)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (19)..(19)
```

```
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (19)..(26)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (26)..(26)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 371

Leu Leu Gln Gly Glu Ala Leu Leu Arg Ala Leu Asp Ala Val Asn Ile
1               5                   10                  15
Ala Glu Ala Val Leu Leu Ser Leu Val Ala Glu Leu
            20                  25

<210> SEQ ID NO 372
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (6)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (19)..(19)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (19)..(26)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (26)..(26)
<223> OTHER INFORMATION: Alpha-Me S5-pentenyl-alanine olefin amino acid
      connected by an all-carbon i to i+4 crosslinker
      comprising one double bond
<220> FEATURE:
```

<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 372

Leu Leu Gln Gly Ala Ala Leu Leu Arg Ala Leu Ala Ala Val Asn Ile
1               5                   10                  15

Ala Ala Ala Val Leu Leu Ser Leu Val Ala Glu Leu
            20                  25

<210> SEQ ID NO 373
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (6)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (19)..(19)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (19)..(26)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (26)..(26)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 373

Leu Leu Gln Ala Glu Ala Leu Leu Arg Ala Leu Asp Ala Val Asn Ile
1               5                   10                  15

Asp Glu Ala Val Leu Leu Ser Leu Val Ala Glu Leu
            20                  25

<210> SEQ ID NO 374
<211> LENGTH: 24
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (2)..(9)
<223> OTHER INFORMATION: Cross-link between residues
<220> FEATURE:
<221> NAME/KEY: MOD_RES
<222> LOCATION: (9)..(9)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (15)..(15)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (15)..(22)
<223> OTHER INFORMATION: Cross-link between residues
<220> FEATURE:
<221> NAME/KEY: MOD_RES
<222> LOCATION: (18)..(18)
<223> OTHER INFORMATION: Nle
<220> FEATURE:
<221> NAME/KEY: MOD_RES
<222> LOCATION: (22)..(22)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (24)..(24)
<223> OTHER INFORMATION: Nle
<220> FEATURE:
<223> OTHER INFORMATION: C-term NH2

<400> SEQUENCE: 374

Glu Ala Leu Leu Arg Ala Leu Asp Ala Val Asn Ile Asp Glu Ala Val
1               5                   10                  15

Leu Leu Ser Leu Val Ala Glu Leu
            20

<210> SEQ ID NO 375
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (8)..(12)
<223> OTHER INFORMATION: Cross-link between residues
<220> FEATURE:
<221> NAME/KEY: MOD_RES
```

```
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (19)..(19)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (19)..(26)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (26)..(26)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 375

Leu Leu Gln Gly Glu Glu Leu Ala Arg Ala Leu Ala Gln Ala Ala Ala
1               5                   10                  15

Ala Glu Ala Val Leu Leu Ser Leu Val Ala Glu Leu
            20                  25

<210> SEQ ID NO 376
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (8)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (19)..(19)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (19)..(26)
<223> OTHER INFORMATION: Cross-link between residues
<220> FEATURE:
<221> NAME/KEY: MOD_RES
<222> LOCATION: (22)..(22)
<223> OTHER INFORMATION: Nle
```

```
<220> FEATURE:
<221> NAME/KEY: MOD_RES
<222> LOCATION: (26)..(26)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 376

Leu Leu Gln Gly Ala Glu Leu Ala Arg Ala Leu Ala Gln Val Asn Ile
1               5                   10                  15

Asp Glu Ala Val Leu Leu Ser Leu Val Ala Glu Leu
            20                  25

<210> SEQ ID NO 377
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (8)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (19)..(19)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (19)..(26)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (26)..(26)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 377

Leu Leu Gln Gly Glu Ala Leu Ala Arg Ala Leu Ala Gln Val Asn Ile
1               5                   10                  15
```

Asp Glu Ala Val Leu Leu Ser Leu Val Ala Glu Leu
            20                  25

<210> SEQ ID NO 378
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (8)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (19)..(19)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (19)..(26)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (26)..(26)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 378

Leu Leu Gln Gly Glu Glu Leu Ala Arg Ala Leu Ala Gln Val Asn Ile
1               5                   10                  15

Asp Ala Ala Val Leu Leu Ser Leu Val Ala Glu Leu
            20                  25

<210> SEQ ID NO 379
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Alpha-Me S5-pentenyl-alanine olefin amino acid
      connected by an all-carbon i to i+4 crosslinker

```
      comprising one double bond
<220> FEATURE:
<221> NAME/KEY: misc_feature
<222> LOCATION: (8)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (19)..(19)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (19)..(26)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (26)..(26)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 379

Leu Leu Gln Gly Glu Glu Leu Ala Arg Ala Leu Ala Gln Val Asn Ile
1               5                   10                  15

Asp Glu Ala Val Leu Leu Ser Leu Val Ala Ala Leu
            20                  25

<210> SEQ ID NO 380
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (8)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (19)..(19)
<223> OTHER INFORMATION: Alpha-Me R8-octenyl-alanine olefin amino acid
      connected by an all-carbon i to i+7 crosslinker
      comprising one double bond
<220> FEATURE:
```

```
<221> NAME/KEY: misc_feature
<222> LOCATION: (19)..(26)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (26)..(26)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 380

Leu Leu Gln Gly Ala Ala Leu Ala Arg Ala Leu Ala Gln Val Asn Ile
1               5                   10                  15
Ala Ala Ala Val Leu Leu Ser Leu Val Ala Ala Leu
            20                  25

<210> SEQ ID NO 381
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (8)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (19)..(19)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (19)..(26)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (26)..(26)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
```

<223> OTHER INFORMATION: C-term NH2

<400> SEQUENCE: 381

Leu Leu Gln Gly Glu Glu Leu Ala Arg Ala Leu Ala Gln Val Asn Ile
1               5                   10                  15

Ala Glu Ala Val Leu Leu Ser Leu Val Ala Glu Leu
            20                  25

<210> SEQ ID NO 382
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (4)..(8)
<223> OTHER INFORMATION: Cross-link between residues
<220> FEATURE:
<221> NAME/KEY: MOD_RES
<222> LOCATION: (8)..(8)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (15)..(15)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (15)..(22)
<223> OTHER INFORMATION: Cross-link between residues
<220> FEATURE:
<221> NAME/KEY: MOD_RES
<222> LOCATION: (18)..(18)
<223> OTHER INFORMATION: Nle
<220> FEATURE:
<221> NAME/KEY: MOD_RES
<222> LOCATION: (22)..(22)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (24)..(24)
<223> OTHER INFORMATION: Nle
<220> FEATURE:
<223> OTHER INFORMATION: C-term NH2

<400> SEQUENCE: 382

Glu Glu Leu Ala Arg Ala Leu Ala Gln Val Asn Ile Asp Glu Ala Val
1               5                   10                  15

Leu Leu Ser Leu Val Ala Glu Leu
            20

<210> SEQ ID NO 383
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (8)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (19)..(19)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (19)..(26)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (26)..(26)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 383

Leu Leu Gln Ala Glu Glu Leu Ala Arg Ala Leu Ala Gln Val Asn Ile
1               5                   10                  15

Asp Glu Ala Val Leu Leu Ser Leu Val Ala Glu Leu
            20                  25

<210> SEQ ID NO 384
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term 5-FAM
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (7)..(7)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (7)..(14)
<223> OTHER INFORMATION: Cross-link between residues
<220> FEATURE:
<221> NAME/KEY: MOD_RES
```

-continued

```
<222> LOCATION: (14)..(14)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (23)..(23)
<223> OTHER INFORMATION: Nle
<220> FEATURE:
<221> NAME/KEY: MOD_RES
<222> LOCATION: (24)..(24)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (24)..(28)
<223> OTHER INFORMATION: Cross-link between residues
<220> FEATURE:
<221> NAME/KEY: MOD_RES
<222> LOCATION: (28)..(28)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (29)..(29)
<223> OTHER INFORMATION: Nle
<220> FEATURE:
<223> OTHER INFORMATION: C-term NH2

<400> SEQUENCE: 384

Ala Leu Leu Gln Gly Glu Ala Leu Leu Arg Ala Leu Asp Ala Val Asn
1               5                   10                  15

Ile Asp Glu Glu Val Leu Leu Ala Leu Val Ile Ala Leu Ala Leu
            20                  25                  30

<210> SEQ ID NO 385
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (6)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (21)..(21)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (21)..(25)
<223> OTHER INFORMATION: Cross-link between residues
<220> FEATURE:
<221> NAME/KEY: MOD_RES
<222> LOCATION: (22)..(22)
<223> OTHER INFORMATION: Nle
```

```
<220> FEATURE:
<221> NAME/KEY: MOD_RES
<222> LOCATION: (25)..(25)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 385

Leu Leu Gln Gly Glu Ala Leu Leu Arg Ala Leu Asp Ala Val Asn Ile
1               5                   10                  15

Asp Glu Glu Val Ala Leu Ser Leu Ala Ile Glu Leu Ala Leu
            20                  25                  30

<210> SEQ ID NO 386
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (4)..(8)
<223> OTHER INFORMATION: Cross-link between residues
<220> FEATURE:
<221> NAME/KEY: MOD_RES
<222> LOCATION: (8)..(8)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (23)..(23)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (23)..(27)
<223> OTHER INFORMATION: Cross-link between residues
<220> FEATURE:
<221> NAME/KEY: MOD_RES
<222> LOCATION: (27)..(27)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 386

Leu Leu Gln Ala Glu Glu Leu Ala Arg Ala Leu Asp Gln Val Asn Ile
1               5                   10                  15
```

Asp Glu Glu Val Leu Leu Ala Leu Val Ile Ala Leu Ala Leu
            20                  25                  30

<210> SEQ ID NO 387
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (8)..(12)
<223> OTHER INFORMATION: Cross-link between residues
<220> FEATURE:
<221> NAME/KEY: MOD_RES
<222> LOCATION: (12)..(12)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (23)..(23)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (23)..(27)
<223> OTHER INFORMATION: Cross-link between residues
<220> FEATURE:
<221> NAME/KEY: MOD_RES
<222> LOCATION: (27)..(27)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 387

Leu Leu Gln Gly Glu Glu Leu Ala Arg Ala Leu Ala Gln Val Asn Ile
1               5                   10                  15

Asp Glu Glu Val Leu Leu Ala Leu Val Ile Ala Leu Ala Leu
            20                  25                  30

<210> SEQ ID NO 388
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me R8-octenyl-alanine olefin amino acid
      connected by an all-carbon i to i+7 crosslinker

```
      comprising one double bond
<220> FEATURE:
<221> NAME/KEY: misc_feature
<222> LOCATION: (6)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (23)..(23)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: misc_feature
<222> LOCATION: (23)..(27)
<223> OTHER INFORMATION: Cross-link between residues
<220> FEATURE:
<221> NAME/KEY: MOD_RES
<222> LOCATION: (27)..(27)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 388

Leu Leu Gln Gly Glu Ala Leu Leu Arg Ala Leu Asp Ala Val Asn Ile
1               5                   10                  15

Asp Glu Glu Val Leu Leu Ala Leu Val Ile Ala Leu Ala Leu
                20                  25                  30

<210> SEQ ID NO 389
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: Alpha-Me R8-octenyl-alanine olefin amino acid
      connected by an all-carbon i to i+7 crosslinker
      comprising one double bond
<220> FEATURE:
<221> NAME/KEY: misc_feature
<222> LOCATION: (6)..(13)
<223> OTHER INFORMATION: Cross-link between residues
<220> FEATURE:
<221> NAME/KEY: MOD_RES
<222> LOCATION: (13)..(13)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (19)..(19)
<223> OTHER INFORMATION: Alpha-Me R8-octenyl-alanine olefin amino acid
      connected by an all-carbon i to i+7 crosslinker
      comprising one double bond
<220> FEATURE:
```

```
<221> NAME/KEY: misc_feature
<222> LOCATION: (19)..(26)
<223> OTHER INFORMATION: Cross-link between residues
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (26)..(26)
<223> OTHER INFORMATION: Alpha-Me S5-pentenyl-alanine olefin amino acid
      connected by an all-carbon i to i+4 crosslinker
      comprising one double bond
<220> FEATURE:
<221> NAME/KEY: MOD_RES
<222> LOCATION: (28)..(28)
<223> OTHER INFORMATION: Nle
<220> FEATURE:
<223> OTHER INFORMATION: C-term NH2

<400> SEQUENCE: 389

Leu Leu Gln Gly Glu Ala Leu Leu Arg Ala Leu Asp Ala Val Asn Ile
1               5                   10                  15

Asp Glu Ala Val Leu Leu Ser Leu Val Ala Glu Leu Ala Leu
            20                  25                  30

<210> SEQ ID NO 390
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 390

His His His His His His
1               5

<210> SEQ ID NO 391
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (2)..(2)
<223> OTHER INFORMATION: Ile, Phe or absent
<220> FEATURE:
<221> NAME/KEY: MOD_RES
<222> LOCATION: (3)..(3)
<223> OTHER INFORMATION: Asp, Arg or absent
<220> FEATURE:
<221> NAME/KEY: MOD_RES
<222> LOCATION: (4)..(5)
<223> OTHER INFORMATION: May or may not be present
<220> FEATURE:
<221> NAME/KEY: MOD_RES
<222> LOCATION: (6)..(6)
<223> OTHER INFORMATION: Phe, Glu, Dpr, Asn or absent
<220> FEATURE:
<221> NAME/KEY: MOD_RES
<222> LOCATION: (7)..(7)
<223> OTHER INFORMATION: Ile, Glu or absent
<220> FEATURE:
<221> NAME/KEY: MOD_RES
<222> LOCATION: (8)..(8)
<223> OTHER INFORMATION: Asp, Dpr or absent
<220> FEATURE:
```

```
<221> NAME/KEY: MOD_RES
<222> LOCATION: (9)..(9)
<223> OTHER INFORMATION: Glu, absent or any amino acid available for
      cross-linking
<220> FEATURE:
<221> NAME/KEY: MOD_RES
<222> LOCATION: (10)..(10)
<223> OTHER INFORMATION: Glu, Dpr, Gln or any amino acid available for
      cross-linking
<220> FEATURE:
<221> NAME/KEY: MOD_RES
<222> LOCATION: (11)..(11)
<223> OTHER INFORMATION: Val, Asp, Dpr or any amino acid available for
      cross-linking
<220> FEATURE:
<221> NAME/KEY: MOD_RES
<222> LOCATION: (12)..(12)
<223> OTHER INFORMATION: Leu, Glu, pL or any amino acid available for
      cross-linking
<220> FEATURE:
<221> NAME/KEY: MOD_RES
<222> LOCATION: (13)..(13)
<223> OTHER INFORMATION: Met, Nle, Ala, Asp or any amino acid available
      for cross-linking
<220> FEATURE:
<221> NAME/KEY: MOD_RES
<222> LOCATION: (14)..(14)
<223> OTHER INFORMATION: Ser or any amino acid available for cross-
      linking
<220> FEATURE:
<221> NAME/KEY: MOD_RES
<222> LOCATION: (15)..(15)
<223> OTHER INFORMATION: Leu, Asp or any amino acid available for cross-
      linking
<220> FEATURE:
<221> NAME/KEY: MOD_RES
<222> LOCATION: (16)..(16)
<223> OTHER INFORMATION: Val, Glu, pL or any amino acid available for
      cross-linking
<220> FEATURE:
<221> NAME/KEY: MOD_RES
<222> LOCATION: (17)..(17)
<223> OTHER INFORMATION: Ile, Glu, Dpr, Bpa or any amino acid available
      for cross-linking
<220> FEATURE:
<221> NAME/KEY: MOD_RES
<222> LOCATION: (18)..(18)
<223> OTHER INFORMATION: Glu or any amino acid available for cross-
      linking
<220> FEATURE:
<221> NAME/KEY: MOD_RES
<222> LOCATION: (19)..(19)
<223> OTHER INFORMATION: Met, Nle, Ala, Glu, Dpr, Bpa or any amino acid
      available for cross-linking
<220> FEATURE:
<221> NAME/KEY: MOD_RES
<222> LOCATION: (20)..(20)
<223> OTHER INFORMATION: Gly, Ala, Glu or any amino acid available for
      cross-linking
<220> FEATURE:
<221> NAME/KEY: MOD_RES
<222> LOCATION: (21)..(21)
<223> OTHER INFORMATION: Leu or Glu
<220> FEATURE:
<221> NAME/KEY: MOD_RES
<222> LOCATION: (22)..(22)
<223> OTHER INFORMATION: May or may not be present
<220> FEATURE:
<221> NAME/KEY: MOD_RES
<222> LOCATION: (23)..(23)
<223> OTHER INFORMATION: Arg, Glu, Dpr or absent
<220> FEATURE:
<221> NAME/KEY: MOD_RES
<222> LOCATION: (24)..(24)
<223> OTHER INFORMATION: Ile, Glu or absent
<220> FEATURE:
<221> NAME/KEY: MOD_RES
<222> LOCATION: (25)..(25)
<223> OTHER INFORMATION: Lys, Glu or absent
```

```
<220> FEATURE:
<221> NAME/KEY: MOD_RES
<222> LOCATION: (26)..(28)
<223> OTHER INFORMATION: May or may not be present
<220> FEATURE:
<221> NAME/KEY: MOD_RES
<222> LOCATION: (29)..(29)
<223> OTHER INFORMATION: Glu, Gln or absent
<220> FEATURE:
<221> NAME/KEY: MOD_RES
<222> LOCATION: (30)..(32)
<223> OTHER INFORMATION: May or may not be present
<220> FEATURE:
<221> NAME/KEY: misc_feature
<222> LOCATION: (1)..(32)
<223> OTHER INFORMATION: This sequence contains at least one macrocycle-
      forming linker which connects at least one pair of amino acids
      at positions 1 to 28
<220> FEATURE:
<223> OTHER INFORMATION: see specification as filed for detailed
      description of substitutions and preferred embodiments

<400> SEQUENCE: 391

Val Xaa Xaa Thr Asp Xaa Xaa Xaa Xaa Xaa Xaa Xaa Xaa Xaa Xaa
1               5                   10                  15

Xaa Xaa Xaa Xaa Xaa Asp Xaa Xaa Xaa Glu Leu Pro Xaa Leu Trp Leu
            20                  25                  30
```

UNITED STATES PATENT AND TRADEMARK OFFICE
CERTIFICATE OF CORRECTION

PATENT NO. : 10,246,491 B2
APPLICATION NO. : 14/843079
DATED : April 2, 2019
INVENTOR(S) : Vincent Guerlavais et al.

Page 1 of 1

It is certified that error appears in the above-identified patent and that said Letters Patent is hereby corrected as shown below:

In the Claims

Column 597, Claim 1, Lines 30-50, replace:

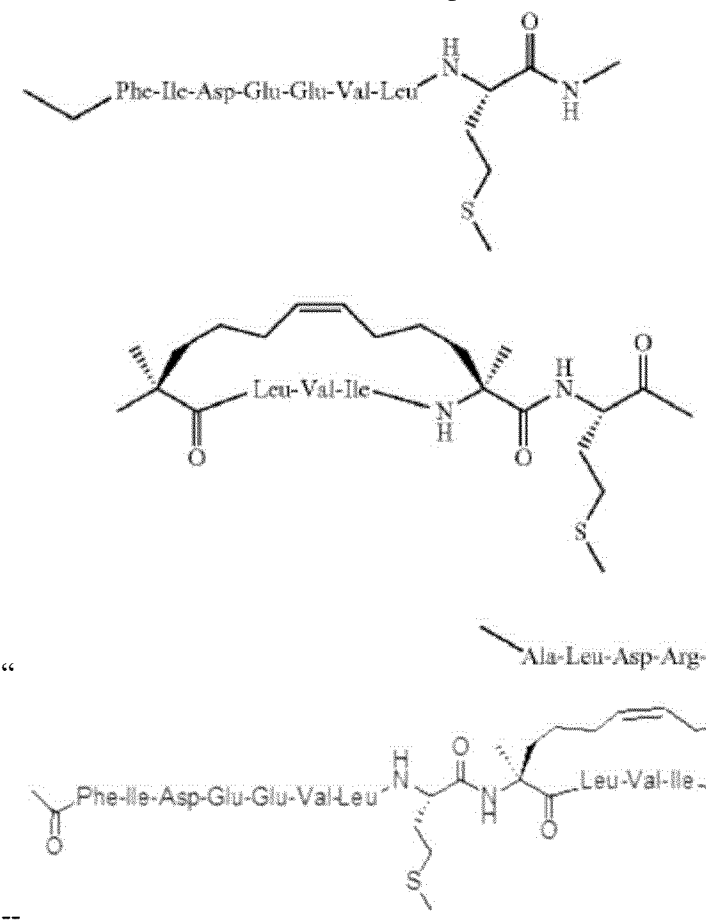

Signed and Sealed this
Seventh Day of January, 2020

Andrei Iancu
*Director of the United States Patent and Trademark Office*